(12) United States Patent
Ruezinsky

(10) Patent No.: US 7,847,153 B2
(45) Date of Patent: Dec. 7, 2010

(54) PLANT PROMOTERS FOR USE IN EARLY SEED DEVELOPMENT

(75) Inventor: Diane M. Ruezinsky, Woodland, CA (US)

(73) Assignee: Monsanto Technology LLC, St. Louis, MO (US)

( * ) Notice: Subject to any disclaimer, the term of this patent is extended or adjusted under 35 U.S.C. 154(b) by 23 days.

(21) Appl. No.: 11/938,045

(22) Filed: Nov. 9, 2007

(65) Prior Publication Data

US 2009/0031450 A1 Jan. 29, 2009

Related U.S. Application Data

(62) Division of application No. 10/810,788, filed on Mar. 26, 2004, now Pat. No. 7,294,760.

(60) Provisional application No. 60/458,828, filed on Mar. 28, 2003.

(51) Int. Cl.
  C12N 15/82 (2006.01)
  A01H 5/10 (2006.01)
  A01H 5/00 (2006.01)

(52) U.S. Cl. .................. 800/281; 800/278; 800/295; 800/298; 435/320.1; 536/24.1

(58) Field of Classification Search .......... None
See application file for complete search history.

(56) References Cited

U.S. PATENT DOCUMENTS

| | | | |
|---|---|---|---|
| 5,608,152 A | 3/1997 | Kridle et al. | 800/205 |
| 5,850,026 A | 12/1998 | DeBonte et al. | 800/281 |
| 6,207,879 B1 | 3/2001 | McElroy et al. | 800/278 |
| 6,426,447 B1 | 7/2002 | Knauf et al. | 800/281 |

FOREIGN PATENT DOCUMENTS

| | | |
|---|---|---|
| WO | WO 96/38573 | 5/1996 |
| WO | WO 99/67389 | 12/1999 |
| WO | WO 03/012106 | 2/2003 |

OTHER PUBLICATIONS

Kim et al 1994, Plant Molecular Biology 24:105-117, provided in Applicant IDS.*
Dolferus et al 1994, Plant Physiology 105:1075-1087, provided in Applicant IDS.*
Johnson-Hopson et al 2000. GenBank accession AC005106, provided in Applicant IDS.*
Benfey et al., "The cauliflower mosaic virus 35S promoter: combinatorial regulation of transcription in plants," *Science*, 250:959-966, 1990.
Bevan et al., "Transcriptional control of plant storage protein genes," *Phil. Trans. Royal Soc. Lond Biol. Sci.*, 342:209-215, 1993.
Cho et al., "Regulation of root hair initiation and expansin gene expression in *Arabidopsis*," *The Plant Cell*, 14:3237-3253, 2002.
Devic et al., "The banyuls gene encodes a DFR-like protein and is a marker of early seed coat development," *The Plant Journal*, 19(4):387-398, 1999.
Devic et al., Database NCBI, Accession No. AF092912, 1999.
Dolferus et al., "Differential interactions of promoter elements in stress responses of the *Arabidopsis* Adh gene," *Plant Physiology*, 105:1078-1087, 1994.
Federspiel et al., Database NCBI, Accession No. AC005882, 1999.
Johnson-Hopson et al., "Genomic sequence for *Arabidopsis thaliana* BAC T25N20 from chromosome I," GenBank Accession No. AC005106, 2000.
Kim et al., "A 20 nucleotide upstream element is essential for the nopaline synthase (nos) promoter activity," *Plant Molecular Biology*, 24:105-117, 1994.
Patent Office of the People's Republic of China, Office Action for App. No. 2004800142878, issued Jul. 13, 2007.
Piechulla et al., "Identification of tomato Lhc promoter regions necessary for circadian expression," *Plant Molecular Biology*, 38:655-662, 1998.
Santo et al., Database NCBI, Accession No. AB18117, 2000.
Santo et al., Database NCBI, Accession No. BAA97167, 2000.
Welsch et al., "Structural and functional characterizatio of the phytoene synthase promoter from *Arabidopsis thaliana*," *Planta*, 216:523-534, 2003.
Database EMBL, Accession No. AX700518, 2003.
Xie et al., "Role of anthocyanidin reductase, encoded by banyules in plant flavonoid biosynthesis," Science, 396-399, 2003.
Ellerstrom et al., "Functional dissection of a napin gene promoter: identification of promoter elements required for embryo and endosperm-specific transcription," *Plant Mol. Biol.*, 32:1019-1027, 1996.
EMBL Accession No. AC005106, dated Jun. 18, 1998.
European Search Report for Application No. 08165538.3, dated Oct. 12, 2009.

* cited by examiner

*Primary Examiner*—Medina A. Ibrahim
*Assistant Examiner*—Brent Page
(74) *Attorney, Agent, or Firm*—Erin C. Robert, Esq.; SNR Denton US LLP

(57) ABSTRACT

The present invention relates to DNA molecules that encode transcription regulatory regions. Furthermore, this present invention relates to nucleotide sequences encoding transcription regulatory regions that promote early seed enhanced or seed coat enhanced transcription of contiguous nucleotide sequences.

17 Claims, 7 Drawing Sheets

SEQUENCE LISTING

<160> NUMBER OF SEQ ID NOS: 17

<210> SEQ ID NO 1
<211> LENGTH: 913
<212> TYPE: DNA
<213> ORGANISM: Arabidopsis thaliana

<400> SEQUENCE: 1

```
gtttgataac tcgtctcttg ttaggatgat tgctagtttg ggtgttgatg agtattatgt    60
gaagcaacaa tggagtttgg tttccgttga gagtaagaag attgttgaag agaagtataa   120
gttgttgcaa gctaaggagt tggaatttgt gttggagaag actaagtttt tgaatgaggt   180
tgcttctatg ttcgttgaag cttcgaagaa caagccatta gatacataga tttatcggtt   240
tttaaaatcg gaatgctatt gccaatgcct tcttttgttt tcgatttagg atttaccctc   300
tcttttttg tcttcttcac tttttatctt tcaatgtaac tttctggtta ttttatcttt    360
gttaaactct gttatggatt tgtagcttaa atatgataaa attgcttaag gccagattct   420
gtgaaacatg gaccagaaca gagcaagtta tgttgaattg actcgtgtaa ttcgtgaaac   480
agaacatagc aagtccaagt tgtgttaaaa actgcagaga atttgacaga ttggtggaag   540
taaaaagcat tcttttgcaa ctcattttaa gatcggcaaa gaaaaaattg aagtaacaga   600
accttactgt aacactattc gttactctaa agctgtgtta tattgtttag acagaaataa   660
tcaaactctt gtgataattt ggtagatgat aacaaatcag aactcagaag gtcaatcttt   720
ttttattctt aggtgaagac aagttggtta tttcaaagat cacgtgctta ccttctaaaa   780
cagccttatt gatctactgt tgtacctaat gagcaaggac tatttgcaaa tcttttact   840
tcttatatag aagtctcaag acgataaact cataacaact aaatctctat ctctgtaatt   900
tcaaaagtac aac                                                     913
```

<210> SEQ ID NO 2
<211> LENGTH: 813
<212> TYPE: DNA
<213> ORGANISM: Arabidopsis thaliana

<400> SEQUENCE: 2

```
atcaaacgtc aaaacatgta ctcccaaata tattttattg gaatatagtt ttggagatat    60
ttttacctgg ggggagatgg aaccaaaata agatctagaa atgtgattgg ctaacgaaag   120
aagcacaata agttgacaag tgacagtgac aatttatccc tcgacaacaa cacacattca   180
catatatctt tttatttat tatttttctg tgtgtcttta aagttacag cacaagtagt     240
ttctaaatct tataatcaat tttcattgat aaacagaaat ttaaaatatt taaatagaca   300
aataaatgat caaatctata tttctataca agagttaatt cacaaaaatt tgttgtgaaa   360
caaactcttt ctatatttct atacaagagt taacatattt ctatataagt tattgtaaag   420
atcaaaatat gaaaattatg gtataaatgc atagacacat atatacgtgc cctattaaaa   480
gaggcagcga aagataata taggaggaag aggaagagga agaagatggt gaagaagaga   540
gttaatgcaa ctgcaagaag atagtaacta atcagcaccg tccattttg tcatctaatt    600
ctttcttact tggccgcaac ttccaaccac atcacacact cttctattc ccttatatat    660
tcccatctca aaagttcttg gagacacata aacattaaaa aagaaaaag aaaaaaacta    720
taaacataaa cgccaatcgc aactttcttg tctttcaatg ggagagaaag gtttgaagcg   780
gtctggtgtt gcggtggtgg ttgcattact agc                                813
```

<210> SEQ ID NO 3
<211> LENGTH: 2017
<212> TYPE: DNA
<213> ORGANISM: Arabidopsis thaliana

<400> SEQUENCE: 3

```
cgtgttggaa ggtgagagga aagaaggcag atcgcggatt tcgagagaag gtagattcgg    60
```

```
gaactcgaaa acggagttgt ttcctgtaga gtaattgtaa taaatgtcga aagcgaaggc      120
tggttggatc cagagatgaa cagagggaag atgaaatcta cgcgccactt ttggaaccca      180
gttgggaaga atcgtgtaga tcaagcaact tacgggagag tcaccattct gattagcttc      240
gatgaaatcc gatagagctt tatcgccatt acgttcgaag tgtaccaacc cggttttgga      300
cgtcgtcggt gttggagatg actccgtcgt cgaatccgtc ggagaaagta aggaaagaga      360
gattttcgac gttgttgtgg tttgggatca tagagcggtg aatgacagag agacacgtgg      420
cgaaagttac acgtgcgcca gttgttttga tgagccgacg agcaaaacgg agagatgggt      480
tcacgtgacc ttgcgccgga aacgttacca gtagaaaatg cggttgcgcc attttttgaa      540
gtgactttct taatacgtac gaggtgtgtc tcctcgtgga tttgtgctgt tatatgtata      600
taaatggaaa atatattaga tgagagtaat gggatttcat ttggggtcat gtgacatgag      660
ataacatgtt ttaccgcttt tggcgtgatc cacgacgtac gccatgatgg agatcataat      720
aagtatcatg ctgaatatac tatataattt atttataaaa aaaatagaac gaaagaaaaa      780
gtatcatgct gtcaaaaaga aaaaaaatat catatttttta tagagaaaaa actcgaaaaa      840
tatctgttta atatctatag ttgtttgaat aatatctaaa ttaattttat gttttttaaat     900 gcttttttaa ttcaaacatt caaattcatg attattatat tttaacggat gttctaactg      960
tggttgaaat ttaactcatg atattcacga aatgtataat ctattttcta aagtttacaa     1020
atatattagt gtaatctaat gggtaaatgt ggattgattc tcttcataaa tctaagttcg     1080
gaatcccccc ttctttccta attaatccaa atttattaag atagtcaatc ccctctttgt     1140
cctaattaat ccaaatttac taagatagtt agtcaatcca cgtttaacca ccatactaac     1200
ctaatatatt tgtaaagttt agagaataga tagtatatat atttataaat accatgagtt     1260
aaattttaat tatagttaga acctcccatt aagtccaaaa tttaaataaa cgaaagcttt     1320
taaatttggg aaaatttaat aatatatgta ttaaatggca aataaaagtt agatgagagt     1380 tttttttaaat tttttattat aaaataattt tttgcatgaa attgttttta agataaaatt     1440
ttgacataac caagtattat tttccgccac gaattgagtc tacgagagat gtcctgtctt     1500
taaacctcgt aaagttttgg tcttacccaa cccaataccc acaaaggtaa acgaccatac     1560
cggttaataa tattctaacc ggtttataag tttacataaa tcatttacta atccgcgtgt     1620
aattaagttt tatgaaatgt ggttattttg taggtcacgt gaaatttatt aatttttttag    1680 tacttgtttt tctttttttgg gttcaactag ttactttttt cctttgacat caaaattatt    1740
gtagacgagt ggtccatata tagatggtga aatgaaatga atattgagta ataaataaat     1800
atagaaagtg aacaaaaaaa attagtggaa aaggtaactg gaaagaaaag gcttattggc     1860
ttggcaagat tccataagtt tatttcacca aaaaggaaag agtacttggc cttgctctct     1920
ctctctttta aaatggtaaa ctggtaaaga taggagactc aatttctagt tcatcaaaac     1980
atatttggcg ttattattc tgtggtcact tgaatac                                2017
```

<210> SEQ ID NO 4
<211> LENGTH: 705
<212> TYPE: DNA
<213> ORGANISM: Arabidopsis thaliana

<400> SEQUENCE: 4

```
aagcttttaa atttgggaaa atttaataat atatgtatta aatggcaaat aaaagttaga       60
tgagagtttt tttaaatttt ttattataaa ataatttttt gcatgaaatt gttttaagga      120
```

```
taaaattttg acataaccaa gtattatttt ccgccacgaa ttgagtctac gagagatgtc    180
ctgtctttaa acctcgtaaa gttttggtct tacccaaccc aatacccaca aaggtaaacg    240
accataccgg ttaataatat tctaaccggt ttataagttt acataaatca tttactaatc    300
cgcgtgtaat taagttttat gaaatgtggt tattttgtag gtcacgtgaa atttattaat    360
tttttagtac ttgtttttct tttttgggtt caactagtta ctttttttcct ttgacatcaa    420 aattattgta gacgagtggt ccatatatag atggtgaaat gaaatgaata ttgagtaata    480
aataaatata gaaagtgaac aaaaaaaatt agtggaaaag gtaactggaa agaaaaggct    540
tattggcttg gcaagattcc ataagtttat ttcaccaaaa aggaaagagt acttggcctt    600
gctctctctc tcttttaaaa tggtaaactg gtaaagatag gagactcaat ttctagttca    660
tcaaaacata tttggcgtta ttatttctgt ggtcacttga atacc                  705

<210> SEQ ID NO 5
<211> LENGTH: 88398
<212> TYPE: DNA
<213> ORGANISM: Arabidopsis thaliana

<400> SEQUENCE: 5
gatcgtaaag ggaaacgata tgtctacgat ggtttgtata tggttgaaga atattgggtt     60
gagagagatg ttagaggtaa gagtgtgtat aagttcaagc tttgtagaat tcctggtcaa    120
cttccattga cttgatatta gtataaaata aaaactgatg atgatggtat aataagattt    180
gagggaaaaa aaaatattat tgaattgtag agcgttttttg ttaaataaaa atagaggact    240
aaagcttctt ttttattttta ttttattatt gtaatatatt catcaaaaga aaagtgaaag    300
gtattaataa gtggaagtcc taacaataac taataagtga aaggttataa atcagacttt    360
taagtgtaga gctaactggt ttttttttttt gtaattatca aattaccttta aagttaatat    420 atataaattt aaaatatcaa tactttctta cactattaga aacagatgga gaaagattct    480
ggtaaggtgt cagatttcta tttactgtgt ttttggacaa aaaaacaaag gttcgagtca    540
atttactgtc gtgaaaaaat gtctatttat tactatattg taatctcttt ttttttttt    600 ccttcgacta tattgtaatc tctttgatat atatgtggta gccattcaaa agaataagaa    660 aaaaattttaa ttgctatatt gtgattttgg attctagatt ttccgatagc taaatataaa    720
acatgtattc tcagaatctc gctgcaatat tatattaaga ctagatttta acccgcagta    780
caccgtgggg ctataatttt tagaaaaaat caaaatgtaa tatacttaat tgattaacat    840
tattatataa cctattattt tgtattttttt gaatttaata tgtggtacaa cgggcaaatt    900
gtttttatta gtataggcaa taatgttaac ttttacgatc ttttttgtat taaagttaat    960
aattttatat aagtacaata aaaaaactaa tgctgataaa atattaaaat aagatttaaa   1020
ccgtgttatt acttttggtt gatgatatta taaatatgta ttaatatcga tccaaaccccg   1080 tcccaccata taactctcat caaatattac tttttataag tttaaatatt attaatgttt   1140
ataaagttaa aatatttcaa taatatattt caaaaattaa tacttttttg cctttttatgt   1200 aatgacattt tttgtaattc ttactaaaac aaaaataagtc tacaaaatgt aattcaatat   1260
tttaaatgca gataatgtta taaataacta tttagtttaa tcataatttg taattgatat   1320
gtacttgagt ttttggatta cctgtatttc acgtcattta atagcctaaa ttgggtagtt   1380
ttgtaacatt atttgaaaca ataatattat cttaatacat gtacatttta ctaactgaaa   1440
aatatgagat tgattatttt tataacacgg aaaatatgag atagattttt tatattacac   1500
tgaaaatgaa tgattcaaaa ctaaaaatca tagtgtaata tagtttagcg tagaaaataa   1560
```

```
ttaaaaggat tttatttatt tattttgttt cctaaatttt agtttagact cagaaaacaa    1620
ttgtttaact tccttagaag atgataaaca tatatggaag atttgaatct ctattcatat    1680
atatttaaaa atcagtaatg tcaatataat taaaggatag attagaagaa attctcttga    1740
atgctaaata attcatttgt tatttataaa cgaaatatta aatgctgtaa aaaatgaaat    1800
attaaataaa tatggaaaga aaatcctacc ttaaagatt gtgtattatt gaaatcaatt     1860
tttattacag caaattaaaa ccaaaaatta ataaatactt aagagaaatt ttaggaatga    1920
tttcgtttga aataatggtg gagttaatat agagagattt taggcaatat ttttgttagg    1980
taaatatttg atttaaaatt tctgcataaa ttcagtggca ttgagtcgta aataagtcca    2040
agtccaagat ttatttgtta aaatggctgc aaaaatgtat atatagattt gcctcataat    2100
caaaaccttt ttactgctta aaaacaaaac aaaaaaaatc cttttaaaaa caaatgtaaa    2160 agtcctttt attctaatta aatctaccga gtataaaagt ttttttttcc aaaaatgtaa    2220
atatttccta aaagtgaaaa cgatttagct ttacaatcta tgattataaa cctataaaga    2280
tggaaatata ctttactta catatatcca ttatggaagt ttgtttactt acaaaaaata    2340
tgaatccctt tgggaaatgt ttttacacaa catattattt tccccacata aatgcacatt    2400
atgaatggaa ataaaagta aattttatat tattttctt atcaattaag taatttccaa     2460
atttgaattt aaagcatgat ttatatggaa agccaataac tttaacaaaa acaatatttg    2520
gaaaaataat atttcattaa ttaagattat cttcttccac tataaaaaga gttttaattg    2580
catagaatca ttcacttcat aaatatttag agcagtcaca tttgaaatct ctcctctctt    2640
attcttattc ttattcttat tcttattctc ctaaacgtgt atctatctat ggagctaatc    2700
agtcatacaa gttgatacat atttttcttaa taacgtcgag tcgggtaagt aacttttgtt    2760 tttttttctta atatcataga atgaaagatt ctaaactatc gctagagttt tctataaatt    2820
ttttagatta ttttttttca taatctctta aaagttttca aacaatctct ttattttaat    2880
gatattttca tgatttattt ttgtgaagaa aagtctataa aatcatatac caataatata    2940
atattttaat tcatcaacaa tcaatttttt ttttaataac acaaaacttt tattgattta    3000
tgaatccttt tattgtgcac tcattgatgt agatgattat ttttctttc aacttatttt     3060 caaacaaatc cttaatagtt tttagattta ggccgtgaat ggttgcggtt tttaaaatgg    3120
ttttacttag ttttttttcat attctatttt acaatcattc ataaattaga aaaagtggtt    3180
ccctaaaata gagaatttag attttgagag ttttttataga tttggaagca ctcttcaaaa   3240
aacttttaag agattttcag tgtttgtcat gaatgtgact atatttctct tttgactaac    3300
ttctaatttt gtttagttaa ttatttagtt tcttgcaaaa tccaaaagct gaaatttaaa    3360
aaccaaaatc taacgtcaac aaaaaaaatc tcaaaaccaa aaactaaaat cttaaaacca    3420
taaacattca tagctttaaa ccagtgttct agaaagagac ataaacttag acgcaaccg     3480 cctaaacttg catatgactc gttttggtgt attttactaa ttttcaacta aatttgtcta    3540
catatatata tacattgtta taacgtttta taaatcgttg gatataaatt aaataaaatat   3600 tttatctaaa ttgtgtttac aaattaaaac ttttctatta taatagatat ttttacataa    3660
ttttatgtat aatatcatat ttataaatat gttataaatg cttaaaccaa gtaaaattgt    3720
ctaggcctct attagatgtt ttaggtacat gaactaggta aacgcctgtg tagcgtttaa    3780
cgctttttta aacatgtttt cacttttttt aattctttg tacatattcg ttttctggtt     3840
tctattagat gttttaggtg gatgcactag gtcaccgtcg acttagcttc ttagaacaaa    3900
```

```
tttttctatt tgtttttaac atattacttt tgtggtttct atttattata cctaaataat    3960
atagtaaata aataaacatt aaaacctaaa aactattgcc caatagttga ataaaaatag    4020
gaaaacccac cacatagtat aatactaaat gcaaataact atttatagca aaagaaattt    4080
gaaatttcta taactataac tagtaataaa gtagatgaga acaaaactta aatgctatgg    4140
aaaaaactta caccaccact actaacgctc cacgtaatca ttaaagttaa ttagtcgcta    4200
atcattcgtt ttgggtattt aatatttaa agttataagt tataaccgaa acaattaacg    4260
tagttaatgg ctccattgaa aaacagattt aaaactcaaa cacacacaat taaccaactt    4320
aagtactgtt cagtgactca tcgttttcg agcctcagag attatcacaa gaagaagaat    4380
ccagagtccg ccgggaaaaa aaaaaaaaa aacaataaga agattacaaa acaaagaat    4440 tactccgttc atcttcgcta ggttctgttt caggttcagt gaattttttt tggttcttct    4500
cttcttccag tgtatacttt gttccctgct ctgtatttca tagttttctt catttctgtt    4560
ccttgttttt ttttttttg cgaattcttc gtttaaagtt cgcttttct gacaaattta    4620 tacaccttt tcgtttttt ctgagactca agcattcttt gatctttcgt tttcttgaat    4680
tttgtgtttt gtagttgaaa ttgcttcgaa ctctctggaa ctttagggtt tgagatcgat    4740
tttcctaata acggttcgtg tttttcaat ctcgatgctt ttacagaaaa taacggttcg    4800
aatttcaaaa ttcaaaattt tcactctccg tcatcttcgt cttttaccat ttgtgttatc    4860
cctaattgtt acagttttaa gatttagccc tagttttact gtgttcacac ttgcgccgta    4920
taaatgctct tactttaatt gtcattttca gccataatct tggaattaca ttgtgggatc    4980
tttctagatt atgtgtgaga acatagaaga ttaagatagt ttctgaattt ggatagatta    5040
gtgattttgt gaaacaattg tatatatgca ggatgatgat gactcaaagg atctctcctt    5100
ctaataagcg tcggagagtc tcttttgtta gagattttcc tcaatttagt gttaaagatg    5160
aaagtgacat tggtggtgat gatgttgcaa ccataaaaga gaactggat ggtaaagaag    5220 atagtaactg tgttggtgtc gcttatcgcg atcaccatag gcctaaagaa gaatcgtttg    5280
attcgataat gaagaaagct ggctttaatg tagctaatgg taatcttggg aatggaaagt    5340
ttcctccatc taagaggaat gttcctttac cttgtgaagg taaagtgcaa cctcttagcg    5400
tggaggaagg tattaaacta atggcttatg aaagccaaag aagacgttgt tttggtaagc    5460
ctttggtatc aaccaaagtt gtgcagaaac atagatactc acctgcgaag aagaagttga    5520
gtaatgcaac tgcgttaaga gtaagacact caccgatgaa gaagttgagt aatgcatcaa    5580
gactaagagc aaatgctcat agaccgactc aacataaaga tgaaagacgg tctggagtcc    5640
tctcggttat acaacgaaac cggctttcga aagatcttac cccacgccag aaggttcaag    5700
aagtgttgcg tattttcaca cttgtgtttg atgagctaga tcgtaacaag gcagcaagaa    5760
gaggtggatc agagactgcc aagagcagga tagattacca aacttggact attctgaggg    5820
aaatggggat gcaagttaac tctcaaaaga ggattggatc agtccccggg atcaaggttg    5880
gagataaaat tcagttcaaa gcagcactca gtgtaatcgg tcttcatttt ggcatcatga    5940
gtgggattga ctacatgtat aaaggaaaca aggaagtagc tacaagcatt gtttcatcag    6000
aaggtaatga ttacggggat agattcatca acgatgtgat gatctattgt ggtcaaggag    6060
gtaatatgag gagcaaggat cataaagcaa tcaaagatca gaagcttgtt ggtggaaatt    6120
tggctttagc taatagcatt aaggaaaaga ctccggtgcg agtgatccgt ggcgaaagac    6180
gattggacaa cagaggaaag gattatgtgt atgatggttt atacagggtg gagaagtatt    6240
gggaagagag gggaccctcaa ggtaacattt tgttcaagtt taagcttaga agaacttgtc    6300
```

```
aaccttatgt ggactttga aagggatagt gtgagataat gaaactttag ttttggttt      6360 tttggtaaga tagtacttac ttaggtccgt gacctgtaat atcaaaccaa ctatagtgtg    6420
gtttaggata acttttcttt ctgacagtag taggttcagg atcttgtgtt gtacaaattg    6480
aatgatcctt ctgatgtctt cataactaat gatccttctg tttctaaact tcataaatgt    6540
tacacctttt tgttaatatt atattctaat gatgtaaagt tacttcgcaa atcttggatt    6600
tcttagtttc ataatccggt aaagcagaag aacttcaata agttccttaa acttgttttt    6660
tcagatatgg taatatgggt ggaaacatga ctttgaaacg tttatataga atcctttcca    6720 acatttttaat ctaatcagaa aaaggcaaaa tatctaattg gtgagaatcc acagcaaaat   6780
gagaaaccta caaggtttag tcacagacag ctaaaaacca aaccaaatta aagaaaaaag    6840
cgccaaagtt tacgaaggaa acttaaagcc cattgacttc aatatctcaa cacagctctg    6900
acttttatca accttgtcct tgtcttcctt aaccttgtca ccggagtttc gaagcagagc    6960
ttcaatgatt tctttaaaag gtataatctc ttctttctct ttctcttttct tcttctttct   7020 tccatcttct ttccatttcc caccacccca ttcgtacgac ggctccatcc acggcggcaa    7080
cactctcctc gctgctgctt caccggcgac tgttgatgtg aacctaatt tcttgtccga     7140 aaccctagtt tcaatctctt ttggtggatt caatctcgca tcgtcagact ctggtgaagt    7200
gggaacagaa accattacga ttccttcttc cggattcacg ggaggagata aatgccaatc    7260
ttctaaaatc tctgaactct ctgtatctga acgtttctcc attctaaaaa gcttcggaat    7320
tcgaaatcgg cgaaactgtt aaaaaggaag agacttctg cttttctgtt tgatttgaca     7380
caattcagta aacttgttta gtatcggacc ttttggggct ttatgagctc taaaattaaa    7440 atgcctatg gactgttttg atttgaaaga ttagagacaa ttcagagaac ttgtttattg     7500
ttggaccttt tgggctttta aaggaaaata tgttatgggc tttaacggaa tatactttat    7560
gggaaagatt aaagacaatc cagagcattt gtttgatatt ggacctttt gggcttttaa     7620 gttggatctt ttggacccaa ttcagatttg ttttataatt tgggcattca cttcattcac    7680
ttaatgatat tgattatttt tttgttaagt acagatttat catttttttt tctcagattt    7740
atcattttta atgactcttg aaatcttgta cccaaattt tttaatagaa tcttaaaata     7800
catgacctta tcagtatt agatttaaat tttctttgaa aagttgagaa accaatgacg      7860
gtattaatct attttgaaaa cacatggatt tttttctata tatttatata taatttcat    7920 tgacggtatt atatatatat atatatatgg taattttgatt cattcattca tttgaagtat  7980
gataaaaaaa agttgataca cccaaattac actaattaat atcatcaata cacaacacat    8040
ataataaata aatatagaaa agatttacgc tttcaaaaac gagaaccata ttcactatta    8100
ttatttttct tcaaaataaa tctcattaga gattgtcatt tttgcctatc atattcatat    8160
attggatgaa actccaaagt tatctaatct tgacaatgat actagatatc ctctctagga    8220
gtatgaatga tgatgtgatt tcatgagaag agagaaaata aaaatcaata caaagatttg    8280
tttctggact agtttgagat aattgagatc gactcatcac atttcatatc agaatggatt    8340
gcaaataaat atctatttta ttaattagtt aatgataatt aatagatagg aaaagaaaat    8400
tttaaattca agaactacaa ggataataac acatgcattt taatttatcg caaggtgttc    8460
tttggacgca tcggcccaat cccttccgtt tctgtaggca tagagcatta caattgccag    8520
caccacaatc tatttcggtt aaagcctcct cacaacgttg ttgttgttgt tgcccttcaa    8580
tttcattcac catcatccct acaaaaaaat ttgtttcaat agcataaaat atcaattata    8640
```

```
ttttttttaa acataaaata catgatttta taatagatta agagcatgct aaatatataa    8700
aaagaaacct agaataagaa tgatgaagaa agcagaaatg atggatttag tcattttgt     8760
gtgataattg gagtttctga attacaatta taatgacaat agttgtagtg tacactgaaa    8820
tatcacaaac aagattatat atatatatat atatataata aagatatatt              8880
tttacaaatt tgattgatga attttggtag gtaaattatt taaaaatctt gtcatctata   8940
gttaataatc tctatatctc ttttttaaaa acaaatccaa tttttcccta acaattgata   9000
ttctagtgtt tcctcaaatt aaaaattcat gatttcaata aaatataatc attactaaaa   9060
tatatcttac ttacttagca aagtaataaa atataatcat tactaaaata tatcttaaaa   9120
attctgcagt tactgctctc tgagagtttc gattctgttt tcttaccgta atctttcttc   9180
aattgttgtt aacttgctat tactaatatt ttttgtttac gactttgaga ctcttccacat  9240
aaagccttag tgattttctg atgaagtaat cttatgcata tattcatgag aagacactac   9300
catattcata aatttaaaca aaagctcata tgctcaagtt ttcatttaaa gacctggtgg   9360
ctaattatac ctttcattta agtgatgcaa tgatcgataa aataattgta acagaattcc   9420
ttcacaaacg ggtaaacaat acaaaggatt agccatcttc aataaagcac aaagaggatt   9480
gaaaaagtgg acaagtaaaa ccaatgatga aagggtctct tgggtcaaaa atgtacataa   9540
tttataactg aaaaaaagaa gaaaatttga tggaagaaac gtgtggaaca ttaggagaaa   9600
gaaagagagg gatataaata acccaaattt agaagattta aaatacccga aaatatgtga   9660
atctgttttg attcggctgt tacatatatt gagatgatag gcgatgtgtt gaagctcaag   9720
agttgttatg tgggagaagc taaggtaagt tttaggatga aaccgatgat gagtccgatg   9780
agtccaacca tagctgccaa cttcaaggat agcccatttc cgctgttcct ctggtttctc   9840
cgcctcctta ccgtttcctg caatgtcgtt caaaaacatt ttaggcagta tcctttgtta   9900
ttaagcactg ttatgttcac atgatttgt ctgaatggta atatgattgc aagcattaac   9960
caatgctaaa ctatcaagga aaaggttcat ggaagcgtac caattcatgt tgcagctgtt  10020
gtgtttgctt aacggctgca tctcgctctt ccttcagccg ctgtatagtc tgttcataca  10080
tattgatggt ataaacgtcc agaaagagga ttaaaacaag acacgaatta atctttctta  10140
aattatgata tgaatgtggc cacttgtgag gttctgtgag atacatttgt tcaccttatg  10200
aagaaaggta taataataac ccaaacaaaa aattaaagct ttgaaaacca gcgtatgtct  10260
cactgtccca accaatcaac tcagtctgtc attacagtat ctatagcttg aaaaccaaaa  10320
gtgcgaatac tagaaagtct aaaatttgat tgaaactttg aataataatt cttgcagaca  10380
ggtatcacaa aaaagggact attcataagg tgtctgtcta tgcaagaggt ccatggtacg  10440
tcaacatact aagtaaatca ttaccacatg cagattaaat aatataggtg ggtactcaca  10500
gagatggttt ccgagctttg tccatcacca tttgttgctc cggattcaga ggatctttgg  10560
gttgtagacg ggtaatata agagactttg agcttacatt ctgttaatgt ctttccactg  10620
tccttggtga actagacaca caagtattgc atatataatg tcaatttgtt ttccaaaaac  10680
tgcagaaaca agaagaatct taataaaaaa agttttaaac ttggatttct tacagtgtct  10740
tgaggaagtt catccacatc agtgtgtgga ggtacaatgg tactttgcag gagaaatttg  10800
tctttgcact gcatatctgg aggatactct cgttgcgctt gtagagtaac tataattaag  10860
aagatcttaa tcatctccat gttcaagttt taaactgcta atgaaagaag ttagagtatg  10920
aggaattact atacctctaa tgatgcaaga gtcccatggc tgaatgacac cagtgttagg  10980
tcttacaaaa tacttctttg gagatgttgt tttcacctga ttgatgaagc caaaaacaca  11040
```

```
aaagaaagaa gccattgtaa caaacgaaat aacttgatca caagacaaag catatgaagt   11100
tggtggtttg atgcagaaat taccttgaaa gcaacatagt tctctgtttt attggcaact   11160
ttaagatcac agtagctttg cttctcaagt tcaactgaaa caaaatcaaa aattccaaat   11220
gtcatccaaa ggaagaccct ccaaaaagtt tcaaacagca atttcttaa taaccaagag    11280 aatcagcctt atctaaagtc agaacctcaa aagctcaaag aagttaacaa aaacttgatg   11340
ctggtgtatg taaacaagag gaaaacaagc attgatgata cacacaattt cgaaatctct   11400
agagaacaaa aagatggtaa attcgagaga agccttttct cattcacatt tcacaaatta   11460
agaatagata tccctagaat taaccaagta tagatgagac aaatgcatgc cattgattaa   11520
cgaagagagt gtagaagaat gcttacagag aaatttgagt tcatcaggtt gaatggagat   11580
aagctgattc tcgccaacgc cggtcatctt ttttttttgt ttgcttaaag ctacgacgac   11640
aaaagtttca caatcaaatc tctattgaaa aaagtataca acaacatcaa aaaatcgaag   11700
ccctaatcca aacaattccg attttatcta acttttttcc agaaaaggta aaaagagggg   11760
aaaaactgag aaatgaagag aggaaaaaaa gacggatcaa acctgaagaa aacaaaagtc   11820
acggtcccaa cgatgaggga ggaagaagct gcttattttt ttctctggct ctcccgataa   11880
tcgctctcca ccaatatccc aaaactctcc tcctatctct ctcctctcgt tctattcgtg   11940
gtaacaaagg caaagaaga gagagaaaga gaaacgggga agacgaaacc caaaggcgct    12000
tcgtggagcg gccacgtgaa gtcgaagcaa agtttccgta cgattttcct ccggcgtcgt   12060
ctccgggaac tgcggggaag aagaaagagc gaaagagaga gaagagaggg aaaaatgtga   12120
cacgtgtgaa aacagttgtg cattgtaaga gacgaaaaaa caaaggttaa aagcgacagg   12180
ctggaaaaaa gaggatgatg acgtggcaga tattgattgg tgtttgattt tatatagtgg   12240
ctaaaaaggc tataatgagc tttcagggtg gtaggccatt tttcgtctct cacgattgat   12300 gatatttaa atttatttct ccgtgtccat taatgattga ttgttagcaa gtaattaatt   12360
atcggacata aaagtcatca tacagaggaa agagacaaga aaaatactca atcattcgtt   12420 tctttttcc tgctttagct ggaaaattca tttacatgaa tgaattacat gatttacat    12480 gtaaaaatc tattttgaaa agcaatttca atgattcaaa agttttattt taatgattaa    12540
atcagtcata tttctgaaaa agaatactaa agggtccaga ttctacatac tcaagatcaa   12600
aacaatcaac attgatttac ttttcttaaa ttactgttac tgtaaattac atgaaaagaa   12660
atgaaatcca aaagacgaaa caaacaaaca attattacaa gagaaaagag agtagctagc   12720
tacctttgga gattgaagac aacacaagac aagactggtg ttgggtttgg tgatcattta   12780
aaagttgaga gacgaggaag tttgtccctc agatagtaaa gtcttgctct tctcactttc   12840
ctgtgactta ccacttttat ctcctttatg ttgggagagt atctgttaaa ttcaaaacac   12900
acatcacatc agatacatat tctaaaccaa gatcaaaaca tattacttga ttgtgtagat   12960
tagtatctgt tcaagatcaa aacatatcag ttacatatta cttcattgta gaatcagcca   13020
atagtactgg aaagttcata gggactagta tgttatgata acggctagac tctagagtga   13080
ttaagattaa aggttggtgc gcgtttctgt agtaaataag cacaaagctt ggtgacctat   13140
aatgctaaga cttccagcat ttatgtacta gttcctatag tatcatactt ggagtagcaa   13200
ttatttcctt ttttcgtgaa gaaagctaat acatatgatc agatatagaa ttgtaaatct   13260
cttaagttct caagaagcga agactatgac tgttcacgat aaaagaagct aattccggtt   13320
tgttttagag ttcctaaaat ctctctcaaa gccaaaagac tccttaacaa ggtcaaagac   13380
```

```
ccttaactct gactatctaa tactatttac atttatactt atcaatatac ccgagtaagt   13440
gtgtgataat aggatagtta aggaagaata aacttacatg ggaaagacga tttcaacacc   13500
aatgcctgca ataatcctcc ggatacggat agtagtgtgg atgcctgcat tttgtctaga   13560
catcacaata cctttgtaga tagatagcct acgtttgttc tcaggaactt cctgtaaaat   13620
caaacccacc atgtcgtatc aaaatcttgc agttaaatgc ataaattgca taagattata   13680
cggggacaat gagttttacc agtttgattt ctacaatatc cccagtccta agtccaggaa   13740
ccggtcttac agtctctgca acctcaatag ctttcttgtt cagtagctac agaaacaaaa   13800
agcaaatcaa catttcattt ctccaatgcc taaaagataa ctgatgattt aagaacagga   13860
gccaaaacaa ctacagtatc agacatgtat aatcagattc agagccaaaa caaaacacta   13920
gacaatctca tagaatcaca ttggataatg aactaacccc catgatatct ccgagcttga   13980
ctctcgtctt ccacggaggt ttagcttcct ccgccgcaac agtggcttct ccttctcctt   14040
ccgcttcagt ttcaacagca ttctccacaa cagcctcagt ttcaccttca gtactctctt   14100
cagctttagc gataaactct tttctcttct tggaatcgat ggcgaaacca aaattggagc   14160
tcgaatgatt gagaaaaacc ctagaaactg atagtcttga gttcactgat gatgctcgtg   14220
gtagaattga agaaacccct aaattcttcg acgagaaaga aggggttctc ggtatcatat   14280
gcaatgcctg gttccataaa tggtagataa atacagaatt caaagaagca taagtatgaa   14340
aatgtgattg agcgtgagag agtgaagaag aagaacctga ggaagaagat gagagctcgt   14400
cgccatgttt gcacaaccca aactcgaaac cagagtaaag aagagcctta tcgcttatcc   14460
gctccgtgta tttcaattta tgggccattt actaatttta tgggcctaga catttaggcc   14520
catattcaat tgatataaca agaaacccat taccaaagct ggttctacca gtctaccacc   14580
acgaaccaag gcttgtccaa gtacactaat gtagaaccaa aaatggttta aataaagagt   14640
ttctgttaca aacaaatgta tgtttatgtg tccttaaatt gatagctcta aataatctac   14700
tttgggcctt ttaaaagtta tgattgacga ataaatttct gctggagttg aaatattatt   14760
ctatgtgact atgttgtata ttcaagtcgt ctacatgttc acgttacatt gacttacacc   14820
gcaagcgatg aaaagctatt atatgttagt ttaatcagaa taccaaaaag ataataatca   14880
aaatattcca tcttctttct ttgtgaaacg aatatatatt ctcttacagg tggtttaatt   14940
aaaagcttga caacagtacg taatattagc atacatataa aaagttacat taattggata   15000
cgaaatttta atctcctaaa gatagttatt ctccgattgt atagaatcaa aaaagaaaag   15060
aacaaaaatc gacaaagaag aagaaaaaag attgattgat tcttttgtcc tccacgcatc   15120
tctctgagtt ggctcggcca cgtcagcatt caaacatcaa aaccaaaacg catttaaatg   15180
tcgaaaagag tgggtcccctt tttttctttt ttcttaaccg tgtcattgac aaaaagagca   15240
cttaataagc caaagccaca tagaagaaaa aaaaagaac attcacgtct ctctcgtttt   15300
tttggccgac gacgatcgct gaattgactg ccggagattc ctttaatcgt cagattctcg   15360
ttgagggata atgaatcctg aatagtaaga aacttgtctt ctcgttgttt catgtatcta   15420
ttgtttcgga tcgatccgcg tttttatttt tttgatgtgt ttggtgattt ggttttgtt    15480
cgattttgct ttggatcttt gttggttgtt aggtttgtga attgaatcta cctaattttg   15540
ctcgtttaag gtattttgta ttagaatttt gtatagattt ggattttcgt tccatggatc   15600
ttatacaggt cagatccgag gaaatttgat cgagatctgc aatttctgtt tactgttgta   15660
gttgaaaattc gcgagtgtga cacaattttc ccttgatct cattagcata ttgtatatag    15720
atgttcttgc gttttatttt cctgacccga attttcatga gtttatgagc ttcactgaga   15780
```

```
ttggtgttta ccgttctgtt gttgcagtga ctatctgttc aagcttctgc ttattggtga    15840
ttctggtgtt ggaaaatcat gcttgcttct aagatttgct gtaagtattc ccacaattct    15900
ggattcatca tctctggtag ttactttta acattgtgta cacacaaaaa tttgaggatc     15960
acatcttgga gttcaatacc tgttgctcaa gactcaaaac tcaaaagtca ttactccatt    16020
ggattagctt agttctcact atggtatcat tgttactcct ttgtgttctt atttcctgat    16080
atcttgaatt ttatgtggac aggatgattc ttacctggat agctacataa gcaccattgg    16140
tgttgacttt gtaagcacct tcatttgctc atcactcatt tatatacagg aatcagaata    16200
ataagtgtta acctttacta atgatatcat gcagaaaatt cgcacagttg agcaggacgg    16260
aaagaccatc aaactccaga tcgtaagtgt tcttcagcta gatatgcaat cataatctgt    16320
taaaattttg gaaagagcag atagttactc ttgttttggt aatcgcctgt gtatacagtg    16380
ggacacagca ggccaagaac gtttcaggac aatcactagc agctactaca gaggagctca    16440
tgggatcatt gtatgtactc ttactctaac caaccaatca tcttcttgtt aaataacaca    16500
tcctatacct cttgctcaca attgcctatc tttgcaggtc acttatgatg tcacagacct    16560
agagagcttc aacaacgtca acaatggct gaatgaaatt gaccgttacg ctagcgaaaa     16620
tgtgaacaag ctactggttg ggaacaagaa cgatctcact tcacagaaag ttgtatccac    16680
tgagacagct aaggtaattt tataataaac taggtgaact ctctatccac gtaaaccttg    16740
tcttaaagag aataacattt ttgttgtctc atctccttgt cccacaggct tttgcagatg    16800
aacttgggat cccattcttg gaaacaagtg ctaaaaatgc aaccaatgtg gaagaagctt    16860
tcatggctat gactgctgca attaagacaa ggttagaaac taaatttttac ttgtgaagtc   16920 attacccctt tacttccata cttaaaaggt tttgttgttt tcgcagaatg gctagccaac    16980
cagctggagg tgccaagcca ccaacggtcc agatccgtgg acagccagtg aaccagcaat    17040
caggctgttg ttcttcttga ttcaattagt caccactcct ctttcgatca tcacaccatt    17100
atgatcattt gtttgcattg catgttagac ttctccaaat taacaactct ttggatcctt    17160
ttgcttgttt ttcatttgct ttctttgat ccgattcttt tctgatgtac gttgaagttt     17220
gaaacccata acttctatat agtaaaaggt cttttatgca aataatgtag agcactcttt    17280
aatgccttcg acgattctaa atcatcgctc aagtatgaaa gatactagat atcgtgctat    17340
tagaaatata cttcatttat gatgtacgaa aagaaagatc gaatgtgtaa taccaaaatt    17400
agagagaaaa atatcttaat aattttttc ataacttaaa aaacgtaata gtttcgcaga    17460
aaagaccttc agaaagtgta acaaaaaatt ataaaactaa caaaattcaa ccaaagagaa    17520
acgaaagaca gagatagcga ggctgaagga ccagggggtct ttactagccc aacgaaggga   17580
actgagctgt gtctccaatc gccggagctg cagcttcttt tgcataccctt tggtttcctc    17640 cttcaccacg accaccgcga cctcctcttc cgcgggagcc tccacctctc ccgttgtacc    17700
tctttccatc agccggcttc aagaactcat taatgctcaa cgactacaaa atcacccaaa    17760
atcactcagg taaaaaaatg acacaaccca aagaaatca tgaagtgaga acagaaagaa      17820
ctaagacctt tttggccttc tcagtagcat ctttgcgttt ttccttgtca gatccctgaa    17880
acaataaaat accaagtatt aactattgct ccgttacagt gaagggaata gataaactga    17940
acagtagatg attttctgac cagcttgatg aagatttctt catcggtgtt cttcttgtta    18000
gagagctgtt gcatggactc aaacactttg gtgtcaactt tcctttcctc aacctttgtg    18060
gcttgcagag ccttcttctt ctcctccaga atttttctcat actcttctag agtcatctcc    18120
```

```
tatatgacaa aaccatatca gttcaaaatg ttagcaaaca ttctacttca aacttaacta    18180
aacctcaaaa gatgtttcaa gagctgtaaa tgattgtacc ctggcttcag cttcttcagc    18240
ttctttctgt gctttctctt ccgcagtgag ttctttcttt gcttcagggg tttcatcctc    18300
acctccttgc ttctcagcaa cagggctctt ctcaacctct gtggtaggtt cctcagacgt    18360
tctaatataa gaacaacaaa agtttataaa caacctaaag ttaaagtcat atggataatt    18420
aaagtgaaga caaggatgct tacgagggga tatcatcttc agtagtgccc cagtttccac    18480
gacctccacc attacgtttc atgccagtac tatcaaacat caagttaaca taaatgaatc    18540
acaaacagaa gaagtcaaac aaagtagtaa ctaaagtagt ggacagaaca aaagaaagc    18600
ttacccatga cctgtcctgc tatggcggtc ataattcctc ggtgggcgtt caacatcacc    18660
agattccccg ttggcaactc caccacggcg aggtccttca cgaccaccgc caacacggta    18720
tccaccaaca gacccaccac ggcttgctcc atcagcatct tcagaaggtc tcctgtatcc    18780
tccagaaaat ccattctcat ttccaggagc atcattgttc ctgttgtccc ggttgtatcc    18840
accattaccc ctgccacggg aaaatccacc acgtccacca gtcccaccac gacctccttg    18900
aggagcattc ctcgactccc tcactacatt cataacaaaa agctttcaat atatatactt    18960
atcctaatct aacaaagtat taagctttac cctaatctaa caaagcagta gagaaacaaa    19020
ataagatacg gaagaaacta acaaagcagc aaatgaaaaa agcacacaca tttgactatg    19080
gatctttcat gacaaccata aacaaacttc actagaacta atcaatcaaa cactagacaa    19140
aacacagctg aatctaaatc tgttaagtat caacataaag gaaagaactt ttacctgctt    19200
gagaaggagg agccggcttg gttgggaact tagcggcctt aggaggctga acagcagcag    19260
cagcttctc gactttctga gacaaagcca cagcgagctg gcttggatcc tcagcatcat    19320
ctcctagaag atcgaaaggg ttcaaagacg ccatcaccag tctggtaaga tcgagttagg    19380
tacaagtcac aggagaaatt ggtttacttt gatgggttta tagagaggga aatcagtaat    19440
tcatggcgat atacagaatc agaaaaaaga ggtacttgaa gagagattat tcggacagag    19500
ctgtttgtgt ttaagagata gcgaaacaag aaccctaaga aaagatgcgg cagtgagaga    19560
gagaggtgcg acttaaaaac ctaatctata aaccccttcct gagttattat tctctgcggc    19620
gggtgctatt taactgtgtt ctggtcctct ctttatctat ccgtgggcta caaactggtt    19680
aagcccatta acaataataa atatcagctc tcgttggtta aagcccatta atgaaaagaa    19740
tattcgttct tagtccatta agagaataac tgggtttcaa tactgaatcc tctaggcgag    19800
acacggtttt tctcattcta aacctttatt gggttcaaag ttttatgtgc ttcaaaaatc    19860
aaagatataa attgattgct taaatgaatt ttctctagca gagcctttgc ttgtcgacct    19920
tagacagctt catcttctca agagtatcaa acagaaacat ttacaagtga ttacacactt    19980
aagctcacaa catttacaac aaaaaaaaat ctaaaataga taggttatta tttattgtcg    20040
cgctactgtt gatggatttt ggtttagta attgttacct cttcgatcaa gttttggcta    20100
cttagcaata tagaactcaa attgagttaa gagattgtat taggggatat ggtgtaatac    20160
tttaataaag ccgtgaatgt catgtaagaa atgaaactag attgaaaaat taacactcac    20220
ggctttatta aagtgtctat tttgtttatg gattgaagat atatggctct gtttagtaac    20280
taatttacat cacgggaaca cttttacttg gtgcctcaac atttatagca aaactattca    20340
actacaaaac acacaagatc aaacttatga aaccaataac tcatcaacac gtgtctcatc    20400
accaacctca cacttcacct gcaccacctc cgacgtcaga ttctctgctt ttctccttcg    20460
tttcaacttc ccgttttcag acgacgacgt agaagaggac gacgacgacg acgacgaaga    20520
```

```
agatctctta gacgtgatcc gaaccgggtc aggttcaccg gaattaaccc tcaacggaaa    20580
attcaataaa gcgcgggaac cacgcatcct aaaagcagct atatcgtaag ctaaagccgc    20640
atcttccgcc gtctcaaacg tccctaacca aaccctagct ccattcttcg ccggatcacg    20700
tatctccgcc gcgaatttcc cccacggtct ctgcctcact cctctgtaat gcttcgcctt    20760
cactgccgtc tccgtaaccg gtatcgcttt ctttggtttc tcctccatcg ccgtaaagtt    20820
ctcagttggc tcgactttaa ccgccggaaa atcaaaaaga cagctcaagt ccgatgatga    20880
cgtgtcaaaa tggaaggcat ctttgaggag tccgtacacc aacatgtcct ctgaatcatt    20940
ctctttcaat ggcaaacctc cccaactctc tgtgaaacac gaactcggtg ttgactcatt    21000
gagtcgcagc tcgttctctc ctcctcctcc tagcaagtga cgtgttatcg actccaacaa    21060
agcgtagtcg gattctatat tgcactgtcc gtacattttc agagaaacta actatagagt    21120
tttttttgtt ttgttgattg atttatcaaa tatctgaact ttttctatg tggaaggtgg    21180 ttaagaggtt tatatagagg gtacgaggtt cacgaacctg gaaaaaaga aaagttttt    21240 catgttttc caaatttgtt ttagtttagt gggtaattaa aaaatatgaa agttgtggat    21300
ttttcgttac tacgaaggtt cgtgaattaa acacgtgcgc tttatccaca gatatcacaa    21360
tgaagaaggg tcaagatgac gtcatgtggt catgacattt ctggaagaaa gatgctgatt    21420
tggttttgtc tctcaacttg tcccttgttt tgtcgttcgg ttttgaatac gattcccggt    21480
tttattaggc aaaactagtg tttaattagt ttgttaatcg aaaaccaagg tcttaattca    21540
ttatactttg ttatatcgac ataaattttc aactaaactt atatttcatc gccttacact    21600
agagtaataa ttttttgctta agtatacttt attagatagt attggcaagt atattatatg    21660
tttaattaca tgaaatctaa gcttagatct tgttatggtg gtgaatgaaa aatcttaacg    21720
aggtgggcca taattatatg aatggggaca ctgaaagtgt ctgcaaaaat cgggatacat    21780
ttctcctggt caccaaccaa ttcatatcat catctttccc tttcacctt catttttact    21840 aatttctaat ttagaatttt cctaattgcc aatgtcatgt ttattttagt acttttgat    21900 acaagatttc atgattaaga aattcattag tgccacttta gtcaataaat atggagtagt    21960
gaaatcatag tgataaagtt ttcatgcaaa gctcaattta caaccacag tttaatccat    22020 atttgttgca tttcttttct ttcttttttg aaaatataac agccttagat cttttgtac    22080 accaatgatt tggaattttg tggataatta ttgaatttcc atctctttct attggctaaa    22140
agtcaataac aacaataagg ctcaaagaca aattaatggt gggtctctca cgtatgtcca    22200
cttgcaaaag ggacctcctt cacggaagca tagttagtc aatagtcact caaactctct    22260
aaaaattagt ttactatata ttttaatct atattcgatt ccaagagtag ttttggttca    22320
aacacatcat tctggtcaga tggttatttc aatttgctg ttttgagtg tatatatgat    22380 gttatgtttg taaacaaatg aaactttaa ttgattacaa gaacatgaat agctctaaat    22440
atgattaaaa acgaatttat ttatttcttt ggtaaagaa taatgataat atacttatgg    22500
atccaatcag gttaagttcc gttttgcaat taaatacttt gattaattaa atatgaaagt    22560
agtagttgaa cttcgttttt tatgtttgaa ctccgcagct aatcctcaaa ttatctcttt    22620
ggacgtttca catacatcca cttttgctgt atcttaggaa tatattgttt tcatattgtt    22680
tcttgtttct ttatgatttg ggtttatata attttcaaat gtcatgatga tcatcattta    22740
atcttagttg tttagtcac atcttattat gctattatt agtcggtgat agtttaattt    22800
taagacgtaa atcatctatt ctcatattat gctagaacaa acttttcctt tgtgcaacct    22860
```

```
cctagaacat atagtcgcct attatccatg gatcccagat actcctccaa gaccaccgaa    22920
aggtttaatt atggatagga acccttttgg ctacgttaac accttgattg acttccagac    22980
gaagaggtgg aaagtagatc gtctacggga gttgttcccc ccccccccccc cccgaggata    23040 ttactttgat tttagggata aaccgaggc taaatgtctc gcgagatgga tatagttgga    23100
cattgactaa gttcggtaat tatactgtca agacaagata tgaagctgcg agagccctct    23160
ctcgcccgtc ttgcgaccac cctcttcagg gacctagtgt tacggcacta aaggcgcaag    23220
cgtggaaatt aaaaactaca cgaaagctaa agcattttgt gtagcaatgt gtgtcagagt    23280
gtttagcaac ttgtcaacgc ctatattttc gccatattgg tagagataaa aaatgtccta    23340
gatgtggggc ggatgaagaa accatcaatc atttaatatt tgaatgtccc ccggcaagac    23400
aagtctgggc gctatccggt attccctcct ctccatctag gtttctttcg tcttctatat    23460
acaataatct cgattatctg tattggagag cgaatgagat tggagcttgt gaggagagct    23520
tacgggtctt tccatggata atgtggtata tttggaaagc gcgaaaccga aaaaatttcg    23580
aaagtatttg cgtgcaacct caagacactt tagacttagc aatacatgag gaagaagtat    23640
ggaggcgagc caataggaga gaagagcaac cagaaggtac caagccaagt ttggaagggc    23700
aacatataga tatggcttcc ccaatctgct tcattgatgg gtcttggcat ataactgatt    23760
cgcggagcgg tcatgggtgg attttgaccc gtggggaaag attgcttcat ttaggattga    23820
agggttcacg tcgttgttta tcaccgcttc atgcagaact agacacatta gtttgggctt    23880
taaagtgctt agtagactta tcaatcaagg aagtccttgt taagacggat tgctctgatc    23940
ttctcactat ggttaatacg ccggaggagt ggcccatttt tgcatcagag ttaaaagatt    24000
tcgagtattt taagaatcaa cttgtatctt ttaatattat gcatgttccc cgtactagta    24060
atatccgagc agattatctt gcgaaatgtg caagaactcg cggattctat ttttcccatg    24120
taagttcaac ggttctcgat tggctctctt taaacgagag cgcttatcca tagaataata    24180
tatagagttt taacccggaa aaaaaaata ctcgcctata gtttgcttta aaaaaaagtt    24240
tcttccaacc aacaaaagca ctcacctaat cttacaactg tgattttga ccaatgtttt    24300 tgttcatatc tcttcaaaaa aaatttata ctataatgag cattataata tattttctat    24360
cacatattat tgtgcagaaa ttaagtatca agttaaaggc aagttttagc aaaaacacga    24420
tttacggaat tagcaacatt tacacggacg atcgcatatt tcagacaaga caaatacaga    24480
ggataaaata tcataaaagg gaaaatgacg acacaaatta tgtaggcagt gattggtaca    24540
cattgttagt tttttttaaa atattactat gtttttgcca aaaaaaatta cgaatcagag    24600
caatcatgca taaaaattag aagaatagcg taaatatttt tctcttttct attcacacct    24660
ttactcgctt ttctattcat tttcttattt ttcctctcaa ttactccaaa aacataccaa    24720
ttagagttta gattcatgat gtaattgacg aaaaaaatca cccatatgat tagttacact    24780
atatccgaac actaatattc ataaatttag tgtctcggat ttatgcatac aaactttca    24840 tggaagatgc ttctcatta caagctgatg ataaaattga tcttacattt tttaacaatg    24900
aaatgtcttc tattttttgt tatagccaaa ataactcagc tttcagttat atataatcta    24960
cagtttagtg tattttgtta actttaatcg attcctaatt cattttaatc aacacatcta    25020
tatgtaggca attggatgca aaaggtacac aaaacaatgc aaaaggaagg atcaaaggaa    25080
agatgttata tgacacgtca gcagtattca aaagtttgaa gttgaacaaa tctagtcatg    25140
tttgactttg accactgact tttcaaacct atctttatt agtagcaaac tcagttccat    25200
acgtgcaaac aacctcacac gtgcgttccc accgcaatgt ttgaggtttt cttcaacaga    25260
```

```
agacgatatt tcttattatt ataacgttag attgagaatt caaagattct cgacaaatga   25320
atggtaactt ttttctataa gaatcacaat aattagtttt agttatacaa ttttataatg   25380
ttggagtaat tgtcacatag atgattggtt ggtgataata gttgtttatg tatgattgat   25440
caattaaact tataattttc cattggaata atattttctt gacctttaaa tttggaatgt   25500
agatttatat ggaaaaagta gataatcatt tttgtgacgc taattaaata tgttgtccca   25560
taacgacaga aaaaaaaaaa tgaaacaaaa atagagacca gattggttca agaaaacgac   25620
acacagttta ggatgctaaa aaagctttgt tagtaccata tgattgttat attgtttatt   25680
ggttccttaa taatgtattt agacgtcaaa aaatgttttt gtattgatat gtgacctcat   25740
aactggttag ctgcttaggg ccattagatt agagttttga ttgtttcaaa tgtcaaatct   25800
tacagtccgt caaattttat ttgatgtgaa gtaagtgagt tgataaatgg gactactttc   25860
tccagttggc tagggtcgac tgctaataac atttctccaa ggaattaatc tcaacgggct   25920
tgttgctcag gcaacaattt ataggaatag agattgaacg aaataattaa cagattacac   25980
aacaatgttt cctctacttt aagcaagcaa tcttcaaggc tatattgatc gactgattcg   26040
agacgcaatc gtcttgtcaa gaagaaccac aaaaactatg atgatatgta atgcaaactt   26100
gactcgtctt tgagtaacac ttcttcatct agtccaatcg tcgcagggtt tcttttaatt   26160
tatttattta ttatcttctc ttttggtaag aaagagcttc tttaatttgg ttaaactttt   26220
ttttttttggt taagtacaaa acttctcatt ccttaataaa attgatatct atattataaa   26280
atatcaaatt ttgtaaaaca aaaataatta agagtagtgt ttcacaacaa caacaaatta   26340
aaaagactac tatataaatt aaaaagacta cttggctttc tagaaattat taaatataaa   26400
tttttatatt aaatctctga tttgctatat catttattaa aagtgtgaac tttattttgt   26460
ttcattgtaa caagtaacaa catgactttc tagaatctag tgagtgagtc gttgattcat   26520
tctacaaacc agttaatgca ccgcgtaaat tcttttcacg tgcatggtgc agtgcatgaa   26580
gatggatcaa attaaatacg aaaccaaaca taattcaata gtatatcatc ttttaaaatt   26640
tgtatgatta ataatctctg tcaataaaag gccgcatgca ttgacttgac tctttcagtc   26700
ttgtcttgct tactaattaa accctccata atgcatcaac ctaatcataa ccgaaaattt   26760
tctgagttgt atttggttag actttaatgc tttactatca ttttagttac gtttgtgttt   26820
acctcgcaaa aaatcttcta gaaggataat ataatactac aatacaatgt tggcattatc   26880
cattactgag cggtgtgaaa ttggttttga ttgtttaaca tatgagttaa aatttgttcg   26940
caatattggc aaattagcat cggatatgct attgtataag aaaacgctta tttttggagt   27000
gcgcgtctac ctgtaactgt ataaactacg taacgaacct ttgaacgcag agtgaatgtg   27060
agtctctgtg acacgactta agcttaatc agaagcagat tattggacct tatggagact   27120
ttatcaagat tagctaatga aggttactat atatgaaact ttgaagtaat tgtttgcagc   27180
cttttgggat caataaacca taaaagcatt ggttttgttt tctctatcta tatccaattc   27240
cggaaagtag aaaactggat tagtaaaaat catattcaca cattgcgaag aaaaactatg   27300
tgcgcgcgga tacgttggga aaatctgcgc atggtttaaa gttttgcttt cagtcaatta   27360
taattcgttt tttatactcc ctctgttcca agatacttga tattttgggt ttttgcacaa   27420
gaattaagaa aagtaacttt tatattttta attattcttt tagttagttt aataatatta   27480
attttacttc tctcatttca ttattggtta caaacaaaaa taataatgat agttttttcaa   27540
aacatcaatt ttggtggaac aaataaaaaa actcaaaata tcaaataact tgaaacagag   27600
```

```
ggagtagtta attaaaaaaa gatatttcac actttgactt ggcgaagcct cataacaatg  27660
aagttatgta tgaactatat atgaagttag aaacaatgga aaacagcttg taaatattca  27720
ttgttgtata tatgttttt tgggtcaatt tggtgcatga acaaaaataa aaacgtagat   27780
gaaaaccgga tattttggtg ttaacatttg catttgaact tcgtgaaaga cggataaaag  27840 ctcattttg ttctttatta tatggctgct attagtacac agagttgaac tttagaatac   27900
taaaaatctc gacatctttt attttatttt tgtcaagcat cgacatcttt tctgttcaag  27960
aaaacgaccg caatagtcga ataatataac tcttggacta gttaatatat atttgcgata  28020
gattttcgat ctcacttata tcttataacc aagagacaaa aacaatattg cagtcaagta  28080
caaaacgaaa acaatcacaa tgtcgactat agatgagtcg gtcattcgat ccaacggctc  28140
tgagtccacg aaacacgcaa ccaagtggtg ctctctttta caccaaatca tattataaaa  28200
aacttaaaag aaagagagga tggttcgttg gctccttctt gttccttaat taattcaaat  28260
tatattcatc acctccattg aataagtcca tttcacgaca aagtcaccaa tgcttctttt  28320
acatgtatat atacttcttt ccactccctc ttctctactc aaatcaaatc ttcttccttc  28380
tctgttttct taagcttttt gaaaattta tcaatggcga ctcctaacga agtatctgca   28440
ctttggttca tcgagaaaca tctactcgac gaggcttctc ctgtggctac agatccatgg  28500
atgaagcacg aatcatcatc agcaacagaa tctagctctg actcttcttc tatcatcttc  28560
ggatcatcgt cctcttcttt cgccccaatt gatttctctg aatccgtatg caaacctgaa  28620
atcatcgatc tcgatactcc cagatctatg gaatttctat cgattccatt tgaatttgac  28680
tcagaagttt ctgtttctga tttcgatttt aaaccttcta atcaaaatca aatcagtttt  28740
gaaccggagc ttaaatctca aattcgtaaa ccgccattga agatttcgct tccagctaaa  28800
acagagtgga ttcaattcgc agctgaaaac accaaaccgg aagttactaa accggtttcg  28860
gaagaagaga agaagcatta cagaggagta agacaaagac cgtgggggaa attcgcggcg  28920
gagattcgtg acccgaataa acgcggatct cgcgtttggc ttgggacgtt tgatacagcg  28980
attgaagcgg ctagagctta tgacgaagca gcgtttagac tacgaggatc gaaagcgatt  29040
ttgaatttcc ctcttgaagt tgggaagtgg aaaccacgcg ccgatgaagg tgagaagaaa  29100
cggaagagag acgatgatga aaagtgact gtggttgaga aagtgttgaa gacgaacag    29160 agcgttgacg ttaacggtgg agagacgttt ccgtttgtaa cgtcgaattt aacggaatta  29220
tgtgactggg atttaacggg gtttcttaac tttccgcttc tgtcgccgtt atctcctcat  29280
ccaccgtttg gttattccca gttgaccgtt gtttgattag ttttttttga gttttttgaac 29340 gatgtgtatg ctgacgtgga cgtacacgta ggtgcatgcg atgaaaaaaa catctatttg  29400
ttcatatttt tgcgttttc tatttgttca ttcttttca caattcacaa tacattattt    29460
cagttaatga ttacggataa tttagcttta cgttaattta ttatgagtac tagaagaaat  29520
cggagtaatt caacatatag attatactag tataaatgtc aattgcattg acattaattg  29580
aggaattata gtagaaccta gtataaaaag aatgattcaa acatgagata ttgaccggcg  29640
ttatgtgaag ttgttcagac aataaatgca taaccgtgat tctgtctgaa caagtcgatt  29700
cttaggataa aaaatggata aacttagtca aaatatttcc cacgtggtta gacttttgct  29760
tagttacatg acgaatgtga aagccatcca tgcatgtatc cagaagaata tatcttgcac  29820
ggcgaattct ctacgtattt tagtatttta gatttgacga catctaattt tcttttggta  29880
tttcgggttt gacatctaat ctgctaagaa ccttttctta taatcgaaga attttgttgg  29940
gtcgtcttgt aagatattat tttcagtaca cactatctaa tcattcatca aggtcactaa  30000
```

-continued

```
tgggccttgt ggtctaaact ttgaatatat actttcacct atgaaatcca gaagttctgg    30060
ctgggtaagt tctaaaccaa cctatcttat acatcgaaac acaaaagata attggaacta    30120
caaacaaact ttacccaaaa attattagtt tgtttttatc tccgtagatg aaattgggtt    30180
ttctaaatcg ttttcgaaga tgaacgctaa tcaaacaaaa gtggtataac acagtttgtt    30240
acgaaatttt gttaggaaaa taaatgaagt atgtgttttg cgtcgacctc aaaataaaat    30300
acatattaaa tcttgcatgc taatattatt gtatagaata ccaatcaggt aagaatcgct    30360
cgtcatcata cgactattca atatccaaac atatttattt ggaaaacccg accacgaata    30420
atggttagct ttacatcatt atccacacat actcaaatgg ttaaattttc tagaattgta    30480
atggaagaca caatgttatc acgaatgagg atcatcatgc acttcaggtt acctaattat    30540
cctacgtgga caatacctaa tccttccatg attttcaatt attgcagata attttctga    30600 acgtcatcat ttcccataac gaataatcat ttcctcaatc aacgcaaacc taactatcta    30660
tgtcatttac atgtttatgt ggtaaaaatc tgcttagaat aagtaaacct tcacatatat    30720
attgtaacaa ataattgag gttaatgtta ttcaatgcga aaaatgtaa acacttgcta     30780 atgagtcgta ataaccctat attattttc caaaacatgt ttctattgaa gttacaaatt    30840
aagtttccac tctatttgga tggagcgtac tagtcgtaga cacggagagc ttccaagtcc    30900
atcggatcaa cttatcaaac ttatcgacct tttggtccac aacaagatat cttttgtcca    30960
tcttcatcat ggctctcgca agaggatggg ttacatatat ggtttgcttt attgcttaat    31020
agggattaat ttctctaata cttttgatta gcttttcgca acattttc agcataagga      31080 cgcatctgac gtacaaatta aaatccaaa tgaactaaaa tacttttaaa cagaaaggac     31140
aaggaatcta agccatcaag gcccatctcc acgtagctcc agcaacgaca agatgcttta    31200
ttatcccatt ctcgtggata cttgtgtgag atacacgctt cagataaatc aacggacgaa    31260
attgtaaaaa gcgtgaggaa gagagagcct ctttccaaag gagagggatt ggatcattga    31320
gatatatccg tttatccatc cttgaactcc tgaagattcc ttcgcacaga caactctctc    31380
gaacatgtta aagattctct gatacctaac tattgattcc tttttccctg cattttcgt    31440 tcactatttt tgcttataac tttttgtact aaaattaaaa atcatgccac catcctgtat    31500
ttcatatcca aaagctttgg attatttat aatatatcat tggcttgatg tgattgatat     31560
ttaccaaaaa tctattctag tttcttttg taacaccaaa tgttatttaa aatttgtatt     31620
ggaaaaatga ttcatttata taagttatta tatccctctt aaaaattgta taaaatctct   31680
aagacattat taattgtaaa agatagacac aacacgtagc tatatgtcta tatccaaaaa   31740
taaaacacgt agctatatgt aatattataa aaatgtacat atattattag ggttgtaata   31800
tttggtcggt tgaaaattga aatcgcagct caattggaaa ttcacgtgta ttttgtcttt   31860
gattgtaaga tattaaaact gttcttcgct ttccttttct catttctcac ttaaccactc   31920
gatccacttt aaaccacaca ttataagtgt gcctcaaaaa aatctaacat tactctctca   31980
acacatctct ctttcttctc catttccttc ttctctttca ttctcttatt taagatttaa   32040
atctgctcaa atgcttgtaa acaaatttca agttctttaa acgatttcct tttcaagaaa   32100
aatccttctc cttcttcttt ttaccacata gatcttcttg atctacaatg gattctgttt   32160 ctcttttctga ggttactgtc attaaaggaa caacacattt gggttttatg cacagtttca  32220
gacagccatt ttgtggtgtc aaaatatctc caaagttcta tttatccaaa ggtaaataat   32280
aacaccttaa aatcacttcc tcttcacaac aagaatcttc attgtctttt ttaaaaattg   32340
```

```
ttttttttttt tttgcattttt ggacgagaag ttgatggacc aaaggcaata tcttcgagca    32400
gcaacacaaa gagtcaattt gtttatggag gaggaagcat agctgcaact tcagattcag    32460
gttataagat gaatggagta aacctaaaaa gcagaacatt gatgagttct gcagttaaag    32520
aaagatcatt acttgatgct tatgatgatg agtatggtgg agtaatagta gatcatggaa    32580
aattaccatc aaaccttat gctttcgctt ctatgcttcg agcttctcta tccgattgga    32640
gaagaaaggt aaaaacgata aaccctataa aagtcttaaa ccctttgtt tttgtacata    32700 tgtaaatttg ggggaaattt ttgtagggaa agaaaggagt ttggttaaag ttacctgtgg    32760
aacaatcaga attagtccca atagctataa aggtaagcaa taagaaaatg gttcttgatc    32820
ttgtttgata aagcagagat ttgtttatgc aagttaatga tttttttgtgg attgattttg    32880 caggaaggtt ttgagtatca tcatgcagag aaaggatatg taatgttaac atattggata    32940
ccagaggagg aacctagtat gcttcctgca aatgcttcac atcaagttgg tgttggaggt    33000
tttgtattaa atcaacataa agaggtatca atatatgaat gattattctc tcaagtctca    33060
acacttaaag tagagtaggt aaaaagaaga gttacctgaa tttttttta aatctcatta    33120 ggtgcttgtg gtacaagaaa agtattgtgc tccttcgatt actggtctat ggaagttacc    33180
aacagggttt attaatgaat ctgaagagat tttctctggt gctgtaagag aagtcaagga    33240
agaaactggg gtaattaaat ccgagaagat tagtatatag tataaatctt gattctgttt    33300
aaaaattcgc aagatcataa ccatgtatgg cattgtgttg tgttattcag gtagatacag    33360
agttctcaga ggttatagct ttcagacatg ctcacaacgt tgcatttgag aaatctgatc    33420
tgttcttcat ctgtatgttg agaccactct ctgataagat aatcatcgat gctcttgaga    33480
tcaaagccgc aaaggtaaat gtaacaagag tctttattag aatgctccag ttgtacatgc    33540
tacaagacgg tcctgattac aatgattgtt gtgttttca gtggatgcca ttggctgaat    33600
ttgtggagca accgatgata agaggagaca aaatgtttaa aagagtgatt gaaatatgcg    33660
aggcgagatt aagccatcgg tactgcggtc tttctcctca tcgacttgtc tctacttttg    33720
atggcaaacc ttcttctctc tattacaacg ttgttgatga tgatcatgat ccttcccact    33780
ccaattgtag cactgagttt tatagataga cgggtaaaac agaaccaaat caagtggttc    33840
gattctgtat atacttattc tcatgtaatg tatgttgtta tttgatactc tctcttcagt    33900
atagtaaata gtaatagatc ctctgcaaaa tccatgtagc atcgaaccgg tactctcagt    33960
agactataca ataaaaagat ctgttcaaat aaataaccgg tgggtcaaca caagtttaaa    34020
caatattcaa actcttggac tgacatattc aacgcatata atataatgta aaccaagttg    34080 taatttaat tcatagaaga agacattatt gcaatggact aattcaacta aaccaagcta    34140
gccaaacatg tcaagatcct gtgcaaaata tctgcttctc tctcaaaccc tgagcacaat    34200
agataacata caattgtggt ggaacatgga aacgttttca ggaatttgac aagacaaaac    34260
aaatgacaag ttgtggaaac atacaagaaa taagaacgta cgggacaaag tgacaggaaa    34320
aaatagctct tgccctcctc cactatccca ttcaaagcct tatatatgag atcatcatcg    34380
atttctttat aatggacgtt gatgaagatt cgggcagttt tctatatcga ctttgttcag    34440
cttcagtttt ggaaaagaga cttgactccc atagatgctt cctagttcct tcaaataatg    34500
tagacgaagg acttgtagct cttgaaaagg atcaacccca acaccttgag ctttctcttt    34560
gtttattaat tctgtcatct taggcgagga ttccacgctt agagactcga gatttgcagc    34620
atacatcagc catgtcaaat cctttagatg tatgcatgag tttattacca cagctgagag    34680
atccttgaac catggattgc ttggagtgat ttcactggat gatgtggatg gagaatactg    34740
```

```
gtctcttctc ttaccttccc attctgttcc cgactctgtg atatcgcagt ttaccatttc    34800
aagtttgtgg agactactca acgtaccaat ggctgcaaat gatactttaa gtccttctag    34860
atatataccc tgcgtcatcc ctgccaatct tgtgcttcct agaaactctt ccaaaacaga    34920
atcgttattc acagtaacgg tcaaaagttg taaacccttc aactgctcca agatcttgag    34980
caagcagcaa tctaatgcag cagcagaacc ataaaatctg agaacctgca acttttgtaa    35040
ttctgaaatc agaccgacgc ttcgaagatt ggaagtggac tccaaattca agtgaatcaa    35100
tttactcaag actcctaaac cttccggcag atgctttata ctcgtccctg ataagttgag    35160
aagccgcaaa gaaaccaacg ccgagattcc ttttggcaac tcggtgattt ggaagttcca    35220
agatagatcc aaaaccacca gagtcgacat gaccagaaag aatttaccaa caatatctac    35280
caacctgtta ttttgaagga acaaggttac aagatttgtc tggtcaggaa attcaggatc    35340
gtctggtatg ttcttaatct cattgttgaa cagagacatc tttgtcacag ttgtccaatc    35400
ggtgacatca ggcagttggc ttaaaccagc atctgttttc acaacatatc tttctccatc    35460
cctaaattca gatactatcc acaatgccat atcacggatc atatcatgca tatacacttt    35520
cttattagac tctaataaca aacctgcccc aacaagatta tcgatgatct catagcctcg    35580
atcttttgct ctctctcttc cgtctttttc atctatgaaa ccctcaccta tccaatactc    35640
taccagctca tcttgtttga tataatatgc cttgggaaat aaagcacaat acagaaaaca    35700
cttggcattt tttgttttca ataatcata gctcaacttc aaaacttgaa atattccctt    35760
ctctgtacct ttcatctcac tccgataaga ctccaaagta tcgagtgcac gacgccattg    35820
aatcacagta gatttagatg ccatagtctt tcttataact tcaagtgcaa ggggtaagcc    35880
acaacactta gccacaatct tttttgcaat atcagaaatt tcatttaacc cgtcgcaatg    35940
gaccttcata tcgaacaaat cccatgcgtc attctccgac aaacattgaa cttctatgtc    36000
ctcatttgcc ctcataactg aacagacatc cttagaacga gtagtaaaca cgactttgta    36060 tttttaccg agcactggga tgcctattgc tgttaaactc acatcctccc ataagtcatc    36120
taataacagc acgaaccggg gcttcatatc tcttagtacc ctgcttattt cactagcttt    36180
cttccctctt gagtatgtag accaattatt gtcacagatg tgtaatcttt ccccgatggc    36240
atcttgaatc ttcccgacat ctgcatcttt agacgattca acccaaataa caacatcata    36300
atcatcactg acttcaacga acttgttgtt aattagagtg aggagggtag ttttgcctac    36360
gcctcccata ccgaagattc ccaacattct gttttcatct tttctaagac tttcccaagt    36420
cttttcaagc gtcgtatcaa gaccgactgt ttgttggcaa agtctcactt ctaccacagg    36480
aggaggaggt tgctcagtca cttcttgaaa atctttaccg gagagacttt taacttcagt    36540
caacttcttg aataccttct cgcctaggtt gcaggttgag aaccagcacc cagatgttga    36600
cagacgtcga cgtacagctg aagcattctg agaagaagca tcccgagcgg acgcaacatc    36660
cattaactgt ttggtgtttt cctcaatgat ttcgacttgt gaaagccacg tagccactat    36720
agctagccgt tgaccacccT taagctcacc agcattgact ctgtttacaa catcttcttt    36780
ttctgcttta agctcatcaa aagcactctt caacaagaca agattttcct tcaacatgca    36840
aatgttaccc acctttacac acaagtaaga caaagcagac ttataacatg gctcaactac    36900
ctgccaacag caattcattg tgctcaagat tgagaaagag aactaagatg agagtagcaa    36960
atttaaaaca gatctttgta cagaacagga tgtctgaatc ggggagtag aaatagggaa    37020 acagaacttt gtgcaggacg aactagagag accagagaaa aggaagagac cagagaaatg    37080
```

```
gagagatgat gaaagaagaa aaataatgga gagaggaaaa gaactagaga aaaaagttat   37140
gtggaatgcc tttaatatcc ctaccccacc cgcatgttgt agaattttt gtaacaacaa    37200 tgatgactaa aaggtgtact gtgtctgtgt ggtaggtaac gttattggtt cattgattta   37260
caaatccata tataattacg caacatgtgc taagatattg acgtggtttg gtgtcagcta   37320
agagacaaat attggttcac tgattaataa attcatatgg gtttgaactc atacatagaa   37380
taatatggtt gttcttaaat ttaaaaacat ccacaaaacc aggttagaca aacaaaaatg   37440
actaacaaag cataaacgaa tactatatgt ccaccaacca tatgcaaaac gaaagaaaaa   37500
aacaatgaaa tccatgaata aagatttata aaatgaaaga tccacaaaag tatcaccaca   37560
agccacgtaa ctcccatatg cattaaaaca tatcaaattt aatttcaaat agtaaccaaa   37620
aaatttcatt ttgtaaccaa aaaatcaaat taaaatttta aaagggaagg gcaatattgt   37680
caacccacaa agccaagggg gaaagtggct gaaaaattca gtctcaattc agttgactcc   37740
taaacacaca aaatgggaaa taatttctca gttgaatctc catctttggc gccgttcctg   37800
tgtgggaaac gcaagtattt atacaacctg gagagaaatc tagaggcttt gcataaagta   37860
atgcaagacc tcaacgcaat gagaaacgat ctgttgaaga ggctgtcgaa agaggaggag   37920
ataggtctac aagggctaca agaagtcaaa gagtggattt caatggtgga agagattgaa   37980
cctaaagcca atcggctgct tgatgaaagt gtctctgaaa ttcagagact atcaaggtac   38040
ggctattgtt ctctgatccc tgcgtcgacc tatcgttaca gtgaaaaggt acttacgact   38100
atggaaggag ttgaaactct gagatctaag ggagtcttcg aagctgtcgt tcacagagct   38160
cttccgcctc ttgtgataaa gatgcctcca attcaactta ctgtttctca agcaaagttg   38220
cttgatacgg catgggctcg tctaatggac ataaatgttg ggactttggg tatttatggt   38280 agggggtggag taggcaaaac caccccttctt actaaactca gaaacaagtt acttgtagat   38340
gcatttggtc ttgtgatctt tgttgttgtg gggtttgaag aggtcgagag catacaggat   38400
gaaattggta aaagattagg cctccaatgg agaagagaaa ccaaagagcg caaggcagct   38460
gaaatattgg cagtcttaaa ggagaagaga tttgtgttgt tactggatgg catacagagg   38520
gaattggatc ttgaggaaat tggagttcct tttcccagcc gagataatgg atgcaaaatt   38580
gtattcacca ctcaatctct ggaagcatgt gacgaaagca agtgggttga tgctaaggta   38640
gaaattacat gtttgagccc ggaagaagca tgggatttgt ttcaagagac tgtcggagag   38700
aacacgttga gaagtcatca agacatacct aagctcgcaa gagtagttgc tagtacatgc   38760
cgtggtttgc cccttgctct taatctcatt ggtgaggcca tgtcaggaaa aaggactgta   38820
cgcgaatggc gttacacaat tcatgtcttg gcttcatcca cagccgaatt tccagatatg   38880
gaagatggga ctcttcccat tttaaagtct atctatgata atatgagtga tgagatcatc   38940
aggttatgct ccttttattg tgctctgttt ccagaaaatt tggatatagg aaaagaagat   39000
ctggtaaact actggatatg cgagggaatc cttgcaaaag aagatagaga ggaagctgag   39060
atccagggat atgaaattat ctgtgatttg gttaggatgc gattgttgat ggagagtgga   39120
aatgaaaatt gtgtaaagat gcatggtatg gttcgtgaaa tggccttgtg atagcatct    39180 gaacactttg ttgtggtagg cggtgagaga atacatcaga tgctaaatgt caatgactgg   39240
cggatgatta gaagaatgtc agtgacgtct actcaaattc agaatatatc agattctccc   39300
cagtgttccg agcttacaac cctggtcttt cgaagaaacc gacacttaaa atggatctca   39360
ggtgctttct ttcagtggat gacaggactt gtagtcttgg atctatcatt taatagagaa   39420
cttgctgagt tgccggaaga agtttcaagc ctggtgttgc tgcggtttct caacttatca   39480
```

```
tggacatgta taaaaggatt gccccttggt ttaaaagagc ttaagagttt gatacacttg   39540
gatttggatt acacatctaa tcttcaagaa gttgacgtga tagcaagttt attgaatttg   39600
caagtactga gattatttca ttctgtttct atggatctca agttaatgga ggatatccaa   39660
cttttgaaga gcctgaaaga gttgagtcta acagtgagag gatcttctgt tttgcagcgg   39720
ttactaagta tccagcgatt agcaagttct atccgacgtt tacatctaac tgaaactaca   39780
atagtcgatg gaggaatatt atcgttgaat gctatattca gtctttgtga gcttgatatt   39840
ttgggatgta atatcctgga gataaccatt gattggagat gcaccatcca aagggaaata   39900
attcctcaat tccagaacat acgcacaatg actattcatc ggtgcgaata tcttagagac   39960 ttgcatggt  tgctattagc cccgtgtctt ggtgagctaa gtgtatctga atgtccgcaa   40020
atggaagaag taataagcaa agataaagct atggccaagc tgggtaatac gagtgagcag   40080 cccttttcaaa atctaactaa gctcgtctta gatggtttac ctaaactgga gagcatctac   40140
tggactcctc tacccttccc agttctggaa tatttagtga taaggcgttg tccagagctg   40200
agaagacttc cattcaactc tgagagcact ataggaaatc aagttgaaac gataattgag   40260
gagcaagtga taaaaatagt tgaatgggag gatgaagcta caaaacaacg tttctcccat   40320
ttcaataaca ggtatcttct tccttatcct acatttcctt ctctatttt  ttcgataagg   40380 tttcttaaat ctataaaagc ttggccatga ataactagca tcttcccacg ggaatgtcac   40440
ttaccatctt cttaattttt tatatatttc aatgtcactc ttattattca tagaatctgg   40500
aaagctgatt tgataagatt ttgcaatggt gatccttatt ttgattgatc attgtttgtt   40560
cgaattatgt aacaaacgaa cggagtgcag agactttgta cagatggctg aagatccgaa   40620
gatggatggt ttgacatcgg agtcacatcc aattcaaacc atagacctgg tcgggactac   40680
aggaagtgga gaaactgcca ctgcaaacaa catccaagga agaaggtgg  tccaatcggg   40740 aacacacgca actgttgtta ccatggaatg ccagacatat aaagttttca caccagattg   40800
ccccatcaac aatatgattg acactcctgg tacgaatttc cttttatgtt atacctaact   40860
aaattatcat gcgtgggaag aaaaaatata aattttctaa taagtaaggt ttgtactta   40920 cgtatacaat tagaatagga tccacgtaaa atgtgtattt ctaattttct atatagttta   40980
aaattaaaaa gtgacaaaac taataatgct gaaccaaata ttataatgta tataactatc   41040
aatactattt tcaattatat aattgatatg attttgtgtc actaccatac gcatatgaca   41100
tatatattta ttatttatat gaacacaaac tctcattcat taaactagtg actaaagttt   41160
actttgctca caaaagagtt gatttaaacg ttttcacaaa caccatccgg acgtaaaatg   41220
tgtaatggaa catacataga gaccaaataa ttataaattt ataatagata atgcttctat   41280
gtatatgtat gtttgtatgt aagattacgt catctcaggt gaactattgt tgagttttg   41340 atattgaaca ctggttaaaa gtcattgaga ctgtgtctct gatgctagaa agtccttcat   41400
ttgatgctaa aaagactttg ggatccgagt tttgtttctg actgtgtcat attttctgac   41460
tttgggaact ggatttaggc aagaggaagg tgaaggagat gctttttaat ttgaacgatg   41520
aggcaagaat tattgggatc tcagggatga tcggttcagg gaaaaccatt cttgccaagg   41580
agcttgcgcg ggacgaggag gtccgaggta atcagtttg  ccctttgtta tgtctgaaac   41640
tatccattgt taatatgctt gggccatctt tgaagtcttt tgagcagttt atgttgttgc   41700
tcagtggcat gtttactggt ttatttggat gatcatgcat ttatctctgt atgttccatt   41760
gtgtcatgtt catctccggt gaactgttga tgagtcgtat agttgagttc ttgatattag   41820
```

```
aatctgttaa gagtcggaga gactgttcct ttgatgctaa aaaagcttta atacaggcca   41880
ttttgcgaac cgagttttgt ttctgactgt gtcacaatct cccaatcttg aggagctgag   41940
atcccttata cgggattttc ttactggtca tgaggctggc tttggtaccg ctcttccgga   42000
atccgttggt catacacgga agctagtgat ccttgatgat gttaggacaa gggaatctct   42060
agaccagctg atgttcaata ttcctggaac cacaacgctt gtggtctcac agtctaaact   42120
cgtagatcct agaaccacct atgatgtaga gttattaaat gaacatgacg caacatctct   42180
gttctgtctc tctgctttca accagaaatc agttccttca gggttcagca aaagtttggt   42240
caagcaggta atgggtctgc tacaagtgtt acatgcatag tagtaatatt ctttgtactt   42300
tcagtactca tcttgactct atttgttagg ttgttgggga gtctaaaggt ctacctttgt   42360
ctctgaaagt ccttggcgct tcattaaacg atcgacctga acatattgg gcaattgcag    42420 tggagaggtt atcaagaggt gaacctgttg atgaaactca tgagagtaaa gtgtttgctc   42480
aaatcgaagc aactctagaa aatctcgatc caaaaaccaa agagtgtttc ttggatatgg   42540
gtgctttccc tgaaggcaag aaaatccctg ttgatgttct catcaacatg ttggtcaaga   42600
tacatgatct tgaggacgca gccgcctttg atgttcttgt tgatctagca aataggaatc   42660
ttcttactct cgtgaaagat ccaacgtacg gttatagaac tctttatgtt ctcatctctt   42720
gtagccactt ttataatttt aaccattctt aactaattta ccgtggataa tgttgcaggt   42780
ttgtcgctat gggcactagc tactatgata tattcgtgac gcagcacgat gttttaagag   42840
atgtagcact tcatcttacc aatcgtggaa aagtaagtag aagagaccgc ttattgatgc   42900
caaaaagaga gaccatgctt cccagcgaat gggagaggag caatgatgag ccatacaatg   42960
cacgagtggt ttccattcac acaggcaaga atttgttatg caacgatctt ctaatgaatt   43020
aattcggttc gtcactagaa tcataaggta ttaatatgga tttctttaca ggagaaatga   43080
ctgagatgga ctggtttgac atggatttcc ccaaggcaga agttctgata gtaaacttct   43140
cttcagacaa ctatgtattg cctcctttca ttgctaagat gggaatgctt agggtgttcg   43200
tgattataaa caacggtacc tctccagcgc atctacatga cttccccatc cctaccagtt   43260
tgaccaatct aaggagtctc tggcttgaga gggttcatgt ccctgaactc tctagcagta   43320
tgatacccct gaaaaacctc cacaagctat atctgattat ttgcaagatc aataacagtt   43380
ttgatcagac agccatagac attgcccaaa tcttcccaaa attgactgat atcacaatag   43440
attattgcga tgatcttgcg gaactacctt cgaccatctg tggaataacc tctctcaact   43500
ccatcagcat aacaaattgt cccaacatca aggagttacc gaagaatata agtaagctac   43560
aagcccttca acttttgagg ctatacgctt gcccagagct aaaatctctg cctgtggaaa   43620
tctgtgaatt gccaagacta gtgtatgtcg acatctctca ctgtctcagc ctaagttctc   43680
ttccggaaaa gataggaaat gtaaggacac ttgagaaaat cgacatgaga gaatgtagct   43740
tatcgagcat accaagttcc gcagtttcat tgacttccct atgctatgta acatgctata   43800
gagaggcttt gtggatgtgg aaagaggttg agaaggcagt tcccggactt cgtattgaag   43860
ctactgaaaa atggttcaac atgacttggc ccgacgagta gtaggttctt aattctccct   43920
ccgagctttt gaaatgcat gttgtattat tatttattaa ctcgattagg accctgtat    43980 gatatacgat tttattaata catgttttgc tcttataacg tcaatatata aattatatgt   44040
tgattttaag tattaaaagt ttctatttgg aatctcaaag atatgttttt aaagattcac   44100
ttataagtaa taacaaacaa acaaaaacta tttagcttaa tggtaaaaag catgagtcta   44160
tatagagaag ggttcataat ttaaaattag tttgaatgtt gtttgttatt aagtgagata   44220
```

```
cattttaaaa taatttagtg agataaatat atcgttaata ttatgcatgt gctgattatt    44280
atatgaccaa ttatatgacc catcaatagt tgtcaacatt ttcttggtgg atcgacgagg    44340
acgaacccaa tgatttagaa acagggatga tatataacaa gtaagtatag tcgcaagtgt    44400
ccctgatcta tagtcataca aggtaaggcc cactgctgaa agagaagtg gcggtcggat     44460 ttaaaacaat acaagtgaag tagtgtatcg agcccttgt aacatgagat tgtatagatc     44520
ccagtaagag atggtagatt tttaatctga gataagaaac tatctctatt tggaaatcag    44580
agaatacttt gcaggggag agggatggga gctacctcga gggcatcaag ttcttcaaaa    44640
ctggagaatc atctttgatt tggatatcag aaagagaaga tatatctatg gttatagtgg    44700
ctgagacaaa cgattctctc tcccaaggat cattgggact gccttggcca tctggactgc    44760
aaggtataaa caggaagaaa taaaaacaac aaaaatatca aggatatagc actaccaata    44820
tgataaatgc attgacaaaa tcagtctttt aagtacaaaa atactttgg tgaagggaaa     44880 actaataaag gaaacttgtg ctattgaagc ggacaaacag ctacccacac accattgtgg    44940
gggaattttg agaaacagat ttgagacttt ttattgttga tagtaacata tacataatgc    45000
tctagcttct tctttctatg cgacgaatca acaatattgt ccatgctatc aacaatacaa    45060
ataatagcta aaaccccaaa aatcataaaa ctaagcaaca agctaatctt cttcagtttc    45120
agagcaagaa tcaaaatgta cagtatttaa aagagctaga cagactttaa cgtagaagaa    45180
aagaatcaat ctccagagcc ttccttagtc atctctgctt cctttttttg catcttcacg    45240
taatgttggt tatgcgattt aacttgttat ggattcctag tctttacaaa ttctctagat    45300
atgacctccc aagctcctgg ccctttcgac tttagtcctt caagaaagag tctgaaaacg    45360
tacaccaaag taaatggata atcagatgag agattcatca tatgatctat atttaccaaa    45420
ttagcaactt taaacaatta atgcctaagc aaagccaaga cctccatcta acattcatca    45480
tcttaaatta gcaagaagac aacttactcg tgttcttggg ctgaccaacg agttcccttc    45540
ttcgccacta tcggcgtcgc tgaacgtggt gagtactcgg gcacaacatc tctgccggat    45600
tcgataacag caatatcttg gagcagctta tcgtagtggt atttgatctc atccaccgac    45660
gttctcattt gtgcagcgat aatctccagc tttgccggcg aatccgggac ttgcacgagt    45720
gcaacctcga aagctttgtt ctcctcccaa gtccacttca tcgtaccagc cattgtagcc    45780
aagaaaagaa agaaaaagaa ttgagagaga gagagagaaa gatcgagcga gtgtaacgac    45840
gtggagttga atctgttacg taacaagaat ctttgcgatt tatatcttta tacagcaaca    45900
acacattaaa ccaagaaatg aaccaagatt acatcttaat taattcataa accggacatt    45960
ccagagccct taaccggaat tatattagta tatcactata tacatgttaa taatagcctt    46020
gataaaataa tagcaaaaca gattagcctt ttagtttttg acgtcatgca tgcacttgtg    46080
ggtctgtgaa atctcgcgt tttctcgtgg aaaagtggat cgcttacaaa acctcaagat    46140 atctttttt ttttttcaac ttgaacctca aggtatctaa gcctttaaac aaactctctt     46200
ctacgtttta taatcaacag aaaaatgtta aatataaaa cttcaaatac aaattaacaa     46260
ttatcaaact agccaaatgt tatatttcaa acatcattgt tcattgactt tttacatgtt    46320
ttcaaatatt tactttaata caaaataaac aaaatactag tggcgtataa aatatcataa    46380
aacacgagca aatatcggag gatactagaa aacatataaa gttgaaaata aactaactcc    46440
gtgtataaag aggaagaagt tatcttatga ctagaaaata tatatatata tatatatata    46500
taatattaaa agtgagagca cgggtcggag caaacaataa aaccctaatt aacaatcaaa    46560
```

```
gccacctgat agagatgaga aacacattga tgttgtcgga ccttccagga gatttgttag    46620
aggagatact ttgtcgcgtt cctgccacat ctctgaagca gttacgatct acttgcaaac    46680
aatggaacaa tttattcaac aatgggagat tcacaagaaa acacttggat aaagccccaa    46740
aggattttca gaatctcatg ttgagcgact ctagggtatt ttcgatgagt gtcagtttcc    46800
atggaattcc atctgtagag gccacatgtg aacttagcct aatcgactct ttttctagtt    46860
ttgaagataa attcgagatt tctcaagtct ttcactgtga cggcttattg ttatgcaccg    46920
acgcagacaa cactgaaatc gtggtttgga acccgtgtac tggtaaaact aggtggattg    46980
aacccaataa tcgttgctac tactatgctt ttggatccta cttggacaaa tcctacggta    47040
atagctacaa aatattgagc tatagtggtt atggctacga gaaccaagaa ctcgcaatct    47100
atgagattaa ctctcaatca tggaggtttc ttgatgtcac tcgtgactgc atcctcgaaa    47160
gatatactga ttacggtgtg tctttgaagg gacatactta ctggtttgcg tcagatgaga    47220
aagagaaaaa tctcagcgta tttctagtca gttttgatta tacaactgaa agatttagac    47280
gtctacgtct cccgtatcag tgccctgatt ataacactgc gtctttatcc gttgttagag    47340
aagagaaact tgcggtgttg ttacaacgcg aaaatacatc aaggacagag atatgggtga    47400
caagtaggat tggtgagacc aaagtggtgt cgtggagcat ggtcttagca gtggatttcc    47460
cgtccgaact attcattttg tctggcataa gtttcttggt cgatgcggag aaaaaattcg    47520
tcgtatgttg tgataattac ttcggagagg atgaatacga taccaaaaac ttggttcaca    47580
ttgttggaga gaacaacaaa gtgagagaag ttaatttcgg agtatccgaa tcatcttggc    47640 cattttttgtt taattatgtt ccaagtttga ttcaaatctg ggaaggtgta ggaggcaaaa    47700
gaaagagagt cgaataagta agcttcacgc aaacctgttt tttttttttc cttctcaccg    47760
ttatctttgg tcatatctag ttatgttttg actaacaaat gtttcataca tcttgttgc    47820 attactttaa gacagttttt ttttttttaa tagtttcgtg atcaaaaaag atctgcatta    47880
atgccgcctc cagcaacatg ggggtttcat tcttcttttc ttaacacata caaagacaga    47940
aaaagcaatt aacctaatga agagaccaaa caaacataat gaagagctac gtgtacgttc    48000
caagtctagt tccccttcca ggataagatg gttgtttcgt gtttctaagc ttaattggta    48060
tgtgattgtt catcttctgc catcatatat gatagtgcat atgtattgaa attgactttg    48120 gttttttgtga tacaacctgg acacgtttta ggtctttgtc cacagttgta tcagtttcgg    48180
tcatgtttgt ggtatcaaca aaactaagat acacacattc caagtataca tgacaaattt    48240
cactctatgc tacaaataac caaggtttgt actaaaatcc aaatacaaag aatttggatg    48300
aaccttacag aagctatatg gaacattcta acttgatata cttaatttga ataaacaaaa    48360
aaagaagtca ttatttagtt attgaatact ttttttccct tgaccttaca gattactgat    48420
taccatatac atacatatat gtgaattttt gaagaagaca acattgcatt tgtaacatac    48480
attgcaaatg agtaacaatg accaacaaca ttaacagatt gttaccaag acttacagta    48540 aatgtacaat gttcagtttg tatagatagg gtccttatat atgctgagtc aaagatgtca    48600
atcctaaagg aaaggaagac gagtaacggc attccccac aaacgctatc atctgcttat    48660
ttcttttcgg atgaaggtgg caacattttc ttggtggatc gacgagaaag tatctgaagc    48720
cgcactttaa ggtgagtgcc gagattctac cgcgagttga taactctata ctagctctaa    48780
ctctacacat aaacataaca cacaaactta tacaaagata aacgtaacac acaaatatct    48840
gaacagagat tcaattgtca tacacataag caaaaacagc aagaattgtg aaccagagtg    48900
atccacatgt gtatttcaca tatctgagtc gatctctaat accctctcgt ggtgtaccat    48960
```

```
atatttggat taaactaaat gatagcatat ttttgtaaat tatcttaaaa ataaaaattt    49020
aattactttt ttttagtaaa aatataagtc tatgtaccgt gattaatata tctagttaat    49080
taacaaagtt gataactatt ccgttattat tacactttgc aatgtcgatc acatcaataa    49140
acgcattgtc cctttcactt ttcgtatccg ccggaaaaaa ataacgtctt tttttttttc    49200
ttccaatctc tctgtctctc tccccaattc ccagattctc atgtaagctc tctccaagga    49260
tttgatttct gtataatgtt tgcgaattga gactaagagc cctctcgatt tcgattttttg   49320 ttcgtctgga tcctttgcgt taggtttttt cttctcgtat aattagggct tccgatttgt    49380
ttacccttag ttcattttct ctaaattttg ttttttgatt gatgggtttt cttgatttag    49440 caattttttaa gatttacttg aaagattccg taattttgtt ctgattcgga ttctttgatc   49500
tgtgctcact agctctctac caaagcagct tccttttctg atccctagtg ttcaattatg    49560
tgaacagatt gttttacttta gcttctcttc cttttcattc tagttttgca gagattttag   49620
gaggaacatg attgtttgaa ttgggagaga cattggttcg tgtaaaatgc gggtgcttgg    49680
tttgagctca agcttatgct ctggtgagga taaggaagaa gaagagatta atggagaagg    49740
ctctctcacg cctgtttatc tcaacgtcta tgatctaact cctgtcaaca attatctcta    49800
ttggttcggc cttggcatat ttcactctgg cattgagggt aattgtggct tcttctctat    49860
tacttacttg acctaactaa attttttcttt gtcattgctt tctatttgct ttcatccata   49920
tctggtttat catgttatca aagtacttct agccttgaat aggaacaatg atattcctca    49980
attgttctcc acaagttgtg atttattatt cattaggtga aaatggtgtt tattatatta    50040
gctatggaat acattattag aaggaaaaag tggaacaagt tttgaggaat ctagaatgga    50100 atgcttttttc aaatcctgcc ttattgtctg aagcattctc tttcaataat tagaacttgc   50160
ctgatgagtt atataactgt acttctgctg aaactgttat tgttgctaaa tgttcatcta    50220
atgtggagtt ttttttcact ttgccatgtg tactactagc tcatggtttc gaatatggat    50280
atggagctca tgagtattcg agcagtgggg tatttgaggt tgaacctagg agctgtccag    50340
gtttcatctt taggcgctca gttttgttgg gaaccaccag catgtctcgc tctgatttcc    50400
gctccttcat ggagaagctt tcgagaaagt atcatgggga cacataccat ttgattgcca    50460
aaaactgtaa ccatttcact gaagaagtat gcttgcaggt aacaggaaag cctattcctg    50520
gatggattaa taggatggct cgagttggta agataacttt cttattccag cttattattt    50580
ctttactggt tcttgttgtt tggcatatct ttttacatgg ttgcttgttc ttgaattttt    50640
tcaggttcgt tctgtaactg tatccttcca gaaagcatac agctctcatc ggttaatcat    50700
cctgaagccc tcgagttctc tggtaagtta atcatgttcg ctcttcttca cctaaaaaaa    50760
actgcaatag gcatttggat ttcggataaa ccagttgtgt ttcatctcca ttgtagatga    50820
taacgatgga tcagaagaat cagttgcatc ttctgtgtca tacgaaacag atggagaagg    50880
atcggatcat catctcataa cagcaccaaa cagcgatatt gcgtatctac aggacagacc    50940
agtgagactt gcccgtgagc tcctccaaga accaaccgat gatacatctc cgcagtactt    51000
gttgaagcgg tcctgatcat cacaagcatc aacaacttgt gttgtctgta aacagtgagg    51060
caatgggtcc atatattgag tattctttgg atctataagt gtaaaaaaag atttaagatt    51120
taaatcagaa cccatctgag atgttggatt gtagtgtaag atttagagac aaatggtgtg    51180
acaaaaattg tgccttcttc ttctcccaat gtgagttcac atttcagtgt cataattcgt    51240
aagatttgcg agactaataa ttagttttga ttttttctatt caatttacag acagttaatg    51300
```

```
gttatggatt ttcagacatt ctttgttctt cggttcactc ttcgcagcta tattttattg    51360
gaggcggtaa cataacttat tgggctagcc tgggaaaata attatacatt gggcccatta    51420
ttttaaataa ccttcatcgg cccagtttgt gtgtaaacag ttatgatcag atccagaccg    51480
tccaaaaata gggaggggtg actctcgaac acgatgctct gaagactgaa aaaggcgtaa    51540
acttttttca cctggctagg gttcttggtc gtcgttaact ggtacgtttc aatggtctct    51600
ctgtactatc atttctgcga aatgggtctt ctctttggag gctaatcgac gttgtgctta    51660
atctaattgc tcttttaggt tgtttagagg aatatatcac aggttttcaa ttagattgat    51720
ctgcttagtt ttgtaatcag tgtaggttac cagtgaatca tgaacttccg ttagggttat    51780
aagctctctg tttctttttcc tgacttatca atgtcactaa tttagatttg atgcgtagtt    51840
tagcttttga agatcaggga actgaatata tctggtttaa ggaagctttg aattttctgc    51900
ttgccatgga cattcgactt atcagtattt ttgtacattt tggttaatgt ttatcgaatt    51960
ggtttgatca gtctgtggat tttaacttta caagttaaga tgctattctt ttaggtctag    52020
ttgataggtc atggatttgt tgttatatgg agtctagaca ttttgccact gctttagtgt    52080
tcttagcttc taagggtttc gttgatatat tgtactgggt ttatcgtttc caggcatcta    52140
gtatggcttt ctgcactaaa cttggcggtc actggaaaca aggggtaaat gttccagtgt    52200
catcaatgct cggttctctt cgctacatgt ccacaaaact ttatattggt ggtaagtata    52260
acttcctatc agattgtttc attttcttac tcttcgcagc tgtggatgtt ttcttctct    52320
tgtatagcag tttaaatgtt ttggtcactt ttataatttt ggtcccaggc ctgtcccctg    52380
gaactgacga gcactccttg aaggacgctt tctctagctt caatggagtg acagagggta    52440
tgccctggat cttactatct ttcttttcac tgttctacaa tagaacgtgg ttttgtttgt    52500
gctagttaat gtataaacca ttcaaggatg tgtggttgga ttgaagccgt cctattcatc    52560
attataccat gaatgattga tggtgatgac catttttagt atggtatttg tgttttgctt    52620
tggtttgcct cgggacttaa ctctcttgtt gagtacagtt aatatattca gtcatttcat    52680
tacttgcgta tttaaccaga accttgccgt atcttttttc tgtgcagcaa gagtcatgac    52740
aaacaaagtg accgggaggt ctagaggtta tggatttgtt aacttcataa gcgaggattc    52800
tgccaactct gctatttcag caatgaatgg acaggttaga aatctaaaga atcattgatc    52860
tatctattta cctatcatgt caattgctgt gttgtatggt taatcttccc cttttgttgg    52920
ttttgggatg gtgaaatagg agctgaatgg gtttaacata agtgtgaacg ttgcaaaaga    52980
ttggccaagt ttgccattgt ctttggatga gagtatagaa gaagctgaga agaaagaaaa    53040
taagatgatg agccgatctg tatggaaaga tccattcgtt gatgcgttcc tgatgaagaa    53100
gaagaatgca gctctgaaca ggaaaatatg gtcaaggaga tcgacgattc ttcccgagta    53160
tgttgattcg gcggtgagaa tctacaacgg caaaactcat gtgcgttgta agatcacaga    53220
ggggaaagtt gggcataaat tcggagagtt tgcgtttaca agaaaagtga agaagcatgc    53280
taaagcaaag tagcatcttt gagaatgaat tggtcagctg cttgaaagga ttgtgttgaa    53340
aagccaaaaa cgaatcaaat caataaattc tcaataggta aaactcatta gctcacatga    53400
tcatgtagac gaatattgag ctttagaaag tctttagttt tcttgtcgat ttcgtatttt    53460
tggaccacaa aagtgccaat gttatttttgg aattcgatta acaaatatca attgtgggagc    53520
ttcaataacc aaacgaacga tgcacctcca tagtgcttgt tcaagaactt gtattgttta    53580
tatacagaag caagccaatg gggccatgtt gagtattcta ttcgatctaa agatgtaaaa    53640
gaagattgaa aatgaaatga gaatccagtt taaggtgttg ttggatggta ctagtgatat    53700
```

```
tagaggcaaa tggtgtgaac ttgttgacaa aattgtgtct tcttctctct ttgagttcac   53760
atttcagtgt cataattcgt aagatttgcg agactaataa ttagtacaag aatttattaa   53820
tcaatattcg tcgttactgg ttatggattt gatatgttta ctcagaaact gtcgtctagg   53880
cttgaaggga tttattattc agttcacatt ttcatgcaat ggagccctca caagacctgt   53940
aataagacga gttctatttg taagtttttt atgatttata aaaagctcag aaattcattt   54000
atagtctata gcttttatgg tttacatctt gagctgaaaa attaaaactt ttgcttgtag   54060
atattataac ttacataagc tatgaattat atatataaat ttgtatttcg gagctaaaaa   54120
tgttataatt ttattcatag atttcatact tctatgttgc ttacctaaaa tgttaattca   54180
accatatatt ttgagtgtta agggggtgta aaagcatatg gaattatttg tgttaaaatg   54240
acaaatcctc tgttattcaa tcatcaatat taaaaagttt tataaaaatc cattgttatt   54300
gaaataatga ttccaaaaaa gtaccatcaa atccagtatt atggaaatat tataaccact   54360 ggattttga atgactttaa ggtggtttat aagattttaa catgttttgt tttttggaat    54420
ttggaagaac tttagaacaa atcataacat ttaatctaaa atcacccaaa aattcatcta   54480
aaaactcatt aaaattcgaa tcattcaaac tatatggttg gataacatag aatttgtcat   54540
ttcaacacca atcatttcaa tgtgatttat tgattatatt ttttatcata gagagagcaa   54600
aaatctctgt caatggcaag taggtaccaa gtagtggcat gagagagtga tgtctggatt   54660
tattgatttc tttggtagct tatacttcca tatgtttcct tatttaattt ttcattccaa   54720
atatgggaca aagttataac aaatagtatt cgatatcaaa cgtcaaaaca tgtactccca   54780
aatatatttt attggaatat agttttggag atattttac  ctgggggag atggaaccaa    54840 aataagatct agaaatgtga ttggctaacg aaagaagcac aataagttaa caagtgacag   54900
tgacaattta tccctcgaca acaacacaca ttcacatata tcttttttatt ttattatttt   54960 tctgtgtgtc tttaaagttt acagcacaag tagtttctaa atcttataat caattttcat   55020
tgataaacag aaatttaaaa tatttaaata gacaaataaa tgatcaaatc tatatttcta   55080
tacaagagtt aattcacaaa aatttgttgt gaaacaaact ctttctatat ttctatacaa   55140
gagttaacat atttctatat aagttattgt aaagatcaaa atatgaaaat tatggtataa   55200
atgcatagac acatatatac gtgccctatt aaaagaggca gcgagaagat aatataggag   55260
gaagaggaag aagaagaaga tggtgaagaa gagagttaat gcaactgcaa gaagatagta   55320
actaatcagc accgtccatt tttgtcatct aattctttct tacttggccg caacttccaa   55380
ccacatcaca cactctttct attcccttat atattcccat ctcaaaagtt cttggagaca   55440
cataaacatt aaaaaagaa aaagaaaaaa actataaaca taaacgccaa tcgcaacttt    55500
cttgtctttc aatgggagag aaaggtttga agcggtctgg tgttgcggtg gtggttgcat   55560
tactagccat ggttcatgtc tctgtttcag ttccgttcat aatgcttcat gggatctcag   55620
ctcaatgttc taatgctagg gatgctaact tcacacagct tctcactaac ctctctggct   55680
ctcctggctt ttgcttgtaa gtcaatccac aaaaatagttt atgcgttttg ataaccaaaa  55740
gatcgggaca tgtagaagaa gagttatgta ttcttgctat ctataagacg ataacgtcca   55800
aagtggctca actatgttga tggatttgtt ctaatgaatc cagagaaatt ggaaatggag   55860
ttgccgattc atggttaatg ccgcttacac gacaagcgga aatagcgtgt gagaaggtga   55920
agcaaatgaa agagttgagt caaggataca acattgttgg aagatctcag gttcttgata   55980
cactttcttg aaaatcctaa aataggttct tgatcattat ttacatagtg tttaagtttc   56040
```

```
atggatgttg attaataatg aacaggggga acctagtggc tcgaggcttg atcgagttct   56100
gtgacggtgg ccctccggtt tacaactata tatccttggc cggtcctcat gctggcatct   56160
cctctgttcc tatgtgtggt gtaagttttt tttataaatc tttttctctc aaatattttt   56220
tctatgattt taatttaatc aatcaatcac agtaacaaca ttgtcttttt cttgttaaag   56280
tctggtttat tctgtaagtt agcagatgag ctaatcaagg gagatatcta tagcgacttc   56340
attcaagtat aaatctcttt ctgtcttttt taggattaaa tcctcagtag ttacaaatta   56400
attaacatat atctttaata accctgcagg atcatcttgc tcctagtggt tatctcaaaa   56460
ttcctactgt atgtctactc accaaatata ttttgatgat aaaaaaacta cttcaaaatt   56520
tgagatatca caaatctttt gtttttgatt tatcaggata tgacaaagta cttgggaagc   56580
tctaagtatt tacctaagct taacaatgag ataccagacc aaagaaacca aacttacaaa   56640
gaccgtttca ccagtttaca taacttggtt cttatcaagg tttggtctcc taaaaaccat   56700
ctagactttt caattatctt ttgattcctc tcttgatgat tcggtttttg tttgttttac   56760
agtttcaggg cgacaaggtt atagttccaa agattcatc ttggttcggg ttttatccgg    56820
atggtgaatt cgaacctctt ctctctgctc aacagacaaa gctctataca gaggattgga   56880
tcggtctgaa acattggat gatgcgggaa aagtgaagtt tgtgagtgta gccggtgaac    56940
atatcagaat ggtagatgaa gatgtcgtca aacgttgt accttatctc caggaccaac     57000
cgtcttcggt gcaaagcttc aaccgcaaga cgaagcagcc cttgcatgct taaaaatagc   57060
aaataccaca atagttatac ttattcatgc aatatatgtc gaaaagctt agtgatgatt    57120
ttgtagaatc cttattctta tagaaatata tacatactta tctgaaaaat cgaattaatc   57180
agtagagaaa cgactcatga gatcttcatc accacatttg tatcaaggct tcaatggttt   57240
tctcaacatg agaaacttcc aatctcattt tttttgttt ttgttgttgt agaagtctcc    57300
caaaatgact cgaagttttt tccttttttgg ttctttagtc tcaccaaatt acatattatt   57360
tttaaataat ctaacaattc tccaaatatc ctaaaaacta attcatatct ctccaaatct   57420
aaaatttcct aaattccacc aaattttcta aaatcatgaa tccaatacac tccctgattc   57480
aaatctctcc aaatctaaaa tttcctaagt tccaccagat aatgaatcca atacacaccc   57540
ctaagagagg caacgcggag atgtcattag aggaggaact aggaagcaga gcgttaatgc   57600
aaaatgttac caaaaacgtt aatgcaagat atcaactgat cagcaccgtc catttcaaac   57660
tgagaatgta aaaaccaatc acaatcgtac atttttttcat ctagttcttc gttcttggcc   57720
acaacgtcca accacatgac gctctttcta ctcactttat atattcccat ctcaaaagtt   57780
cttggagaca caaaatatca taaacatata aacgccaatt agaacttttt tacttgtggc   57840
ggtttacaat ggagaaaggt ttgaagcgat cttgtgttat ggtggtggtt gcattcttag   57900
ccaaggttga tatctcagtt tcagttccgt tcataatgct tcacggaatc gcatctcaat   57960
gttctgatga tacaaatgct aacttcacac agcttctcac taacctctct ggctctcctg   58020
gcttttgctt gtaagtcaat ccacaaaata gtttattcgt tttgataacc gaaagatcgg   58080
gccatgtaga agagttgtgt attcttgcta tataagacgt gcaaagtgac tacttatttt   58140
tgttttatat agcatgaaca agatgatgta tttggtttga tctgattctt gtttttttt    58200
tggtaatgga atccagagaa attggaaatg gagtaataaa ttcaatgttc ttgccactta   58260
cacaacaagc agaaatagca tgtgagaatg tgaaggaaat gaaagagttg agtcaaggat   58320
acaacattg tggaagatct caggttcttg atacactttc ttgaaaaccc taaaataggt   58380
tttttgatca ctataacacg tttcagtttc atggatgttt gatgaatgat ggaacagggg   58440
```

```
aacctagtgg ctcgaggctt gatcgagttc tgcgacggtg gacctcctgt tttcaactat   58500
atatccttag ctggtcctca tgctggcatt tcttctcttc ctaggggtct tgtggtgta   58560 agcttttttt attttcctc aaattatcta aaacttttat ctgtaattta attttaatca   58620
atcaaggtaa caacaacgat tgttttgttt tgtttcttttt cttttaagtt aacgtccgat   58680
ccagcatgta agaaatttaa tgagttgatc aagggagctc tctatagcga gaccattcaa   58740
gtatatatat ctctttctct atatatatca tgattaaaga ctcaattaga aaataataaa   58800
aaatcttcaa tgactctgca ggatcatctt gctcctagtg gttactacaa aatccctaat   58860
gtaagtccat tcaccatttg tttataagaa aacttgcaaa atcaacaaat aagtgattga   58920
tgatcaaaac aacaacataa agttttaaca aaatctttgt ttttctttta tttattctca   58980
ggatatgaaa cagtacttgg aaagatctaa gtatctacct aagcttaaca acgagatacc   59040
aaaccaaaga aaccaaactt acaaagaccg tttcaccagt ttacacaacc tggttcttgt   59100
caaggtttgg tctcatcaaa accatctaga cttttcaact atcttctcat tcctttcttg   59160
atgactctgt ttttttttt tacagtttca ggacgatgag gttattactc caaatgattc   59220
aacttggttt gggttttatc cggatggtga gttcgaaact cttctctctg ctaaccagac   59280
aaagctctat acagaggatt ggatcggtct gaaaacattg gatgatgctg gaaaagtgaa   59340
gtttgtgagt gtacccggtg gacatgtcag aatggcagaa gaagatgtcg tcaaatacgt   59400
tgtaccttat ctccagaacc aacagcctgc cgcacaaagc ttcaaccgca agaccaagga   59460
gcccttgcat ccttaaaaca gagcaaaaac ctcaattgtt atacttatac ttagcaaaaa   59520
aaaattgtta tacttgttca tgcaatatcg aaaaagccta gtgatgactt tgtagaacaa   59580
gaatccttat tattgatata ttgatatata catacctata tgaattgtcg aattaatccg   59640
ttgagaaacg acgaatgagg tcttcatcac cagttttctt caagacttca atgattatct   59700
caacatgaga aacttccaac taatctcatt ttcttatcaa gcatcggttt cacaagctta   59760
tagctagcag cttcccaaga aagcccattt ataaattaac tttggccaat cttttgcaac   59820
atcttcaata tacataaact aaccaatata atgcatcttc tcgatgcttg ttgaagcagt   59880
attgatcaga gtcatcaata acttatattg tctgcttaca gaagtgagtc aatgtgtcca   59940
ttgtaagtat tatttctatc taaaaaatat ttagagattt tattctttac agaaggagca   60000
aatttatttg tatatttagt tgtcaaatta aaatttagtc tatacattat acaaggcgca   60060
agtttgtgga tttaagaatt atataaaaac ttgaaatata tagtttttat gcattctcct   60120
cttgtgtaat acataaacca aatatgagat aggttaatct gtatttcaga taatattaaa   60180
ttccaaacaa tatttttact tgttataaga aggcaattaa tatctctctg ttaatggcaa   60240
gtggtaccaa gtagtattaa actattaatg caatggaaga gtactgttgg aaattataat   60300
cctctatcac acattcaaac agatctcctg aaatcttctc ttccaaactt gtacttctct   60360
gatccaaatg taggctccaa aatatagaca tttaccattt actaagtcca caactccttt   60420
cttgtctcct tcaaaaatga ctcttgtgta accatcatat gactccgaca gttcggcatt   60480
gccatgatga gagcttaaaa attcaccttc ctgagcattt caagtcttca ctcccttagc   60540
ttgacctgaa ccaagataaa atgcctttgt cgtcccgtaa tatccatcct gctttggacg   60600
gcatcatagt tacattcgat ccatcctatt tacaatgtta ttttagtatt aaaaacatga   60660
caataaattt gttgttaaac atattcaaat acaatatgat tggatttata agtaattgta   60720
atatgaaatg tccttagtaa tatgttaaaa aatacataga tacacacacg tactaaaaga   60780
```

```
ggcaacgcgg gagatgtcat tagaggaaga actaggaagc agagcgttca tgcaaaatgc   60840
taccaaaaac gttaatgcaa tatctcaact aatcagcaca gtccatttca tactgagaat   60900
gtaaaaacca atcagcatcg tccattttt catctaatta tttgttaact cttaattggc    60960
cacaacttcc aaccacatga cgctctttct attcccttta tatattccca tctcaaatgt   61020
tcttggagac acaaaatatc ataaacatat aaacataaac gccaatcgca gcttttgtac   61080
ttttggcggt ttacaatgga gaaaggtttg acgatgtctt gtgttttggt ggtggttgca   61140
ttcttagcca tggttcatgt ctctgtttca gttccgttcg tagtgtttcc tgaaatcgga   61200
acacaatgtt ctgatgctcc aaatgctaac ttcacacagc ttctcagtaa cctctctagc   61260
tcacctggct tttgcatgta agtcaatcca caactctttc gtccttttga taatccaaag   61320
attatggcta tttatgtgtt cttgatactt aagacgtgca aagtgactat ttatgatgat   61380
gtctttggtt tgatctgatt cttgtttttt ttttttggta tggaatccag agaaattggc   61440
gagggaaatc caataggcgc ttcatggtta ataccactta cacaacaagc ggaagtagcg   61500
tgtgataagg tgacgcagat ggaagagttg agtcaaggat acaacattgt tggaagagct   61560
caggttcttg aaaaccctaa aatcgggttt tgatcattat atgtacatat tgtttaagtt   61620
tcatggatgt tgatgaatga tggaacaggg gagcttagtg gctcgaggct taatcgagtt   61680
ctgcgaaggt gggcctcctg ttcacaacta tatatccttg gctggtcctc atgctggcac   61740
cgccgatctt cttcggtgta atactgtaag cttttttatt tcctctaaat atcaaatata   61800
tatctttgat ttcatttta atcaatcaat cacagtcaca acattgtatt tttctgttgt    61860
ttttggtttt ccttgttcaa gtctggctta atttgtgaca tagcaaatgg gataggcaag   61920
gaaaatccct acagcgactt tgttcaagta ttgatctctt tctctctctt tacatcatat   61980
gattaagtcg tcaattagaa aattaattaa aatctttgaa tgactttgc aggataatct    62040 tgctcctagt ggttatttca aaaccctaa agtatgtctc tattcaccat agtttattag    62100
gaaacttgca aaatcaacaa attagtatct acctaagctt aacattattt tttctgtttc   62160
acagaatgtg acagggtacc tgaaagactg tcagtatcta cctaagctta caatgagag    62220 accatacgaa agaaacacaa cttacaaaga ccgtttcgca agtttacaga acctggtttt   62280
tgtcctggtt cgcttctctt ctcttaacta ttatagttgt ctactatctt ctgattcctc   62340
tcgtgatgat ttgtttttct tttatacagt ttgagaacga tacggttatt gttccaaaag   62400
agtcatcttg gttcgggttt tatccggatg gtgacttaac acatgttctc cctgttcaag   62460
agacaaagct ctatatagaa gattggatag gtctgaaagc attggttgtt gctggaaaag   62520
tgcagtttgt gaatgtaacc ggtgaccact aataatggc ggacgaagat ctcgtcaaat    62580
acgtcgtacc tcttctccag gatcaacagt ctgccccacc aagactcaac cgcaagacca   62640
aggagccctt gcatccttaa aatgagcaaa tagttcaatc gctatactaa ttcatccaat   62700
gtcgaataag ctcagtgatg attgtgtgac acaataatcc ttcttcttat atgaataata   62760
aaagcatact atctgaataa attgaattaa tcaatagaga aacgactcat gagatcttca   62820
tcaccagttt tcttcaaggc ttcaatgatt ttctcaacat gagaaacttt caatctcatt    62880
ttcttgtcaa gcattgattt cgcaagctta gcagcttccc aagaattccc ctgttggcag   62940
agaccgagca aaagaaccgc atgtatatcc gagtctattg ttgatttcac atccttcttc    63000
tcgatttctt gatacagaag gaaacaatcg agatacctttt ccaacaaaca taactccctg   63060
aaaacatgac tgcacgcaag accatcaggt ctaaccccgc ggaccaacat cagacggaaa   63120
atcttttcag cctcttccca tcttttcata cggattagcg acacagtagc cgaactaaaa   63180
```

```
cactcagaaa gagaaacacc gcctagtttc accaacttat caatcaactt agaaagagcc    63240
ttcacatcct catcattctc caaaaccccc tgaatcaaaa cacaagcagt aacacgattc    63300
ggcatgcacc ctcggtttcc cattctatcc aataccaaca acgcctcttc aaccctcctc    63360
ttctcacaaa acgcttgaat caccaaagta taagtaaccg cattcggact aatcaatcca    63420
ccaccgtctt ctttctccat ctccgccaac aactctaacg ctctctccat atcaccagac    63480
ttgcaaactc cttcaagaat cctagaatac gtcacactgt taagcacgca atcatgctta    63540
ctcatctcct tagctaacct ccaagcgtca tcaatcttac ccgcattgca atacccattg    63600
atcatcgacg tataagtaat cacatctgga taaagaccaa cacaatccat ctctttatc    63660 aacatatcag ctatattcaa atctccctta tcagcaaaca acctaatcac caaattatac    63720
gcaacagtgt ctgcacatac attaaattca ggaaacttcc ttaatacccca caatgcctca    63780 tcagcgagat tcgcttgatt acacagagtc agaacaatcc tcatcgtctt aacattaaca    63840
aagcattctt ctttccgata agattcaata acgtatttga tcaaatctgg ctttgctcta    63900
atcttaagaa tgtcgcaagc tttggtatac atgtaagcac tgtgtctatg ctggatagaa    63960
gttcctgccc atatgaaaaa cctaagaccc gattgaaatt gatttggatc gcatcttctt    64020
agtacctcgt tgatacaaga gggtctaatt tgtacattag ccgaagctaa ttctttctcg    64080
agattacttg tgcatccttg aagctggccg tataatctct cggcggctga gacagttgtt    64140
aaaaaacgta aagctgagat ttttgagggc tgagatcgta atgaaggaga taccagacga    64200
gaaatcaatg aatttggcat ctgggtcgct ataagtgtag cgattgatga aagatttcgt    64260
taagaaaatc gtaagaatga gacttgagtg agagaaatag gagagtttcg ctttcgcaga    64320
tggaaacgac gacgaaagac taaacgtatg ggccgacata ataatgtagc ccattaagac    64380
ccaataagaa ttgctcatac atctttgtca gatctgaatc ggaaaagcaa ttgaagtcag    64440
attaggtcac aagatttcat gatttcgtta agaacttcaa ataagctaca cttcttttc    64500 ttttctttt tgagcaactg catataagct acacttatac catgctcaga aactgtgtat    64560
ttatctagaa gacgtttgtg aattttggt ttaatttaga actcttgtaa gatatcaaaa    64620
aaagatagtt tcataatttt tggttaatat agcaagtttg taactaattt ttgctaattt    64680 aaatctttt aaggttgcat catacatagg actagttcat gagaaggcca atcatccaaa    64740
attacaatga ccccacacag atagactata taacgataac gaaaaatacc aaaacaccct    64800
tttcccacca ctaaaataaa aaatcacgat cgtggacgca aggcttcaaa attcagccca    64860
tgagccacct gaccagcaca agcaacccac ggattgatag aaacgggcct gtgattgtgg    64920
tgatggttcg atgatgatgg gccacccaca cgctcgcacg aaggacacat gatgagtgta    64980
gttggtggag tcatctgacc gtagaattgt ggagacagct tgagagttcg aagctccata    65040 gcctcttct gaagtctccg gttctcttcc gttagcttct ctacgcaccg tttcaagtat    65100
tcgcaatcta cctccgtttg ctttaacttg gttctgtaaa accaaatcgg accttgtaag    65160
taaaaacttc tacacaaggg ggtataaatg taattttaca attttggtgt taagacaaga    65220
aaatctcacc tagctcttct gttttggaac cacacttcca cttgtcttgc cgtcaagttc    65280
agcttcttag ccaaagctag cttctgtttc tgtaaattat gataataacc ttggttattt    65340
caaagtaatt acgataatta tcatttgatt cctctgactt ttttacactt acgggattga    65400
gagtgttgtg ttctttgaaa gtctcttcga gaaaagcaga ctgatctttt gataacctga    65460
gcttcttcct cgacgtttcg cccccgtctt cttcttcatc tgaggttcca cgtgagtacc    65520
```

```
ctcgatccgg agtgatctcg tcgtgatcgt cgccggagcc aacgccggtt ccggagattc    65580
cttctctctc acttctcttc ccgctaatgg tgcttgagat cgtactgttt ggtgacgaaa    65640
ctcctgtgtc ttcctcgcag ttaaccgttg atggaaaact gttcacgtct atcttgcgaa    65700
gatctgcaaa gagcaatcaa attttaagtt tgagatctgt ttttatttta cttggaaacg    65760
aagaaaagtc tcatacttca attctgaaat ctgttctgtt tctttaaaaa aaaaaacaga    65820
gaagatttaa gtatatacct gatgtaggat cgaatgtttg gttccatggg agtctctgga    65880
gattgtttga taatgaagag ttaggattca gattcatctg aagaggattg tgattttgtg    65940
aaaaccctaa gcttaggctc aaacctagat cttctttgcc catcatcatg ttttttattt    66000
cctttcacaa gaactcaaca gtttcaggaa ttatatttcc ttatgagaat agagaaagaa    66060
agaacacgaa atggtttgtt ctttctgaga tagagatgag aaatggtgtt tgtttcaact    66120
cgaagttagg actctttgtg gaagagaaat agagagagat gtgagatggt aatgaagaag    66180
agagggatt aatatagtac tttgaatgat gagagatttt gtcaggtggc taattacaat    66240
ccatcattat tgtttctttg ttttttggact tgtattactt tatctccaac ttgtgtcccc    66300
cctttggcct ttgccatgtc tttctttttg tactttctca atatttgtgt ttttctttt    66360
ctttcacaaa catttttagt ttattcctta caagaaccca tgcataataa gatggcagtt    66420
tgtccaaaac aaataagatg gccaatatgt tttcaagtgt acacatgtat atgtgtttg    66480
tgtctgaaga tttaaagcca atgtctttaa aaccaataga aatgtccgga ccactctgag    66540
aaagtaatct acaattaagt gaatcatcaa ggtgcgatgt tttttgtata tggataacgc    66600
aatttgcact acttgtgtta attttcatga tccatatcat gtagtatgtc tcaaagttga    66660
taaatacaat aattctcgta cttcgttttg tcttaatcaa gtcacgtca ttatactcaa    66720
agtacatgta ttatgtggat atcaataaaa gaaagtatag aaaatagtat cttgattagt    66780
tacggcatac cgagctgagt caaatctcca atagtgtagc caattatttg tccaaatatt    66840
tttaaagag aaaagggaaa atagtatttg aggttggata taatggaata ttgactaatt    66900
ggagtggttg gtacaaaaca caatcaaaaa gaatctgaac ttgttcaaag ttgtggacca    66960
accaacggtt atgaaccaat gatatacgtg tgagatgaat atttgcacat aaatatcatc    67020
atcatggttt ctactttcat caacaatgac atttttaaagc tactactttt tttcgtttct    67080
tccgtcagta aaacctttaa atgtttgtgc ttttttcctt agaaataaaa atttaaatgt    67140
gagcaatatt ggtcaagtgt gtgtaaatgt ataaccactt tgcgtacagt aacatggaga    67200
taggagcatg tgggtcataa cagcgtgatc gtgcgtgttg tgttgtttcc tcactcgcct    67260
gctccttatc atgtgtaacc atccgcctca atcaatgcta acttgttaat tatttgattc    67320
ctttaactgc tgcctacttt tttatcgtct aatattcctt tcttttcaca aaaactagtt    67380
gtagactaac ttcagttttt gtaaatagtt gttttacaat gcctgaagca tgtaaactta    67440
attgttctag taaactacta gtgatcgttg cataatcata attcacaatc caaataaaag    67500
tgtcattagt gtatatgtaa acaataaaaa aatgatggtt tggatatact tttgtaaata    67560
tatttcatgt ttatttagaa aaaaataaca tgtaaactaa aattccaaaa acaatttaat    67620
aatttccgcc taacgtagac atgtatatag tgaaattatg aagagatacg gcaatgagcg    67680
acaataattg agagcaaaaa gatgggtttc gtggtgagag atattatgaa aagtgggacc    67740
caacgcttta cataagatcc gacaagatgt cggagttgtg tttcagtgtg atctggctgt    67800
cccacgtgtt cactctgact tgtgccacac gcactgacca agtgcgttat atccacgcgc    67860
gcatgtttat ttgtaatcat ttacccctca acgaaaaaga gagtccgcaa agcatgatga    67920
```

```
ttgatgatca atcatttatt agtgatcctc caatagcttt tatgtaagta ttggcaaaaa   67980
catcgagtgt tcttggtgtt gaggttcgag catgtctaag tttgagttcg gcaccaaggt   68040
aatatatata tcggattcaa atttggtcta ctagtctaac ttttagcact taattgagca   68100
tgaccgcgga tcttgcacta gggtgaaaca attcttaacg agaacatatt caagtagcat   68160
agcttaaatg agaatttcat gttctatccg taatggtgaa tggcttaaat ttctgcattt   68220
agcccctact agcactttgg tatcgttaat ttgtagatat agcaaattga gatatggcgt   68280
ccaaacagca acttgttatt tcacattatt ccgattttt cagtagagcc tcgtctattt    68340
ggaggtagtg cagaagggta tgagcattct cttacagtct taccttagtt tctcaattta   68400
catgataagt gaaatattga attgaataca ccatttcgat tacttagttt ccttcggaaa   68460
taaaatatat atatattatt tgaaataaaa gctgcaggcc tacatcacag atccaaatcc   68520
aaagttgagt accacaacac aaaacaaaat cataggcaac ggaatatttt aaaagtatgt   68580
gttgtaatca ttttatatgt ttggcaattg cgtaggacta ataatcatgg ttttagttgc   68640
ttaatcatat gtttcatgca tgtgtatatt agctttgaat gttctttaca gcattttggc   68700
tgtagaacga ggtcatcatt ggggatattt tatactctct gttttttcct taacctaact   68760
aaccaattat tctctaaaca aatagtacat tagattttgt ctaattgtcc tctcacatgt   68820
actgagatct gttaactgga atatttgatt attttttaga tttaggaaaa atcaatcaac   68880
atgcataatt atgatcatca cacaaagcag cttattctta ttctagagaa gctcggaatt   68940
tgaggtttgc atcacatgat tgttggactc ttatagtatt ttaaaaataa acactaagct   69000
ttaattatta acgaaaatgc gtatgtgaca gttttgatta tttttttgacg ttaaaattga  69060
ggcttgttat tactaatggt aataatatga tcgatcattg agattcccat gccaaaaata   69120
aagataggga ttataatttc ttcaatgatt ttgtttaaag tcataatttc ttcaatgatt   69180
ataaggataa aaaatgaaaa tcatattgga gaatcttgag agagagcttc gaaagttggg   69240
tggtgcgtaa atcttatgg gctacccatg tggaattgac gtggcgcaca tattcttatg    69300
cgacccaaaa ccaccactc cagcgaagca cacgtgtgtg tagtgacacc cgcacgtgca    69360
ttccccactt acatatagat ttccagtcaa cggtcaaaca tccgtctctt attttctac    69420
tcacaagaat aaacgaaatg tttgtttaat gaacgtgtac taattagatt attttcatat   69480
aatcttgaaa atgatgatcc agaagaaaac tattaacctt gaaaatgcaa agtatcacca   69540
agaagaaaaa tcagattatg ctcttctcgg cttataaatc tataatgatg caaagttgtg   69600
aataacttaa acattgttgt tttgtgaccg ttcactctta aattcaaacc acaatctctt   69660
cactcttgtg ttatattaca tcgaccaaaa gtccaaaatt gtcaaatctt gtcgtcgtat   69720
caacaatgtt ccactgtctt atcaaactat acatgtcaca ttatgatttc acaattagca   69780
gttagattag ttagttttgt aaaaaaggaa aaatcaagcc agagcggtct gggaaagaag   69840
atagtttctc ttgtacacaa ggatagcctt tttcattgtc tcactataaa catacaaggg   69900
agagaattag ggcatcgaaa gctttcatta taacacaagc aatatccttc taaacccacc   69960
agggcttttt ctccatcaag tccttggaga aaacataacg gaattttgaa ctgtatggca   70020
accattcgac gacctgcgat gctttcttgt tgtttggttt gccttgtacg catttttgta   70080
ttgattctcc aagcttttcg tctgcgttat ctattaacca tctcatcagg tcatcaaagc   70140
tcagagaagc ttccttttgta aacctctcta taatcttagg taataacact ttcttctgca   70200
tctttacaac cacgtttgct ccaagaaact ctctttttga agcatctaat tcctctttaa   70260
```

```
cgtttgatgc agtgtaggct tttagctgca atcacttcca tcatgtaatt tcccattaca   70320
agctattctt ttgctcaagt aaaccaacat attctgactg aaatgtgaca aaatttaata   70380
tatgtatgtg aataagatta gtaataaaac gtcaaaagaa gttaccactg gatctgatag   70440
agcaccaatg caaagagcaa aacagacaag tggctctggt ttgtcaaggc taaacattga   70500
ctttacttta tcttcagctg gtttcttcct caaggcggtg gaaataatgg tctcaagcca   70560
ctgcaacata ggattctttc aatgattctt ctttctgttt gaaaaaggat aaggagtaaa   70620
gactcttaca cgtccattcc gtggagtctg gaagcagaag atagagtatt caatggtgtt   70680
tgcattgatg atgtgcccac cgatattata cgcagactgc actagacatt agacaatgaa   70740
acccattagt ctctgctcaa atatgaatct gttctcatgt caagcattga gatcaaagta   70800
gaataccttg tgaaacaaag ctaaccttct gagggaatga gcaggtacac catatgctaa   70860
gtatgccttg agaagatata tagaagatta tcctcataga agcatgaatt agcagatgta   70920
aagggatttt gtatcagatc aatatattct tacatgcatg aggagagcat tgtatatgtt   70980
gatccaaaag gctaacttgg cattgccttc catttgattt atagtaactc tctctagttg   71040
ttcaacaagg agcctgcaag ttaaaatcat gagttcttgt gatggaacta aattcagatg   71100
ttgttttcaa aaactgctat tgttggacta acctatagtt gttgatagca tacgttactt   71160
gagaaaatct tttcttgtct gatgagatcc aagatacttc caccatggat ctgcaggacc   71220
aagctctgtc ttcattcata atgttcttgg ggatgatcac attgctagta gatgatcttg   71280
ataggattct cttttcagga tctgctgaca tggcactgca gcagagccag aagtacactg   71340
aagacataca cttgaccata tcttcagaca acttgtttgg gcattggtac aaatgatcct   71400
taagagttct ctgagatgga gacttcactg ttactgaatc ctttaagaag tgggactgac   71460
agaaaaatca acagaatata taaaagttag aagaagtatc aacaatgact aaattagggg   71520
gaagttagtc tttattcatt tacttttgct tgacttgagc aacttgttgt tgaaggaata   71580
cagtttctga actggaactg agaagattgg tcctttttgg aagttttttct actcgaatct   71640 ttaagagtaa ccatagcatg ccacggcttt agagggaaat tattggagga acaaaatgca   71700
tttgaaataa catttgggtc ttgttttctt ggtggctgct ttatatgatg agctggagaa   71760
gaaatgcttg agctttgttc ggaaggtgct ctgcttactg tctgttcaaa tatacttcga   71820
tatagagaaa gcacatgatg ctcgcgattc gtgacctctg cttcaagcaa ctcaatctcc   71880
gtgataagtt catttgcctg aatcatccaa attcacatgt aaaatctaaa gtctcacaat   71940
ttctatttac tcttaagtaa aatgcagaaa tactgaagtg ttttacctga ccagcaaaat   72000
gtctgtgccc tggagacaaa ctgctcgaag cacggcccat tgctctctct aacaccattc   72060
tcatagattt ctcctgttga agacgaaggt gaagctgctc aacctgtgta gccaagtcac   72120
aaagatcatt cagatgagat caattcactt tttggacatg ataatgcatg ttaaagacga   72180
ggagatacga aacatgacgc gcttacatcg cgttccaagg atgctctgtc gttagaagac   72240
acattgtttt tagttaacat ctgacaatta tgcagtggtt ttggtctctt gtttgctgtt   72300
gtttgaacag aggatgccta tggaccagaa aaatacaaat caacctcaaa agaaaaaaac   72360
aatcatatga aatacagctt taaagtgtct tacttgcatt ctagtgaagt tgtttgcaga   72420
ttgtgaagct ccattaccag aagtgtgaag atcccgctct gacgacgcac tgggaagatc   72480
ataaacaaga attcgttcta gcctctagga agaaacattc taaacagaaa aagctctaaa   72540
acagacttct ttgcataaca gtctctatct acgtcgtttt catcatagag acgtttaagc   72600
aaacattggt gtgcaagaaa catcgagaga taatctcaaa aacccattaa tggatttaag   72660
```

```
ataaagattc aatattagtg aaaagattga gcttaaacta ttgaagcgag agtacctttt    72720
agagcggcca tgtttatgag aatccaggca atgccaagaa tctccgtttc ttctctgctt    72780
gttaccgtct ttattcaaat caaaaccacc catatatctc agccaaaacc ttaaactcag    72840
atgatgaaag taatcaaagt ctccaaaaga atctcagtaa aagaagaaat tgataaagga    72900
gtgaattcaa atgcagcaaa ggagaagaaa gaatgaagaa gtaaatgcag agacgaaaac    72960
tgaaactgta gcttagccca taagaaaggg gaccaggtta gtagtatcag agtgcctgcc    73020
aaaattcaat tacatttcac tttatggttg ttgtattgca tttaattcga ttttttttt    73080 gtctcatttt aaattcatag ttccatttcc ctccttttt cgagaaatac aacacttcta    73140
ggttaggaaa attcgcataa atagttatac tcttaatttt ctctggtcaa ataatattaa    73200
gaacacgcta cagtaggaca gtgcagtagt taatgttgtc atgtcggtcc gagtacattg    73260
agaatttaat gttccgatat aaatttcctt gtttttccc aatttgaaa agtccgttaa    73320 attttcatat ttattcaacg agacactgta ctttcagttt ccaccgaaaa ataattcatt    73380
actcatcatt tattcaatgt tcgataattt cttggaagca gacagcattt gggcctcgag    73440
atttaaattg gcccaaggtc cacgtttact tgggtcaatc acagtcaaaa cgttttcccg    73500
gggtttctct caattttttt gtcaaagtct ctcaacttt aaaaatacaa acactgggat    73560
cctccacggc atgcaaaagg atattataat gaagatgaaa tcaaattggt ataaaaagtt    73620
ggagaaaggt ataaacacta tgtatgtggc taaaaatagc tagaaactta aatttaggt    73680 gaaagaagat ttgagtaacg ttgttgttgt tatataataa gatgaaataa tgacaagaaa    73740
tctgaaataa tatgcgaata tgccaccgac gggagaaata cacgtggacg gctgataaag    73800
ctttgtgaag gaatcccaca ataatataag aagatctgac caaaggttcc tttctggata    73860
agccgctctc ctcgtgtcca cgtggcattt tcaaacgtgg gacctcctaa tctatatcac    73920
taaacccatc cactcatatt atctctcttt ctatcatcta aaatccaaaa tgttcgtcca    73980
tttttttttt tctgttcata aacaaaaact gcattgcctt ttaatttatt cttcttctaa    74040
tccatacaaa tgattatgga actataaatc tataataata atacaattaa ccacaaaata    74100
aaatatatct tagtattata agatatgact tttggagtta gggggtgtct aatacaaata    74160
ttatggtatt tgtaatctta gcaagaaatg aaatcacaat catgtttatc tttcttaaga    74220
taacatattt tactcagtca tgggtctact tttattttca gtttagatta ttaaataaat    74280
aacaatagtt ttgtcgcctt actatatgac caaaaattag atttttctcta tgtgtaggat    74340 gttggcattt gtttaccatt tttcttatga taacttatta aacagatgtc atatttact    74400 tatttgtgtt tataactgtt aaaatctagt caagctttct gtatggaacg cgtgaagggc    74460
tattaagata tttttaaaatg ttgaatagtg taattaatct tgtggctaat aatattcatg    74520
ccaattgtta atttctggtg gagggttaac acttgtacat aaatacttaa ttttctttt    74580 tgcagttttt gtatagatat ccatccttat ataaatagaa aaatataagg aaattgtaat    74640
gatttagcat aagacaattg gataatcaca aatgcattaa acctattaac tagtctatat    74700
agaaagagtt attagttaca gctatactat ttgtggtggc attaatatat agtaacttat    74760
ttaagatata tgtcataatg ttaaaaagaa atcacagaga aagctgttat ttttttaat    74820 cctaaattta aaactttgga tattgagatt agcctgtaat acatcttttt ccaaaaaatt    74880
tatacaaaaa tggccattaa taattaatag taatagctag ttggacttct tagttcaaag    74940
taattcaaca tttttctaa aataaatctt ctaataatag aacacgttgg attgactaat    75000
```

```
taagtcaaat atgaaatatg gaaaaggaaa aaaatccacc aacgatacac caaataatttt    75060 ccgattttta tatatataaa taaacatact aagagcaaaa gaaaaacaaa ctgaaaataa    75120
aaaaaataaa taaataaaaa aaaaaatccg gccagataaa tcgaatttat gtaataaatc    75180
cgaccagata aactgatatt attgtctttc ttccgctcct ttgtctctct atctctttct    75240
cacaattaga ttctgtgctt cttctgcgat caactaagat ccgatccgcg agcgtttcag    75300
acttcgatca gatccgatta agagaagcaa atcgggtcgg gtatgactcg tcgatgttct    75360
cactgcaatc acaatggcca caactctcgg acttgtccca atcgcggcgt gaagctcttt    75420
ggtgttcggc tcaccgaagg ttcgatccgg aaaagtgcaa gtatgggtaa tcttagccat    75480
tacacgggtt ctggatcggg tgggcatgga accgggtcca cactccgggg ttctccgggt    75540
gatgtccctg accatgtcgc tggtgatggt tacgcttctg aggatttcgt tgctggctct    75600
tcctctagcc gcgagagaaa gaaaggtatc ttcgtttgat ttctgagatt aaatttttta    75660
tcaaattcca aattttttgta attgagttta ttttgcatca aagtcgttga ttgcattatg    75720
taacaagtgg tgatctggtt tatgtaacaa gattttgatg tgtgtttgat attggttttg    75780
ttgtaggaac tccatggaca gaggaagaac acaggatgtt cttattaggt ttacagaagc    75840
tgggtaaagg tgattggaga ggtatctcaa gaaactatgt gaccactagg acacctacac    75900
aagttgctag ccatgctcag aagtatttca tcagacaatc caatgtctct cgtcgcaaaa    75960
gacgttctag tctctttgat atggttcctg atgaggtttg ttccttcttc attcaaaaac    76020
accattttta tttatattgg agtggttaca aaatgtgttg agatactgat ttaaaggatt    76080
cagaagctta ttaggtggat tggtttgcct tctacatttc aatatgaaaa gttgaagtct    76140 gttgggttc taattgatat gcttgaggat atcattttgt agccaatcct gcttaagcat    76200
tttggtcttc tcatgggaat gtgatcttga aatgtaattc tctttcttta ttctgcttat    76260
gctgtgtgat ttgtccttgt aggttggaga tattcccatg gatttgcaag aaccagagga    76320
agataatatt cctgtgggaaa ctgaaatgca aggtgctgac tctattcatc agacacttgc    76380
tcctagctca cttcacgcac cgtcaatctt ggaaatcgaa gaatgtgaat caatggactc    76440
cacaaactct accaccgggg aaccaaccgc aactgccgct gctgcttctt cttcttccag    76500
actagaagaa accacacaac tgcaatcaca actgcaaccg cagccgcaac tacctggctc    76560
attccccata ctatatccga cctactttc accatattac ccgtttccat tcccaatatg    76620
gcctgctggt tatgttcctg aaccacccaa gaaagaggaa actcatgaaa ttctcagacc    76680
aactgctgtg cactcgaaag ctcctatcaa tgttgacgag cttcttggta tgtctaagct    76740
cagccttgca gagtccaaca acatggaga atccgatcag tctctttcat tgaagctagg    76800
tggcgggtca tcttcaagac aatcagcatt tcacccgaat cctagctctg atagttcaga    76860
catcaaaagc gtgatacacg ctttataaaa gacctgagga agtgatggtc taaaatggga    76920
tctggtttgg ggtttacagg ttagttgttg gtcacagtaa cttaaataag ttttctttg    76980 ttaggttgtt taacttgggt aggatgtttt agttcagctt tgatcattag ggaaaagaaa    77040
aaagaaaaaa aaagggaga aaaacaaatt attattttt gcttacattt ctttatattt    77100
gtatgctttt attttgactc taggatgcgt taattttcgt ttaatctgta ctaaaaatta    77160
gaatttatta gtttgaata aataaaatca cagtttgttt atcctctgac caaaactat    77220 aactggattg aaaacggaaa ttaaaccaag acgaaccgga tttaaccgga ctccagtgtt    77280
gtaagagaaa gtaaacaagt tcccaagcgt ttcgtaagta aaaaaacgaa tgggctaaac    77340
aattagtcta aatgggccttt aaaagagtga ataacgtgtc ataatcagga gcgttaaatt    77400
```

```
tagggcgatg agtgtcgaga gtgttcccgc gttcaccgat tcactccact ctttggttaa   77460
aaagtccact gtcatggaaa attaatcgcg gtgatttaca cagatgccac gtggcacgtt   77520
cgctttcttt ttcttcctcg tgttgatttt ttttcttctc ttttgtccct ctttggtttt   77580
tcttttcccc ttcacaaggc gcgatttgag tcgcctcgca tttcaaaccc ttcttctccg   77640
gcgtaaacct ttgctctatc tctcgataaa aaccccttgtt tcgttttcac cttcgtattt   77700
agcgatgctt ccacactcct acaccgtcga ttcgctttcg caatcacaag acctagcttc   77760
agctatactc tcagcttcca cgccgtcgag tatctccgct gcttgctctt ccgtcgaatc   77820
gtttcttcag tcgcatacgc ctgatcagtg tcgccatttc ttctctgtta cttttccgag   77880
tttaatctgt aagatcttcg gtttcggcga cacgaccgcg gcatctccgg cacagtcttc   77940
ttcgctgcga ccgaacggtt ggatcgatgt aatctcggcg gccaacgatt tggatttagc   78000
ggagagagta tacaatctct tatcccctag tggaatactc atgagctcaa tcttcgctgt   78060
tgataaatta gctcttgtta agtatgtttt cccgacggaa cgtttaccgg agtatgctag   78120
attcatgctc tccagcgaga aggatcgaat tgcgttatcg aatctgtgcc cctttttgaa   78180
aggtaaaatt gaggaggatt cagttcgtgg ttcattgtgt gaagttaggc taaatgtttt   78240
tgagtattac atgttttggc tctcttatta tccagtttgt agaggaaaca atgagatttc   78300
agctgtgaat ctgaatccta tccaaaagag aaacaagttt aggctagaga attggacact   78360
tatcaaaggt tttccaggga gtaacaagcg tgattctgat cagaaattgg agtgtaatct   78420
ctacataagg cttctttact cttatttgaa agcatttgtt cctgttttcg acttaaacgc   78480
tcaccagcct tatcgtagtt ctcttttgca ttacggaaat gggtatgatg ggtcagtgat   78540
gacaagagct gagttcttgg tgaatgtttt cgtgcattat tggcttgttg agaatgactt   78600
ctcaccattt cctgttgtta cggctaaatc ttttggtgtg gctcctcctt tccgttctgc   78660
tgtggaggag attccaccta cttgtgggtt ggaagaagta gtgaagttgc ttgtcaagta   78720
tctgaatttg agttgggtta caagtggtgt tgggagtgaa aactacattg agtatggcga   78780
gagtccacgg tggaagacac cgacttcagg atcgtcatcc catgtcgcga atttgagcct   78840
caggccgctc acttcctgga cacccatttt acagaggccg ctttatcgtt atatattgag   78900
gagtttcttg ttctgtccca taggaagctc aattaagaat gcatctcagg tgttctccat   78960
ctgggttacg tacctggaac catggatgat cagtttggat gatttctcag ttttttgaacc   79020 tgctttaagt ggatctgtaa aagatatgaa aaaggaagat tcttatgaat cacgcgtttg   79080
tggatacacg cctttgtggc agagctatgt gatatccaat tatctctact atagttctct   79140
ggtcatgcat tttattggct ttgcacacaa gttccttcac acagatccag aaataataac   79200
tcagatggct cttaaggttt gatccctggc ttaagctatt ttctcaaatt catgagttta   79260
tctgtagaat atggattgca agacttctgt ttgaaatctt aatgtgactg aatggttcta   79320
ctgtgtctcc ctaaataggt gatgagtacg ttgacatcgt caaagagct tttggttctg   79380 atgaagaata ttgataaagc ctttcactct aaacaaactg gaccaggaaa ctcaaaagtg   79440
aacgaattgt ctagattttc tccatctatc cgtgagcagt tgaaggtatg cctatatttt   79500
tcctcaacac cagttgttat ctgttctccg gtcatagaac gcttttccag tgattttact   79560
cttatgtatc cgccatcctt tgtcttcata cttatttagc ttttttcatca taacacccett   79620 ggaagtttaa caaagactg taaaatcaat cttttttttca cataagtcac ataagtactc   79680
aaactctata ctgaaaaatc atgtttaact gcttgtggaa cttcaggatt gggaagatgg   79740
```

-continued

```
gttgtgtgag agcaacgctg atggctcata cttgcatgaa aactggaaca aagacttgaa    79800
actctttagt gatggtgaag atggcggaca acaactgctt caggttaatg tcttcctttt    79860
ataacctact gtagtgataa gttaggaata aaaaaatgga agataatctt tgtaggatga    79920
tatcttcaaa tgtacttaaa atagctctat tatggaatga tctagttgac aaatatatag    79980
ataaaccttc agatttactt gtttgttgtt tgtagccttc tatctatatt aacaggagaa    80040
tttgttactt gacaattaga tgagtacgca gtcatcggca atgttgtgag ctattaactt    80100
gggaatttgt ttttttgagaa attgttcacg gaaatatact ttgagaacta gttctcctac    80160
atttgttttt cagtaaccta gttgtatcgc atgttttctt gtttccgata ctctacttta    80220
gtttatacga ctcttgaatc ctttagctca taggggggga gtggagctta aaacctgttt    80280
tactttgctg aaggcgtttg ttctttgcat ttgcagctat tcatactgcg ggcagaagcc    80340
gaactgcaaa ctgtatccga taaaaacctc acagaggccc ttaagtgtgt agattcacta    80400
aaatcagcgg tttccaactt ctttggcggg catgtcgtaa aaccaatcgc tttttttccta    80460 gagccggacc atcctcagaa aaaccgtgac gagctcttca agccacgtgg tgctggtaac    80520
caaacagcag gcggtgtgaa gtacaaaggg gactggatga cccgtccggt gtcagaagac    80580
gaggttgcat tgatggctaa actgctaatc aacatgtcta tttggctcaa tgaacgcctc    80640
gggctgaaca atctgagac gagcaacgac aagaaagaga attcagagtc agtatcatat    80700
gtagatgtat caggggaaga tgtgggaaac gttgcaggac ctggagatgc tgcgaagatg    80760
ctgttgcgag ggatggtgat ggtatgtggc acagtgttgc agctgatgag aagattcggg    80820
attcgagtca atcttcgggt tatggcttca aaaaagtttc tgatgctttt atttctctat    80880
gtcctgtttc ttgtagtcaa aagggtagtc acaaggatga tttggtagat gggtgtccaa    80940
aatgtgttaa aagttgaaga agtaaaagga aatagacact ctaactcgcg tagagcgttt    81000
gataggaatt ggaaagctta tttacgaaac agggactgag tttttttggta atttacatgt    81060 tcgcattaca aattgaagcg tgtctttact tgttacaacc aatgagaatg gtccacgtaa    81120
tcagtctcca cgtgtcatct gccaataaga tccacccatc agcaaaattc atcggtcgtt    81180
cgtcgctgac tatcacaatt ccgaacacca aatttcgaat ttctgccact tgctttgtga    81240
tctgatcgtt cgaaattgac cggagaattc ttctgtgttc ttagatctgt cgcgaatttg    81300
ttaaagctcc tcagaaggtt ttggttacag atcttctctg tggtcttcac cactatggcc    81360
gctccgtttt tttcaactcc atttcagcct tatgtctacc aggtgtgctt cttctctctt    81420
tgatcatttc gctttcaaaa tgatgaggtc gtgttcttct tagttgcaat ttgactaaat    81480
ttgaggttca ttgtaagtag gatttagaga aattccatct ttgattagtt taacttagct    81540
gggagaacgc ataatcgggc caattaggga ttttagatca tgacattgtt ctagtgttgt    81600
ctaataagtg gccatttgat gcagagtcaa caagatacta ttacaccgtt ccagattttg    81660
ggtggtgaat cccaagttgt tcaggtacat ttgctttctt aatatagcgt gatcttcgta    81720
tttgtgggtt atatgccata taattttaac ttctctaacc attgctcgta tgttggcaga    81780
taatgttaaa gtcagaggag aaagtcattg ctaagcctgg tacttccact gaataactcg    81840
cttctctact cagttttgta taatggtttc aagtttcaac taattttgtg ttatggtgat    81900
gtagcttcca tgtgctacat gtctggctcc atcgagatgg aaaatacata cactcctgaa    81960
caagaagttg gagttctgca gtggattttg ggcaagagtg taagcagtgt tgttcttcgg    82020
aatactgggc aaaacgacgg gtttgttggt attgctgcac cttatttggc taggattctc    82080
ccggttagtg atttttagctt gtccatgttg gcataatcat cttccatttc acccttaatg    82140
```

```
tataccgcct gattccttgt tgtttttgtg atctttgttt tccatgtaga ttgatttggc   82200
aatgtttgga ggtgagatct tatgccaggt agagtctttt ttcctagatt ttgaacactt   82260
agctatcagc ttcttcttca ctcagatcaa gctcttacag agtcgcctga ccttttcttc   82320
actttctgta gccagatgca ttcctttgtt ctgtccatga tgtgaaggtt gtcaactccg   82380
ttgaccagag agcaagaaac attgttgccg ctggtgcaga ggtaagaact aagaaggaaa   82440
atacgttgat ttggtttctg atgcaattat tattcttaac aaaattctgc aacccgttgt   82500
ctggcttcta ctcacaaatt gctgttgcag ggatttctga dacaacgcct atctggacaa   82560
ggtcttgctt tcatcctcgc aggtggctct ggtgagattt tatcccaatg aaatgctgtt   82620
tccgttgagg cctcatcccc ttcaataaaa ctgacattta acatcccaaa catgttagtt   82680
gtacaaaaag ttctggaggt aggagaagtt ttctccattg acgtttcctg tattgctgct   82740
ctcacaccct ctatcgatgt ccgaatcaaa aacaatgctc cttttagacg agcactattc   82800
ggggtacatt ttcacatata ctttgtttca atgagaagaa gattcaggtt tttgtttgt   82860 ttctcaactg ttttaatctt tcaacattca aaagggtgat aacgtagtaa tggcgactct   82920
aacggggcct ggcattgtct tcattcaaag cttaccgttt catcggctct cgcagcgtat   82980
tgcaaggtaa agcaaccaac aatccaaatc tccatttatg ttgcaaatat gtttatataa   83040
agtgtgaatg gttttctgt gacaggtcgg taacgtcgcc aaacatgaga gagaatccaa   83100
aattgctgat acagatagct atatttgcgt tcctagcata cgctgtgatt ttgtcatcgt   83160
tgatcttaac cgaagtttga aagcagagag atagaaagaa ttatccgacc aacaaactaa   83220
cgttgtaatt gttcaaatta tctcgggttt ggactttgga tggatagagt gaagatgaat   83280
tagacacatc tcaaaccatt ttcttttcgt ttactagtga gtttaggcac ttgtgttata   83340
ttgatattgc tcctatatat tgaaaagtga aaacgtagat accgagttga acaaaaattg   83400
gattctttac ttaaatcaca catcaattta aattaattaa tttgattttt tgttttgtta   83460
aataattaat gtctaatgat attattgatt aatttcatc ggatggttaa gaaattggat   83520
taattcaaaa aaaaaaatct ggattaattc gttaccaatg gatcatatag tcaagactca   83580
agagaatgtc tcaatgatat catggactaa ttttcagaaa atggattata gcaggagtta   83640
atagttttcc aaaaacattg aactgtcaaa aacagtaaac atgctcaagc aaaaattcac   83700
aattttgaaa acagcgaaat gtcataggtg ttaacacacg aatttcaaca atatacaata   83760
ctccgttttt tccgtttact ttttaaacta ttcgaattac tcatggatac ggatcttacg   83820
atacgatgaa tacatttacg ttataagaag tgactacaac cattcttaaa catgtttacg   83880
attcgcacat aagatctctc aaatcagtga agctagacca acaagaataa atttgatatg   83940
aatcgtcgtc aaaacaaaca ctaaatttct cactgtaaat tcgctggtct catagattaa   84000
gaataaagta gttacgaaat cgaattccac tacaaaaatt aaaaaagaat tcgatgacaa   84060
aagaactctc tctctttgtt cgttacagca aaacaagaag attctcattc tctgttttg   84120 attatacaaa aaaaaaaaaa aacatgtttg aaaatccatg tcaagctcga gatctctccc   84180
cctttccacg ttttgagtat cggagtttat cttcactcac atcactaacc accaccggtg   84240
gtgatcgcgc gtaccttgac ggcttcctct tgaaatgcct atcttcatca ctagattcat   84300
aatctgctac ttctatttcc ttccgactac tgtgtcggtg aactgatgtt cccacggcgg   84360
ctgcggcaga ggcggaagca gatggatccg taacagaagt agaagaagag gaaggcacct   84420
ttcttcgttt accagaagat gtttcttcct ccggaaaact tatccgagcg aatacgctag   84480
```

```
acttaagatt attctcgatc tctgctttag tagcagggac tggtggctcc gatgaaggcg    84540
gttccgatct cttgcggtgg tgatgttggc tgcgttcggt ttcaccacgg tggtggcgat    84600
gatctcggct tctgtcttca tcgcgacggt cgcgagtacg gtcgtgttca cgatctacgt    84660
cttggtgacg tgacctctca cggtcgcgtt gccgatctcg ttcatcagga taacgctcgg    84720
atttctctt ggagtcgcga gacggggaaa tgttttacg cgtaggcgga tgctctgggg    84780
atagtctctt ctccggtcgt ctccggcgat cgtaatcgtg gattggtggt ggaggtgctt    84840
gtctctgtaa acaattgtt agcccaaatt attataataa aatatgtatt gaattcggcc    84900
cacaaataaa aaggaaatgg gctcaatagc ccagttaccg tcgtcacctt tcggttccta    84960
cgcctactat tttgcatttt aggctttta gccatctacc cttctatttc ttttccttt    85020
tattcacagc ccttagtttc tgataaaccc caattttata tttcagaaaa ttacgttaga    85080
aaccaatata ttttccccta gttttcttca agttttttt tttttttttt tgggttttca    85140
aaataagcaa aatgagggaa tcagggaaga gaatttggag ccattttctg atataataat    85200
aacatataac caaagtaaa tgggagagag cgaagcacag gtgaacaaag aaaagaagaa    85260
agagagagcg agaggggaag atgagtcaaa caaaaggaga catacagatt tattagggtt    85320
gatggatgat gcagaggctg aagtaccgtt gttcatcatc attctgctat tctctccatc    85380
cctaaacatc ttcccactgt atatacaacc aaacaacaac caatgtttag gttttagcat    85440
atccttgttt gaatctgtag taaaaataga gtgagtgttt tcttttacc cttcaggtcg    85500
tctctcgttt tcacgttttc ttaacatctc agcgtttcgg gcttcggctt catctctgcc    85560
catcatagca cgttggagat tcattcggtt tcccatttca gctaggtccc tgcgcatgca    85620
cagaaagttc catcatgaga cttgttgaga aagctttatt gctcttcttt gatagagtga    85680
gtgttttacc tatggggtgg tggtatatta gggaacccaa atccttgtgc catgaatgga    85740
tctggatgca tcatattcat accccacca aatcccatgt ccattgggtt taatccgtaa    85800
cccataaatg gaggcattgc gcctggaaac gggcctccaa atccattgaa gccagggtga    85860
aagccattga agccaggttg aacaccgttg aagcctggtt gtacgccatt gaagccaggt    85920
tgcatgccgt tgaagtactg cggacctggt cccatttgca tcatatagtc agggcctgct    85980
agatctggca caggattcca ttgcatgtct gcaataaatc acataaacaa accatctttt    86040
agacctccca ttcgattcac atagacttcg aaactgacaa tgtattgcct tcagcgtagc    86100
aaagaaagct tttaccattc ccaggcactc ttggtttctt tttcttcttt tttcctgtat    86160
agagacaata agtacgtatt acattgatga atgacaacaa gggttcctca gtaattgaaa    86220
aaaaaaggt tcatgtgagg tccagcttga ttaatctcag tagggaaatc tgaactggac    86280
tatcagtcac caatcattcg caatgtccag tgaagctaat attagtacat ctttatttta    86340
cctggctctc cagcagcaac ctgctgctgc atttcttcct tgggggcttg cgtattcaac    86400
tttgacactg ttgcttcttt cacaatcacg gacccttgag tgctttcaca tgcatcaact    86460
ggcttttcta cattcacttc tgcagatgca cgaggggcac ttgtgatctc tgcaacttcc    86520
attggcgcct ttaaagttga agcatcatta ttgttactaa gtactggttt cttctcgcct    86580
ttagatgcaa cagatgtagt aggagataga gccttgggag gtggacagcg tgcagactcc    86640
aaatctatat tgtccatgat aattcagtag tgaggactaa tcaaacaaag tttaaaaaca    86700
catgaattta aaataatgac ggacctggga tatggccaac gctgcccaca ttctcagtgc    86760
tatcgtttcc agcttccaaa atacggttta tggtatccct gagggtcttg tttggtagaa    86820
ggtcgtcagc aagtacatct gatcttccac aaacacacat tgactttgaa ataatgtgat    86880
```

```
ctctgataccc tgaatcagtg aaaaaggata ataatgtaga actggaactg acaacggtca    86940
gaaaaggttt ttgtggaaca gcagaatgca ttaaaagaac ttacacttgt cacagaagct    87000
cttgtaacaa catttgcttg taagcgcagc atctttcatc acttctttgc ataatgggca    87060
ttttagctca ggtggaagtt ctcctacaga acgtgttgtt gatggcaatc cctccatttc    87120
cttctcaaaa gcatccctga atttgttgaa gacacaacaa acatttaaac tataatcaat    87180
atatgtgaag aagtacccaa tagcaacatt cccaaactaa ttcagtacaa cttactcatt    87240
tggtttcaga actgcaactg cgccacttgg caaggaataa gaaccatctg ggtcgccat     87300 caacatggac ttggggatac cagtaggtgg cttaactctc ttaacatcat agttagggtc    87360
tccatttgtg gggcaatgct gaataaaatg tcctgagaca gcaaagaaaa tgctctcaac    87420
acttcttatc tattatatat ccatctacaa aagtgagaga aaaataaaga ttttcagagc    87480
tgacatacca gggatattgc aacgatggca cataaccct ggaggtggcg ttttcctttc     87540
cattcctatc cagccagcaa aaccaaacta agtatcttac aacttgagca aatagaacaa    87600
aaatataaaa tattttgaca gaagtaaatg ttttgtatac tgtattttga cattccagaa    87660
ttcaaccaaa atcaaagaat aaaagtaagt ataagttacc aaaaccacgt ccattcatcc    87720
ttccaggcat acccctccca taacctctac cagctccaaa agtatcttga ccttgtctgt    87780
tacattgaat aaatataaga ggtctgttaa accttctcac aaaatccaac agtttcacct    87840
gcaccatttc tggaagattg cttaccgttg ttgccagtca agtgctggag tgtcaatcag    87900
cgcctgaatt ttgctttctt catctacttt gtcgtctgcg gttgcaagat gaggacgtgg    87960
aataatatgc tgggcatctt gggtatcagg aatggaataa agatcagtcc caaactcgtc    88020
atactcatct tcaggctaag aggtgaatac ggatgacatt agtactttttg tagtagaaga    88080 aaattaggtg cagtcaatgc caacagaagc cgagaaaagt tcactataat caacttacaa    88140
attcagcagc agatggatca gcaacaggaa aattggtggt tcagcctga acgtcttcca     88200 ctttattctg gattctaggc ctgcaaagtt aagatatttg catcattgag gatcccgaag    88260
tttcttaaat ccgatagtca gacaattaac ttatgtttag ctaaaacgat gcaccagtaa    88320
aatgcaatgc ttttaatatc atgtctattt aagtttaata gctaaataag tagacaaaga    88380
atatagaaac taaagatc                                                   88398

<210> SEQ ID NO 6
<211> LENGTH: 87394
<212> TYPE: DNA
<213> ORGANISM: Arabidopsis thaliana

<400> SEQUENCE: 6
aagctttgaa agctgcaaac acaaatcctt attaaaccga tcaggtcgcg tagcaatcca       60
ttgaccaaat ttgataaaag caggacctgc tttctccaga gttcgatgga ggacctcata    120
ctgcagctgt ctgtaacgag gcccgcaagc aaatcccaac aacgccataa taacatttgg    180
agaaaacaaa attgctaaat aaagagctct cccgatcaga acaacaccct tgaccgcaga    240
aaacactaaa gacgagagaa cgatagggaa gtttatcgaa ctcctataag gagaaatgtg    300
tgaaggagaa tagaccacag gatttggaac caccctttgc gcatacgcca cttgtctata    360
ggtaagagcc aataaaccag gtaacaagaa gtgcgaacgg gctaaagaca agctacacgc    420
ttgagcaatc tgacttatcc gaggtaagtt ccaactacga ctcagagtta ctctctgtac    480
aagccttccc caagagactt gagcatgttg cttaactaca ttactcgcaa ctgcaatcga    540
```

```
atagctccta cgcgcaagct gatgatgatt actacctaaa aaccttcctt taacattatg    600
aagaagaccc aatgtgtgat atccattact ctgaattctg aattgtggca actttacaga    660
aacattaata gctgttctat tattctgatt cgaaaacaga gttctactaa tcactctaga    720
gatcaaaaat ctgcaaaaga aaccaaaacc aaacccaccc aatgaagatc taatcaaacg    780
aagactttgg agaaaagttc aaaactttat aaacaaaggt tcaattttta aacatagcaa    840
tcaatttaag caatctccgg ctaaaagggc aatcaaaatt aatcggatta gagattcacg    900
agagaccctg aatatgagat tagagacgaa ccttgagatt agggtcatgg cgagaggaga    960
cacgcaaaag gttgagttttt tggaatgatc tttaaaccgt taaacgttgg gagcataatt   1020
tcatcgattt agcgattagg gctgaggaag ctcttccctc gccggaaaaa gaaggttctg   1080
ggttttagga gctgaagaaa gatacggaga aagagaagtc agtgatttgg tgcggagaaa   1140
agtggggccc ataaaaaaaa cctcgtgggc ttcacgctaa aatttt attt gtcggcttat   1200
tcgtttattg gattcacttt gacatttcaa tttatttat taattggatg aatgtttttg    1260
aaataaaaag cttggtagat agaaattaaa aatatatgga aaattctact tttccatagt   1320
tttcacagag gtaattcact aatttcgaat tatttattta attattttga cttatttatt   1380
ttatatgaaa acatacttat cttttccgtaa agaaattatc aattgttttt gtgtccattt   1440
tcccaactga aagtgctaaa taatttgttg tgaaaaaata atttcacatt tttataataa    1500
caaaatttaa ttttggtcga tactccctct attcattatt atttgatttt ttagaaaaaa   1560
aattgttttt aaaaagttga tttttaagtt ttctagacac tattttagt tattattgat    1620
gaattttaaa ctttaagaca aataattatt ggtttagaat tataaaaaaa tctacatcac   1680
aaaaactaat atatttataa ttagttttaa tatgtgtttg tgtgttttc tagaaaatca    1740
attaaaaaat aacagataga gtaataagta acttgaccag ttaaacaaaa aaaaaaaaac   1800
cttaaaagag aatatggtaa ttgcaaaaga tggagagaca cgattgattt atctgatgtt   1860
aatagttcgg gtagataggc gcaatcactc tctggcccct atgatcccat gatctattta   1920
aaaaaaaatt ggttgtaaaa tcttaaaaca gttgctgcct aagctttagg ttaggttctg   1980
cacatgccct agcttggtgt acactctacc atccctaaat acatccattc catatttcca   2040
tggatctaaa ctctcttttg atagttttag tcttcatgtt gaagtagagc aaataaaaag   2100
gaaagaatag agtgcatcaa gatttcgtca agtattagtc actccaacaa taattcgtcc   2160
tcagcaacta atctaataaa tacgaaattc ataatttaat tcttagtatc cacccataat   2220
tcaagatgtg tactttcttc actaagttcc tcaaacctat ctaacaaaag ctgaggatcc   2280
ccatagtatc atgaaaccta gcagataatt tagagttatt aatgaaatca tttaaaagaa   2340
aaaaaataaa cagtcctaaa tcctaatata aatccaagtc aaagcaagat aaacaatgaa   2400
gaagttatta agagatgaga tcacaacagt tgttttggaa tcctctaaag gaagataata   2460
agaagaaaaa atcctctagc tcaggaagag gtttcttcaa tactcccttta ctcgacactt   2520
agccactttc cataattttc ttcttctcac agactctcgg ctttctcccc ttagtcctca   2580
atttcctttt catgaactga attgggatct ttaatctatc agaatctacc tttctcttaa   2640
gacattcagg gatacatgaa agggtagtct atgacaggtt tatcatcaca caaccttga    2700
ctcgccatcc caaacatgta tcctaaggca atcccgactg aacagcaac aacatgccac    2760
tttccacaat cttcatcttc tcccaaactc tagcctttct tcccttagtc ctcatttcct   2820
cttcatgaat tgatttggga tccttaatct accgatacta atacaccatg tacctacatt   2880
gaggaacatt gtatgcacca gcagccatta tgcctcatct tgcttggtaa ttcttgttta   2940
```

```
caagacgagc tacaacataa cgaccaacaa atctttccat gaaacctaaa agatttacaa    3000
cgttctccat caagacgtat ttgggcttca agtatagtct atgatattca tgaaaccgtc    3060
acttcattgt ttttttcat cttgaagtgg tttatcttta tttctaaatc ggtgtaaaac    3120
cactaagtcc ctggcatgga agaccccac atacaagatg cacatattcc taaaagaacg    3180
acacaaggtc gaaagttac gaaaagtggg gaacaagaaa tatttggagg atttacatgt    3240
gtaattaaca tgacttagct tacaagaagt ggcaataaat ttgacttgaa acccttcgtt    3300
acgaattcct taagttttta tttgtatttt ctaatgaaac catatacaga ttagaggaca    3360
acatgagaag gccaaagcag taatttaaaa aaccttaccc caatccatca tacggctccc    3420
aagtatcttc ttctgatttg tattccttct aatacaccta aaaatgatgt aacataagag    3480
aaagttgata tatagttaat cccatgcatg atgactagca tttaaaaaga ggactcttat    3540
aaacaatata cgtgctgatt gtcttgcaaa aaaggcaata gcacgaggtt ttatctttt    3600
catgtaagct ctttatttt ggactgattt ttttccaaag aaaaccgtac agttctagtt    3660
taaatagata attttatttt accgttcata taaaaaaaa gccaaaaata aagtaatttt    3720
accaatgtta tctttgtaac actatgtcac aatttaaagg ttacttctgt gattctaaat    3780
atattgggaa caattaacaa acttcataaa ctatatgagc aatttcattc gaatgtttta    3840
tggaaaaaaa ccttcacgta aaagattttc aaaagaaaat ctgtaaatga tatcaatata    3900
taaaggatat caatataaaa cggatatatt ttgattcatg atagtagaga atatataaac    3960
tctttggagg aaaataagcc gtgtgtcttt gtgatactcg gaaacttaaa caatattaga    4020
atcaatgtga tttatttata gaaaaaggaa taaggctttt aagcttcaat caaacgaagc    4080
ttatagctga agatattaag aacttgttgt attcacataa agcaaaaaag atgaaacttg    4140
ttcgtccttt attgtacatc taaaagacta aaaatttatg ctcataatgt tttcttttgc    4200
cttttatatt catattacat tatacatgat cctcctttct tttggcgcat ggcatatttt    4260
gtcaaactct attacaacat tgattctaat cgatctacag ttgaaactag tgaatcgaat    4320
tttcaggtag aagttaaatt tgatttgaaa tgtactcaag tttatgctat ctttctcata    4380
taatatccaa tattttagac tagttatatg ttgtttatgt cgaagattgt tatttgttag    4440
gtacgaaaaa tttatatgag ccaccacata tatagttgta atcgaccatt ttctgtaatt    4500
tattggttaa gatttaagaa gactagaaga gggaccgatg tcactagatt cacaaactta    4560
gcaacttaaa tttacatgaa tccaagttac atattaaacc aatgacaaga gccgaagcac    4620
ctcatgaatc caaaaaatct acgtaggacg gtaacttttg ttgatcctga gacaaaggat    4680
atagccgaat atgagttgca accaaatctt aacttctctc tatcaacgac gataatctta    4740
gttgcaacat gaaaaacatt cataaacaaa catttgccgg ttctcctta gtcgcggaat    4800
gatctctttc caatggccag agacatgttg tggtaatcaa gcctagtact tctttaatttt    4860
atggttccga gaaccatatt tgaatgtgta gattcaccgt tccatacgtt cactttcgac    4920
cttaactcca ttttcacttt ttagaatctt gaatcctgac tccatgctat gttcttttaa    4980
tttgtttgta ctttggagaa aaccaacatt aatttccaat agggcataat ttgagatttt    5040
gtttttaat aataaatacg tactaatcat gcatgggact tgttgagtat tttatcgata    5100
ttgagatcta aggtaagaat tctgttcttg cattgcatat atttttgagt ggcatttgat    5160
agattagaca cacatatatg tctttatagt aacatatgaa taatcttttt tctgtaaaca    5220
taaatgatgt tgaatgcaaa tcagtatata tttatcggta tctatactaa aatcatatat    5280
```

```
gtatattcaa atcataaagt aggaagcagt gtgggccgct attctactgg cttccactac    5340
tgaatttcca taatatatag ttcttaatcg aaccaacaaa aagttgaatc catatggaca    5400
catatttata catggatatg tacgaacata aatacatgca tgtatccaga aaatgtgcaa    5460
gtttgcaagt ttggacataa atgtaactat gtaagagtaa cggcactatc acaaacaatt    5520
aggttataag tgttggtttt gtgattgtta aaattaaaat ttatgattaa acatgaaaaa    5580
aacaactcta taaaacaac aaagaacttc atatgacaaa ccaccaatta ttatgttctc     5640
taactttaat aagtgattaa caaagatgtt accaacgaca aaatatgta tatatatata     5700 ttcaagaaca atgacaggaa caaaaggtta ttcaacataa aaacaaccca tatatgctaa    5760
attcagcaat aaaccccct taaaatattg aaagaagaag aaaatacatt aaaaattatt     5820
gttatgcttt agagtctcca agctgaattt agcatatgtt cccatccgtc ttgcaaacca    5880
caaccctctc tctttaatca cctatatata attaaaaagt gaaatttagg ttaattatta    5940
catatataac atgagagtat gtaagttaat gttttaaaa atatatctat ctattagttt     6000
atgatagatt attatcccaa attttctaag ccctaaatca ttcttgcttt cgtagttggt    6060
cccctccaac actattgttg cctctgccca cctttgaaga gtcaccttct tcttctccca    6120
tctctacttt ttctccaagt aatgattcaa tctttgatca tgacttgtga attttatttt    6180
cttttatttt tatgctaagc attattaaat aatatcttaa tgctaattaa gaaccgtatg    6240
atatacgtaa ttcaccttct ctacctgaaa ttgttgcccc caaacgttgg tgtccaaaaa    6300
tcggctgttg tttcgttagc caccggaaac gtgcttgata ttgggacgag acatagacca    6360
tgtcctctta gttcgtgatt ctcatttca tcttgactct tcgatttacc agatatctac     6420
atgaatccat actgaaatta gtacttattt aaccatgatt atagcacgaa gactccaact    6480
tggacaaaac taaaacacta gatcgtgtat tgaacctgct gttgttgttg gttcgaggca    6540
ccttgtttca tgtatggagt gcttagaacc tgtatttaaa aaacattaat atgcttaaaa    6600
atttgctcat ttctagggtt ttatgaattc agtgagttag gagagaaatc acaagaaacg    6660
tacagtgact tggtcgtgaa ggaacttgat gtactctata gcttcttgga gaacagatgc    6720
agtatctgtc tgaagtttaa cccaaagata tacaaaataa acaaactaag aagctcaata    6780
cataaccaag ggaaaataaa tgcttttggt tgtatatatt aagccatata aaataaagta    6840
aacacataaa tcattcacct ttccgaaagg tgaaactagt tgttgtaatg aagttatctg    6900
gtcccttaga ttctctttc tcacctgtta catatacaat ccatttatc caccaagaaa      6960 ttgaattaaa ataaaaggtc ttaaacaaat cttgaaatat gatcatgtac cttgaaagtt    7020
ggcaacggtg aaggcgtggt gactctcggt ttcttcgccg cagattcatt atcctttgct    7080
ctcttcaaag actcactctg agctcttgtc ttcagattct tctcaacaaa aataaataaa    7140
taaataaatt caataatata gccacaaaac ttatatagta gcaaaattat tttgacatat    7200
atgagataat ttaccttggt tttgtcctcc aaacgagtag atattatctg cggagtggtt    7260
acaaaattgc tcggcgtcgt gttgtttaag ttagtggttg atgaagaatt ccaaagggt     7320 cgagagtttg cgttgttaga gaagctgtta attagtccat aagctacttg atgatgagga    7380
tttgtcttat tagcccaaga aagttgagga tcgttgattg aaccacttgt ggtggagaca    7440
aagttgtatg gacttggttc gggatcgtaa aaggttcgta tcaagcttga ggacgaagaa    7500
gttgatggag atgaagaaca agctggatta agtatataag gtgaagtagt tgtggataag    7560
aatccttggc catgatcttg atcttgtgag ctccttatga agcttgagtt taagtcttct    7620
tgtctgaaaa atacaaaaca agaacaaaag agatctcatg attattatta aaaatcttca    7680
```

```
atcttgttca tcaagaaagt gaacaaaaaa aattaagtta gggttttttct ttaagaagtt    7740
tacaaaatgg tttggttcca atctgaagaa caatttgagg aaaaccctag acccatcatc    7800
tgcaacgtcg agtccatcgt cacggtactt cctccactgt cagaatccgc ctctcgctgc    7860
ccgaaaacga tgttgttgtt gtccgtacaa gtcatcctag atttgagatg attctcttgc    7920
gagctaaaat cattggaagt gatagccgct ccgaagcatg gtgacaagaa atgatccgaa    7980
ggagacataa cgctccttgg cgagttccac cacgcgccac ctccgccacc acaaatcgat    8040
gccgtagctt taaactcctc cgccatatta agagaatcag aaagttttag tataagcttt    8100
ctactagatc gttgctatac gaaggttaaa gtttttatat atatgagttt gttgtatgtg    8160
atatgaagag cataagtgta aaattttgat atatgtttat gagggtgtgt atgtttatat    8220
aggcaagtac ggacaagtgt gtggaaatta ccggaattta gttgacattt aagacaaaa     8280
acttatatca tcataacatt cctatgtgat tttttaatt aaataatctt gattttaaat      8340
tttttcctta agctaaatat tttatttgac agaaagatgt tgtaataata gtgttcctaa    8400
tccctcaatt ttcttctatt attataagaa caactgtctt tgtgagattt gtttctttgc    8460
tgcttagctt ttcgaagaag tgataatgat cctcatttta taaatattta aatatttaat    8520
ttgagattag ataggtgttt ggtactatta tgcaagatgc caaaaggggga tactatttat    8580
atatagacat tatatctaac ggtaacctt gattggttgc catcaaattc tacaaatcga     8640
tcgtttatat taagtggtca gaaatagaaa acatatcacg attttgatta aatcagtttt    8700
tagtaattgt atagacaaaa cacgaaaatg actgattata gtctacgcat gcgtatatat    8760
ataaatgtac ataaatatga aagactaaaa ttttgaaact tgatattttt ttattacttt    8820
catgcttcca tacatgattt ttatcagatc actttagtaa gcttaggaaa aaaaaaaact    8880
aattagtcta tgcaagcgta ttaataattg ttttattatt ttggtaatta taaacgacta    8940
accaattttt gaacaacgtt tcttctaatt aattatccat actttcatac agtaatgatt    9000
atcttgaagt taaaatatat gttttctcaa tcgcatttgc taaaaaaaac tttaaaacat    9060
atatcttcaa ggattagact cacttatttt caaaagtaat attcaaagat tctttcgaga    9120
taaaagttga gtcctaggct agctcgttca ggtttgagtt ttcagtactt gggagggata    9180
tttatacttt aacaggtatt actattacta aaaattagtt ttagatcgaa aaagcgatca    9240
taggaatttt tatttttta atagacgatc aattgttttt agctcgattg gaaaacgcaa     9300
aattaatggc aaaacctaga gttagcactt gatatgagtt cgatatttat ttcattgtcg    9360
atcggattct ttcggttaaa aatagtacta taaaataaga tttgttcttg tggcttgagg    9420
ctaaagggat aaatggtata tgatgacgat cgtcgatcga tgctgagttt cgatctgtgt    9480
gtcacgtcac cgtttctgga cctattgtgt ttgtgacttt tttcacaatc tctttatacc    9540
aaacggtcct tattcttttc aactagcttt ttctaaattc cgtaaatatt ttattcttct    9600
aataaatttg ataagtcaat caattattgc actttaatta caagtcattg ttttgttttt    9660
cttctttctc ttaattcttt ttccatttta tgtgatagac tgatagccac acaaaatatc    9720
aaaaaatgga tttgttgaac ctgataatag taaccagttc tgttctttat gatcattata    9780
cggctcgagg catagtgaac cgggctgtgt caccgtccat aaaatataca agttttatca    9840
aacgataggc atagataata aacataattt caccgatatc catgtatata atatttatat    9900
atctatctcc tttcaaaata aaaaaaaaaa ttggacatat tctaagctaa attgtgctag    9960
tatcgttatt acgaaattca aatttacgtt atgtatcttg acaaaaaaaa aattgttatg    10020
```

```
aatgcttgaa gaatggtatt tttacgttac atgtaataca aaaaagacac taatcattta    10080
tggtagtcca atgattcaaa aatatatttt gtaattggga gaccattgtt catggttagt    10140
agaagtgaaa gtcttaaatg tattcggcaa aaaaaaaaaa atatcaaatg aaactcgtag    10200
atttttattg ttcatggcta ttcgaattgt gaaaagtctt aaatggtaaa aatatgacac    10260
aaaaatatca aatgaaactg gtaatatttt attggataat ggctattgag gacaaatgaa    10320
gactataaag gccccaattt atctaattat tattaaaata ttaattaaga actaattgaa    10380 ttttttttctt aatggtctct ctatgcgaca caatgcattt tgacttaaaa cttaaaagag    10440
ctttgaagca ctgaaataca gagacagtta ggtcagatcc atgcgactga ctagtaagtt    10500
ttcatcgtgc aattaaaatt aattttaata taaactaaga aagtgtcaaa acaaatttga    10560
tcaatttgct taagcccacc agtccactcc gccaaaaatg aaaaaaataa taattcatta    10620
ttgcaacgtg actaactttt tatttattta tgaaaacact tgtttcgttt aggttgatat    10680
cgataaaata aaagttatga aatgaacgtc aaaagaatgt gtcacagcca ccgtatgaca    10740
acataagtta aatccgaaga atctttgtca gcccatcggt tgttttctct aacggtctgg    10800
tcgatcccat cgatatgtac accgacactc ctctaagctc ttgtcggtcg atatttggat    10860
tttattatta tcggacacat atgctaaatt ttatagtccc caatcttatt cagctttctt    10920
ccattttctg tttagtatat tcatggtggc aacatatata gttgaatcaa cgactagttt    10980
tgaaatatac cgcttttcac aatgcaagta tacgaacact ttcggatgtt ggagtaaaac    11040
ttgatcacga acaatgagat tcatgcactc gttgtatgaa aaaaacttag ttgacgaaga    11100
attgctccaa aatacgtatt gctatatacg tatataaagt gatatagaca cgtatatacg    11160
attagaagca atatgaacat gtataaaatt taaagtaggt gaaggaaaac gacaagtagt    11220
caaaaaatag gacccacacg gcaaatatga gtggagactt tgtttggcgc agatagtcgg    11280
ataagtgtca gcgactcatt cttttcttca aaccccaaaa tcaaatcatc atatgtccta    11340 acaattttt gttttgtatt tggaaaagca catgtttctt tgttttttatg tttatgataa    11400 cattcttttt acacgtaagt aacgtaatgc tgttttttggg actcacggga gctcatatgt    11460
aattattatt ttcatgtagt tcacataagt tcgaaaacta ataaataatt aagttatcta    11520
aaaagagtcc tagtattata tgaatcaaat tctcaaaatg tcccatataa caaattatgt    11580
caacaacata cgtactaatc tcttttgcaa caaactcagc cttaattttt taaacaaact    11640
aaacatatcg aaatttaaaa ggaatacctc atattaaaat atactataat cattaaaatt    11700
gatataaata ttcgatatat tgatatatat aaaccaacaa aaaaacccaa gtaatattgg    11760
aattcaatta atactgttac taaagagtgt atatcatggc gagatgtgtt aaaacttgta    11820
tagttacgta atttttagt gatggtgcgg ataaaaactt cgaaccatta attgtcaatt    11880
atacagataa tttgctatct catacataaa ctataaaata ttattatgag gctttttaaca   11940 tgcaaaagat attagaacac aaataatgtt ttgttttatt tttattggtt gaaatgaaag    12000
tcactgaaga ataacagtcg aagaatacaa gcgtaacgca tatttctctc atgacatgcc    12060
atttctacat ccgattttac atatcagttg tatttctatt tttatttatc tatcaaattt    12120
ttattgatcg taatattata tatctcatta tctcatacta tgtaggatat atgtcatact    12180
gacgtaagga tgaaatgcag aaaactacaa aaacgaagct ttttttttttt gcacgattac    12240 agaacgatga tgatacgatc ggaaaaaatc atcatggccg tgacagacac gtggggtagt    12300
gagctccatg aataaagaaa cgaaattgta ttccttgtag caatgacggt caaaagaaaa    12360
gcgctttaat tagtccactc ctatcttaag ttatggttat taattatgat ttacggtcag    12420
```

```
tttaattatt cgcttaatta attacagttt atatgacaaa atcaacataa tgttcttatg    12480
gtttctttgg taatttatca atttaaaatt tattacatgc cactcattct cataatagat    12540
gtcgcaaatg taatatcaca acatttgtag agtgtttgat gacatgacaa tgacatagtc    12600
ataaggtgtg tacatctata ctttgcatct tgttttcctg ttgaaacctg aatttacatc    12660
gaattcaaat atttataaaa tggattgtgt atgatttgct acttcttatt tttcatatag    12720
atatattaat ttacatgtga catataatta cttaacttat atctattata gtattattat    12780
acaactagct aactaaaagt tacaaatatg ttatatactc ttagctgaat cttttgattc    12840
atatatgtta tatattaatt tgtgtccatt tacgatcaat ataagttatt ttgtcatggt    12900
gaaattaagg agttgttaca ttttagattt tacttgtatg ttttttttg ttcacaattc     12960
atgcaatcat ctaactgata aaacaaatt tggcaataaa ggtaagattt taagtttctg     13020
tgtttgtaat tttgcttggt tatttttatc acgaattcgt ggagcaaaac gaattttggg    13080
acagcaccgt tccaagaacc gtctacatga aaaatattta catgaagtcc ccgatcatca    13140
ttatgcaatt ggttctaccg gtaccacaca ttatcaatac aactggctaa aaactaagca    13200
tggtcagact cttagtaggt ggtgtccaga atactgtggt cgatcaaact aatgttttt     13260
atgaacccaa aatgttataa acttgacaca caatttcttg gacgccaaac acaaaaatat    13320
gtaaattagt catgtttcct atatcaaaat ttgaatacgt gaccttgagg cgcactactt    13380
ttgagaactc tcatagacac caagagaact acatatgatt aggtaaaaac tgagaattaa    13440
ttgggactga gaaaatatgg aattattcac atgtaataag tcacatttgt tttgtagaca    13500
ttctacaaat tatataacat ctaaatatgg aacagtattt tatggttcat gaacttataa    13560
acatgtaatg atttttttatt tggctaaaac atgtgaaact ggtgatagtt gaaaaagtac    13620
ttataaactt ctaattgtct tctgagaaag taatttaaac aaaaaactgt aatcatttga    13680
cacgctaaaa ttttggttta tgtactactg attagtggtt gaccagtgaa aagtagtagt    13740
cttcttataa gttttacttt ttttttaggt aaagttgact cctagtttat ctcttattca    13800
atttattttc ttgattacaa ttaaaggtca acgcagaact caagatcaat acgactcttc    13860
tagatatcgt gccaagaaca cgacaagagc cgccccacgc ttttactcta gttttgtcat    13920
tttcatttgt tcttttttgtt ttccgaaaaa ttctaataaa tatgaataaa attcaaagtt   13980
agtagtaaaa cccaggatca tttgaaagat caaaaataat ttattctaat cgaagattat    14040
gcctatagtt tttgaagtaa tagttgagat ataagagag agcgatctct tgctatactt     14100
ggatataaca tttgcaacta aaaagaatat agtttgcaaa tattgttgtt ttataataga    14160
gcatgttatt taagtcaaat tacatacact aataaaactt gaataaaata ataacatttc    14220
actaaccttt gttttttctt taaacatata taaatcactt tctctaacct tgttatgca     14280
aaaatatcct acgttcctaa aatacagtta tatgtttaaa actctatacg aaaatgcagt    14340
cattattctt cttgagctat tttgcatccg caactcatca ccttcacact agtataagaa    14400
ggttacaagc tctgatagac tacaacattg ataataaatt gtaatcatct tcatcatttt    14460
taaaataaga ttatatattg cccctatatt aattgtaaga acattttaca aaatctgttt    14520
aaatgttata cagtaattaa taaaaccgtg tataaactat acagtactag tatctttttt    14580
tgttcacttt atagacatag taaattgtac tataattaaa ctttatgtct ttttttttcct   14640
atattcgtaa gaacaacacg tagtcaacat taataaatat tattttttgtt gccgcaatat   14700
atttcacttg tagtctatga ctaaaaacaa ataaattatt tttaatgaga tgcgaaatga    14760
```

```
gataagtatg cttgattgca tcaggccgaa attcggtaaa cttgagaatc tctattactt    14820
atttaatttt catttgttat agattttctc cgtaattttc gttttagtag agaaagcaat    14880
catcataatt tcgcagactt ctaagaaggt ttcgagagaa gaaatgaata aacaacgtca    14940
atgggtttta gagtcttcgg ggtgtggtag tctccatggt cccacttgta agttgtaagt    15000
caattccggt ataagttgcc aaaaactaat acaatttgac tcgttctatt tcttactttt    15060
taggcactga ttttaaaatg taatgaaaac aatatgagtt aacatttttac tcggttgaag   15120 tttgtgtatt acatttgtga agtgacatca ggaatgagct ggatttgtga acgagcttct    15180
cgcaaagctg gagatcctga tttgggttat gcatgcatgt ggagtctact agaattgtgc    15240
tatttttaga caaactatta gaccatctcc aacaatattt ttttagtaga agctctaatg    15300
aattttttaa tattaatttt gaaaatttta tacttaagag gttgtgtaat gatttttaatt   15360 tttttatgtg tccaatgcta gacagactct taagttagag ttcttaaaga attcaatttt    15420
tgaaaattat tttagtttaa atgtataaaa aagttgaagt gtatgaaatt tgtgtttaag    15480
ttaaaagata tgaatatgat tcatttggtt acaacacata tgattcattt ggtgtttaag    15540
ttcaagagat ttatttgagt aaaataaaca cagaaatttg taaaacatct tatctaatat    15600
tagcatagag gagaagaaga agatttgtga tacatcttca gtttaatcat ataattgttg    15660
tttctatttt gaaatttcgt gttcaaattc acatgacttt agatttcttt tgttcaattt    15720
atttgattgc actatgccag taagagcatc attattggtt aactcttaaa ttagttctta    15780
ggctaagaat gagatgttct ttgcaatcaa ttacaaaaaa aaaatcctaa gaattaatct    15840
aagagacaac caataatggt gctctaaggc actaaattct ggttttgttc ggttcataac    15900
ttcatattgt aatttgtaac ttgtgtaaga aaactcataa atatctagag tggactggac    15960
tataaatgtt tcttgtttct tatctcggcc catcaaaaac acgaagccca cgataattga    16020
ctaagtcgtt ttatacagct tttgaatttt atgtattcat cagtagtttg accaaaaaaa    16080
aaaatgtact catcaggata aataatttgc gacgtcggtt gtcggacctt ttgaagttta    16140
tacctaattt gatttctatt gattatcgaa tttgtttcgt ttactcagat tcatattcag    16200
cacatacact taagttaagg atgattattt ctaagggttc aaataaggtt gaaatcttca    16260
cattcagttt caaatttgat caaattcata ttgaattata catgtgtatc caatgaattt    16320
ttattgggat ccactcaaat tactagaaca tcttgcttca cttgtcttga cttgataatg    16380
ctctttgaga ttcttgaatc ttaagcctgt tttttttaa aaaagaacat atttgaatct    16440
gtgttagctg atatagaata agagtaagaa actcgaaata ccagattaag aagtatgaga    16500
gacaaaaata gatggtctgc ctcctgaaca aagaagacaa agacaagaac cggctgcttc    16560
tgattcacct tgaacgatag aaagattaca aaggttcgta ggaaagatat atattatcta    16620
ttggttagtt gctaatttgc tataagctct tagtgttttt cttgtaaaat catctatagt    16680
atcataaaac cttcttgaac aacatcgacg ttttgaactg caaacgttaa agattgttaa    16740
aggtccaatg caaggcttgc atgcaactgc atgggcaaac attttctac ttttgaatgc     16800 tcttcatctt acgatgaggc caacataata aaccttcttt cctacaaaat tttctttgcc    16860
acgtatgaaa agatttattt ttgcaacttt tttaatttttt tagaaagagg atcgtgtgga   16920
taaaacgaga agaactacac ttatacactt tcctctttct aaagaagatg caaaaaaaaa    16980
aatgaatctt tgtggtaaaa taaacttcgc aggaaaatgg ggttgttgcg ttggcctcac    17040
cgcaaaatca aaagagcatt gaaaagagaa atcgtgctta aagtgaaaat ttgagaagtt    17100
gtagaatgat atcaaattga gaaccttaac gaagcactta taatgaagca cttgaggacc    17160
```

```
ttgagtaacg ttttataaat tgagattttt ctatttattt agatagtata gtctttatga    17220
gataataaat aacttttttgt tggtgttgac tgttgaagtt ctacaattca attaagaaaa    17280
cgttatatgt gcattaattc ttgattctca taatgatcat catacggttt tgtttatgta    17340
tatattgatt tttgtataga actgaggaaa tggagatatt ttacttttat aggttttaga    17400
tattttccaa agttttattt ttaacacact tttttattta cagagctacc caaaaacgat    17460
acttaataag cttatataaa tgaaaaatgt tcatcgtcgt acaaagtttt agggagaaag    17520
caagattgat ttaacattgc tactatatag ttcataaact aatataaatt ttaggaagcc    17580
attattccgg actggtatca tttttttgtg tgttaaaaaa agttttttt ttctaaaaga    17640 aatggtttat tatatcgtca aagaattcta aatgtaaata gttttatatt tcattcaaat    17700
ttatataaac tttacaaata agcaatgaat tttaccacta cttttttttaa aatacaaaca    17760 aacatgtaat gttaaataca ttttagtgtt attagcgata tgttttcatt gtttttgcag    17820
aacttcggca atccattgtt ggctcaaggt ttggatgact cacatccact aagtctagag    17880 ccatttttcca taacaacccc atctttaatg tctccttgcc atatgctatc acactcaaca    17940
cttttggtct ttacattttg cgcatcccat gaatatggag atctattttt tctgcgtaaa    18000
aaattcagac tggtatattt catccaaaat aaatatatta aactgagaat ctattggctg    18060
caagatctat tacttctcac cacacatctc attatcgaaa tatattacaa catcacagt    18120 ccataatcca ttcacccgat gaagaaaagt taggtggtta atactaatgg ataaggcaat    18180
gtagtgcatc tctgaagtat gctctgaagt tatatatagt gagtttgttg taaattatac    18240
ctcaccattc ttttgttgca ttttcagcaa tagtctgaag aggccgctaa atcatcactt    18300
gatcgatgag ttgtggttat aatgatattt gattttgtat ttgcttggat aattaaaaaa    18360
tttggagggc gagaaaaaaa atcacatata catgtgtgca aaacttgcaa ttaaattatt    18420
agaaaaagag ttttatgcta taatttaatt taaattctat gtcatttatt taaaactgaa    18480
aataataatt ctgctagtga atgaattaaa atgtggagta atgtcggatc attttaactc    18540
tcagatgttc tctctgtttc attattttat ttgatgtttt ggcacaccaa ttaaaataaa    18600
attaaatatc gtttaatttg aaataatttt tcttctaaa acatcactta atttaaaaca    18660
gaggaagtat tacaagcttt agttggaaat caaaataatt tttaaatatt tattttatgt    18720
aatttctgta cttcatattt caatatagaa actgtgtcat tttcagttcc gtttgggttc    18780
cttttttgat cccacagccc aagttccttg taccatttttt cagacaagac aaaagaataa    18840
cgtctaaatg gaagactgac ttaacgaaac cttttaaaaa gaagtaacga aactattcat    18900
tagcatacta atcaaaatca gtaggcgaaa tttggtgaga agtttacact gtccatgaat    18960
catgataatc aacaacaaca tttataaatt caatacaatt aatgagttac tattggaatg    19020
agtctggatt ttttttagat aagtaaaatt tttgcaatct ttatcttgat tagtatttaa    19080
aatcaattaa tttatgtttt aagtgtaaac taaaataagg tagaaaaaag agataaaaac    19140 ataatgtgt gatacactta accatgattg gtactttgga tccactaatt tatgttttaa    19200
gaaaatgata ttccattata atgtttcccg gaaacaaacc gtgatttgcg gatgttacaa    19260
cgtcaattag ttcaacatgg ctttacttaa ggcaaaagac tacaaattca aatagtgaga    19320
ctatacagat aataatatta ttaaaaatta agtggattgt ttttcaaatc attaacatgg    19380
tacaaaaatt atttaaatat atgtatattt gaaataatca caatttttca caaacacaa    19440 ctcattgcta accagctcat atgctaaaaa agacaactca tttctccact cttttgacaa    19500
```

```
aaacagagca ccaaacatta aacccttcaa aaacacaaat ctcaccatca cacgtaaaaa   19560
aagaaaatat gtctatgctt cttcttcttc ttcttcttgt cccattcatt actccatctt   19620
cgcaatcttc cattcgaaac ctcctcgaag ctcgcggttt accaggtggt ttgtttccag   19680
acaacgtgga gagttatagt ctagatgata agacaggaga gctcgaagtt cagctacaaa   19740
atccttgttt cgctcggttc gaaaacagag tatattttga tcgtgtgatt aaagcaaatt   19800
taagctatgg tgggcttgtt ggacttgaag gtttaacaca agaagagctt tttctttggt   19860
tacctgttaa aggcattgca gtgaatgatc cttcttctgg acttgttctc ttcgatatcg   19920
gtgttgctca taaacaaatc tctcgttctc tctttgaaga tcctcctgtt tgttatcctc   19980
ctggtgagtc aaagtttgtt cctcaaaacg ttttagtgtt taatgccaag tgttttattt   20040
attggtaaca tatatatgat cttgaacaga atattttgt agtaataatt gtatgttttt    20100
atttgtagga tctataatgg agaagttaga aaaagcaag atggatattc agctcaagag    20160
atgaatgagt tttttttttt ttggggttgt gtaagattca aaactcaaac ttgtctcttt   20220
gaaacttgaa caaaaaatgt gttttttttct ttcttcttt accttttgt tcggggttgt    20280 ttgggaaacc gtgaaagtg tcgggagata tgtgtaaaat ctggaaagaa gggaggaaaa    20340
ttttggaact ttgtataaat tatggggtcc ataaagtaat caattttgtc acttgtcaat   20400
tatttttctt ttctttatat agagggaata tagagtactt tagatatttg tttaactttt   20460
gctttaattt ttgaggaatg atgttttcgt ttaatcatta tcctctagca taatcattga   20520
catagaatta ttctttgaat ggaagctcaa agctgcattt gttaccaaac aggcaatcac   20580
agctgttaac ctaaacacaa ctgacggatt ataaaattct agcactgaaa tacctattta   20640
aaactttcac tcattttac acaagaagtt taaaaaaaaa aaaaatcagg tagatatttc    20700
gggtaaaata aatactccca tttgtaccaa aataaatgat gtttaacttt tttacacaaa   20760
gatcagaagt tattatattt ttttccgaaa taaaaacgta atttatttat ttatacatat   20820
tcaataaatg ataaaataaa atataaatag tcataaggaa aaaatataaa aattttgcat   20880
agaaaaaaaa gaacacgggt caatttcaaa ccaccaatta ttctgatatc acagatgtca   20940
atacgcgtca gagtgtgata tatgttagtt atatgcgatt ttagtaacat ttttggaatt   21000
ttcagtgttg aatatcacat gtatatcgtt gatcaaatta ttttagtaaa catgttttca   21060
ccagttttat ttgaatttat agtcatttca ccaattgatt ctagaatata tttaaaattc   21120
ttaaatgata taaggtagt tgaaattaga taacctaaca ttttttatgt taaccaaact    21180
ttttaattaa aaataatata tttataggca caacctattg taaattttt aatttacata    21240 gttttaagta aacgagataa aagaatcagt tggtgatctt caaatcggat aaagtgttat   21300
gagtgtatag gagattttga tacaaattga attcttttg gagtcatata ttttgtctat    21360
gctcaccaca gcatcggaag atcttccatc acaaaacagt tcacatttgt ggtggacacg   21420
agagatgaag aatctgtctc aaggtttaat cactgtggta ttatatagta aaatttat     21480 gatgatatta aatcatgatt ttggctatgt taaaatttga ggttttggt tctaaggatt    21540 ttttttgcta gatttatgtt aatatctaaa gtttaagaaa tttgataata attatagtta   21600
cgtgacataa ttcaaattta tgatgaacta catttactat atatagccct cgagataata   21660
atgttataca tttatttagt agatatatta ttagataatt caaaacttaa attacattat   21720 tttgttttata tatttcatat tatgttaaag tttaattgat aaatgatatt tttacgaaaa   21780
atttgtataa tactaaagat aaattttaaa aacatcaatt tcgttttatt tttattaata   21840
gtacataaag aaaaataaat aaattaaatt aatttgtgac tattttggta tatgatcaat   21900
```

```
gctcgtcttt taagtagta atcgtgtctg ttacaggtga atgaacccaa caaaaatctt    21960
cgacgagcat cttctgcttt cttcatctct gaatgatcaa tttctagaat cagatcggat   22020
atttcgatga agaatcgttc tttagggttt tgggcgatcg gggttttgct catcggaagc   22080
ttgatcggag ctacggaagg ctcgattcat gagtacaaca acgaaaagtt cactgcaaaa   22140
ttcaatgctc gcttcttcca tggtggtagc gaaggtcttt acgcttccaa atctcaagat   22200
ctaaactctt cttcttcttc tgataattct tttaaaggca agtcctttat aaggtcagtt   22260
tcactctttc tgaatcagct tcataattca aagtttgtgc atttggaatc gtactgattc   22320
aaagtttgtt cctttaggt ttgatgatgt aacatttgtg aggacaaagg aatctgctag   22380
taaacagaat gcaatgcagt caacttcagg attagtggaa gcaattatac ttgaggtaaa   22440
agaccgtgat agaatcggtg gtacttttct caaatccgaa gtgatttgtt gcacgccgga   22500
gctagctgat actggatctt gtagtcttgg ggaagttatc attaagagag agtctaatga   22560
tgttgagtgg ccaagacaga tcaagacatt ctttaaaggg aataagactg aagttaacat   22620
gtcccctgaa actgtggtta tcaataagac tgggatgtat tatctttatt tcatgatatg   22680
tgacccggaa ttggatggta ctaggatcaa ggggagaaca gtttggaaga accctgatgg   22740
ttatttacct ggaaaggttg ctcctttaat gaacgttttt ggcttatgt cgttagcgta    22800
tattttgctt ggtctagttt ggtttgtgag gtttgttcag ttttggaagg atataattca   22860
gttgcattat catatcactt tggttattgc tcttggtatg tgtgaaatgg ctgttcgata   22920
cttgtagtat gttaatttta actccactgg gatgaggcca atggatgtta ccctatgggc   22980
ggtgaccttt tcttctataa agaagacgct ttctaggctt cttcttctgg tagtctctat   23040
gggttatggt gttgtaaagc ctacccttgg tggtataacc tcgaggatac ttctacttgg   23100
agtcatatat tttgttgcaa cagaggctct tgagttggtt gagcatttgg gaaacatcaa   23160
tgacttttcg ggaaagacga tgatagtttt ggttattccc gtggcattac tggatgcttg   23220
ctttattctg tggattttct catcattggc aagaacactt gagaaacttc aggtaagata   23280
ccacacttat atcgaatatt ggatactcat gatccgtcac attattatat cagaaggatg   23340
tatatatacc ataggctttc atgggtttta accatgttat cgtacttaga ttccaattta   23400
tgcagcctat tcgagggaaa atcatataca attgctgctt aagccatcta tgacgatcca   23460
gttcttcgta ctctttttt cagctgctta tctgtctaaa tttcactaca gattaagaga    23520
aacatggcca agcttgagct ttataggaac ttcaccaatg cactcgctat ctctgttctg   23580
ctctctatcg cttggattgg ttttgaggta acaaatcgct actctagtga ctgtgtctcg   23640
tgtataacat gaaaccccta gtcagaggag tgtaactgaa atcaaattct tctatgtgtc   23700
tgtatcagct atacttcaac ggaactgacc ctctaatcga actctggcga atggcgtgga   23760
tcattccagc ttttttggaat ttactctctt atggtctgtt agcagtcata tgcatccttt   23820
gggctccatc aaataatcct acaaggttct aatacttcca ttagcgttta ctcaaatgtt   23880
ttggactccg atggtcccaa tgggtcaact gccaaagatg tcaagattca agacacttat   23940
ttgctcttca ccgagagatt atcatttttgc actcagctta cctctaattg gtttaaacct   24000
ttcaggtact catacttagc ggaaacaggg gatgagtttg aagaggaagg tatctcattg   24060
acaggtagtg gaattaagag tacagaagat gttgaaagga atgaacttct atttgggctt   24120
ccagacgacg ttgaagaggg caaacgtgag taagctccag atagcaagcg ttagatagtc   24180
catacctcgc cgagtagttt ttagtgtatg taaccttatg tcttttatcc gttgtacctg   24240
```

```
agtaagttgt ttactgacct ttaaggactt gtttaccaga tcgaagttct tttagtctta    24300
tagaaagatt tacagactgc ttatttccag agcgtcaaag ggaactttt tacattagag     24360 acttgagata ttcgtcggga agtcgttgat catcatcata gctgtacatt aaaggaactg    24420
ttcttgcaat gttgagacaa gcttttgaga atgatcttga aatggacat ggattcagac     24480 actccctgtt caagcgtttc catgctctag atatcttctg gcaacatgt gttcttgctt     24540 catcaacagt tgatcccttg tactcgttca ggtaacactc tacatatgat ccatcagttc    24600
catcttggtt ctcatcctgt taaacaacaa aaaccatatc taagattcga tatcaagttt    24660
cagattctct ctagtcacat tagttatcag tagttcaata taaccttggc acttccgaga    24720
tcatcccaga gcctgagaat tgtagctgca gatgatacaa tccccgggtt actctctatt    24780
agttcgactt tctcttttgt tagttcttcg cctaacaaga tataggcatg aagcatcact    24840
aaatgaacac ctgaactcac aaccccattc ttcatatact cttcagtggt gggtaagtaa    24900
cccgaattaa accactttgc ttctaccaag aatgctttac acaaacttgc ccactgagaa    24960
acaaagacat catatttta gtagggtttg aaccagttga gctatatgat acaaaatata     25020
tatacacatt acgttttgaa tgataattac cgattgtcga agagcgtatg tcgggttcca    25080
accatgtgat ttgtagatct tcatgctaat ctccgttgtg atcatatcta gagcttcaaa    25140
acaaaccctc atgtatttgg gtagcgtctt aagccccta tgatcccatc tagacgaatg      25200
atttcattat gtttgacaga atgttaatca agaaaatgta taaagtaatt tgtatgtacc    25260
tctcaacaac tcgtgtgaag atggttagtt cttctagctc cccatagaca tcgaaaatgt    25320
catctataac ataaacaagc gatattggtt tggtaagatc aagcctttgt tcggttaagg    25380
tcggatcttg aagaatttc atggaccacg tatgccattt taacggctgg cttcttgcct      25440
tctccacatc tttttctaaa ccaagttctg tccaccatct gaaacatcaa aaaccataca    25500
aaaacaaaat cgtatatcgg aattcaatta ttttcgacaa aaagttaaca ttgatcttca    25560
gggagtatca tcattgattt tacttaaatg tttgagacat ttctccttga gtcaatgact    25620
ttagcctaat ggaatcgatc tccgccactc gtaatagaga ctgtaaccat tctggatctt    25680
cttgacccgc gattttgatc atgcttgtga acctcttgga cgttaatcct cttacggttt    25740
tgtggcgagg ttgcgccaaa gacttcatta tctcttgctt ttgatgactt tctctacctg    25800
agcaaagttc attaaggcgg ctatatgtga attctctcgc accgtcgagt gtttcttcac    25860 cttctcacg gagctcagaa gcttcaaaca atttctgttag acccttgacg tcattttta       25920 ctacgtcttt aaatccaccc ttcttgtcta ggatgtttt gaaataact aaatgtttta       25980 taaaaattgt aacagtaaat acgcatatct catacgagca atatagtaag taaatatata    26040 tataacat cacatactt cttgaacata gtgaccctct tgtctcagca atcgaaagcg        26100
aagcgctatc tcatggagat caccgttgaa ttggaggcct tctttgtaaa tcatgtgaag    26160
ggtttgctcg atctcttgtc gaaaatggag atcaatgcct aaactttgaa tgacatcgat    26220
catctccagg ttctcggatg aacatctac gtttgcactt agtatattct tgatcttctt      26280
gatattcaac tcgtgtaaat attcctacgt acaagaacaa acacattctt agttctgaaa    26340
acagcatgag caacaaaaag taagcagaat atatatacta aggatgtctt attatgaaac    26400
tgcttcgaag ggttagaaac tgaagcatgg acgtttctca agatcgatct tttagcagta    26460
tttgcaggcg acaaagaatc gaccgtattg ggaaatttgg atatcagaaa cgttggagaa    26520
ttgtttggat aagcagaaac aaaacaagaa cgtgaactta ttttggtagc tattaaggcc    26580
atgatgtatg aacttaagtt ttgttttgtt tttgtatgaa cttaagcttt taatgagaat    26640
```

```
ggtgttaaac ttcaaacgaa atgctctata catatagcga ttatggatta taaaggagtg   26700
gtggatgtag catttagggg acggggccat gcataataaa attcgttatc aactatgttt   26760
tgtatatata tatataattt gtatcatgtg catactagtg aaaagcatta aacttcaagc   26820
ctcaaccata tataaatgaa ttataaagag tctttgtact aagcttttat ttgaattact   26880
ggagtcgtaa ttttaagatc ttatagaact gatacattcc aataagtttg gctagctaac   26940
attaagatta attgggtaaa tattaaatgc attatgtatc atgtttggtg gcttcactat   27000
atttttcaac ttaatataga aacggttttgt atttattgtt agacaagttc ggaagacatc   27060
aattgtggaa gcaaatccga agaacgtgaa gaaccaaatg atcaacggaa caaaccaata   27120
atgatgactg acactgatat ttttttttcca tttttctttc agtttaaaaa gtttcattag   27180
aaaattggta ttacaaaaac aagtacaaag tgcactacaa aacttcagat tttttctttt   27240
aattatataa gccaagttat gtgccatata ctaaagaaaa caaatacgaa aaaatgaatt   27300
taatgatgct tccttgcgat aagctatttt ctattatcat gttaattttt gaaacaattt   27360
tttttatata atgatttgtc aaagtttttc attagttatt tacatatttta attgttcaaa   27420
aattaaagat ggaaaaataa ctcaattttc ctaagcaata tattaatgtt agtattcatt   27480
ttagataatt attctagtat aagatttaat taaaccatta gataatttg atgtattta   27540
tattattaac attcataatt atttgacgtt attttttgaat taaatttctt aactattttg   27600
acagatttga ccaaaaatca caaaaaagaa agttcagttt gattccggcg gtttggaaat   27660
gtaaaagttc agctagatcc atctgaaaat cactaaaatt cagttagtca gcaattcagc   27720
ctgactcagc cagattttc ggttactatt tagaccagtg ttttcacgcc cgacccgaac   27780
cgtccggtcc gaccggttaa cccgtgaccc gaacacgttt ccggtttggg tttagtgcta   27840
aaacccaaca agttcaaaac cgaaaaaacc cacaaaaact cgcaattaac ccgtgacccg   27900
gtgaaccggt tgaaccggcc gagtgtgggt tttaaaaagt tctcttgatt ttacaataaa   27960
atatgggatt ttagacttta ttcaattatt tttaaaaatt tttttcagtt cttaaattca   28020
tttgatgttt tagattttgg tgaagacttt acaataccgc cttaaaattg aatcgaatgg   28080
tgagagagac aatcgagatt agttgtttga attcacgatg ttttattaat ttatttctgt   28140
cattgatgat ctcctaatat atttgttacg gtgttagaca tttagttgga tttcaaattt   28200
ttaaccactt tattattatt gtttgattat atatatatat atatatttgg gtgtaaatga   28260
tttttatttt tgttaaacat aatataattt tatatttgat taaatatgat atgattattt   28320
ttgttttata tttataatac taaatttttt tttatataaa atactctaaa atttctatta   28380
atattaaatt tattaaataa attttaacta attaacccgt ggtccaaccc ggttgacccg   28440
atgacccggt gacccaaaag gtagtccggt tcatcgtccg ggtcgggttt cattgtgtaa   28500
atgatatttt ttgtggtcaa agttgagagg tactataacc tttccattta ttttttttata   28560
gatttataat caaaagaata taacttatac tttcaattta tttccttata taattagtca   28620
aaagaaacta gaaataatg ttttttaattt cttacctaat tacgtttgaa caatggtaaa   28680
gtgctagtat tatatatttt ttttttttggc aaatatatat tatgttatgt acactgtttt   28740
ctctacattt caatttttt tcacattacg aaaatggttg tagcatatat ttaagatttt   28800
gtattacaat tccaaatttt agtggttcca acttgatgtt atgggtaaag aatgttgttg   28860
gtgggaggaa agtttacaca ttccaaacca aattttacac attctttac caaaaaaaaa   28920
aacatttgca aattcaaagc attatgtttg cagtttttgc tggggaagaa caagctaccg   28980
```

-continued

```
gccgtactgt gaaacttttg atattagaaa catcaaaaca agaaagtgaa catatcgtgg    29040
gacctatgat catgggcatg atgtatcaag gctaaacttc aaaagaaatg ctctttata    29100 actattacag tcgttaatgg ggatgggga taacaaacat catcattttc ttttataacc    29160
actacagtcg ttaattaaat aatttaacca atacaaatta attgtaaaac ttcggttaca    29220
ggaatatggt ggtgcatgtg gagaaattta taaaaattaa tttggtcatc tatgttacta    29280
aaacacactt atcttttttg tcaaacgtct taaagaaaat tctacaatta agcatttta    29340 agctgggaaa gtcttatgat agataacttt cgaggaaatg attgtcggaa ccgtgtgagt    29400
gagaacaaaa tacgggagaa aatcatgtgg tgatttgtaa ggtaagtacc aagtttttaa    29460
agcctctcag acatggcgta tcgatcgttg gacagaaata gacccacaga cccgagaaaa    29520
tacatgagac ctactagtag agactcttgg aacattatat tgataataaa taatggtta    29580 gattggaaac tcaaaacggt acaaggtttt taataaaata gacgaccagt aagcaataaa    29640
tacaaaatag attaaagtcg tagaaaatag ctatatatat ataagtatac aaaaaattta    29700
tgagtatcac ttaaaattgt ttttaggttg atattagacc atctaatatt cataacgtat    29760
aaaaaaaaaa taataataaa aataataaa gaaaaacaa ataaatattc attcctccgt    29820
gtttcaattt tcttttagat tttgttctaa tgcgaagcaa aatatatcac taaattttt    29880 aactgaaact tccattgata tgtaaaagtt tatgttcttt atatcttata tatatatata    29940
tatatatata tatatatata tatatatata tatatatata tatatttggt aggaatcttt    30000
tatatatatt gagaacatat aaaaactgtt gatgttattt cttaggcaga aaaaattaca    30060
tttggttgga ttatttcaca ttgaacgcat tcttatcatt atcataagtc ataacaacaa    30120
catcgtcctc taccaataca tttgccataa gaatactcgg cttcattaca aaacacaaga    30180
caacctagtt gccctgcgga ataacacgcc attagcatga agcaaaacca gtgttttcac    30240
gcccgaccca aaccgtccgg tccgaccggt taacccgtga cccgaacaca ttccggtttg    30300
ggtttagtgc taaaacccaa caagtacaaa accgaaaaaa cccacaaaaa ctcgcaatta    30360
acccgtgacc cggttgaacc ggccgagtgt gggttttaaa aagttctctt gattttacaa    30420
taaaatatgg gattttagac tttattcaat tattttttaaa agttttttca gttcttaaat    30480
tcatttgatg ttttagattt tggtgaaaac tttacaatac cgccttaaaa ttgaatcgaa    30540
tggtgagaga gacaatcgag attagttgtt tgaattcacg atgtttttatt aatttatttc    30600 tgtcattgat gatctcctaa tatatttgtt acagtgttag acatttagtt ggatttcaaa    30660
tttttaacca ctttattatt attgtttgat tttatatata tatatatata tatttgggtg    30720
taaatgattt tatattttgt taaacataat ataattttat atttgattaa atatgatatg    30780
attatttttg ttttatattt ataaaactga atttttttttt atataaaata ttctaaaatt    30840
tctattaata ttaaatttat taaataaatt ttaactaatt aacccgtggt ccaacccggt    30900
tgacccgatg acccggtgac ccaaaggta gtccggttca tcgtccgggt cgggtttcaa    30960
aacattgatt ataacatttt gccatgtact actaaaaata aatcaaaatt aaatttataa    31020
aaacaaatta aggaaacaaa atctgtatac atttaattaa acaaaattaa tgtttataaa    31080
taagagtttg ggtttagatt tacaactaaa tgaaactaga tgcggtttgg gttttttatg    31140
gtttagattt tatagttaat tcaatttaag agtttgtaat gaattaatga attttattat    31200
tattagataa taatgactgt tttagttttgt ttaataagat gatatggcaa attttgatgg    31260
gctacttaag agggggggg ggaataagaa aaataaatgg gttgatttga actagttata    31320
ttttgattgg ctagttaaga ggagggaaca agaaaaacaa attttgattg tttttttggt    31380
```

```
tgattttag tttaataaaa aaaatgacta gtaatttcat gtgattaact atcaaattct    31440
tacgagattt tgtataataa tgaaaacaaa atataataag aattagagag attgttaaga    31500
ttacccttcc aaggttacct ttttaattct acccttcat  ttagttcatt tttatttata    31560
cattttaaa  ttattaatga ccattttatc tttatttgaa aatgttttcg gttaacataa    31620
tgaaatattg attttttccg ccaaaaatat tccgacgata cttcttattt aattgtatat    31680
aaaagatag  gttgaacttc ttgccttgtt aaaaacctac agaagccatt atcatgaatc    31740
ggaacaaagg agtgcgtaaa gaataccaca tctctctatt aaaattttag aagcaggcaa    31800
catatgctcc ttttgtctgg cctcatatcc agtgaataat ccacatcatt tcacaaaaag    31860
caatcctcgt gccaacataa ttgatgcaca agaatatgta atatgcatac gtttaacacc    31920
atgtgagccc aaggttgaca acacatattg aagcttgcca agttttctca atctagcaat    31980
agttgattcc gaaagacatt tctattggga gatcgatgag atcgacccaa accgaattga    32040
gacacataga aattacaaac caaaattaag atataattat ggagatattg tggactgtga    32100
atatacgagt ttataaaatt tgatattatg tcttattata ttatttacat ttaagttttat   32160
cattttaaga gaacttagat ttatttcatc tctttataag acaataaatc ttgcatcttt    32220
attctgatga gagtctaaca taattcttcc taaacatttt tattttcttt actctcatca    32280
atttatcggt tactgaaact gtctcaaccc ataggcctac acatcgaaaa cctttccact    32340
tgtgctctct tggagttatc atctatcgct tttggaattg gtatatacat gtactacatc    32400
agtagaggtt accaattaaa cccaaatttg atgaaacaac acgtttacca aatggacccc    32460
gtataacatg tgaaagtatt tggattttct aatattcatt atgttatatt ttcgatttta    32520
gatttattc  aatacaaaaa aaagatatca ctcaaacatt taatcaaact atactttga    32580
ttggtaaagt ttatctattt tgttatttga tctttatat  agatattgag aacataggaa    32640
aactgttgat tattttttca agtagataca tttacatttt cgttggatta tttcagctcg    32700
gacgcattct tatctgtatt ataacaacaa catgatctat taacacattt gtaatgttta    32760
taatgggatt cgtgacaata cacaatgcaa cctatttcat attggcctgg ggcaaaacac    32820
gctggtgtta cgaagcaaat cccatcgttg tcgtgcgagt gcttcgaaag tgcaggacct    32880
aattattaat aaaaatcagt acaatataga cattcattta aaaaaaagga caaaatatg    32940
ttcataatta taaatgggt  tataagaata cactaacaca ttaaaagtta aatatataat    33000
aatggaacat agaattctta tcttcaaatg aaacaagaat gaaagaggat ggaaactgaa    33060
aaatcaacaa cagtcactat aaaagttttg ctctaaattc taaatggttg gtaaagttta    33120
cctgttgcgt atgttgttgg ttcaccactg cttggggcac ttgcaattgt tgtatgacaa    33180
tgaacataag atatgatgac aataacgctg aaaacaaatg cgattagggt ttttggggtg    33240
ttagccattt tttatattct tattttttt  tgtcaatgag gtcttcaata ctttgattga    33300
ttatatatat atatatatat atatatatat atatatatat atattaatac aaatatacgt    33360
aaatggttgt tttcctagtc aaagatgtaa ataacttatg atactataat ttacaatta    33420
ttttcatatg gtcaaaataa atatcttatc ccttcagttt atttctttat agaattgtag    33480
tcaaaataaa atacatagaa tgttttttct taccaagcac tttagaacac cggcattacc    33540
cttactaata tttatgaagt gcataattaa aattaaccat atttcatatc aaaaattaca    33600
tcaaattttc attaaaatat aggttttcat taaacaaatt aataataatc attacaagta    33660
aaatagtaaa cactacggcc atgaatgttt gtagttttta aaatggtttt tggattttgg    33720
```

```
tttttggttt ttaattttg attttcttgg tttttgtttt cggtgtagat tttagtttct    33780
taaaaacttg aatgataatt tgtttagatt ttggttttta tgttaatgaa taatatatat    33840
ttttttaaac aaatctaaaa taaaataaaa aatgtgatc aatggtttt gagaaagaaa      33900
ctcccataat tatagatttt ggttttcttg aaaaattgtt caaacactca aaaactagat    33960
tccctatttt ttaggaaaac ttgtttttct tttaatctta aatgggtaca aaatagattt    34020
tgtacaaaat agatcttaaa tgggtacaaa atagattttg ggaaaaacta aaaccaaaaa    34080
ctaatttaaa aaccacatcc attcgagggc tactttctta aaacgaacat gctttagtag    34140
ttttcaaaaa tatttaatta atcaaattaa ataaagaaga tttgatatct aatttaacat    34200
attaatttt atttaatcat tgtacttcac cgctcatctt cgtttaattc tacttttctg     34260
aaaaaacaaa tcatcacatc atcttttcgc gtatgctatg atttgaattt ttttgtagga    34320
tgttgtttgt acatcagatg ccttggtctg atggggagtg atcaatgggc tcctctccaa    34380
aatgtttctt cacctttcat gaatcataat acatgatttt gctctttcta cgatcaaaac    34440
ttcctcttta agctcattct tcatgataca tgctccaaac cctaggaaga acctaagtaa    34500
tgcaaaatac acaactgagt tgatataaac cacaaagata tcaacaggta aaagagaaag    34560
ctctgattca aatgtacata tgagtcttct gtgttgttcc atcgacaaaa tatgactaat    34620
gaaaaaactt ccgactctcg tcagtttaca aatcagatga taaacactcg agtaacatga    34680
aggttatgtt acaaatatcc aatgaactgg agagttgaat caacttgaag caagagcgtt    34740
tagcttcttt tcatatagtt ttgcccgtcg aagagcatct aatgcctcag cttgtttccc    34800
tgcacgtttg aaggtcacag cttttacctt ctctgctttg attcgttcct ccaattgact    34860
tctctcttga ttattagtat ttctattact ctccttcact gggtttggtt ttgccgcagc    34920
ttgtgttgtg tctgttttac ttaccggtgg aggattcacg ggattgtcta atccaatagc    34980
tttgagggca gacaggagtt gaggatcgag aaaatcttcc accgctacat cgtccaccgg    35040
ttctggttta gaggatgttg aatcttccaa ttgagcttca agagttttgg cgatttcaaa    35100
ctcagcttca gcttcctgca ttttaccttc cctccgaagc ttcatggctt gacgtttgtg    35160
acttagtgac tcttgctgca gcttaaaacg gtcacgacct gacattgcct ttggagctga    35220
acttgaagga ctattctctt tctctcgagc aggaggatcc tccgttgtgg aaaccatatc    35280
atctcgtccg agcttttcag gagagggatt ttctccttct tgtagtctcc tctccaacaa    35340
ttttgcttct tgcaatgcct ttttggcttc acttatgttt ccttctctct ttaaggcaag    35400
tgcctttttc ttatgagcca gaatctcttg tttaagggtg ttctgaggag atgtattttg    35460
aatcgaagct gattgaatat gactgggctc tgactcttca cgtgccactc tttgttcagc    35520
gccgtgattg tttcctgaac gaaagcctga catagtctca gcatttcctt tttctgcatg    35580
aatttgagac ctctcagaat gctcaccagt cagcaaatcc atcatacttg gttgctgctg    35640
gccaggttga gaaacaacgc cagaggaacc agatttagca ggggagataa agtctcctaa    35700
caagtcataa ctatcttgag gagcatgaga aacactagca gattttatcg ctttatcctc    35760
catttgcgat ccaactaata aatcaacatc catgtagttt tcaggtttaa ttgcagaagc    35820
tgagcctttc atctccatct tgggggtttc cagttctgct agctgtgcct ccaaaacact    35880
ggccttactg tataattcat cagcatctcc agttttccct tgacgcttga aggcaagtgc    35940
cttctttttt aagtcaagaa gttctctttg gatttgtccc ttgcttttgg ctgctatccg    36000
tggaccgctt gactgcacag agccgaaaga agcttcttct ttctttggtt cttcatcctc    36060
ccatcccaaa ttcttaagag tcgacaataa cgctgggtcc ttcatatcat tttctgtaac    36120
```

```
gctatcatct cctccattga gccgactgtc ggtggcaaga tcattggatc gttttttcgg    36180
ctgatcactg tcagcatata gattcttgcc tgaatcaatc tccattatct gagcttccaa    36240
tatttgtgtc tggttcagaa cttcctcagc ttcatcaaca ttaccctgtc gtcgcaaagt    36300
taaagccttt cttttcagcc ctaagagttc tcgttgtatt tctgctttag ttctccttgg    36360
tttagtaaca cgtacttcat atgcaccttg agcttctgct gttttccctg gtcgagaatt    36420
tagtgggtca gattttttctg atgaaggacc tgcaggatta ttatcttcat cattccaacc    36480
taagctcttt agcatcgaca agtaattcgg atcatttaac tcctcatctt ttacatccac    36540
ctctccatca tcatccagag aactaatatc aggcagatca tttccttttt cacgagtggc    36600
cttccctgtg gcagctaact tgacgaatt gtccagctca tcaagctgat tttggagaac     36660
cgctcctttc ttcaattctt cttctgcttc gttaaacttt ccttcccttc tcaaagtaag    36720
tgctttcttt ttcactgcaa gaagttcttt ctgaatcgct agcctgcttc tgggaggagg    36780
tttaagactc gtatccctct ctgccctagt tgtgtcaaca gtttcagagg aagtatcagc    36840
agcctctagt tccttctcaa gtaattttgc cttcttagt gtagccatgg cctcaacgac      36900
atttccagcc cgttttagat taagggcctc tcttttcaat gtctgaattt cagctaaact    36960
ttcatctctg tttttaggag atggtcgaga gtggacattc tcatggtgtc caggatcctc    37020
actccaaccc aaagatttca atgcagcagc gattgctggg tcctccatat cttcatctgt    37080
gacatcatat tcaccatgaa ctccaatatc atctaaattt cccacaaggt tactaatgtc    37140
gaaatcatgg cttccctcgt attgagctaa cagatcatct tctttgtcat catccatact    37200
attaataagt gcagatagct catcatctga tccatcagct ccacccaaaa gttcctgctc    37260
ttccagttcc ctttccaaaa ttttagcctt tttcagttca tctttagctt ccgcaagctt    37320
cccttcacgt ttcagcgtaa gggcttttct cttaagggca attacctgac tcttgtcaat    37380
accccccagtc ttctgaggat tagcacttcg cggaatttca cggagaagag acgaaaattc    37440
gccctccaaa cttatagttg ctggtttctt atcttcatcg tcagaccacc caagctccct    37500
caggtcagct gccaaatcat catttccttt acccccttga cgtagaggct tttgtgattt    37560
gctagattct ttggtagcag ccttgttctg cgtctcagca acatttcgca tagacagttc    37620
ccttttccgg ttccttctta aagatatctc taatgcgtcg gcctctctct caagttccct    37680
ccctctctta aatgctttta gagcttcatc agatttccct tctcctttaa gaattctgta    37740
cttattcttc gcttctactg cttgtttacg caattcttca ggactagcat ccaactccat    37800
accttattta ctactgctac ttgccatttc tttagaagca ttcctgtctg tgctagacac    37860
agattcagat gaagaagata catcaacatc agagcctaga atctcactga aacatcatc     37920
ctcattcttt acagtccttt tcgagctacc tcctgaacaa attcacaatc tctttacatc    37980
aaaaactagc agataacaca aaagtgtcat aaataagatc actataggta cataaatacc    38040
tttagcagct ctattttttgt aaccatgacg caactcaaac cgtgcagctt cttcaatttt    38100
cttcatggt tcatatatac gcacaggtga gtcaccttgt ccacgtagtg acaacctttg     38160
ctgagtgcag gttccacaga acaatccccc acatctccgg caatgatgct gctcgctcaa    38220
aaaaacaaag ccaacagaaa ctaagaaaaa ttaagcaaat tcaaggtttt tgggagaca     38280
tagaagaatc cagcaagtca caagtctagt aatacacaaa ccacaaaaca tccagattca    38340
ccaaatttac tcaaaaatat ggaatctatc aaataggcac atcaccagaa accgatcatt    38400
cagtgaagtt ttccgataaa cagattctga attagatctc gaagaagaat cgactaagac    38460
```

```
gaaactaaat ttcgatcgaa gaaactaaga atctaaagat cgcgatagca ataagcaagt    38520
accaattgat agagagagta aggaaattaa gagagaggaa gaccttgcga ttgatgaaag    38580
tgaattgaga agaacatcct tgacaatgag aagcatcaac gacccaacta tttcctctta    38640
gagatggctt cggcggtaat ccgatcttct ccaacatttt cccgtctgat tcttcttctc    38700
ctccgccgcg aaacgaactt ggttttgatt ttgatcttac cggaaatgta aaagatcgag    38760
cagatgaaga agaagaagaa gaagaatact tttcctcctc tattgtcaga tataaaataa    38820
ataattttaa ctaatacggt atcgttttag ctaaaacaca taataggact caatatataa    38880
agcaataata attagacatg aaactaattt ttgctttgag acgagaacga agttagaaag    38940
agacaagccc taaagatcgc tttgagacga taaactctta aagtttcgat tcgttcacga    39000
tgatcgtccc tgttcgttgt tttacttgtg gaaaggtttg tttttcttc tctctttttg    39060 tacgatttcg atttgttata tatatatgtg tgtgacaaat ctctagggtt tgtagtattg    39120
agatttatga agcttttgtt tatgattttt tgtaggtgat tgggaacaaa tgggacacat    39180
accttgaact tctccaggct gattacgctg aagggtaagc gatatatagt ttatgattag    39240
aaaaagaatc ataatttgtg agaatttttt ttggtgaaca tgagagtgat tgaatcttgg    39300
aattttgaac gttttctgac attttcttag ttgaaatgag agtcatgtaa aagatgaaac    39360
aatagtggaa catgacaata gaatgatttg atggttttgt gtagtcaaag agattgcatg    39420
atcttgtctt gtatgatcat cttgaaagtt tatacatgtt ttagccttgt tactaaaagc    39480
atgaagttag atcattggga ttttttcgatt ttccttgtttt aatcgctagt gtaatcttta    39540
gcccgtttgg ttctaggtgt taagctacat gatttggaat tgcgcaattt cgttttttgtt    39600 ttagttgcaa tttgatcatc ttgaagttca tagatgttat cttaagtgtt agtaaagagc    39660
atgatggtag gtgatcactg atatattcca ttctcttgtt tctatctaat cttttagcta    39720
ctttggtttt aggcattatg ctaaaattgc attttgttga actgaaaatc tgaattttgg    39780
ttttggaata cgcagggatg ctcttgacgc gcttggatta gtccgttact gctgcaggcg    39840
tatgcttatg actcatgtcg atctaatcga aaagcttcta aactacaaca gtaatatctc    39900
catacccggt tcttttgcct tgtgttgcct ctgctctatt ctttttgtta acttgcttat    39960
tcgaatactt ctcttttgca gctatggaga aatccgaccc caattaaaaa aagatgctat    40020
aatgaataac aaatcatcaa gagctgaagt gaaggagtga tgcatctcat ccatgtgggc    40080
gtcttaataa aaccacaatg tttcagaaat tttggtttaa tttataacta ggaatgttga    40140
tatttcaatg ttttctgatg ttcttgttcg gttttagaaa tctagacaat ttttcgagcc    40200
aaaaataaag ctcaagcctg tagagtcatc atctattgat ttgttttttgg taatctaatc    40260 ctgataaata gtaaagatca cacatttgat aaggttcaaa tctacaatct agatcacgag    40320
taggaagcag ctcttttgt acgatatcaa attggtaatg agaacagagc acataaaaac    40380
aatttgaatg gagctcccat tttataaccg gagaatatca agttttttta gttacaagtg    40440
gttgtattaa ttcaaggaaa ccatttaaca aaagaaatat aaatatttat attaaatata    40500
cactataatt agttgaatat atatttattt tggatcaaat gttttattaag atatattttt    40560 attataaaaa tttattctga aatatgttta ttgaacaata tactgaactt aacaaaccaa    40620
ggagactttt tttatttat ttttttttcaa acacaaacca aggagacaaa tatgaagaaa    40680
acaaattaca tttgaataga gaggtagagc tatataactc actgaatgct tggaaatatt    40740
gtctattagt ctattacaga ttaagatttt ctaaaagaat ttgagcccgc tgaacccaga    40800
atttgagagt ttggcttaga ctcaaattcg agttttttacc tagtacgcat tcaatatgga    40860
```

```
aaatggtgca gcactcaacg caccaataga acactttgt gtttgtgtct cttaaattac    40920
gttcacatac ttcgcaccaa tcttttttcac ggacctcttc ttcccatata gctgtgagaa    40980
agtgtttgtc atgttcatac cttgctctat agggtaatgt agcacacttc atacaaacaa    41040
taaaatcaca tttgatgcaa tttaattgat tatgacgttc tgttttgcat acgcgacata    41100
tgagttttcc gtctcggcct acaaatatga acaatggatg tttatgacct tggaaacaaa    41160
acggctcagc aattgaagca cattttacat ctagagtgaa gatacatccc cttatgcaac    41220
actcatagac aaagccacga caaccacgat tacaagaact gcatccaaaa cgatccatac    41280
catatctact tgcagctttt aatgttagtg gatgaggatg taatgcatgt tgtaatatcc    41340
tgcaaaattt tgcacatgtt tcatggaaga tgaaatcatc acactccaca caagaataga    41400
aattaccttc gaaaataggt aaataacacg cttgacaaag tttttttttcg ttataaagta    41460 tactgacttc gagccggaaa tgatggtcat ggagaaaatg aagtatcact tccttagata    41520
ttatattgaa tgatccaaca tcttgtgtaa tatcatcttt gtctggtaaa ccttcgagat    41580
cttttccatc ccacacattt ttctctagag cacatctcga atgaacagca taatgaccac    41640
acttatcaca agtatatgca ccataatcac cgtcaataat ttgatgaaaa actccacaag    41700
accattcaca tgatcgtaga gaaaaagtgt aggagatacg atggttgtga cgtgatatct    41760
tgatgacgct tggagagtac atacaatcac tatgaaacac aaagttgcat ctgacacata    41820
tgtaggtggg atatagtttt ctcaccaaac cacaaaagtt gcaagttaaa gaagtttgtc    41880
taggaaaaaa agtgagagga tggtcggcat gccttttttgg tgggtctata acaaagggta    41940
ttggcttcac tgcacatact ggatgcatga aaacgttaca tatggtacaa taatatacca    42000
ggaagtttac tcttcttcta cagcataaac aattaatact gtaaagaagg aagtgaaagt    42060
aaagttggag cgaatgctga gggtgataag ggtgtttgat tttaagtgga gactcgacgc    42120
attctttgtg atactttttc gtgcaaatgt cacaaaaata atagtcagtg ccaaaatttg    42180
agtgacggca tatattgcat ccaccatcaa tatcgaattc tttattgttg caccaaaaca    42240
acgggagtac tgaatgatat gtagcacttc ttgtagagaa gacgaactcg ggggaagaat    42300
tgagcgggaa aatattccca gttctatctt taaattttcg tgcacttggg cataaaaaaa    42360
gaggttgaag aagatggtca tcgctgactg cttcaccgga tggagatagg ctatgtgttt    42420
ttggtttggg atgatacttg ggatgatgat attccagaaa taggttacca tccttttcct    42480
cctcatgaaa tccaccgaaa tccatggctt ctcctagtct ttgtttacta tacttctgtt    42540
aagatctttt ttttttatat aaatgcaaaa tactagtttt gagagttttc cactatacat    42600
aagaaaatct gataccaaag gtctccttct acgtttaatt attggatcct taaccgtgaa    42660
aatgagttga attatgttct tttctttgta ttgaatggta attttctttc cacgcaagta    42720
aagaatactc ttttccacat agttttcacc cttacggaac ttatatatcc gactcgtcaa    42780
gattttaatt ttacgatcaa ttacaataga gaacaaattg agaccttaac ttaaatggta    42840
actacttttt tagtcagttt ttggtttttg ttatcaaaag aaatcattag tcatccaatc    42900
aagattcttt tacaattgta ctcttagctt tcttctcttc tcgaggaaag aatgattcac    42960
aatggggaaa tgtgaagtag tctttcaggt aatagaattt acaaagcagc ttcctagagt    43020
aatagaatta tcatgtgtgt atgatcaaag aatcttgttt ttcacaagtt catttcaaaa    43080
gtatgtaata tttatgtatc aaaagacatt aaatcaacca acatataata cataattatt    43140
caataccatt ttatagaatg agaatgagac caaagactca tatactcttt gaatccattt    43200
```

```
tgacattata aaagtcaagt ttatttagct ttgatcaatc cttttgactc gaagtactct   43260
atcatttgat catacatctc attgatccca tattcgaatc gaaagccttc attgataagt   43320
ttttgcgaag atagtgtcaa tttcggaatc gacaagccct cttcgaatct gccaaatttc   43380
acaaaacaaa aattgattag acaaaagaaa atcgaatttt caattaatat ttttgcaatt   43440
tctgtagaac ataaaggctt actctgacaa cacattgtac ttaggatatc tctgtatgag   43500
aaaatccgca atctctggaa cacttgtgtt gtaagcacag caaatgtagc gaccagaagc   43560
agtttctttc tccgcaagaa acaaatgggc acgagctaaa tcgtctacgt ggacgaacga   43620
gatcgagcca gatagcttct gcatttcctt gagaccggtc acatgcattt ctttccctga   43680
caacaacacc aaatcatctt gattatttat cgtgaaacag aatgggataa aatggtaaat   43740
tcgtgtttac cggtgatgaa agacatcgag agagataagc tactcggagg atcggagagg   43800
agagagtttc cggctataag tgccggaatc acggtaacga gattgatctt attctctttt   43860
gcaaattccc aagctgtctt ttctgctaac accttcgaga ttgggtaacc ctagaaaaga   43920
acagagaggt aagttggttt atgtatgaaa aagccctagc ttgtgtaaca agaaacgtaa   43980
ttacccagtt aaaaggcttc tcctctgtga gaaattcaac gtcagtccag ttttcttcgt   44040
tcatcacgat tccggttcca gaaagattgt tgatggaaac agcagcagct gaagatgtgt   44100
agatcacacg cttgactgat ttcgatttta agcaagattt caacacattg atcactcctt   44160
gtatcgccgg cttgatcatg tctttctgta tattgaaaca aaaacaagat aagcttgata   44220
atgtttctct tatgagtata taaaagcctg cacattctgt tcaagataga cctcgggatc   44280
ttcggattta aagttgatcg gagttgcgac atggaagatg tattcacagc cggagaatga   44340
ggattcgaaa ctgtcttcat cagtcaaatc tgccttgaag atcttcaggt cgccaagctc   44400
ttgaagtttc ctaaggtgag ctatttcctt ctcgttttct gcagtttcag aataaaaaaa   44460
atccattaaa cattcaaaat gccttcgagag aaaaagaaa gaagaagaga gtgaagaacc   44520
tggatctcta actgtagtgt taactttgta gccactttga agcaaatgct tgatgagaat   44580
agaggctaag tttcccgtgc caccaatgac acaagccttc ttcgatccgg tgtgtgtaag   44640
agtctggtcc atgattgtac ttttgaaatt acagagatag agatttagtt gttatgagtt   44700
tatcgtcttg agacttctat ataagaagta aaaagatttg caaatagtcc ttgctcatta   44760
ggtacaacag tagatcaata aggctgtttt agaaggtaag cacgtgatct ttgaaataac   44820
caacttgtct tcacctaaga atcaaaaaag attgaccttc agagttctga tttgttatca   44880
tctaccaaat tatcacaaga gtttgattat ttctgtctct aaacaatata acacagcttt   44940
agagtaacga atagtgttac agtaaggttc tgttacttca atttttttctt tgccgatctt   45000 aaaatgagtt gcaaaagaat gcttttact tccaccaatc tgtcaaattc tctgcagttt   45060
ttaacacaac ttggacttgc tatgttctgt ttcacgaatt acacgagtca attcaacata   45120
acttgctctg ttcttgtcca tgtttcacag aatctggcct taagcaattt tatcatattt   45180
aagctacaaa tccataacag agtttaacaa agataaaata accagaaagt tacattgaaa   45240
gataaaaagt gaagaagaca aaaaaagag agggtaaatc ctaaatcgaa aacaaaagaa   45300
ggcattggca atagcattcc gattttaaaa aaccgataaa tctatgtatc taatggcttg   45360
ttcttagaag cttcaacgaa catagaagca acctcattca aaaacttagt cttctccaac   45420
acaaattcca actccttagc ttgcaacaac ttatacttct cttcaacaat cttcttactc   45480
tcaaccgaaa ccaaactcca ttgctgcttc acataatact catcaacacc caaactagca   45540
atcatcctaa caagagacga gttatcaaac caatcacatc catcatcacc accatcttct   45600
```

```
tcaacttttt taccattagt tgaagaacca ccggcaaaca ccaactcttg cttaacagaa   45660
tcaatcttct tcttcgccac actctttttc gatacaccgt tcgacttaac attagaatca   45720
agagctattc cttaggtcc ccaaataaac ttagacaatt caaaagcttt cttatcatga    45780
gctttcacaa aactaggttc gttccttcct tctttaccaa tatacttctt ccttaaactc   45840
ctaatcttat ccatgaattg attcttacta acctcaaagc taatcgattt cttcaagaaa   45900
tcgtaaaacg cattagtatc tacataagga gacttccctg tatcagcttt gaaatcaatc   45960
attccttgta acactaagat ttcgtcttct tcactccata gtctttgaaa acctcctggt   46020
ttcttcacac tctcttcatc tttcttcact cgtttcgttg aagtcgtagc agcagcttca   46080
ctcgctggcc gttttgttcc tgatttcatc gccggtaaag ctaaagtagc tgacgacgac   46140
gttggatcct ctttcttctt tagattcact gtgtttaaag cgattgtctt cccagatcca   46200
gaattcggtg gatttgttga ttcagaatcc gaatctgttt cagtctcgga tccagaatct   46260
gaatcagcgg cggtggagac ggcggtggat ttagctggag gagcggcggc ggttgtggcg   46320 gaagggggatt tgattcgaat tttgattggt acgtcttctt cagatgaaga ggaatcgtct   46380
gaagcttcac cagcttcgga agtctcgacg tcatcttcgt cgcttgaagt tgccgttggt   46440
ggatcttcca gtggattgag tttcttcgtc attggaaatt ttcaaggagg caaatcggaa   46500
tccttcaagc agaagagaag agagaagctt tttagggttt tgtgaggagag gacggcaaaa   46560 gtgtttggga atataaaggt gttaacttta gtttaaagtg gttgctgtct tccaatagat   46620
attttagggt ttttaatata gggaattaat tatttttttc tcttttttctg ttggtcaaag   46680 taatttagta ttttattac ttttgctttg gtaatatttt atctctttct tttggtcaaa   46740
gtaatttagg attttatta tttgctttgg taaatatttt ctctatttt cttatgtata     46800 accaaaaaaa aaaggcctaa gccaaggcta tggttttgc ttttagcttt ttccaaaaat    46860
ccatttttta aaccattcaa gatttttgagg aaagttgatt ccctatataa attagggaat  46920
ctaattctaa gagttttttac taatttctta acaagatcca aaaatctcat gttatttaca  46980
aaaaccaaaa tctgaaatct aaaatctcct aaaatcttgg cctaaatttc tcttttcagt   47040
atcaaactga agtatgggct ttcaggcttg tacatgctta acttctgttc ttctgttaaa   47100
tgaggtgtaa atccaattgt gtagagccca ttactaggcc cagagaccat tttgacccag   47160
atacaatcag ctcacaaaat agaaaacata acatcatgtg tcgttgaaga aaatatggta   47220
caaggcatga tgggccttgt tgatgaaaat atggttagat tattattaaa tgagcatggt   47280
gaaacattat ataaaggaac gaaagatgat aagtctaccc acattactta ccaccattct   47340
taattatacg tttcttttg cttttgattt tggttcctct tgtattttcg atctaagagt     47400
aatactttag aggaagtaca tacagagaca acctcttaaa caaatccatc ggaaccctaa   47460
acatctcctt gtggcagagt tatgactttt tacttccagt gatgaaattt ggttgggatt   47520
atagccacga actcaataga attcttaaga tcatgtgaaa acgttgacaa gatcgtctac   47580
gattttccaa gattctaagt cttctattga tgttcatggc tttaacctga ttttttttt     47640 cctactaaat cgacactcga tggctacctt agaggttaac taaggcacct aagacattca   47700
tggaacgaag ttggctctag cggtgtgtct tagagccaac tctgttccat gtagagatta   47760
ggtttcttag tgatcatgag tctctggctt aaccaactac tcaacaatca agcaacatgg   47820
ttgttggttt gatgtcagtt gaaagccggt tcaagctcaa ggtgttaacg ttttgctgt    47880 tgatcattct tgtaatcttt tctcggattt tgagagagtt ggggtcttat ttttaatgta   47940
```

```
accattaaag atgagagtga attttgtaga gaatcaagct tagacgtatt attcactatg    48000
tgagctcgaa ctacttaaga tcgtcttttt cctctgtttt gctctgtttc tgtttctgat    48060
tccgtgtatt attgagtgca tgtgacaaca agtaaagatt tgatcgatta tttcctgcgt    48120
aaagtgacaa tagcaatttc aagaataatg ttataagttt aatgatgaca tggcattatg    48180
gactaataac caaatggatg aaggaacaac caaagaata tgatgatatg gttatacaca     48240
tctattttga actatttagc aaagaaacca aaactttatt tctgtggtaa tttgaaagtc    48300
atgtaactac agagacaaat cattccaaac atatatccat agctagtcat caacactgtt    48360
caataccatg acaataccaa ccaagaacat aataatcgaa gctcttccat gctcggttat    48420
aaccttttga accaccttt agtcccacga gggaagacac aaaaacaaat aattgcatat     48480
atacttgtgg ttccagtatg ttatatgcct agcaacatgt gttgaatcat agacattgtt    48540
tttttttca tatattgttg atgaaaacag aaccatgaaa taacaagtct tttaacttga     48600
gatatatcaa aaacatatta ttttctgatg gagccaagaa cttgactacg gaaggagctt    48660
gcaaggacgt atagtccatt ggatttaagc caccaataac aattgggtca actgcaatgc    48720
gagcttcaaa atgggtgtag aaggtacata ggcatgatcg gtcttaaaag ttcaagtttt    48780
gttttttcttt tttgtgtgtg tagaaaata caaagccatg atgggtctta agagttcaag    48840
gggtcaagat caaagtaaga tgtgtatatt caacaccatt agaagcagaa tttcttagag    48900
caaaggtatt gcacgatctt gtatccttgt taacgacaag actgactaat tggctaaagc    48960
tctaataccct attggttgtg gttatgtatt tccctttcat tggctaaata tccgaacgtg    49020
aggaacacca tgactgttgg atgattttga tcattttttca acaagtttct tttgttattg    49080
gtcaataact tttgctacaa atctacttgt gtaattaatt tcttacgtgg ccaaaatgcc    49140
caaaacataa catgtgccgt tcaagaaaaa aaatgctcaa tgcatgatcc ttgtcccaca    49200
aattaccaca ctctagtgct cccacataca accttcgata catgcgagat atggtagaaa    49260
tttattgtgc ctttcatttg aggatattgt aaaataaaat cataaaggaa aaagaggaag    49320
aagaactcat ccggattgta gttatctcca ttatccaaca acaataatcc ggatgaattc    49380
ttgtgttaga gacgtagagt cttggttggg atcagagaaa cggtcttgag atcatggtgt    49440
caaacaaaga tctttcctac aaaattgaaa ctcgatcgag tgctttctca gagtcagagg    49500
tttatgtgta atagagatac acttaaccat tagacccaca cgtagtgcaa gaaccttact    49560
ggtaagaggt cccagaacga tatccattat tttgtagttg gaggccacac caaccgccgc    49620
aatgttccaa tatatcaaag ggattataaa tcataatgag atactagaac attggcgtgg    49680
ttaatgtcat ctccagcaac ccaagaataa tggatatcat tatggcccgt atacacctct    49740
gaccagagca attttcacca tatgttatgg tctgcgacac tagtttctga accaagaaac    49800
tagtttagct ttcttttcttt tttgacttgt gatcagcaat gaaatcttga tttcttggga    49860
agaaaggaac cgattgtgag acctgatctt tatgttgaga agagtgtcac aagcgtttta    49920
atccaagaac ttctttgttt ttgaataact caaagcattc tatagttcaa atcaatctct    49980
ttctgaatgt agttgccaac gacggcaatt gtggacaaca ctatgacaat aaaactacac    50040
aaacaaatgc atagaattgg atattgaaat ctgaatttag gtccagaaca taacttttat    50100
ttgaccatat attcgaatgc acgagatgtg cattctgaat agtgatttaa aaatcataca    50160
aaagaaagaa atagaaagct tgttaactct aaatgaccaa atggatgaaa gagcaacaac    50220
atggtgatat gatatacaca tgtattatga aacttggtct caacaaggta acttgaaacc    50280
catgtaacga ccagagacat aatcattcca aacatcaaga gctccatagc ttgtcatcaa    50340
```

```
cacaatactc aatgccatga cgataccaac cgagaacaca atgatcgaag cccttccata   50400
ctcggttatt acctttttgaa ccacctttag tcccacgagt gatgccacaa aacatataac   50460
cgcaaatata cttgcggttc cggtatgttc catgcctagt aataagtatt gaatcgcaga   50520
catcgttgat gaaaaaagaa ccatgaaaga acatgtcgct gcagttacct ataacaatat   50580
aaacagagta tttaaactag agatcgataa acaaaacaga gtattttctg atcgagccaa   50640
gaacttaatt acctcgggag cgataccaac ttggagaaga agaggactaa tgagcattcc   50700
acctccaata ccaaaaacac cacccaaaac tccagctaat agagccatta cagggaacat   50760
acacttgttt gatcttgctc catcatttga tctcaaatct tctacatcct gcaagcacaa   50820
aattgtttta agacattcat cgattctcgt cctttttta aaaactattc aagtgtttgt   50880
tagatttgtt tgaaatctaa cctttactga gacatggtaa tctgattgtt gttggctttg   50940
aacattgtca ctgaagcaga tccagagagt gaagaagaga gttagtggta tttgagacga   51000
tgaaatgagc cagtaggcgt ttccacatgg ctcgatcgat atgattccct gcaaatacaa   51060
atcatgaaat tcttaaaaaa taaagaaaaa tcttgaattt gttcctttca tatattttt   51120 tatgaagtca catttcaatg tcactgtaga gaaatactgt gttatacttt ctttcttgaa   51180
aatgacataa aaatagtagc cctaagcatc attgaaaggg taaggaatct aaaaaagtgc   51240
aaatcttaaa gaagatccta ggaagaaaaa gacacgtaag tagtgtttgt attttgatt   51300 cccttttatta ggaccatctc aaaactaaca aacattattg atgacctgtc tttcacgtga   51360
acaagttcgc tatcgctttt catcaaaaaa aaaaaaaaaa gttccctatc gttttcaaa   51420 cgcatcttta ttcttcacca cgtgattcca aaaacaaaa aacatataca agactaaaaa   51480
aaaaagatgt catgaaggta gatgagaaaa attcaaacgt gtttcattta cttctcaaac   51540
attaaacata aatcttaacg ttcacctaat tactccatca acgtgatttt gacatatact   51600
ttctctgtat aatcttttac gtctttgaaa tatacctaga taaagcaaaa aatgtaattg   51660
gtatataaaa accaactgaa aaataaagga atatcttaca gaatcatcat tttgacatat   51720
ttttattctc ggtcatagtt ttttcctttt atggtaaaaa aaattacttt ttatcaaata   51780
gttttagaaa gtttggttag aggtattagt gaaatgaaat ttacaagtca gccaattaaa   51840
aataataata actcaatgaa aacaatatta actattccaa aaaaaaaaat cattcaaata   51900
ttatgcaaat aattcttttt tttctggat aactatgcaa agttgcaagc cttttggct   51960 ttttcttct tgtttttttt tcctttaatt ttctgtgttt tgtctctagt agtctaaatt   52020
gtcaattcca aatttcaaac ttttaagcag atctataaaa gacattaaat acgattcatt   52080
aaatgcaggc aacattaatt ctaatactaa taatgaaatt aaattaaatt aaatgaaact   52140
ttttagttac ctcgccatat ttgtttcctc gaagaagata aactgcgaag taagaaagcc   52200
aaataatgac caaaactcca agcttaatcc atggaaacct ctttggtctc tgataatcct   52260
ccaagagagg caactttaga ctctcaatct tatcttcttc atcatcttct tcaattctat   52320
tcgattctct aatcttcacc atctccgatt ccaatctcca ataataaagt ccatttccaa   52380
aagtcttcaa cgtcgaccac gcaagaaaca cagcgaagag actcgtaatc aaccagttcg   52440
gaaaaacaag attacagatc acaccaatac taactccaag aagcatacat ggttccaata   52500
aaagagctaa atcgaagtcg attagggttt tgccaccaga tttagggttt ctaacgaata   52560
gattgcatcc cacgttagct atagatccac cagtaaccat aaaagctgag aagcttgaag   52620
ctgtctttag atcgagaccg gccacgattg tcattatcgg aacatataaa cctccaccgc   52680
```

```
cgattccacc ggcgcttgag attgatgaag ctaggaaaga gagtaagccg gcgatgatcg    52740
ttgatgttgt tagttcgatt cttggttggt tgaattttgt tgaaaaatcg aggtatgagc    52800
ttgttttgtt gaggagttga tcgacgggag aaagaattga aggttcttgt tctgcgattg    52860
atggagtcaa gaagatgatg aaggagagaa ttatagggac gaaattgttt ctcattttt    52920 tgtttggggg ttttggttaa cttttaaaa gtttgggaga ttttaggaga tgttgggatt    52980
tttatgtatg ttatttctgt ttataacact ttatatatag ccatatagga gagtgtgtga    53040
tgcttggatt gtcaagtaga aagaaaaaa aaatatatta aatagaaata gaaatagaaa    53100
tagaaagaag aagataaaaa gagacaaatc aacaattggc aagtggtgag aaaatgaaat    53160
aataccacat agaacttgtg tgggcattat gttatttgct cccaccatta cctattactt    53220
tctcatactt gttaaatatt attatgtaaa accagaataa cttaggagcg agacttttat    53280
ttaaataaga tccactgatc ttaaaagtga gacttttgta ttttttaaaa atatgctaca    53340
gattttttta tatagttatt atataaaaaa tataaatata attaatatct acaatacttt    53400
tgaaaactgt tagcctcaaa aaaatattat ttcattaaca ataaaatttc agttaaagag    53460
actatataaa tttctaaatc acatttcaat tcaattaaaa actaaattct ttaatctttg    53520
agtgaaatta aagtaaacat atatatagtt ttattttggt ttgtctgctt tttcaacccg    53580
aacagagtat tataactatc aatattagta aatgataagt gatagtattg gttcacttca    53640
tcacttagaa gaacaaaatg ataagtgaat gatttcaatt tctctgattg atactttaga    53700
cagtacctac ctagaaactt ccagacatca tgaacggctc aatactaata gtctggtttt    53760
agcttcttcc aaacaaaaca gttttataag agatattata aaattttgat atattacttg    53820
caacatgctt tatttaacgt tcgtctctcg aaacccatat aggttaaccc acaagccaag    53880
tgtaaaattt tatatctttt ggaaatcccc atgttccgac cacatgcaga cagtttattt    53940
ctctaatgtc aaacccacat gcaaaaaact ataccataaa cctccaaagc cacatgcaag    54000
taaaatttaa ttcttttttg atggggagta aatatactta tgtgttttaa tcgaaagatg    54060
atgaaacgaa tgacgtaatg agtcattctc gtgttatttt cccaaatata tgtctaactc    54120
aagtaagcag gtaattgtca aatcaatgta atagtttata tgaaactttc ctttattcaa    54180
tggcatactt atcttagag tcatgagttg gcgaaaaaat aaaacacttat ctgttgtgtt    54240 tcgtttatg tagatcaact tgctctttgc atatacgacc aaattgataa taatataaac    54300
tatatatatg cttatgtata tgtttgcatg taagtataca atgtttgtcg acattattaa    54360
ccagatatta ttggatcctt cacttctacg ccgactaact tgatctagct agtaaccgat    54420
tatataattg aataactatt ttaagttttg aataactatt ttaaatttta cattttctga    54480
tggtattaag tttgaaatgg ttatatagac tcgttgtaag aagatgtagt taatatgaaa    54540
attctccaac gataatcaat tgtctggtgt tatatctttt tgttatagat ttcttggatg    54600
gaaagtttat aatgccggcc aattctaagc tacacaaatg aaaagaaatt atttgtacgt    54660
gacccacact ctaactgcta acctcgcttg aagttggaat agtatctagt attattttg    54720 ccatctgata gtagattgat cttaaagatt tacctaacta aaagagatcc ttaaatcaag    54780
ctttcaattc ttattttcc aaaaatataa ctgtcttgtg tgtaagtttt ttattatgtt    54840
ttgtagaaag cctcaagatt gcaatatagt tctgaaattg caacaaattt tgttttattt    54900
ataaccaaga ttaagtaatg gttgattaac ggtaacgttc gattctactc agttttcagt    54960
atacatatat agatcggaaa cttcctacct aatttaaacc aaaaaattga tctaaatatc    55020
aaactatatc gatcttacct aaatataaaa agattttta tacgtacctg aaaagtggaa    55080
```

```
accaaaccca ccatgaaata atttgaactg aaatttaact ttatttggaa aaacaaatgt  55140
atgtattttg attaaaggaa ccaaaattta aaactacaat catatcacgg cgccaaattc  55200
tcctatttaa atatgattac cgtagaagca ttgaaatatt ttataatttg taaactatac  55260
attatcatgc tgctggataa atagtataag gtttaaatac gagactggta tatattaaac  55320
tggagaatat acaactatac aagcattcca taagacatta atctttaggg gtctgataac  55380
ctgaatctag dacaacgaat attccaatta ttggttgtac aactacacaa gataaatttt  55440
aacaaagaat acaagttgtc tgtttacaga ttttttatata tagccatatg gagaattaga  55500
tatttcgcta aacctgaaag aagacttaaa tttcttctaa ttttcttatt tttagcaatc  55560
atgatcaggt aagttcttta cattatctag aacaacctag tgtacacaat tttccgatgc  55620
actttcttat attaatcaaa agtgttgtga acttttggt taaagtcgta gtcgtgtatt  55680
cgtaataaca ttattgtaat ctcgaactgt ttcgatatga ttttggctct tggaaagtct  55740
cctgagtcgg gcttgtacta tgatccaata gtaaataatc acttaaaaag caacataaac  55800
gataaaaata tgataagtat gagccggctc taaaagtcac caattttcca ttctcatgat  55860
caaacataat tagcaagtat tatatttgag atctcataat agatcgtacg ttttcattac  55920
ttgttgaaat accaagattt taaaacaaac ttatttagtt tctacaccat caattttttct  55980
aagcttatct aatcgataca acttttaata aatgaaacaa gctgtataag tttattgata  56040
attgttatct ataacatggt gtataagtca ttctggcgcc gaatgataac gcgaactaaa  56100
tacatatttc atataaaaaa attgttaaaa aaaatatat ataataggag tatctttcaa  56160
gtatatatag ggtttacacg caacacgtat taccatttac caacttgcac tagtctaatg  56220
atattgtgtt gtgatgtatt ggtcaagtga aggggatca atttctataa tacaaaaagt  56280
taacaccaac ggtttggaat tgtccagact tttagtttgt tgaaaagttg tagttttaact  56340
ttaagctcaa aatcattcgt ttatggtata aagaacaca tgtacaaatt aatttggcaa  56400
cgataaacag atggctaatt aattgtgtgg gtttcaacag tgatcagtac aattgaaatc  56460
tgatttaaac aaacgagttt actttcgtaa atccgattcg gtgttcgtta ttggtgatca  56520
accgtgagat tctctccagt gttaagcgtg ggaatttcta tcgatgcttc tctttggttt  56580
gccttctttt tctttttaat gcaacaacaa caaagagaac acacggaaat taccaagatt  56640
attaccaccg cagctatcac cggagctatg attcttctaa acactttacc tacacacata  56700
aaacaaaact ctatgttata aagactatca aaggaaattt gtttaaatta gcatttcaag  56760
gttcataaaa tatttaaatt catatttaca tacatgtata gcagttgtta taagagaaa  56820
atttcgtcaa gtacaatata tttaaattac acttccatat catcaaaact accatatctt  56880
agctaaaatt tatataagta cgcttacatg tattatccat agcaatctgt gtaaaaaatg  56940
ttgattttga taaatagttc caatcgttga caaaagaaag agataaatga tccacgttat  57000
atatataaga tatgttttaa tgttaattaa aaaaaaaata tgatatataa catgaatatg  57060
ttgctccaat cctaagtgtt cgtcaaggaa cacgatgaat attgctaccg atctttatc  57120
agggtgaata tgaatattag tcggtaaatt cagtttggac aaaaacaaaa caaaagagtc  57180
cgttacttct aattcttgat gattagtcaa acacctaatt atattatcat atgcataagt  57240
tgctattaac cctaatttca catcagttac acttacatgt ttaggtaatt ttcagtgaag  57300
acacaaacat aaatgaaaaa aaattcaaac cctagcgtag aactatattt tatatatatt  57360
tattctcacc taacttgaat gaaaatgatt cgtcggagct aggagtatca ttttctccgt  57420
```

```
aaagacgttg tgggggtggt ggaggtggtg gaggtggagg aggaggggggt ggtggcgcca  57480 aaaaagtggc tttatatgtc aacatacagt tcgaagagta aaccagagca aaacgtttac  57540
cataacaaca atccttagtc tcattatacg ctgatttcaa gcacctatag caatcatact  57600
gattcagatc gggtgtgcac tgtaccaatc catttagatc gtaaacttct ccaagataac  57660
tgacatgata agtttcttcc gcaaaatatg aagagctcga ataggcttct tgtatcaacc  57720
ggtccatacg atattccacg gtgttaatga aataaaactg gtacaacgtg gtatcgtaag  57780
atgtccatgt aacaaatgga ccttgatcaa gaatcgagaa aatcttacgg ctggagtacc  57840
tgaggaagca ttcttcatac catatgatag cttcttttg gaccggacac catataaaaa  57900 cgttttttgga tgctcttgag atgcatgttt cacaagttga ggacgagata tctccgcgac  57960
atagataact tccgtacact gttgtggttg gggaagaacc cgaggcgtag ctataaaagc  58020
ctttgttgga tgattgagaa tcaagaacgg atattaaagt atctagattg gatttgtacg  58080
aactgttcgg tgtgtagttt cctgatgtgt agcaatagct aaggaggtat gttggttgtg  58140
cattaagggt tttgatgaga agaaaagaga gaaggaagat gagttttgat tgatgaagag  58200
ggagagagaa catcttcgtt tgagtaaact tgttgtgttc ttcaacataa tatcgagcta  58260
taggtctata ttatttgaat tgactcttct tatgtatatc cttttagtag acgatatagt  58320
ttggttcgca tattttcatt tttaaaaaaa ctatacacta ttttgtttcc ctcttctaat  58380
ggtcaacttt gggccaggct gtcctaattt gactttaatg attatgaact tgataatgta  58440
taaataagga cgaggtttca aacttaatat aaaattatat gcatgcctat atgcctttta  58500
gctgattttt tttctataag aaaagtccaa tcccttttac gagtaaattt tttaagtttg  58560
ggaaaactat tgatttgatg aaactaggaa tttattattt taaagtatat cttgaaagat  58620
attaataaag ataaactatg taaaattatg acttaaataa tcgttttact aaagtaattc  58680
gtgtggcaga gatttatttt gaaagatcga attcaaaatt aacataagaa ttttgcccat  58740 tttcttatt cgattttgat tttaataaaa caaaaatcat attactttta gattttagta  58800
cttttctttt aaaatgtacg taatcatttt aacaaaagtt acaaaacgtt tattttctttt  58860 tacaagttca atttaaaatg actaattctt ttctattatg ttgttcatga taatcatatt  58920
atctattgca cagtctcaat ctctcaaatt tcaataact atctttaata ataagttcta  58980
cgacgtgaca acataagcat aatttttttt tcccaacgta tattaatcaa acgcgtaaat  59040
tgtgcaaata attaggtgac aataagatta tataaagcac taatgtcggc cgtcaacgaa  59100
aacaaaaaaa gaacactaac gtcgagtcat atatagataa tggctagtaa aaacaaaaac  59160
aaatatcgta gaggtcatca ggccgaatgt tacaagttac aaccaaattc aatacacgaa  59220
aaccaataaa atgttccaat aatttttgt aagcattaaa aacaaaatgt aatttcataa  59280
tgttaataca tatctatgta aattatgttg gtgacacata cacttttgtt caaatcaagt  59340
gaaataaact ggacatctct tgtctttagt cgcactcaac aacattccat cccaaccgat  59400
ctcaatataa cagcttgcgt acatcttgtg actcttacta tgccatgtgt acaccttaaa  59460
acgtatcatg gaccttacct tcaaacggaa cattatcttc ccttggttcc tgtctcgttc  59520
catctccatc caacggtcct tattcacggc cattgcgggt cgacttaagg ctccgtcgat  59580
cgagctcgtt tcttgggt cttggtaaaa cggattagta agtttagtcg aaccgatccg  59640
tttctctttg tagtaaacgg atccttccat ggaatcgtag taaatgccga cgttttggtt  59700
cgggttatga gccgttatct tgaagcttat gtgtgacgtc tcgaacccgt cgggcctgga  59760
tagaccagag attgagaacc cgcggatatg gacgcgtggt cggtgtggtt gtagactgat  59820
```

```
ccataagatg aaagtgataa tgcctaaaca tagtaaaaga gataagaaaa tggcacatat    59880
gagtttagag actcttgttg tgaggctttc tttaacccga tgaacgatgt tactcgccga    59940
gtggtgacgg gatatgggtc gcgttgatgg gttcgatcga accggtaaag aatcgacctt    60000
gttgtgcatt tttttttttgg gggtagattt agtgttagtg ggtcatggga agtaaaatga   60060
tgtaatgtga ggtttatgta gcaattttttt ctaaaagaaa aacattgttg gtagttaaga   60120
agaaagcaaa agataccttg gaaaatatta tggttattac actttgagaa gaaaagaata    60180
gacaactaag tatctaaatt tttaactaaa aagatagagg aaaactaagt agctaaaagt    60240
gcattgcttt tccgtatatg caatgcaaag atttagatgc aatcataaag ttcattaaaa    60300
aatttagacc aaactccttg tccttactag ctagttcctg aaaccaaggc cggcccaatg    60360
cctgaaactt gtaaaatttt taatcgatta attagctatt agctatgtgg attatcaatt    60420
aagttgatat atttgcatgt aatttttcttc tctaaaaatc gattaattta tttttgagcgg  60480
atttgaggtt tcttgctgga gggacatact cctgcaaagt gtccatatgt taagagtttt    60540
gctaacatgt gatgtgaagg agtgcttgag aagtatttga tattataaaa aagaaaagtt    60600
ttagaatttt gtgtaagatt tcgaattaac atatgtccta atacctgtt agaaattttg    60660
aaaaaggccc taagtccaaa attagatttg cttcgagcta gatagaattg aggtacttct    60720
ttatttgatt ttcttgtcaa gtacttcatc ccaactccca agtagcccat atgtccaaaa    60780
ctaattaact ataaatgcat aatttatatg agggtttgta aaaatattct attttcttag    60840
ggtttgtata ggcatctaat ttaacaacta caagttagac tttagctctt agataatagc    60900
ctagttttac aagcaaggat aaaatactca tcttagaaac aactcttaat cattgtagtt    60960
tagcttagtt acttttaaac aaaacaaccc aaatgtatgg gcttgactaa tggcccagta    61020
atggccttct tgactaactc cattttgact ttcttcttcc tcttcccatc atttcttctt    61080
cttttttcatc ttgatttatg atctctgctt ttcatcttct tcttctcact taatcaaaag   61140
actcaattga gtcaattctc aattctcaac agtaacattc ttttttttgct acaaaattct   61200
tcaataataa cttcaaaatt atgttatctt agagcttaag tatatattat aaggatactt    61260
tttgtttctt acattgaatt tattgtatct atgatgttct aattatttct tgtgctttga    61320
agactaacat cttgatatat cattttcaga attacttttta gaaaattcgg aagtatatag   61380
tagttttttt ttggtaaacc ggaagacgaa agtatatagt tgaaccataa ttcagtacta    61440
atttgtcctc aactttttttt tttttggtgt gttcctcaat cttatttaat agtagcacta   61500
atttcacaaa aaaacgacaa aatgaaatat agatcaacaa taattaatat ggacccatta    61560
atatatacag ttttcaagac taggatgaga caataaaatt gtaaactcta ctaatttag    61620
caatatctat tgtcaaaaat taaacaatct gctatccata ctttcaatac gcatacacaa    61680
acaatttatt gtttcgaagc aaacacatat acagcacaaa actttatatt agtattgtct    61740
ttgtatgact attaaaactc gatgttatag tggtaagtat taaaatgtat ataataaaag   61800
aaaaaaccaa aacatatata attatctttc atctaaatag taaaccaaat atataaatat    61860
atagtataat gttttgtaag tttttaaatt cctattattt tgcacgataa gactcaatta    61920
tttaagaaga gaatatacta ctaacgtaaa atctataatg gcccaacaaa attaaatatt    61980
ctaaaaagtc acatttattg ttgaccttca caaaaaaaaa aaactctcaa ttttctgttt    62040
cttataacaa cataacaaac aaaaaaaggc ccaaagagta ttttcctccg aattcgccga    62100
cgactaatca cgagatggcg ccgccggtga cggagcggtg gtgcttagct ttgattcttc    62160
```

```
tctttctctc cttgttcgtc caatcttcaa cggcaattta ctgcggtgct gaagattgtt   62220
atgctcttct cgggtttgtt catcagcttc cgatcttcat tttcaaattc agattttgat   62280
ttcgttctct taatcgtttt gcattatcga tttcagagtc gctcaagatg cgaacgcatc   62340
ggatatcaag agatcttatt ataagctctc tcttcaacag taaggatgat ctggatttg    62400 tttagacatt gttcagattt gattttgatt agtgttttgc taatctttgt ttctcaattt   62460
tgatgattcg atttagtcat ccagataaga atccggatcc tgaatcgagg aaactgtttg   62520
ttaaaatcgc cactgcttat gaggtacttc aatatttta tgattctgaa actttggaat    62580
ctggcttagt caatcccatt atatatctct gcgtataatt tcttaggtat gatccagttt   62640
tagcgaatcg agaatcatta cattgggaga tagatttgat agtgtatggt ttttttgtta   62700
tagctgagaa taattgaaca tgaaagtttc tcaaaaggat tcgtcttgtt gcagattttg   62760
aaagataata ctactcgggc acaatatgat tatgcaattg aacatccaga agaggttagt   62820
agaccattat tctgagaatt ctcaactgtt attcttggtt tgtgactttg tgtacattgc   62880
ataggtgaaa gatctttgaa aaaaattctg taccgctttg tgtttctttg tatataggta   62940
ttttacaaca ccgctcaata ttaccgcgcg aaatatggac ataaatcggt acgatgttat   63000
tgaatgtttc tgatgacttt tcttcggaa  aaccattggc tttttttaact gatgttacga   63060 ctgcctaatg tgtgttctag gatcccctgt ctgttcttgt tggtctattg gtggtttat    63120 ctgcatttca atatctgaac aacgtggcaa ggtataatga ggtacgtatt agagatcggg   63180
attctctcac tatgtgttaa tagtctcaag tagttgttct gtatcgtttt tctgatgcat   63240
gccagaccta tattgttata tatttaagca tcagtactac tcatctatat atcacatgta   63300
tgtgcaatac ctaatcacat gtatgtgcaa tacctaatca catgtatcat agcatctcaa   63360
gaaacgtaga atttgacctc ttgaatgtga ttcatatact ttgttatgag aactttatgt   63420
agcttaaact cttaaagcct ataattagaa attatacaaa cctcggctca ttttcttaat   63480
gagatcttgc attattgttg tgatgcaggc tatagcgacg gttaagcgaa cacctgctta   63540 caaaataag  ctcaaggcat tagaactcga acgcacaggt ggagtaagta acaagaagaa    63600
gggttcaaag cagattgacc agtatgtacc cccagttatt taaattgcct ttttattagc   63660
tgagaatgtg tcgtatcgct gaataaatca taatcattta ttgttttggc aggaaactac   63720
aggaagagct aagcaacgaa cttgacttac aaatcaaagg agctgaaaaa ccatcggtct   63780
gggaacttct cggtgttcga ttcattctcc taccatacac tatcattaag gtttcatttt   63840
cttaaaatac tttcactgtg ccacatttca cagattcctc catatcctac tttcccgaga   63900
tagctgattc aacattctgt tatcttccag cttctagtat ggtacagcag ttgggtgtgg   63960
agatataagg tcaagaaagc tccttattca tgggaagacg catcatacct aacccgaaga   64020
tcacttagtg tgcctgccga cgcatgggct aatctaggta tccttctatt ctctaatttc   64080
caacctgaac cgacatattg ataaagattg atgtctaata caatgtgatt aaatctattg   64140
tgcaaattcg atatttttca gatgaatata ggaaggaaga tctggtgcag aaaaggctgt   64200
gggagaagca gaatcttgag aattactttg cagaaatgcg taaagaatcg aagcggagaa   64260
gataggtcac ttgtcgctta ccatgcaacg atacaaaata caattcgagt tcagagaca    64320 ccattttac  cattatcact ctactttaat gttataagaa cgaaccagtt acaagaagag    64380
acactagtat aattgtacgg taccaggaac caaatctcaa tttgtcatat acaagatgaa   64440
atcatgtctg tcaatggaca tggtccagtt ttgactcagt tttgtttaaa accaatttgc   64500
tccgtggaat gttcaaatct atctttgata cttgaattcg agttctaaaa cgaaacatta   64560
```

```
actttatgat cagtcaagaa acacagtgaa gcaacaagat tctgtttggt tatattaaaa    64620
ccggaggaaa ccgatacaaa aaaatacatg agtgagagga tacaacgttg acatcaaagg    64680
gacaaaaact aaaatgtgaa acgcttgcgg atttgtttat acattgcttt gcttgtacat    64740
cttggtgtcc aacacttgct tcccgcacat tgcgcacact cctgcacaac cacgaagagg    64800
caattccatc agttgttaag ttactctata atatcactat ccaaccagag gtaagaattt    64860
agtagagtaa aacagatgta ttaactattt acctttgcta taggcacatg tgtgacagta    64920
tttaccatct tgatgcactt gctgcttgca gatcatacat tttgtggtac aggtactgta    64980
aggtgaccat ctacaaggca aagaaatatc acaatagaaa attagaagca gaacaagagt    65040
aaacaaaact aataactcaa ctcaaaaaag acaacacaaa cattcacagt tacaaatatc    65100
gctagttcca tgagaagttg tacatttact aatgattctt attaaaccct agaggactag    65160
cgaagcggtg gagttctaca ccctagatgg caagagtcca gtagcctaat caactcaaca    65220
gataatacaa acatcccaaa cttaaaaaat ttatcgctat ttccatgaga aattctataa    65280
ttactaatga ttttttagaag aacctggagg gatcaactca aaaaagacac tacacgaaac    65340
tacaatacca atatttctta gaagaaacta caggaaacaa aaccaatacc aaactagacg    65400
atacaaacat ccccaaagct acaaattaat cactatttcc atattgcaat tcaaataatg    65460
aaaagtagta aatgaagat ggataaacat aagaaatgca tacctattct tcttggagag    65520
aagcttattc tcattgattt tacgaccacc accttcagtt acattacgag caccatcctt    65580
ccacttatca ggaactatca ctttcgataa cttcttctca cctaaaatta aaagataaaa    65640
acaaattgag tcaaaaggtt catactttga actaaattag agatcctaca actagggttt    65700
cgatctaaga aaccaaaatc gaatcagaga tcattaaatt tcttcctgaa acatgtaatc    65760
gattaagcta gaaacgaaac gaatcacaaa tcctaacgcc aatagtatag attcaattag    65820
aattaaaacc gatccaagta tagattgatt caattagaat atggaattca aagagaagat    65880
tattgatgga cttacactta tcgcaaacca tcttcttctt ccgagagaga aatatgaaga    65940
aaccctaacg cctaaatcaa ttcgaatggg ttagagttac gacgaaaact tatcggtgtt    66000
gaaatttta tctatgttta aatatatttt ttttccttttt ctggatttgg aaagtcggat    66060
atgtctcgtc aaaactcata gcctcacagg tattttatgc cacgaatcgt aataatccac    66120
gtggtacatc aaccaataaa aacgttccac gtggtacaac cagcgagata ccaagaactt    66180
cgagaccttc ttctccagat agaggctttc cggtaaacgg caaatacccct tttccttcac    66240
tttcttcgtc ttctcgaatc tgagagaacg agagatcaac aacaatggcg ctcaaatcaa    66300
aactcgtctc tcttctcttc ctcatagcaa cactatcatc cacattcgca gcttcgtttt    66360
ccgattcgga ttccgattca gatcttctca acgaacttgt atctctcaga tcaacaagcg    66420
aatcaggcgt aatccatctc gatgaccatg gaatctcaaa attcctaacc tccgcttcca    66480
cgcctcgtcc ttactcgtta ctcgtcttct tcgacgctac tcaactccac agcaaaaacg    66540
agcttcgtct tcaagagctc cgtcgcgaat tcggcatcgt ctccgcttca ttcctcgcta    66600
acaacaatgg atctgaagga actaagcttt tcttctgtga gatcgagttt tcgaagtctc    66660
aatcttcgtt ccagctcttt ggcgttaacg ctttacctca cattcgtctt gtaagtcctt    66720
cgatatcgaa tctacgtgat gaatctggtc aaatggatca atcggattac tctagattag    66780
ctgaatcaat ggctgagttt gttgagcaac gaactaaact caaggtcggt cctattcaac    66840
gtccaccgct actttcgaaa ccacagatcg gtattatcgt tgcgttgatc gttatcgcta    66900
```

```
ctccgtttat catcaaaaga gttttgaaag gagaaactat tcttcatgat actagacttt     66960
ggttatctgg tgctatcttc atttacttct ttagtgttgc tggtacaatg cacaacatta     67020
tcaggaaaat gccgatgttt cttcaagatc gtaacgatcc gaataagctt gtgtttttct     67080
accaaggatc tggaatgcag cttggagctg aaggatttgc tgttggattc ttgtatactg     67140
ttgttggatt gcttttggcg tttgttacca atgtgcttgt tcgagtgaag aatattactg     67200
cacaaaggtt gattatgctt ttggctttgt tcatatcgtt ctgggctgtg aagaaagttg     67260
tttacttgga taactggaag actggatatg gaattcatcc gtattggcca tcgagttggc     67320
gttgattaca tcacacttga ggatctctgt ttcacaaggt aatggcttta gttttggaaa     67380
aacagttatg ggaattgagt aatgatgttt ctggatgttt tgtgtttcga tttgaaatac     67440
ttttgaatcg gtgtagtact actatttcag atggtttaaa actccttact gttacattag     67500
tccattgtta agttatttat ctgaatgagt aacttatata accaagaata tgggatcttt     67560
agtcgattga atataggaac catatttgga aattcaggta ctgtttcttg agatcagtct     67620
aggattgttg ttatttggta cattgacact tttagagttt ctatgtgtct tcagccttgc     67680
gccccttgct tactgcatct attcagaaaa agggactttg tgattgagga tagtgttcct     67740
gtttaagcat tatgggacct tatgttttgt cgttgactgt gtcctcttct cgttttgctc     67800
tctgttttag aatgagtcta agtaaaattt aggttcaagt ataaatttgt gatagagatg     67860
gagtttcgga ttaggtttag ccattcgaca tgacataggc ttgcgcaggt gggaaccaag     67920
tctcttcttg ataggctttt catttgtgta cacacatttt gtgagatcat ttcaacttga     67980
aaattgcaaa gcatgcctct ctgatacatc agtatgactt tgattgtttg tttgcgttta     68040
ttgtgcaatt aattttttt tcatcaaatg aatttacaat cttcagcagt taaaacagat     68100
tatacttgtt tatggtaaaa aaaaaaaat gtcacactca cacgcaaaat tgaaaaagtt     68160
tcagatttca ctcgagaaag tgaagtaacc tatgatttgt cttttgtcga atcaaatggt     68220
tgatggaaat tttctttcgt cttttgaattt agttggacaa tctcgactta gttagctcat     68280
tcgatccatt tctagcccac acagaaaaaa tgagcttaat ccatatgagt gtttcacttt     68340
ttctaataag ttttttggggg cttctcgact tgggccttga gttttatttg tacgttgtgt     68400
atgggtctaa gtcttgctaa tccacgtttc ttacatattt cttttaggtct ctcatttgac     68460
aatttcgggt cagattgatc ttcgtttgag ttggactggc gcatgttcgg gtttcgacat     68520
attgctatgt ttaatggatt tacgactcta atttaatta accactagta aatttggtat     68580
gtatgcttct tattattaga gcagcccaat cattatcata aaaatagtcc attagcccat     68640
gtgtttaagg tttcttttcaa gatagattca gagataaatt tgtgtaatga aagaagaga     68700
agtaactta gaattgctga tggtacaact ctcttctcca tctttatatg aaattaatct     68760
aataagattt cattagtgct cttggcgaac atttaaatat actctggact aacaaaacaa     68820
aatcactagt ctaccataat ttaggttgc aaatttttaa agaatactca tttagtaaaa     68880
tttaggtaaa taaatatta aaaactaaat tcattttcga cgaggatatt gaactaaccc     68940
aaaggcacga ggtgtcttga aagtgactaa gcacaaattt tcaacctata taaaaaaaaa     69000
acacagcctg tctcacacag tcacattgta tgttattaca atttaagaca atgacgattg     69060
catatacata aaaattattt atacacacat atatcttgaa aacgtgaagg ccacaactca     69120
aatatctcaa tatgtatagc tttcaaaatc taaatagaaa agagcaaggc taatcatttg     69180
atttgacagc aatataagtt tttgttgcgt cttgtatgga ttatgaatat attattagtc     69240
actaattagc tatggttaat ataacaataa atgacaactt tattgattat tattgataaa     69300
```

```
caaagcaaag tcttttgtta actagcataa aagaaaagat gtttagaggc atgtatttga   69360
aaactgtgaa taataaaaat tcatatgatt tggaatttat gttttctaat gatcggatag   69420
ctttatccgt gaacttccca ttttcttgtc tgttttagat ttgtggatct tatttt cttc   69480 aaatggtagc aaatcatttg aaaaagcccc acaatatttt gttgcattaa aagaaaaaat   69540
tgtcttcagt tatacgatat tagttatatc ctgatctttg tatgatcatc tattacgcag   69600
ttactataga tttagtgcag acttt caaaa ctataattgt gctttgaaaa tatgagtatg   69660
taaaatcagt tattttagtt ttttcacgtc accttttcag attactatag ttttt caagt   69720 tgttggacca aatcttatga ttgcgttgca tatatacttc catattggtt agttagtgaa   69780
cgaaaaaaat aattaaacac aagaaaacta taccatagtt gaaccaattt ttaaaaataa   69840
aaagaccttt ggactagtat gtagttaacc actatggtgg ttaatttcct tgaacgtcta   69900
agattcgatc ctatctttgc ttcacgggac ataccatat taaggtataa accctatttt   69960
taaactttgt caactagcta tgtgaaccct cttggtgagc ccaaaattag accacttttt   70020
aagaaaaaat ttcagagaaa tatatgcttt tgagtcaaaa tattagatcc atcttcattg   70080
tctatacgat atatttctaa ttagcaaaaa aactttgttt ataaagaaa acctaaatgg   70140 tagtcatttt attaatatct ttccatacat aaccgataaa aagaaaagat tcattctaat   70200
aaacaaatta aaaaattcac acttttt aaa attgacatat tattaagaaa agataggtgt   70260
cttgaggaca tatcaagcgt ttaaatgctt aatcaaaatc taaaacgctt ttaagacgtt   70320 tcaatttt ta taagaaatat tataaaataa tattaatgaa atatcatgat ttatatatat   70380
atatatatta attaattaca tatttaaagt tgtaagaaaa accaatgatt gtattttata   70440
ttgaaagaaa ttttgtttag ctaaaaggat aaaagtttgc ttctttt ttt agtctaataa   70500 tttcttactt tttcaactcc aaattctagt tgttatactg tccaaatcca gtattataat   70560
tgacatcaaa actttataga attaggcata cgcaacattt agttgtatat ataaaagtat   70620
gtattagagt agacgaagaa aatccctaga atgcttatta catgcgattt cgacaacata   70680
tactgctaaa atgccaccaa aattttt gtc tattctttag atataattgt tacaatatga   70740
ttcatttaac attttgttga attgtggagc gaaaatatct tggattcgtt aatcgatcca   70800
atgagcgtgc tagatgcggt ttaaccgaag cggttatgtc gacgatggac cggaaaacct   70860
cctcccattt gagagttgcg gtcatgacca aatttgttat agtgttcttg aatagtatat   70920
tttcagaaaa tttcaagctt attaattatt tgtcgttgtt tcctattaat tattgtttat   70980
aaagctaaca taggaaaatg aaagttgtaa atacattttt atttt cttag ttttt gagta   71040 aagaagaagt tttgagacta gatttgtaca taatcctctg atcaacgacc aaatcatttt   71100
atatgatatc ttctcaaatg tcactcgaac tgtgtaaaca ttcgtttaat cataacgaaa   71160
ccgaaccatc ataattttca cattaaaatg aaccattata aatcatttct gttttttta   71220 ttttctctaa tcgtttacga aaatttagat ttttaaaaat aaattgctaa attcctaaac   71280 gcattcagt ccaattttt g aacagttgta ttggagtgga tgataactag taaacgaatg   71340
gaattggtag ttgaactaaa actcgtggaa tggatcacct aaaccttta a ctaatttctt   71400 attgtcttat acataacatc ggtaaacaaa actgtaaaca ctattctcct tgtccttggt   71460
cggataagat attcgttttt ctgttttccg ttaaaatata tacaaatttt atatcctcca   71520
ataattgatc aagaatatat atactttcat ttttatttat atattaccac tactctttca   71580
tgtctccttc caattttt ct ttgtcttcaa atactattcc aatctcaaac gaaagagtat   71640
```

```
tttgtctctt ttctctttct tcttcattttt catcatcctc ttcaatcatc tctgattctt   71700
ttcttctgtt cgattcattg cgttctttac caaatttttct tttggtcttg ttaacaatat   71760
catcttacat tttttataga agtgtttcag ttctttataa gtagacagat ttttattgtt   71820
gcgtcggatt cttgagcatg gctacaagat tcaaggggct ttataacaag agcttcaaat   71880
gtttctccga cattttttggt aaatagataa aacctctaat cttgtttagt tttatcttta   71940
aatggacatg aataagcttt ctaatgatta caaaatggat taaatttgta gatgtggagg   72000
aggaggagga gatggaaatt ggttatccga ccgatgttcg acacgtgtca catatcggtt   72060
gggatagttc atcaagtagt gcacctagtt gggtaagaca ttttttttgca acaattagaa   72120 attatggtgt gtgtttttta attacaacgt taatgtgctc tgtgttgtgg atttcatcat   72180
ttgtactctg ttttgatgtt ttaagatatc agatgagcaa aaaaaataga acgtggatcg   72240
atttaggtta agttttaacc tatttatgga attttgcagc tacatgaatt caagacgagc   72300
aacaatgttt tagagccaaa ctcatcgtgg ccatttcaag gcaagttttt ttctattata   72360
ttcctttttt aaaagaagct ttctgtcaat aataagcaaa tggtttccac gtattactag   72420
tccttattga aatttatatc aaaaaataaa taatttaagc agacctccaa atgtattact   72480
tgatagatgg atgcataaac taatatatgt gtttgacaac atagatccta atgaaatgta   72540
attttaaaaa tatatagatt tgaagtcagc gatggaggca tttggagaag ttgaaagcag   72600
caaagaaatg gaaagagaat caactaaaca aaatctgaag aagaaactct cttcaaaagc   72660
ttctctattg tgtaattcat ggtcaccaag attctcaaga tcaagcaagg tcctggctta   72720 attattttc attttaattt aatttcccat gccattgttt atataataat atatagagcg   72780
tatagtaaga tatcaatctt aatgttttca ttcgagatac gtatgtcttt tcacaagtgt   72840
gtacaaatta atattcatac tgtcttcgca atgatattgg gatggtttta ctaatttcac   72900
aaattattgt ttcaaaaagt atccattaag aaaactttca caaatctaat gattatgact   72960
tgttttagat ctatattttt gttttcgaat ttcgaagttt ctttgaaaag aatgaatatg   73020
gtgaaaatct agttcagtag ggttgtgaat gtgaaaattt actatacgac attccgtttg   73080
ggacagcggg ggaaattggg atgatcaagg attagtgtat attggtcgta agtgcaacaa   73140
taatcacaat ttattgagtt agtggtttga gtgaagaaca tttgatggtt atgggtttta   73200
aaatgtaatg aacccttgat ttctctattg cacttttgaa agttttttaaa cttcgcagct   73260 caattttat caagtactta gtaatttata ttatggtgtt tgtaatcatc gaaagtttga   73320
tcaaatgaga tgatgcttaa cagaaaaaaa acaaataatc aaaaaaagaa gttaaaacta   73380
atttagttat aaatggattg aatgacctcc ttcacaaaat ctaaaatatg ataaaatggt   73440
ttcattaatc aagtgatact ggttaagtgg ttcttactta aggaagaatt gcttcttatg   73500
tcgccaaaga ggcaaagatc aattcttctt aaacgtgtga tttacaaaat cattttattt   73560
gatcaatcga aatggtgtta tatttttacg ctcattaaaa aaccatgtga gtggactatt   73620
caatagctaa atttactata tacagagatt tttcgggtgg tagaaacccc cgattacacc   73680
tgatttcatt ggcttatatg gccttgtgcc gatatagtag tggacatact ctaaagtctt   73740
gaaaaatgca ccaaaaagct aatactttgt taacatgggc taaacatttt gcctagcata   73800
tatgatccgg cccattttatt aatatgtatc tacatcttta agaagtaacg aatttgtagt   73860
agcaaagaat gaatggaatc gatattgttc agtgaccatg aaattctcat atattgccat   73920
aagcccatac cttttttttta ttatttatac tttttacggt cgaagaaaaa gagaatagta   73980
gcaggattcc tactgcaggc aatgataata aacttataga aattttgaac agcgaaaaga   74040
```

```
aaacgacttg agattcaata tcaatcgttg gtgctgtcca attggcaatg aagtaaaatt    74100
tatgaacatt gaatttttt aatttaccta ttaagcttcg atcgtattca acctaagaat    74160
attacatttt ataaaattta acagtaaaaa tatctaattt aagagataat tattaaaaat    74220
tatataaaaa agtgactgac tttttaatct aattttaatt tattaggaga aaatctactt    74280
tgaaaattat tatatatata tatatatata ttgtgaggta gaattttta tttcttaaaa    74340
aggtttacta ttttaactga acattgtgta aacgatgaac atcataactc gattgtgtcc    74400
aattcatatc taatagttaa atgaatcaac gactcatata tcacggagca aaacgcgcat    74460
gcagaaaaat ccaccaagcg aacaatttgg aaagcgatat ttctgatgaa tcgttgattt    74520
ccccaatatt acgaactttc ctgaaatctt tcctagccgt cgaatatgaa ccaaatttat    74580
tacctgacct ataaacacac acatatgcag gcaaatggac acatgtgttc tatgaatcag    74640
tgttggtgaa gagagagctt gtcgtgtaat gagagttgca tgtgttcaac aactttgtgt    74700
atgttttgta attttcctct tgtgatattt tctacggtga gaattccatt tgcaaggtta    74760
catcaatggg tgaagcctgt acgtccaaca tgtgaccaga ccttctttta tatcaacggt    74820
ccaaattaac attacattaa catacacaaa tatattatat atttaatact attgttcctg    74880
ttcttctttt tattgtcgtt acctcgttag catcaatgac gaatgaaaat gacaaacgat    74940
acattgtgtt gttcgaattc gtgttattgt tgccaaaacg atgtgataat aatgaaacta    75000
tgttcattgt attggcgttg cccgctggtt tacaacgatc tatttcatcg atgaattttg    75060
gtaattaacg atataaaatt ttcaatacta aaagacacac cttttcaac atttcttttt    75120
ataacttatg atgttcccat tccattatat tatagctcaa cttacaaact aacttgtcac    75180
atgtaaatta ctcattgact cgtgacaact attgacggca atattatcaa actcgtggtt    75240
ggaaatattt taagtccaca aaggaggaga aaataaaatt cttgaatatt gaaaattctt    75300
atacctctat gatataaaag aaaataaaat caaagagaag taccacaaaa acaaattttt    75360
agtatttaaa aatgccatta ctttggaaaa ggtcccaaaa tatcacaaaa tctaggctta    75420
ggaagggtct ctaaacgttt attaagaatt actaagccca aaacttgaaa actcctaaaa    75480
ctctttcttc aaatttagac taatcatttt taattctctc caaaatatta gtaacccttg    75540
taaagcctaa acatttagt aaattttatg attttggtg gtaattttgg aaaataaagc    75600
ataaaatgtg gtattccgag gactgaccaa atttcaaaaa ttcaaataaa tgattaatat    75660
cctaaatcaa tcattatttt ttataattgt ttttgagaaa cttatattaa tactatttc    75720
aggcattttc ttataaatta ccctatggtt ttagtaggca acaaaaagat gaacgtctca    75780
gatttttttg aattcaattt aatcttaaca aaagcgataa atatcaagaa gataattggg    75840
tacgtgtatt gtgtactatt tcaaaattga tatttgcttc cataacgtaa cgtaacgtaa    75900
gacccaaaga ttaacacttg gtttcttcat ggtcgtagat tattaaaagt ttataactaa    75960
tgacgacaaa gtttaaacga aaacaatat tttctcaatt ttcactagtt ttttttttt    76020
attccagaaa attattagta tacaaccaac tatttttacg attataaact ttatttgat    76080
gatattcata atttagaaaa accttaaacg gatcttaatg tcaatatcat cagctcatgc    76140
accgcctctc ggatatgttg acaaaattac cccatacaat ataaaccacc aaaccataac    76200
cacaaagggt atattcgtat attataaaaa tatctgaata gtcgaacttg tcgttacact    76260
caaaaacgaa atctttccct cctctgttct caatctttct ataaattctc ttcttcttct    76320
tcttccattt tcccaacaac acaaagtctc tctctctctg ataaaatctt aaacccacc    76380
```

```
tcgagatcat agtcttcatc aattagccat aaaaaagcac aatgcttttct tcaatcaaac    76440 catcttcgtc ttccttctcc accgctatct ccggcagcgt aaggcggtca attcctacaa    76500
agctcaagtt ttctccttta ctcatcatca aaaactgcca taaccaaagc tttaacgcta    76560
atgttgtctc ccatcaaaag cctctacaca tttcatctgc ttcgaatttc aagcgtgagg    76620
tcaaagtcga agcttacgag gccgatcgtt cccgtccact ggacatcaac atcgagcttc    76680
ccgatgaaca atccgcgcag aaactgaaaa tcggaatcta cttcgcaact tggtgggcac    76740
ttaacgttgt cttcaacatc tacaacaaga aagtcctcaa tgcttttcct tacccgtggc    76800
ttacttcgac gttgtctctc gcttgtggtt ctttgatgat gcttgtctct tgggctacta    76860
gaatcgcaga tgctcctaaa actgatctcg agttctggaa aactctgttc ccggtaagta    76920
attagggttt attgtgtgta gttgttgcct caaaagtttc aatcttttt ttttacgatt     76980 gagagctcag tttctggaat actctgtttt tccggtacga attcatgatt tattctgttt    77040
tctggtaaaa agtcatgatt tactctgttt tacggtaaga attttagatt ctctgttttc    77100
atgtaagtat tttatatctt ctctgttttc atgtaagaat ttagtgtact ttcgagcatg    77160
aaactgatct tgagatctgt cttccggtaa tggtttaggt attttcatga tgttgttgct    77220
tgatggattt ataattttgt ttgttgtctg ataatgaaag agtgtgtttt gatcgatgtt    77280 cccgttttt cttattcttc aaggtcgctg tagcacacac gataggacac gttgcagcaa     77340
cagtgagtat gtcaaaagta gcagtttcct tcacacacat cattaaaagt ggtgaaccag    77400 cttcagtgt cttagtctca agattcttca tgggagagac tttccctctt cctgtctatc     77460
tctctctctt accaatcatc ggaggctgcg ctctcgcggc catcaccgag cttaacttca    77520
acatcactgg taaaactcac aatcctagaa tattggtttc acatggtgac atttctttga    77580
tttatggtct tatgtgaaac tttgtggaat ttttttgta gggtttatgg gggcaatgat     77640
atcgaatttg gcatttgtgt tccggaatat cttttcgaag aaagggatga aagggaagtc    77700
agtgagcgga atgaactact acgcttgctt atcgatgatg tctcttgtga tcctcactcc    77760
attttctatt gccgtggaag gtcctcaaat gtgggctgct ggttggcaaa atgcggtttc    77820
tcaagtcgga ccaaactttg tctggtatga tctaaaaacc aaatcaataa tctttaattg    77880
tttgttaagt tttatagact ccaactcaaa tgactatgag tggattggta tatattgctt    77940 tagttcccctt ctaacttaag atataagatt ctaacttaat gtgttgtttt tgtttttga    78000 atcaataggt gggtagtggc acaaagtgtg ttttaccatt tgtacaatca ggtctcatac    78060
atgtcattag accagatttc gccgttaact ttcagtatcg gtaatacgat gaagcggatt    78120
tccgttattg ttgcatcgat catcattttc catacccga ttcaaccggt taatgccctc     78180
ggtgctgcca ttgcgatttt tggaactttc ctctactcac aggtaaacaa acaaacttat    78240
tcttgtttac ctacctctag tacttggttc tttagtgaac aatttctagt tctaatataa    78300
ttcattgacg ttcttcctat gttctttgca atcattgagc aggcgaagca gtgaggatgg    78360
tttaggaggc agttttttgg gtttgttttg caaagaaaa tgaaaactaa caaagagta      78420 gccggggagg agagaacatt ccggtgagat caacatcgga aaatgctttt ccccggtcca    78480
tggatatgaa gaaactggag cttgaagttg atagagtgtt tgcttttact tttttttca    78540 ttgtctcata atagattctg cacaagacag gctaattcta tattatctat gttttattta    78600
gatgatcgta ataataaaga tatcagtgtc atttcttgat cagaccatct actgaattat    78660
ttttgaggta tctatcagtt gatgcatgtg taatagtttc agaaatcact gaattataaa    78720
tatattgagg tgtgtcgcta ctggcctata tacatatcat attaggccat taggttaaaa    78780
```

```
attctactca atccattcct tataattggt ctagttagct atattggtct ctcacacact    78840
ctcttattcc aagaagaaca ttaggaaact ccaatattgg gcctggtcca tgtactcttc    78900
taagttcgtc tatacttgga cactgtctcc attttgtggg ctagggatct acaatccaat    78960
gactgcaaaa tatttacggc atgcaaaact tcttatgaca agtgtgtttg acacacgtct    79020
ctaaaatttc aattatgtgg atgtgcttat ttgtatcaat gcatttcatg cttgcttggc    79080
ttcgtatgga aaaagtatga gccatcataa aaatttgtta aaaaagattc gagtcattta    79140
cattgtttta ggagcctttt ttgatcggtt agggtgctag agaacccatt acatactagt    79200
catctggggg tattagtatt ttgtaagctg ttttaaacga ttccgaattt tgtttctata    79260
ttttgtggtc agatctgatg gcctgaaaat catccccaat aatcaaatct taatgcgcgt    79320
ttaatatttt actaaattat gatcatatta tttttttgcga tctagtcagt agtcactgta   79380
gtgaagttgg tgagacgaca cccacccaaa aggagtacgt aaagcaattc cggcttccaa    79440
ttatttatg ctaatcttgt cggcagatga gatggataca tttatacata tcatatataa     79500
taggttggga aattgttagt ttcgttgata aaataattaa ggttttgact tttgactgat    79560
tctggatttg atttcaggaa atgtaaaatt ttccagattc tgtatgtact ttttgataag    79620
aaatttcaag ttgctgcatg tcaaaaattt caactaatct cttttgtagt gtataaattt    79680
atttactgtc caatagacaa ttgccaccga tcctaaggag caacgtacaa taccaaaagt    79740
ttgcatgcat aataaaagtt catttaaaca taacgtataa taattttcag agtgattatt    79800
gtaactttca aattttcaca taaattttag agtattaaat caaatagcct ttgtaatttt    79860
tgagtaaact aaatgacggt cttttttttac tcaaaatcaa ttacaacccct ttaaaatatc   79920
ctaaaagctt tgttttaaaa aagaagataa attatcacaa caagaatata atctaactca    79980
ctacaaaatg taaggccaaa gaagagatac gttcactgat tggacgtgat ggagagagct    80040
cacatctcgt ctggccttat catcatcgta atctattgaa gatatatata tggtaagaca    80100
aattaacttt actcacggat tctattcttt ttacccattc tcggttttgt aacgaacgac    80160
gaaccaccaa ctagacaacg aaacgtccca cttgtttcca ttagttaaat ttgggtaaca    80220
ccaaaatcgc attaacttaa taaaacactg ttccaatatc aaccactgcc atattttctc    80280
ccttattttt ttttgacatc aaaactgatt ttggagaggc tttgaaaccc cgactataaa    80340
tttgatttag gtgttattct gatttatgag tgaatagtta cacagtcgga gtttgaactg    80400
aaagttatag gattacattt ttggtaaaaa attgttgagt cgtattttg gtagaaaaca     80460
gtaaaattat gttttttgac agaaaattgg aggatagtaa ttttggagga aatcatatat    80520
atgaaaattg gccaactctc tccatatgat tgacacataa tcactttagc atttgacatg    80580
tgtctattaa ataattaatg taagctcttc aacttctaat ttataggtta aagatatatt    80640
tattatttaa ttttacatct tatttttattt tacgtattta attatactat tactatattt   80700
atttaatat tacatgattt ttcaataaaa ccatttaat agttttctta tactctgaag      80760
ttttttttttt tttttttgtaa tccaaactca aagtatgagt gtataatagt cgtggattac  80820
ttaataattt gagtaagtta ttctcttaaa tgaatattta tattttctta aattgatatt    80880
tatataataa atcactaagg gtgaaaaatg cgtaaggagt tccatcatca aattcttagg    80940
tttctagaat ccaacactaa cctctgttaa attggtttaa aacaaacgtt gtttatgaat    81000
tatgtatatg atgcattgtt gagaacgttg ctagaaaaaa atattttttaa tactaaaagt   81060
aattgtttat tgcatgattg aatgattaga taaatataaa ttatatttaa attaaacact    81120
```

```
acaaaagaat ccgaaaaaac cgcgacgtag cgcggataat tacctagtag tgttaaaaca   81180
aaattggagg aaattttgga gatcacattt ttaacataaa attagtagaa atatatattt   81240
taattattaa ataaaaaatt aaagtaagcg ctaaatgtca ttaagaaaat tttgtgaaag   81300
gcggaaacaa aaattttaaa agaaaaagaa aggactaatc acatcatcgc cattcaatga   81360
tatagtttga caatgatatg attcattaac taccattcaa taaatcggtt tatgaaatct   81420
aacggttaaa tattagttgg taaagcatga ttaattaaga taatcactca acaatcaatt   81480
caggaccaac gtcacctagc taccaccacg aaggaaaatg ctaatacaag aaccaaatcg   81540
tcttattaac cagttatctt tttctcatgg accacattta aatcgtcacg gcaattaagc   81600
tagattttaa gaaagaataa atgggatact caactaattg ccacaaattt tattacttt    81660 aaaactcggc tgctcggccc aaacttatcc ggtacggatg gatagaccta tcttttatcg   81720
tgtaaagaaa ctcttgggct ccactcttga cgttgctcat tttatctact tttgttggtt   81780
tcttagtgac ctttgacgtt tatttacata gagttgacag atttgaattg acgttttctc   81840
aataatgcag accaaaattt tcacgtttct tacatgtaca tatatatagt aaaacaaatc   81900
tctgaagaca cacaagagaa tcaagaacaa tgaaaaattt aaccagtttc gtaattgtta   81960
tcttactaca aagcttattg tttcatgtat atggtcgtca tcaaagttct tcgaagaaca   82020
ttttagtaga ttcatctcca tttccttctg atttcctctt tggtacagct tcttccgctt   82080
accaggtact tattttgcgt cccactgata atttaatatc agatttattt agtgtatcgt   82140
cattacgaaa tgtttatttt atatataaaa aaattgtgaa tagtatgaag gtgcgttctt   82200
gactgatgga aaaagtttga acaattggga tgtctttacg cataaaaatc ctggtatgta   82260
ttttattttg gtttccattt ggtttatttt ctatttgaaa tagtttaaga ttagtttaag   82320
atttttattt ttttttaatt cacttattct attgacaagt atatatattg gaactgcagg   82380
gaaaatactt gacaagaaca atgcagatag agctgtggac caatataatc gatttttggt   82440
tattttctta tgataattat ttctttctat ttttgttctt gtcaacttct tttatcatat   82500
tatattctca tattatttga tgttgttatt tattttatat tatcttctat gcttaggagg   82560
acatccaatt aatgtctttt cttggagtga acagttatag gttttcaatt tcttggtgta   82620
gaatcttacc tagtaagtcc ttcttttagtt aaatcagcag tattattaat actacattgc   82680
attgcatggt aaaaaaaaga aaatattcga ttgcatctca tatactaacc agagttgata   82740
aattaaaata ctgaaactca atcgacgaat agttatttag atttagctta ttatttgtga   82800
gacaggagga agatttggag agattaatta tttggggata aagtattaca acatatttat   82860
cgatgctctc attagtagag gtactttttt gtctttccgg tttataataa tttaagtttt   82920
tttttaaaat attgtaatct cataaagtta atgaaaatac ataattgtat caactaatca   82980
ctatccaggg attaaaccat ttgtgacgtt gaaccatgtc gactatcctc aagaactcga   83040
ggaccggttt caaagttggt taaaccccga gatgcagtga gtggtaaat agaattagta    83100 tttttatgaa cccctaatta cttagaatgg caatgaactt ataaacactt ttttttttt    83160 ttgttatttt tgataggaag gaatttggtt atttagccga tatatgtttc aagcattttg   83220
gaaaccgagt taaatactgg accacgctta acgaaccaaa tcaacaatta atcttaggct   83280
atctaacagg taaatttcca ccctctcgtt gctcctcgcc atacgggaac tgtagccagg   83340
ggaattcaga aaccgaacct ttcatagccg cacataacat gatccttgca cacgcaaaag   83400
cggttaacat atacaagacc aaatatcagg taataaaact catacatcaa attaagacct   83460
ggtttcgtga gttatcgata taaatataat gttttttgcag aaagaacaaa agggaagcat  83520
```

```
tggcattgtg gtacaaacat catggtttga acccattagt gattccaatg cggataaaga   83580
agctgctgag agagctcaat cattttactc taattggtat gttatattac tatatatgtt   83640
gagatcatat ttgtagatat gaagtatagt acttcaccca catatggaat atatattgtt   83700
ttatctattt gtattctaac atgtactagg attctagatc ccgttatata tgggaaatat   83760
ccaaaagaaa tggtagatat tcttggacca gccttgccac aattttcgag caatgaagtg   83820
aagaacttag agaagtcgag ggcagatttc gttggtatta atcactatac aagttacttc   83880
attcaagatt gtttgacctc tgcttgtaat actggacatg gagcttttaa ggccgaagga   83940
tatgctctca agttagaccg gaaaggcaat gttactatag gagaacttgt aagtacattc   84000
attcagtttc ttatattcaa tattttacga ctatattcaa atgttttagt aaattttatt   84060
gtttattgac catgtttcta ttgttagacc gatgtaaatt ggcagcatat tgatcccaca   84120
ggattccaca agatgctgaa ttatttaaaa gataggtacc caaacatgcc aatgttcata   84180
actgaaaacg gtacaagacc tcaaatttga tcaatgatcg agtcatcaac catatttgaa   84240
attatcatga aaattatta ttaatggctt gaaggttttg gagacttgca aaaacctgaa   84300
acaacggata aagaacttct aaatgataca aaaaggatcc aatacatgag tggatactta   84360
gaagctttac aagcagcaat gaggtaaata atttatgtaa atttatgcag aaatccaatt   84420
cttaaaatca tgcattcaaa tagtctttaa accaattttt atctaatgaa aatttactaa   84480
ttctatataa gttgtgaatt gttttggtag ggatggagca aatgtgaagg gttattttgt   84540
gtggtcacta ttagacaatt ttgagtggtt gttcggatac aaggttcggt ttggtctatt   84600
ccatgtggat ctaacaactc ttaaaaggtc accgaaacaa tcagcttcat ggtacaaaaa   84660
ttatatcgaa gaacacgtga atcgaagaga tatcgtagat aattattaaa cacatttatt   84720
tttaattcgt attcactgcc aaagaaagtc aaaaattaca aaagcattta aaattgatac   84780
ttatcattgt tgttgattgt tgaatgatta aatttgtctt ttcctcctaa aagtgaatgt   84840
ttaatgtgtt acatgattat ttgtctaatc ttgcacaata attctattag cttaagatgt   84900
tgaagaacac gtgagaagag aatttaggtt ttttttttgg tcaaaggaag aatagtaatt   84960
cgtattccta agtaaagaaa gtcaaactag gaaagaattt atgtaacttc gttaaatgaa   85020
tgattaatgg ttttctttac cttaaagtga atgtttaatc agtgttacgc gccatacgga   85080
agtaattgtc taatcttgca caatcattca acacgttttc aaagaaaact ttttttgttc   85140
tctatgatga taatagtgtt aaatcaaaag tagtacaaaa gtaaactaaa cttatttttag   85200 attaaaaatc accgaaaaaa ctaaacacgc gttagaaagc atttgacatc acctccaaat   85260
ttaatttcac gcaagcaagc gtttctaaga tatggattct aaacgctata tcactgtttt   85320
ttgtaagata aattcttctt aattttttca ataaaaaaat ttaaattaa aaataaaatc    85380 ataaactaac tgataatgac caaaggaacc ataaacacct agaaaattat atttctgtgt   85440
tttctatctg cggtttaacg tcagtaacat ctaggaaagt tatttttacga aagtgaactt   85500 ggttttttgtt tgattgaaat atgtttcaga cttctcagaag aaaaaaaaag atacttattt   85560
aaaatatgtt aagattttag ttcacttcaa attatgtaaa catgctgatt tttttttttt   85620
tttttttttt ttttttttgca atcatccttc aatattgtct gcgaaacagt caagtttcaa   85680
gtacgattca caacattttt caaaaaattt attcattcat ttcactccca aaacttttta   85740
atttacaaaa ctacccgtac acgtatattg gttgaataga aatttttttga atatttatta   85800 tattttgagt tacatataga ctatgattta atcaaataca caatgagtcg ttaaacaatc   85860
```

| | |
|---|---|
| taaagaaaaa gacacacgaa caaactgata acatagataa catataagca aaataggtcg | 85920 |
| gaatcaacaa ttacatatat aaatggttgc gtggttaatg atttcatttg gtattttcac | 85980 |
| gacaagatcg tttctaggta catagaagtc aacttcgttg ccatataaac tgtataacac | 86040 |
| ttagtcatac aatctggttt atttatcaag ttcaaaaatt taatttaatc aaaatatttg | 86100 |
| tttgcgaaat tttcaatcga gaattaaaaa attaaaaaaa gttgcgtggt tgagttaatc | 86160 |
| gtttggtctc catcgctgat atcttcaatt tctctgaatt aatcttcaca tagctgtata | 86220 |
| aagacctaga aaagaaaaca gatatactag taaccaaact tagaatcaag aaagaaaaaa | 86280 |
| acagctatag agttgaataa gaagaagaag aagatgacat tttttaaacc aattagaatc | 86340 |
| atcaattttt tattcctatt tttcatattt cttgtggtat acgcaaccgt gttctgcaaa | 86400 |
| ttttgttcag acactggaaa cttcaaaaga agtaagttga ggtacgaaac ttccgatgat | 86460 |
| agttatgaag ctaggagtag ccatgtcacc aaccatatcc tcagccgccg caacaccaac | 86520 |
| cccttcacca aatgggtcaa cgttctccgc cgcactagca cttcttgtac gaaaccgtaa | 86580 |
| gtttcttctt tttacttgaa tttatataaa cgtatgaatt agtcgtgtgt tgccaaaaa | 86640 |
| agaaaagaaa aagaattagc cgtgtcatag aattgtaaat tatggcgacg gatgatataa | 86700 |
| tatttaacac gtgagtagta ttgaagacat ttattaaaga atatgtttgt tgttaaaaag | 86760 |
| taagatatca gtaattaatt aatgtttcac actgtcaata acataaaata tgtgattttg | 86820 |
| aattcgaagc atagtaacaa caatattaaa aactattacg ccataaacta tagccatagt | 86880 |
| attttttattt atacttattt atactttcta acttccaaat ttttatattt tatataataa | 86940 |
| tcatcaacgc tatatatcta gaaagtaaaa ccagtaaaat ctaacgtacg aaattagatg | 87000 |
| gagttgttag gcacatttca tatattaaaa ttttaatgat tttctttttaa actttatgat | 87060 |
| atttaaagca tgtacatatt ctttttttgg ttataatata tgtaaaaatt tggtatgctt | 87120 |
| tgtctatagt tgtaaccaaa ttgatgcata gtttatgata tttaatagtt tcgaatatat | 87180 |
| tcagtaggta gaaattgggg aattttttaaa aagttgacaa gactgcccca aaatcgcaat | 87240 |
| gatgcattta aaatattctg caatttttttc atataaatat agacacgtat agataagagt | 87300 |
| gcacacaaaa ccacagacga catacacgag aaagaaaaaa aaccaaaatg aaaactttg | 87360 |
| ccaactttgc aattctgttt ttattacaaa gctt | 87394 |

<210> SEQ ID NO 7
<211> LENGTH: 26
<212> TYPE: DNA
<213> ORGANISM: Artificial
<220> FEATURE:
<223> OTHER INFORMATION: synthetic primer

<400> SEQUENCE: 7
atcggcaact ccatttccaa tttctc    26

<210> SEQ ID NO 8
<211> LENGTH: 27
<212> TYPE: DNA
<213> ORGANISM: Artificial
<220> FEATURE:
<223> OTHER INFORMATION: synthetic primer

<400> SEQUENCE: 8
tagcatccct agcattagaa cattgag    27

<210> SEQ ID NO 9
<211> LENGTH: 20

```
<212> TYPE: DNA
<213> ORGANISM: Artificial
<220> FEATURE:
<223> OTHER INFORMATION: synthetic primer

<400> SEQUENCE: 9
gtttgataac tcgtctcttg                                                   20

<210> SEQ ID NO 10
<211> LENGTH: 22
<212> TYPE: DNA
<213> ORGANISM: Artificial
<220> FEATURE:
<223> OTHER INFORMATION: synthetic primer

<400> SEQUENCE: 10
ggtgtgtgta agagtctggt cc                                                22

<210> SEQ ID NO 11
<211> LENGTH: 28
<212> TYPE: DNA
<213> ORGANISM: Artificial
<220> FEATURE:
<223> OTHER INFORMATION: synthetic primer

<400> SEQUENCE: 11
ccatggttgt acttttgaaa ttacagag                                          28

<210> SEQ ID NO 12
<211> LENGTH: 24
<212> TYPE: DNA
<213> ORGANISM: Artificial
<220> FEATURE:
<223> OTHER INFORMATION: synthetic primer

<400> SEQUENCE: 12
ccatggttat tcaagtgacc acag                                              24

<210> SEQ ID NO 13
<211> LENGTH: 17
<212> TYPE: DNA
<213> ORGANISM: Artificial
<220> FEATURE:
<223> OTHER INFORMATION: synthetic primer

<400> SEQUENCE: 13
cgtgttgagg tgagagg                                                      17

<210> SEQ ID NO 14
<211> LENGTH: 39
<212> TYPE: DNA
<213> ORGANISM: Artificial
<220> FEATURE:
<223> OTHER INFORMATION: synthetic primer

<400> SEQUENCE: 14
aggcggcgcc taaaccatgg tccgtcctgt agaaacccc                              39

<210> SEQ ID NO 15
<211> LENGTH: 39
<212> TYPE: DNA
<213> ORGANISM: Artificial
<220> FEATURE:
<223> OTHER INFORMATION: synthetic primer

<400> SEQUENCE: 15
```

-continued

```
agtcgactca ttgtttgcct ccctgctgcg gtttttcac                          39

<210> SEQ ID NO 16
<211> LENGTH: 24
<212> TYPE: DNA
<213> ORGANISM: Artificial
<220> FEATURE:
<223> OTHER INFORMATION: synthetic primer

<400> SEQUENCE: 16
acttcacttg agcggaagcc atag                                          24

<210> SEQ ID NO 17
<211> LENGTH: 26
<212> TYPE: DNA
<213> ORGANISM: Artificial
<220> FEATURE:
<223> OTHER INFORMATION: synthetic primer

<400> SEQUENCE: 17
tttaaaacaa tggcgcaagt tagcag                                        26
```

PLANT PROMOTERS FOR USE IN EARLY SEED DEVELOPMENT

The present application is a division of U.S. application Ser. No. 10/810,788, filed Mar. 26, 2004, now U.S. Pat. No. 7,294,760 which claims the benefit of U.S. Provisional Application 60/458,828 filed Mar. 28, 2003, which are incorporated herein by reference.

FIELD OF THE INVENTION

The present invention relates to the field of plant genetics. More specifically, the present invention relates to early seed development gene expression. The present invention provides promoters capable of transcribing heterologous nucleic acid sequences in seeds, and methods of modifying, producing, and using the same. The compositions comprise novel nucleotide sequences for plant promoters, more particularly the seed coat promoter from *Arabidopsis*, pBAN; and the early seed promoters from *Arabidopsis*, p26, p63, and p63tr that are useful for expression of transgenes of agronomic importance in crop plants.

BACKGROUND OF THE INVENTION

A large number of genes are known which are expressed only in developing seeds, or are expressed in developing seeds at much higher levels than in any other organ or tissue type. Much of the information about seed-specific gene expression has been derived from studies of genes encoding storage proteins (reviewed by Bevan et al., *Phil. Trans. Royal Soc. Lond. Biol. Sci.*, 342:209-215 (1993)). For instance, DNA sequences that confer embryo-specific expression by the soybean conglycinin promoter in transgenic plants have been identified (Chen et al., *EMBO J.*, 6:3559-3564 (1988)). Similarly, the storage protein napin is one of the major protein components of *Brassica napus* L. (oilseed rape) seeds. The 5' regulatory region from napin has been published (Kridl et al., *Seed Sci. Res.*, 1:209-219 (1991)). A 152 bp fragment from the napin promoter directed strong expression of the β-glucuronidase reporter gene in mature tobacco seeds (Stalberg et al., *Transgenic Research*, 7(3): 165-172 (1998)). The napin promoter has been used to control expression of genes in transgenic plants designed to produce novel fatty acids (e.g., Voelker et al., *Plant Journal*, 9:229-241 (1996)). However, because storage lipid accumulation begins substantially before the maximal level of expression of the napin or other storage protein genes is reached (Post-Beittenmiller et al., in *Control of Plant Gene Expression*. Verma, D. P. (ed.) Telford Press, pp. 157-174 (1992)), the promoters of storage protein genes may not always be preferred for controlling expression of genes related to oil accumulation in plant seeds.

Current technology permits the transformation of plants with heterologous genes. The expression of these genes is either ubiquitous if the promoter is constitutive, or is regulated in a temporal or spatial manner if the promoter is stage- or tissue-specific. Continuous expression precludes production at particular stages or in specific tissues, and can adversely affect yield due to increased energy demands associated with prolonged synthesis of the product. Tissue- or stage-specific expression permits greater control over the temporal and spatial accumulation of desired products. Thus, promoter sequences that control the expression of desired genes in a tissue-specific, stage-specific manner that can be employed in recombinant constructs for the transformation of plants, and that would facilitate greater control over the location, timing, and duration of expression of introduced genes and reduce the possibility of deleterious effects on overall plant growth, are highly desirable.

For production of transgenic plants with various desired characteristics, it would be advantageous to have a variety of promoters to provide gene expression such that a gene is transcribed efficiently in the amount necessary to produce the desired effect. The commercial development of genetically improved germplasm has also advanced to the stage of introducing multiple traits into crop plants, often referred to as a gene stacking approach. In this approach, multiple genes conferring different characteristics of interest can be introduced into a plant. It is often desired when introducing multiple genes into a plant that each gene is modulated or controlled for optimal expression, leading to a requirement for diverse regulatory elements. In light of these and other considerations, it is apparent that optimal control of gene expression and regulatory element diversity are important in plant biotechnology.

SUMMARY OF THE INVENTION

In the present invention, we provide DNA molecules that encode transcription regulatory regions useful in driving expression of selected polynucleotide molecules at specific times and in specific tissues in plant cells.

The present invention provides and describes compositions and methods for regulating expression of heterologous polynucleotide molecules in a plant. The compositions comprise novel nucleotide sequences for plant promoters, more particularly the seed coat promoter from *Arabidopsis*, pBAN; and the early seed promoters from *Arabidopsis*, p26, p63 and p63tr.

In one embodiment, the present invention provides a promoter comprising a polynucleotide sequence selected from the group of polynucleotide sequences consisting of: a polynucleotide sequence from the group of polynucleotide sequences consisting essentially of SEQ ID NO: 1 and SEQ ID NO: 4, a polynucleotide sequence substantially homologous to SEQ ID NO: 2 or any fragments or regions thereof, and a polynucleotide sequence comprising SEQ ID NO: 3.

In another embodiment, the present invention provides a plant expression construct comprising a promoter comprising a polynucleotide sequence selected from the group of polynucleotide sequences consisting of: a polynucleotide sequence from the group of polynucleotide sequences consisting essentially of SEQ ID NO: 1 and SEQ ID NO: 4, a polynucleotide sequence substantially homologous to SEQ ID NO: 2 or any fragments or regions thereof, and a polynucleotide sequence comprising SEQ ID NO: 3, wherein said promoter is operably linked to a transcribable polynucleotide molecule. In a preferred embodiment, the transcribable polynucleotide molecule is a gene of agronomic interest. In a preferred embodiment, the transcribable polynucleotide molecule is a marker gene.

In yet another embodiment, the present invention provides a transgenic seed-producing dicotyledonous plant stably transformed with a plant expression construct comprising a promoter comprising a polynucleotide sequence selected from the group of polynucleotide sequences consisting of: a polynucleotide sequence from the group consisting essentially of SEQ ID NO: 1 and SEQ ID NO: 4, a polynucleotide sequence substantially homologous to SEQ ID NO: 2 or any fragments or regions thereof, and a polynucleotide sequence comprising SEQ ID NO: 3, wherein said promoter is operably linked to a transcribable polynucleotide molecule operably linked to a 3' transcription termination polynucleotide molecule. In a preferred embodiment, the dicotyledonous plant is selected from the group consisting of tobacco, tomato, potato, peanut, soybean, cotton, canola, rapeseed, safflower, flax, sugarbeet, *Arabidopsis, Brassica*, sunflower and alfalfa. In a more preferred embodiment, the transgenic dicotyledonous plant has seed with altered protein content. In a more preferred embodiment, the transgenic dicotyledonous plant has seed with altered oil content. In a more preferred embodiment, the transgenic dicotyledonous plant has seed with altered micronutrient content. In a more preferred embodiment, the present invention provides seed, oil, or meal of a transgenic dicotyledonous plant.

In another embodiment, the present invention provides a method of making a vegetable oil and meal, comprising the steps of incorporating into the genome of a dicotyledonous seed-producing plant a promoter of the present invention operably linked to a transcribable polynucleotide molecule conferring altered oil content, growing the dicotyledonous plant to produce seed, and extracting the oil from the seed to produce extracted oil and meal.

The foregoing and other aspects of the present invention will become more apparent from the following detailed description and accompanying drawings.

BRIEF DESCRIPTION OF THE SEQUENCE LISTING

SEQ ID NO: 1 represents a nucleic acid molecule encoding a pBAN promoter.
SEQ ID NO: 2 represents a nucleic acid molecule encoding a p26 promoter.
SEQ ID NO: 3 represents a nucleic acid molecule encoding a p63 promoter.
SEQ ID NO: 4 represents a nucleic acid molecule encoding a p63tr promoter.
SEQ ID NO: 5 represents the P1 clone: MQL5gi|3702735|dbj|AB018117.1| from chromosome 5 of *Arabidopsis thaliana*.
SEQ ID NO: 6 represents the BAC clone T13M11.
SEQ ID NO: 7 is a primer sequence for PCR amplification identified as Clone 26 GSP1.
SEQ ID NO: 8 is a primer sequence for PCR amplification identified as Clone 26 GSP2.
SEQ ID NO: 9 is a primer sequence for PCR amplification identified as BAN+1500.
SEQ ID NO: 10 is a primer sequence for PCR amplification identified as pBAN GSP1.
SEQ ID NO: 11 is a primer sequence for PCR amplification identified as BAN-Nco.
SEQ ID NO: 12 is a primer sequence for PCR amplification identified as p63-Nco.
SEQ ID NO: 13 is a primer sequence for PCR amplification identified as p63-fwd3.
SEQ ID NO: 14 is a primer sequence for PCR amplification identified as GUS 5'.
SEQ ID NO: 15 is a primer sequence for PCR amplification identified as GUS 3'.
SEQ ID NO: 16 is a primer sequence for PCR amplification identified as CP4-Dra.
SEQ ID NO: 17 is a primer sequence for PCR amplification identified as CP4-Kpn.

DETAILED DESCRIPTION OF THE INVENTION

Figure 1:
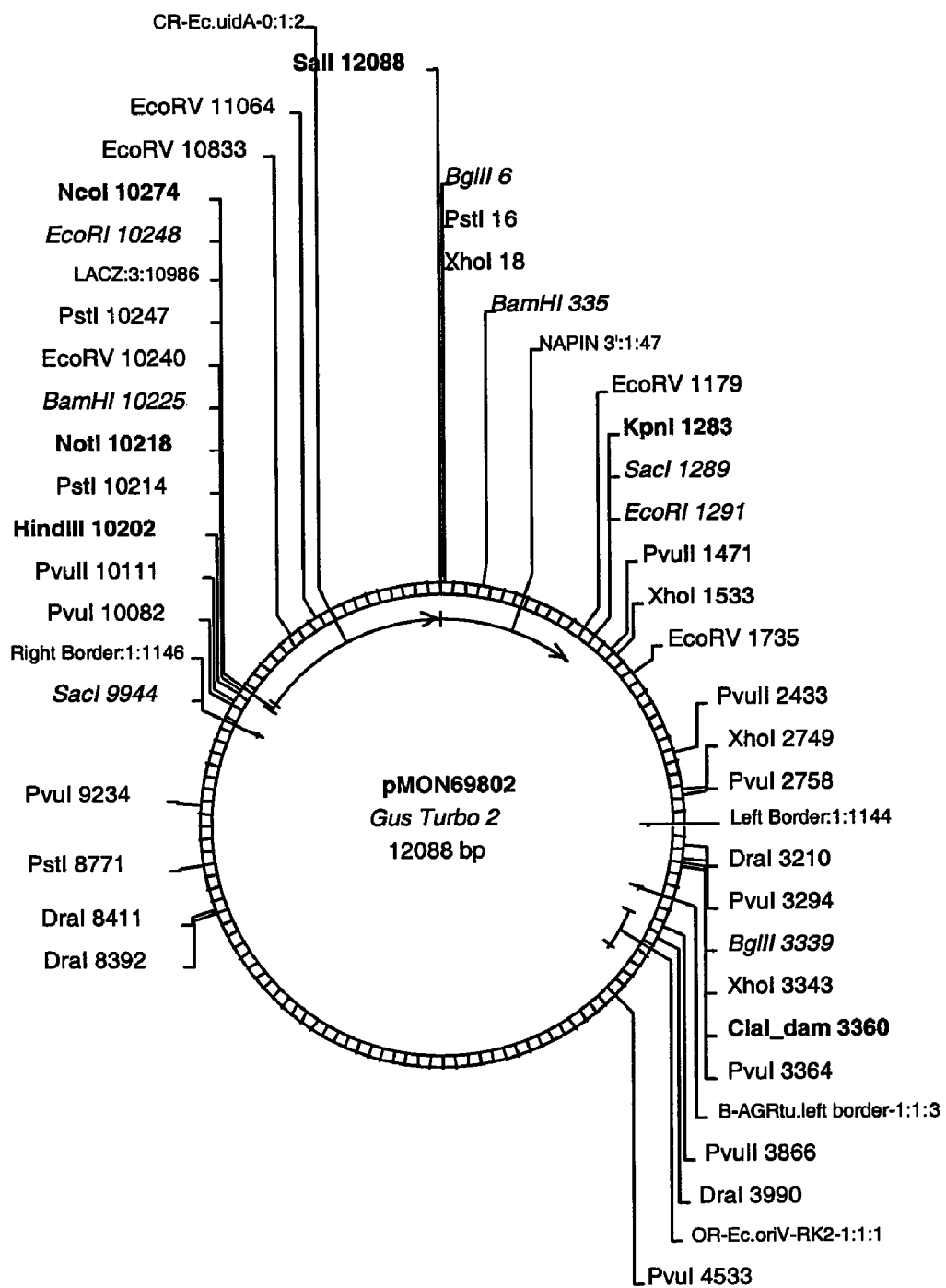
FIG. 1 is a schematic representation of pMON69802.

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the phrase "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the phrase "polynucleotide sequence" refers to the sequence of a polynucleotide molecule. The nomenclature for DNA bases as set forth at 37 CFR §1.822 is used.

As used herein "heterologous" DNA is any polynucleotide sequence which is not naturally found next to the adjacent DNA. Heterologous DNA is often found in a DNA construct used for transformation. A p26 promoter operably linked to a reporter gene is an example of a heterologous DNA as the p26 promoter is naturally and normally associated with a p26 gene.

Promoters

As used herein, the term "promoter" refers to a polynucleotide molecule that in its native state is located upstream or 5' to a translational start codon of an open reading frame (or protein-coding region) and that is involved in recognition and binding of RNA polymerase II and other proteins (trans-acting transcription factors) to initiate transcription. A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a transcribable polynucleotide molecule, a promoter typically causes the transcribable polynucleotide molecule to be transcribed in a manner that is similar to that of which the promoter is normally associated. Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. Thus, the design, construction, and use of chimeric or hybrid promoters comprising at least one cis-element of SEQ ID NOs: 1, 2, 3, or 4 for modulating the expression of operably linked polynucleotide sequences is encompassed by the present invention.

As used herein, the term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

In one embodiment, the promoters of the present invention comprise multiple cis-elements each of which confers a different aspect to the overall control of gene expression. In a preferred embodiment, cis-elements from the polynucleotide molecules of SEQ ID NOs: 1, 2, 3, and 4 are identified using computer programs designed specifically to identify cis-element, domains, or motifs within sequences. Cis-elements may either positively or negatively regulate gene expression, depending on the conditions. The present invention therefore encompasses cis-elements of the disclosed promoters.

As used herein, the phrase "substantially homologous" refers to polynucleotide molecules that generally demonstrate a substantial percent sequence identity with the promoters provided herein. Of particular interest are polynucleotide molecules wherein the polynucleotide molecules function in plants to direct transcription and have at least about 70% sequence identity, at least about 80% sequence identity, at least about 90% sequence identity, or even greater sequence identity, such as 98% or 99% sequence identity with the polynucleotide sequences of the promoters described herein. Polynucleotide molecules that are capable of regulating transcription of operably linked transcribable polynucleotide molecules and are substantially homologous to the polynucleotide sequences of the promoters provided herein are encompassed within the scope of this present invention.

As used herein, the phrase "percent sequence identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20% of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "homology" refers to the level of similarity or percent identity between polynucleotide sequences in terms of percent nucleotide positional identity, i.e., sequence similarity or identity. As used herein, the term homology also refers to the concept of similar functional properties among different polynucleotide molecules, e.g., promoters that have similar function may have homologous cis-elements. Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology. The phrase "stringent conditions" is functionally defined with regard to the hybridization of a nucleic-acid probe to a target nucleic acid (i.e., to a particular nucleic-acid sequence of interest) by the specific hybridization procedure discussed in *Molecular Cloning: A Laboratory Manual,* $3^{rd}$ edition Volumes 1, 2, and 3. J. F. Sambrook, D. W. Russell, and N. Irwin, Cold Spring Harbor Laboratory Press, 2000 (referred to herein as Sambrook, et al.). Accordingly, the nucleotide sequences of the present invention may be used for their ability to selectively form duplex molecules with complementary stretches of polynucleotide molecule fragments. Depending on the application envisioned one would desire to employ varying conditions of hybridization to achieve varying degrees of selectivity of probe towards target sequence. For applications requiring high selectivity, one will typically desire to employ relatively high stringent conditions to form the hybrids, e.g., one will select relatively low salt and/or high temperature conditions, such as provided by about 0.02 M to about 0.15 M NaCl at temperatures of about 50° C. to about 70° C. A high stringent condition, for example, is to wash the hybridization filter at least twice with high-stringency wash buffer (0.2× SSC, 0.1% SDS, 65° C.). Appropriate moderate stringency conditions that promote DNA hybridization, for example, 6.0× sodium chloride/sodium citrate (SSC) at about 45° C., followed by a wash of 2.0×SSC at 50° C., are known to those skilled in the art. Additionally, the salt concentration in the wash step can be selected from a low stringency of about 2.0×SSC at 50° C. to a high stringency of about 0.2×SSC at 50° C. Additionally, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little mismatch between the probe and the template or target strand. Detection of polynucleotide molecules via hybridization is well known to those of skill in the art, and the teachings of U.S. Pat. Nos. 4,965,188 and 5,176,995 are exemplary of the methods of hybridization analyses.

Homology can also be determined by computer programs that align polynucleotide sequences and estimate the ability of polynucleotide molecules to form duplex molecules under certain stringency conditions. Polynucleotide molecules from different sources that share a high degree of homology are referred to as "homologues".

Methods well known to one skilled in the art may be used to identify promoters of interest having activity similar to the promoters described herein. For example, cDNA libraries may be constructed using cells or tissues of interest and screened to identify genes having an expression pattern similar to that of the promoters described herein. The cDNA sequence for the identified gene may then be used to isolate the gene's promoter for further characterization. See, for example, U.S. Pat. Nos. 6,096,950; 5,589,583; and 5,898,096; incorporated herein by reference. Alternately, transcriptional profiling or electronic northern techniques may be used to identify genes having an expression pattern similar to that of the promoters described herein. Once these genes have been identified, their promoters may be isolated for further characterization. See, for example, U.S. Pat. Nos. 6,506,565 and 6,448,387, incorporated herein by reference. The electronic northern technique refers to a computer-based sequence analysis which allows sequences from multiple cDNA libraries to be compared electronically based on parameters the researcher identifies including abundance in EST populations in multiple cDNA libraries, or exclusively to EST sets from one or combinations of libraries. The transcriptional profiling technique is a high-throughput method used for the systematic monitoring of gene expression profiles for thousands of genes. This DNA chip-based technology arrays thousands of cDNA sequences on a support surface. These arrays are simultaneously hybridized to a population of labeled cDNA probes prepared from RNA samples of different cell or tissue types, allowing direct comparative analysis of expression. This approach may be used for the isolation of regulatory sequences such as promoters associated with those genes.

In another embodiment, the promoter disclosed herein can be modified. Those skilled in the art can create promoters that have variations in the polynucleotide sequence. The polynucleotide sequences of the promoters of the present invention as shown in SEQ ID NOs: 1, 2, 3, or 4 may be modified or altered to enhance their control characteristics. One preferred method of alteration of a polynucleotide sequence is to use PCR to modify selected nucleotides or regions of sequences. These methods are well known to those of skill in the art. Sequences can be modified, for example by insertion, deletion, or replacement of template sequences in a PCR-based DNA modification approach. A "variant" is a promoter containing changes in which one or more nucleotides of an original promoter is deleted, added, and/or substituted, preferably while substantially maintaining promoter function. For example, one or more base pairs may be deleted from the 5' or 3' end of a promoter to produce a "truncated" promoter. One or more base pairs can also be inserted, deleted, or substituted internally to a promoter. In the case of a promoter fragment, variant promoters can include changes affecting the transcription of a minimal promoter to which it is operably linked. A minimal or basal promoter is a polynucleotide molecule that is capable of recruiting and binding the basal transcription machinery. One example of basal transcription machinery in eukaryotic cells is the RNA polymerase II complex and its accessory proteins. Variant promoters can be produced, for example, by standard DNA mutagenesis techniques or by chemically synthesizing the variant promoter or a portion thereof.

Novel chimeric promoters can be designed or engineered by a number of methods. Many promoters contain cis-elements that activate, enhance, or define the strength and/or specificity of the promoter. For example, promoters may contain "TATA" boxes defining the site of transcription initiation and other cis-elements located upstream of the transcription initiation site that modulate transcription levels. For example, a chimeric promoter may be produced by fusing a first promoter fragment containing the activator cis-element from one promoter to a second promoter fragment containing the activator cis-element from another promoter; the resultant chimeric promoter may cause an increase in expression of an operably linked transcribable polynucleotide molecule. Promoters can be constructed such that promoter fragments or elements are operably linked, for example, by placing such a fragment upstream of a minimal promoter. The cis-elements and fragments of the present invention can be used for the construction of such chimeric promoters. Methods for construction of chimeric and variant promoters of the present invention include, but are not limited to, combining control elements of different promoters or duplicating portions or regions of a promoter (see, for example, U.S. Pat. Nos. 4,990, 607; 5,110,732; and 5,097,025, all of which are herein incorporated by reference). Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

In another embodiment, a promoter comprising the polynucleotide sequence shown in SEQ ID NO: 2 includes any length of said polynucleotide sequence that is capable of regulating an operably linked transcribable polynucleotide molecule. For example, the promoters as disclosed in SEQ ID NO: 2 may be truncated or portions deleted and still be capable of regulating transcription of an operably linked polynucleotide molecule. In a related embodiment, a cis-element of the disclosed promoters may confer a particular specificity such as conferring enhanced expression of operably linked polynucleotide molecules in certain tissues and therefore is also capable of regulating transcription of operably linked polynucleotide molecules. Consequently, any fragments, portions, or regions of the promoters comprising the polynucleotide sequence shown in SEQ ID NO: 2 can be used as regulatory polynucleotide molecules, including but not limited to cis-elements or motifs of the disclosed polynucleotide molecules. Substitutions, deletions, insertions, or any combination thereof can be combined to produce a final construct.

Polynucleotide Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner.

As used herein, the phrase "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. Preferably, the two polynucleotide molecules are part of a single contiguous polynucleotide molecule and more preferably are adjacent. For example, a promoter is operably linked to a gene of interest if the promoter regulates or mediates transcription of the gene of interest in a cell.

As used herein, the phrase "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed for transcription of antisense RNA molecules or other similar inhibitory RNA in order to inhibit expression of a specific RNA molecule of interest in a target host cell. For the practice of the present invention, conventional compositions and methods for preparing and using constructs and host cells are well known to one skilled in the art, see, for example, Sambrook, et al.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see, for example, U.S. Pat. Nos. 5,659,122 and 5,362,865, herein incorporated by reference). These additional upstream and downstream regulatory polynucleotide molecules may be derived from a source that is native or heterologous with respect to the other elements present on the promoter construct.

Thus, constructs of the present invention comprise promoters such as those provided in SEQ ID NOs: 1, 2, 3, or 4 modified as described above, operatively linked to a transcribable polynucleotide molecule so as to direct transcription of said transcribable polynucleotide molecule at a desired level or in a desired tissue or developmental pattern upon introduction of said construct into a plant cell. In some cases, the transcribable polynucleotide molecule comprises a protein-coding region of a gene, and the promoter provides for transcription of a functional mRNA molecule that is translated and expressed as a protein product. Constructs may also be constructed for transcription of antisense RNA molecules or other similar inhibitory RNA in order to inhibit expression of a specific RNA molecule of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or DNA molecule that is introduced into a recipient cell. The type of DNA included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

The promoters of the present invention can be incorporated into a construct using marker genes as described and tested in transient analyses that provide an indication of gene expression in stable plant systems. As used herein the phrase "marker gene" refers to any transcribable polynucleotide molecule whose expression can be screened for or scored in some way. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate promoters or promoter fragments operably linked to any transcribable polynucleotide molecules, including but not limited to selected reporter genes, marker genes, or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

Any scorable or screenable marker gene can be used in a transient assay. Preferred marker genes for transient analyses of the promoters or promoter fragments of the present invention include a GUS gene (U.S. Pat. No. 5,599,670, herein incorporated by reference) or a GFP gene (U.S. Pat. No. 5,491,084, herein incorporated by reference). The constructs containing the promoters or promoter fragments operably linked to a marker gene are delivered to the tissues and the tissues are analyzed by the appropriate mechanism, depending on the marker. The quantitative or qualitative analyses are used as a tool to evaluate the potential expression profile of the promoters or promoter fragments when operatively linked to genes of agronomic interest in stable plants.

Thus, in one preferred embodiment, a polynucleotide molecule of the present invention as shown in SEQ ID NOs: 1, 2, 3, or 4 or fragments, variants, or derivatives thereof is incorporated into a construct such that a promoter of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep), and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061; 5,633,435; and 6,040,497; and aroA described in U.S. Pat. No. 5,094,945 for glyphosate tolerance; a polynucleotide molecule encoding bromoxynil nitrilase (Bxn) described in U.S. Pat. No. 4,810,648 for Bromoxynil tolerance; a polynucleotide molecule encoding phytoene desaturase (crtI) described in Misawa et al., *Plant J.*, 4:833-840 (1993) and Misawa et al., *Plant J.*, 6:481-489 (1994) for norflurazon tolerance; a polynucleotide molecule encoding acetohydroxyacid synthase (AHAS, aka ALS) described in Sathasiivan et al., *Nucl. Acids Res.*, 18:2188-2193 (1990) for tolerance to sulfonylurea herbicides; and the bar gene described in DeBlock, et al., *EMBO J.*, 6:2513-2519 (1987) for glufosinate and bialaphos tolerance.

In one preferred embodiment, a polynucleotide molecule of the present invention as shown in SEQ ID NOs: 1, 2, 3, or 4 or fragments, variants, or derivatives thereof is incorporated into a construct such that a promoter of the present invention is operably linked to a transcribable polynucleotide molecule that is a gene of agronomic interest. As used herein, the phrase "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648), low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference.

Useful nucleic acid sequences that can be combined with the promoter nucleic acid sequence of the present invention and provide improved end-product traits include, without limitation, those encoding seed storage proteins, fatty acid pathway enzymes, tocopherol biosynthetic enzymes, amino acid biosynthetic enzymes, and starch branching enzymes. A discussion of exemplary heterologous DNAs useful for the modification of plant phenotypes may be found in, for example, U.S. Pat. Nos. 6,194,636; 6,207,879; 6,232,526; 6,426,446; 6,429,357; 6,433,252; 6,437,217; 6,515,201; and 6,583,338 and PCT Publication WO 02/057471, each of which is specifically incorporated herein by reference in its entirety.

Preferred seed storage proteins include zeins (U.S. Pat. Nos. 4,886,878; 4,885,357; 5,215,912; 5,589,616; 5,508,468; 5,939,599; 5,633,436; and 5,990,384; PCT Publications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576,203), brazil nut protein (U.S. Pat. No. 5,850,024), phenylalanine free proteins (PCT Publication WO 96/17064), albumin (PCT Publication WO 97/35023), b-conglycinin (PCT Publication WO 00/19839), 11S (U.S. Pat. No. 6,107,051), alpha-hordothionin (U.S. Pat. Nos. 5,885,802 and 5,88,5801), arcelin seed storage proteins (U.S. Pat. No. 5,270,200), lectins (U.S. Pat. No. 6,110,891), and glutenin (U.S. Pat. Nos. 5,990,389 and 5,914,450) all of which are incorporated herein by reference.

Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), diacylglycerol acyltransferases (U.S. Patent Publications 20030115632A1 and 20030028923A1), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249) all of which are incorporated herein by reference.

Preferred tocopherol biosynthetic enzymes include tyrA, slr1736, ATPT2, dxs, dxr, GGPPS, HPPD, GMT, MT1, tMT2, AANT1, slr 1737, and an antisense construct for homogentisic acid dioxygenase (Kridl et al., *Seed Sci. Res.*, 1:209:219 (1991); Keegstra, *Cell*, 56(2):247-53 (1989); Nawrath et al., *Proc. Natl. Acad. Sci. USA*, 91:12760-12764 (1994); Xia et al., *J. Gen. Microbiol.*, 138:1309-1316 (1992); Lois et al., *Proc. Natl. Acad. Sci. USA*, 95 (5):2105-2110 (1998); Takahashi et al., *Proc. Natl. Acad. Sci. USA*, 95(17): 9879-9884 (1998); Norris et al., *Plant Physiol.*, 117:1317-1323 (1998); Bartley and Scolnik, *Plant Physiol.*, 104:1469-1470 (1994); Smith et al., *Plant J.*, 11:83-92 (1997); WO 00/32757; WO 00/10380; Saint Guily et al., *Plant Physiol.*, 100(2):1069-1071 (1992); Sato et al., *J. DNA Res.*, 7(1):31-63 (2000)) all of which are incorporated herein by reference.

Preferred amino acid biosynthetic enzymes include anthranilate synthase (U.S. Pat. No. 5,965,727 and PCT Publications WO 97/26366, WO 99/11800, and WO 99/49058), tryptophan decarboxylase (PCT Publication WO 99/06581), threonine decarboxylase (U.S. Pat. Nos. 5,534,421 and 5,942,660; PCT Publication WO 95/19442), threonine deaminase (PCT Publications WO 99/02656 and WO 98/55601), dihydrodipicolinic acid synthase (U.S. Pat. No. 5,258,300), and aspartate kinase (U.S. Pat. Nos. 5,367,110; 5,858,749; and 6,040,160) all of which are incorporated herein by reference.

Preferred starch branching enzymes include those set forth in U.S. Pat. Nos. 6,232,122 and 6,147,279; and PCT Publication WO 97/22703, all of which are incorporated herein by reference.

Alternatively, a transcribable polynucleotide may be designed to down-regulate a specific nucleic acid sequence. This is typically accomplished by operably linking with a promoter, such as a promoter of the present invention, an exogenous DNA in an antisense orientation or a DNA designed such that a hairpin-forming RNA molecule is generated upon transcription. Gene suppression may be effective against a native plant gene associated with a trait, e.g., to provide plants with reduced levels of a protein encoded by the native gene or with enhanced or reduced levels of an affected metabolite. For example, a promoter of the present invention may be operably linked to a heterologous DNA designed such that a hairpin-shaped RNA is formed for suppression of a native gene in dicotyledonous seed. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest is useful for the practice of the present invention.

As used herein "gene suppression" means any of the well-known methods for suppressing an RNA transcript or production of protein translated from an RNA transcript, including post-transcriptional gene suppression and transcriptional suppression. Post-transcriptional gene suppression is mediated by double-stranded RNA having homology to a gene targeted for suppression. Gene suppression by RNA transcribed from an exogenous DNA construct comprising an inverted repeat of at least part of a transcription unit is a common feature of gene suppression methods known as anti-sense suppression, co-suppression, and RNA interference. Transcriptional suppression can be mediated by a transcribed double-stranded RNA having homology to promoter DNA sequence to effect what is called promoter trans-suppression.

More particularly, post transcriptional gene suppression by inserting an exogenous DNA construct with anti-sense oriented DNA to regulate gene expression in plant cells is disclosed in U.S. Pat. Nos. 5,107,065 and 5,759,829, each of which is incorporated herein by reference in its entirety. Transgenic plants transformed using such anti-sense oriented DNA constructs for gene suppression can comprise DNA arranged as an inverted repeat, as disclosed by Redenbaugh et al., in "Safety Assessment of Genetically Engineered Flavr Savr™ Tomato, CRC Press, Inc. (1992). Inverted repeat insertions can comprise a part or all of a T-DNA construct, e.g., an inverted repeat of transcription terminator sequence.

Post transcriptional gene suppression by inserting an exogenous DNA construct with sense-oriented DNA to regulate gene expression in plants is disclosed in U.S. Pat. Nos. 5,283,184 and 5,231,020, each of which is incorporated herein by reference.

Different types of exogenous DNA arrangements resulting in gene suppression are known to those of skill in the art and include but are not limited to the following. PCT Publication WO 94/01550 discloses DNA constructs where the anti-sense RNA was stabilized with a self-complementary 3' segment. Other double-stranded hairpin-forming elements in transcribed RNA are disclosed in PCT Publication No. 98/05770 where the anti-sense RNA is stabilized by hairpin forming repeats of poly(CG) nucleotides and U.S. Application Publication No. 2002/0048814A1 describes sense or anti-sense RNA stabilized by a poly(T)-poly(A) tail. U.S. Application Publication No. 2003/0018993A1 discloses sense or anti-sense RNA is stabilized by an inverted repeat of a subsequence of 3' untranslated region of the NOS gene. U.S. Application Publication No. 2003/0036197A1 describes an RNA stabilized by two complementary RNA regions having homology to a target sequence.

Gene silencing can also be effected by transcribing RNA from both a sense and an anti-sense oriented DNA, e.g., as disclosed in U.S. Pat. No. 5,107,065 and other examples as follows. U.S. Pat. No. 6,326,193 discloses gene targeted DNA which is operably linked to opposing promoters. Sijen et al., The Plant Cell, 8:2277-2294 (1996) discloses the use of constructs carrying inverted repeats of a cowpea mosaic virus gene in transgenic plants to mediate virus resistance. Such constructs for post transcriptional gene suppression in plants by double-stranded RNA are also disclosed in PCT Publication Nos. WO 99/53050, WO 99/49029, and U.S. Application Publication No. 2003/0175965A1, U.S. application Ser. No. 10/465,800, and U.S. Pat. No. 6,506,559. See, also, U.S. application Ser. No. 10/393,347 which discloses constructs and methods for simultaneously expressing one or more recombinant genes while simultaneously suppressing one or more native genes in a transgenic plant. See, also, U.S. Pat. No. 6,448,473 which discloses multigene suppression vectors for use in plants. All of the above-described patents, applications and international publications disclosing materials and methods for post transcriptional gene suppression in plants are incorporated herein by reference.

Transcriptional suppression such as promoter trans suppression can be effected by expressing a DNA construct comprising a promoter operably linked to inverted repeats of promoter DNA for a target gene. Constructs useful for such gene suppression mediated by promoter trans suppression are disclosed by Mette et al., The EMBO Journal, 18(1):241-248, 1999 and by Mette et al., The EMBO Journal, 19(19):5194-5201, 2000), both of which are incorporated herein by reference.

The constructs of the present invention are generally double Ti plasmid border DNA constructs that have the right border (RB or AGRtu.RB) and left border (LB or AGRtu.LB) regions of the Ti plasmid isolated from Agrobacterium tumefaciens comprising a T-DNA, that along with transfer molecules provided by the Agrobacterium cells, permits the integration of the T-DNA into the genome of a plant cell. The constructs also contain the plasmid backbone DNA segments that provide replication function and antibiotic selection in bacterial cells, for example, an E. coli origin of replication such as ori322, a broad host range origin of replication such as oriV or oriRi, and a coding region for a selectable marker such as Spec/Strp that encodes for Tn7 aminoglycoside adenyltransferase (aada) conferring resistance to spectinomycin or streptomycin, or a gentamicin (Gm, Gent) selectable marker gene. For plant transformation, the host bacterial strain is often Agrobacterium tumefaciens ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this present invention can include any of the well-known and demonstrated methods including electroporation as illustrated in U.S. Pat. No. 5,384,253; microprojectile bombardment as illustrated in U.S. Pat. Nos. 5,015,580; 5,550,318; 5,538,880; 6,160,208; 6,399,861; and 6,403,865; Agrobacterium-mediated transformation as illustrated in U.S. Pat. Nos. 5,824,877; 5,591,616; 5,981,840; and 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (Gossypium hirsutum), soybean (Glycine max), peanut (Arachis hypogaea), and members of the genus Brassica.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this present invention can be harvested from fertile transgenic plants and be used to grow progeny generations of transformed plants of this present invention including hybrid plant lines comprising the construct of this present invention and expressing a gene of agronomic interest.

The present invention also provides for parts of the plants of the present invention. Plant parts, without limitation, include seed, endosperm, ovule, and pollen. In a particularly preferred embodiment of the present invention, the plant part is a seed. It is understood that even after separation or isolation from other plant parts, the isolated or separated plant part may be contaminated with other plant parts. In a preferred aspect, the separated plant part is greater than 50% (w/w) of the separated material, more preferably, greater than 75% (w/w) of the separated material, and even more preferably greater than 90% (w/w) of the separated material. Plants or plant parts of the present invention generated by such methods may be processed into products using known techniques. Preferred products are meal, feedstock, and oil.

In another embodiment, the present invention provides a method of making a vegetable oil, comprising the steps of incorporating into the genome of an oilseed plant a promoter of the present invention operably linked to a transcribable polynucleotide molecule conferring altered oil content, growing the oilseed plant to produce oilseeds, and extracting the oil from the oilseed.

In another embodiment, the present invention provides a method of making a meal, comprising the steps of incorporating into the genome of an oilseed plant a promoter of the present invention operably linked to a transcribable polynucleotide molecule conferring altered protein and/or micronutrient content, growing the oilseed plant to produce oilseeds, and producing the meal from the oilseed.

Methods to produce feed, meal, protein, and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than about 5% w/v, more preferably greater than about 10% w/v, and even more preferably greater than about 15% w/v. In a preferred oil preparation, the oil preparation is a high oil preparation with an oil content derived from a plant or part thereof of the present invention of greater than about 5% w/v, more preferably greater than about 10% w/v, and even more preferably greater than about 15% w/v. In a preferred embodiment the oil preparation is a liquid and of a volume greater than 1, 5, 10, or 50 liters. The present invention provides for oil produced from plants of the present invention or generated by a method of the present invention. Such oil may be a minor or major component of any resultant product. Moreover, such oil may be blended with other oils. In a preferred embodiment, the oil produced from plants of the present invention or generated by a method of the present invention constitutes greater than about 0.5%, about 1%, about 5%, about 10%, about 25%, about 50%, about 75%, or about 90% by volume or weight of the oil component of any product. In another embodiment, the oil preparation may be blended and can constitute greater than about 10%, about 25%, about 35%, about 50%, or about 75% of the blend by volume. Oil produced from a plant of the present invention can be admixed with one or more organic solvents or petroleum distillates.

In a further embodiment, meal of the present invention may be blended with other meals. In a preferred embodiment, the meal produced from plants of the present invention or generated by a method of the present invention constitutes greater than about 0.5%, about 1%, about 5%, about 10%, about 25%, about 50%, about 75%, or about 90% by volume or weight of the meal component of any product. In another embodiment, the meal preparation may be blended and can constitute greater than about 10%, about 25%, about 35%, about 50%, or about 75% of the blend by volume.

The phrase "micronutrient content" means the amount of micronutrients, i.e., vitamins A, E, K, tocopherols, tocotrienols, or carotenoids, within a seed expressed on a per weight basis.

The phrase "oil content" means oil level, which may be determined, for example, by low-resolution $^1$H nuclear magnetic resonance (NMR) (Tiwari et al., JAOCS, 51:104-109, 1974 or Rubel, JAOCS, 71:1057-1062, 1994) or near infrared transmittance (NIT) spectroscopy (Orman et al., JAOCS, 69(10): 1036-1038, 1992 and Patrick et al., JAOCS, 74(3): 273-276, 1997).

The phrase "protein quality" means the level of one or more essential amino acids, whether free or incorporated in protein, namely histidine, isoleucine, leucine, lysine, methionine, cysteine, phenylalanine, tyrosine, threonine, tryptophan, and valine.

The following examples are included to demonstrate preferred embodiments of the present invention. It should be appreciated by those of skill in the art that the techniques disclosed in the examples that follow represent techniques discovered by the inventors to function well in the practice of the present invention. However, those of skill in the art should, in light of the present disclosure, appreciate that many changes can be made in the specific embodiments that are disclosed and still obtain a like or similar result without departing from the spirit and scope of the present invention, therefore all matter set forth or shown in the accompanying drawings is to be interpreted as illustrative and not in a limiting sense.

EXAMPLE 1

This example sets forth the isolation and characterization of the nucleic acid sequences for the plant promoters p26, p63, p63tr and pBAN.

p26

A cDNA clone, designated clone 26, was identified from *Arabidopsis thaliana* using a cDNA-AFLP procedure. Briefly, SMART cDNA libraries were prepared from mRNA isolated from *Arabidopsis* according to manufacturer's instructions (Clontech Laboratories, Palo Alto, Calif.). The mRNA was isolated from open flowers (inflorescence), stem, whole seedling, and developing seed harvested at 4, 7, 10, 13, or 18 days after flowering (DAF). Five hundred micrograms of amplified SMART cDNA was used for AFLP analysis using the Gibco-BRL small genome AFLP II Kit (Invitrogen, Carlsbad, Calif.) according to manufacturer's instructions. The resulting bands were visualized after electrophoresis through 6% acrylamide/8M Urea sequencing gels. A single band, designated band 26, visible only in the lane derived from cDNA from 4 DAF developing seed tissue, was extracted from the gel. The DNA was eluted by placing the acrylamide band in 50 μl of TE (10 mM Tris-HCl (pH 8.0); 1 mM EDTA) and allowing the band to elute at ambient temperature overnight.

After a brief centrifugation, 0.75 µl of supernatant was used as a template source for a PCR amplification. Twenty microliters of Preamp primer mix 2 (Gibco-BRL small genome AFLP II Kit, Invitrogen), 2.5 µl 10×PCR buffer with 15 mM MgCl (PE Applied Biosystems Foster City, Calif.), 2.5 units AmpliTaq DNA Polymerase (PE Applied Biosystems), and 2 µl water were added to the DNA template. Amplification conditions were as follows: 25 cycles of 94° C. for 30 seconds, 56° C. for 60 seconds, and 72° C. for 2 minutes followed by 1 cycle of 72° C. for 2 minutes. The resulting DNA fragment was subcloned into pCR2.1 Topo (Invitrogen) according to manufacturers' instructions. This cDNA clone 26 was hybridized to virtual Northerns that were prepared from SMART cDNA libraries, according to the manufacturer's instructions, using the SMART PCR cDNA Synthesis Kit (BD Biosciences, Clontech, Palo Alto, Calif.). Clone 26 was characterized as being expressed in early stages of seed development. The sequence of clone 26 was determined using standard sequencing methodologies as set forth by PE Applied Biosystems BigDye terminator v.3.0 (PE Applied Biosystems, Foster City, Calif.).

The entire sequence of clone 26 was then used as a query for a BLAST search against public and proprietary genomic DNA databases. A single EST clone, LIB3176-P1-K1-C12, was identified from the search. The clone had homology to a palmitoyl-protein thioesterase in *Arabidopsis thaliana* (GenBank protein_id BAA97167; gi:8809616). The entire genomic sequence of clone 26 was contained within the P1 clone MQL5 (SEQ ID NO: 5, GenBank Accession AB018117; gi:3702735).

To prepare a genomic library from *Arabidopsis*, genomic DNA was isolated using a modification of a genomic DNA isolation protocol (Dellaporta et al., *Plant Molecular Biology Reporter*, 1:19-21, 1983). Soil or plate grown *Arabidopsis* seedlings were harvested and kept frozen in liquid nitrogen until extraction. The tissue was ground to a fine powder using a mortar and pestle while keeping the tissue frozen with liquid nitrogen. The ground tissue was transferred to a Waring blender containing 200 ml of cold (0° C.) DNA extraction buffer (350 mM sorbitol; 100 mM Tris; 5 mM EDTA; pH to 7.5 with HCl; sodium bisulfite (3.8 mg/ml) added just before use, and homogenized at high speed for 30-60 seconds. The homogenate was filtered through a layer of cheesecloth and collected in a centrifuge bottle. The samples were centrifuged at 2500×g for 20 minutes. The supernatant and any loose green material was discarded. The pellet was then resuspended in 1.25 ml DNA extraction buffer and transferred to a 50 ml polypropylene tube. Then 1.75 ml nuclei lysis buffer (200 mM Tris; 50 mM EDTA; 2 M NaCl; 2% CTAB (Hexadecyltrimethyl-Ammonium Bromide, Sigma, St. Louis, Mo.); pH to 7.5 with HCl), and 0.6 ml of 5% (w/v) sarcosyl was added. The tubes were mixed gently, and the samples were incubated at 65° C. for 20 minutes. An equal volume of chloroform:isoamyl alcohol (24:1) was added and the tubes were mixed gently. The tubes were then centrifuged at 2500×g for 15 minutes, and the resulting supernatant was transferred to a clean tube. An equal volume of ice-cold isopropanol was poured onto the sample, and the sample was inverted several times until a precipitate formed. The precipitate was removed from the solution using a glass pipette and residual alcohol removed by allowing the precipitate to air dry for 2-5 minutes. The precipitate was resuspended in 400 µl TE buffer (10 mM Tris-HCl pH 8.0, 1 mM EDTA).

*Arabidopsis* genomic DNA as prepared above was used to prepare Genome Walker libraries (Clontech) according to the manufacturer's instructions. The p26 promoter sequence (SEQ ID NO: 2) was isolated from the libraries according to the manufacturer's instructions. Primers were designed based upon the sequence of the P1 clone MQL5 (SEQ ID NO: 5). The following were used as the primers for the PCR reaction:

```
Clone 26 GSP1
5'-ATCGGCAACTCCATTTCCAATTTCTC-3'     (SEQ ID NO: 7)

and

Clone 26 GSP2
5'-TAGCATCCCTAGCATTAGAACATTGAG-3'.   (SEQ ID NO: 8)
```

After an initial PCR using the Genome Walker libraries as template and primers GSP1 and AP1 (supplied by the manufacturer), a second amplification was performed using the first round amplification product as template and primers GSP2 and AP2 (supplied by the manufacturer).

The product of the PCR reaction was purified according to standard methodology well known in the art and cloned into pCR2.1 Topo (Invitrogen) according to manufacturer's instructions. The resulting plasmid was named pMON69803 and contained the sequence of the promoter p26 (SEQ ID NO: 2). The sequence of this clone was determined using standard sequencing methodologies as set forth by PE Applied Biosystems, (Foster City, Calif.).

pBAN

The promoter sequence for pBAN was identified from a BLAST search of the coding region of the BANYULS gene (GenBank AF092912, Devic et al., *The Plant Journal*, 19(4): 387-398, 1999) against an *Arabidopsis* database in GenBank, the NIH genetic sequence database containing an annotated collection of all publicly available DNA sequences (*Nucleic Acids Research*, 30(1): 17-20, 2002). The search identified BAC clone T13M11 (GenBank AC005882, [SEQ ID NO: 6]) that contains the BANYULS coding region in antisense orientation. The following primers were designed to amplify the sequences corresponding to T12M11 base pairs 44629-45570 from *Arabidopsis* genomic DNA prepared as described above.

```
BAN + 1500
5'-GTTTGATAACTCGTCTCTTTG-3'     (SEQ ID NO: 9)

and

BAN GSP1
5'-GGTGTGTGTAAGAGTCTGGTCC-3'    (SEQ ID NO: 10)
```

The reaction conditions for the PCR followed a protocol recommended by the enzyme manufacturer (PE Applied Biosystems, Foster City, Calif.). The Banyuls promoter was isolated from *Arabidopsis* genomic DNA using 30 nanomoles each of primers Ban+1500 and Ban GSP1, 10 micromoles each of dATP, dCTP, dGTP, and TTP, 2.5 units of AmpliTaq Gold in 1× Opti-Prime™ Buffer 3 (Stratagene, La Jolla, Calif.). After an initial incubation at 95° C. for 10 minutes, 30 cycles of PCR were performed with 92° C. for 30 seconds, 56° C. for 30 seconds, and 72° C. for 2 minutes followed by 1 cycle of 72° C. for 7 minutes.

The product of the PCR reaction was purified according to standard methodology well known in the art and cloned into pCR2.1 Topo (Invitrogen) according to manufacturer's instructions. The resulting plasmid was named pBAN1.

To add an NcoI site at the predicted ATG start codon of the Banyuls gene an additional PCR reaction was performed. pBAN1 was used as template DNA with the following primers:

```
Ban-Nco
5'-CCATGGTTGTACTTTTGAAATTACAGAG-3'  (SEQ ID NO: 11)

and

Ban + 1500
5'-GTTTGATAACTCGTCTCTTG-3'          (SEQ ID NO: 9)
```

The reaction conditions for the second PCR reaction followed a protocol recommended by the enzyme manufacturer (PE Applied Biosystems, Foster City, Calif.). Approximately 10 nanograms of pBAN1 is amplified using 30 nanomoles each of primers Ban+1500 and Ban-Nco, 10 micromoles each of dATP, dCTP, dGTP, and TTP, 2.5 units of AmpliTaq Gold in 1× Opti-Prime™ Buffer 3 (Stratagene). After an initial incubation at 95° C. for 10 minutes, 30 cycles of PCR were performed with 92° C. for 30 seconds, 56° C. for 30 seconds, and 72° C. for 2 minutes followed by 1 cycle of 72° C. for 7 minutes.

The product of the PCR reaction was purified according to standard methodology well known in the art and cloned into pCR2.1 Topo (Invitrogen) according to manufacturer's instructions. The resulting plasmid was named pMON69809 and contained the sequence of the promoter pBAN (SEQ ID NO: 1). The sequence of this clone was determined using standard sequencing methodologies as set forth by PE Applied Biosystems.

p63

A cDNA clone, designated clone 63, was identified from *Arabidopsis thaliana* using cDNA-AFLP. SMART cDNA libraries were prepared from mRNA isolated from *Arabidopsis* open flowers (inflorescence), stem, whole seedling, and developing seed harvested at 4, 7, 10, 13, or 18 days after flowering (DAF), according to manufacturer's instructions (Clontech). Five hundred micrograms of amplified SMART cDNA was used for AFLP analysis using the Gibco-BRL small genome AFLP II kit and following manufacturer's instructions (Invitrogen). The resulting bands were visualized after electrophoresis through 6% acrylamide/8M Urea sequencing gels. A single band, designated band 63, visible only in the lane derived from cDNA from 4 DAF developing seed tissue, was extracted from the gel. The DNA was eluted by placing the acrylamide band in 50 µl of TE (10 mM Tris-HCl (pH 8.0); 1 mM EDTA) and allowing the band to elute at ambient temperature overnight. After a brief centrifugation, 0.75 µl of supernatant was used as the template source for a PCR amplification. Twenty microliters of Preamp primer mix 2 (from the Gibco-BRL small genome AFLP II Kit), 2.5 µl 10×PCR buffer with 15 mM MgCl₂ (PE Applied Biosystems), 2.5 units AmpliTaq DNA Polymerase (PE Applied Biosystems), and 2 µl water were added to the DNA template. Amplification conditions were as follows: 25 cycles of 94° C. for 30 seconds, 56° C. for 60 seconds, and 72° C. for 2 minutes followed by 1 cycle of 72° C. for 2 minutes. The resulting DNA fragment was subcloned into pCR2.1 Topo (Invitrogen) according to instructions. This cDNA clone 63 was hybridized to virtual Northerns that were prepared from SMART cDNA libraries, according to the manufacturer's instructions, using the SMART PCR cDNA Synthesis Kit (BD Biosciences, Clontech, Palo Alto, Calif.). Clone 63 was characterized as being expressed in early stages of seed development. The sequence of clone 63 was determined using standard sequencing methodologies as set forth by PE Applied Biosystems BigDye terminator v.3.0 (PE Applied Biosystems, Foster City, Calif.).

The entire sequence of the clone 63 was used as a query for a BLAST search against public and proprietary databases. Public database searches indicated that clone 63 was annotated as a putative protein. The entire genomic sequence of clone 63 was contained within the BAC clone T25N20 (Choi et al., *Weeds World*, 2:17-20, 1995), which was then obtained from the *Arabidopsis* Biological Resource Center (Columbus, Ohio).

An overnight culture of *E. coli* containing the BAC clone T25N20 was grown from a single colony in LB broth (10% bacto-tryptone, 5% yeast extract, and 10% NaCl with kanamycin (25 mg/L) and ampicillin (100 mg/L)), containing 12.5 mg/liter chloramphenicol at 37° C. with vigorous shaking until late exponential or early stationary phase. Clone 63 (p63) was then isolated from the BAC clone T25N20. The cells were collected via centrifugation resulting pellet was resuspended in 0.2 ml buffer (50 mM glucose; 10 mM EDTA; 25 mM Tris pH 8.0; 5 mg/ml lysozyme) and incubated on ice for 5 minutes, followed by the addition of 0.4 ml of 0.2 N NaOH; 1% SDS solution. The tube was mixed gently and incubated on ice for 5 minutes, followed by the addition of 0.3 ml of 3 M potassium acetate. The tube was mixed gently and then frozen at minus 80° C. for 15 minutes. The debris was pelleted by centrifugation at 20,000×g for 15 minutes, and 0.75 ml of the resulting supernatant was transferred to a new tube. Isopropanol (0.45 ml) was added and the mixture was incubated at minus 80° C. for 15 minutes. DNA was pelleted by centrifugation at 20,000×g for 5 minutes. The pellet was rinsed with 1 ml of cold 70% ethanol, then dried on the bench for at least 15 minutes prior to being resuspended in 40 µl TE buffer.

The following primers were used to PCR amplify p63 from BAC T25N20:

```
p63-Nco
5'-CCATGGTTATTCAAGTGACCACAG-3'      (SEQ ID NO: 12)

and p63-fwd3
5'-CGTGTTGAGGTGAGAGG-3'             (SEQ ID NO: 13)
```

The conditions for the PCR reaction followed a protocol recommended by the enzyme manufacturer (PE Applied Biosystems, Foster City, Calif.). The p63 sequence was amplified using 1.5 µl of T25N20 as template, 30 nanomoles each of the primers p63-Nco and p63-fwd3, 10 micromoles each of dATP, dCTP, dGTP, and TTP, 2.5 units of AmpliTaq Gold (PE Applied Biosystems) in 1× Opti-Prime™ Buffer 3 (Stratagene). After an initial incubation at 95° C. for 10 minutes, 28 cycles of PCR were performed with 94° C. for 15 seconds, 62° C. for 10 seconds, 52° C. for 10 seconds, and 72° C. for 3 minutes followed by 1 cycle of 72° C. for 7 minutes.

The product of the PCR reaction was purified according to standard methodology well known in the art and cloned into pCR2.1 Topo (Invitrogen) according to manufacturer's instructions. The resulting plasmid was named pMON69811 and contained the sequence of the promoter p63 (SEQ ID NO:

3). The sequence of this clone was determined using standard sequencing methodologies as set forth by PE Applied Biosystems.

EXAMPLE 2

This example describes the construction of the vectors used for *Arabidopsis* transformation.

pMON69802

An 1861 base pair (bp) fragment containing the *E. coli* uidA gene (GUS) was removed from the donor plasmid pCGN10906 by digestion with EcoRI. The fragment was isolated from an agarose gel using the QiaGel Purification kit (Qiagen) according to the manufacturer's instructions. The purified DNA was eluted from the column using 30l of Buffer EB (10 mM Tris-Cl pH 8.5). New restriction endonuclease sites were added to the *E. coli* uidA gene using primers:

```
Gus 5'
                                            (SEQ ID NO: 14)
5'-AGGCGGCGCCTAAACCATGGTCCGTCCTGTAGAAACCCC-3' and

Gus 3'
                                            (SEQ ID NO: 15)
5'-AGTCGACTCATTGTTTGCCTCCCTGCTGCGGTTTTTCAC-3'.
```

The purified fragment (0.5 g) was used as the template for the following PCR amplification. Thirty nanomoles each of primers Gus 5' (SEQ ID NO: 14) and GUS 3' (SEQ ID NO: 15), 10 micromoles each of dATP, dCTP, dGTP, and TTP, 2.5 units of AmpliTaq Gold (PE Applied Biosystems) in 1× OptiPrime™ Buffer 3 (Stratagene) were added to the DNA template. Amplification conditions were as follows: 25 cycles of 94° C. for 30 seconds, 56° C. for 60 seconds, and 72° C. for 2 minutes followed by 1 cycle of 72° C. for 2 minutes. The product of the PCR reaction was purified according to standard methodology well known in the art and cloned into pCR2.1 Topo (Invitrogen) according to manufacturer's instructions. The resulting plasmid was named pMON65400. The sequence of this clone was determined using standard sequencing methodologies as set forth by PE Applied Biosystems.

A 1278 bp fragment containing the napin 3' UTR was removed from the vector pCGN 7770 by digestion with SalI and Asp718I. An 1861 base pair fragment, containing the *E. coli* uidA gene, was removed from the vector pMON65400 by sequential digestion with BstXI and SalI. Prior to SalI digestion and gel purification, the BstXI overhang was blunt ended using Pfu polymerase according to the manufacturer's instructions (Stratagene). Both fragments were ligated into the vector pCGN8541, which had been digested with Asp718I and SwaI. The resulting plasmid, containing the *E. coli* uidA gene and the napin 3' UTR, was named pMON69802 (FIG. 1). The nucleic acid sequence was determined using known methodology and confirmed the integrity of the cloning junctions.

pMON69804 (p26::GUS)

Figure 2:
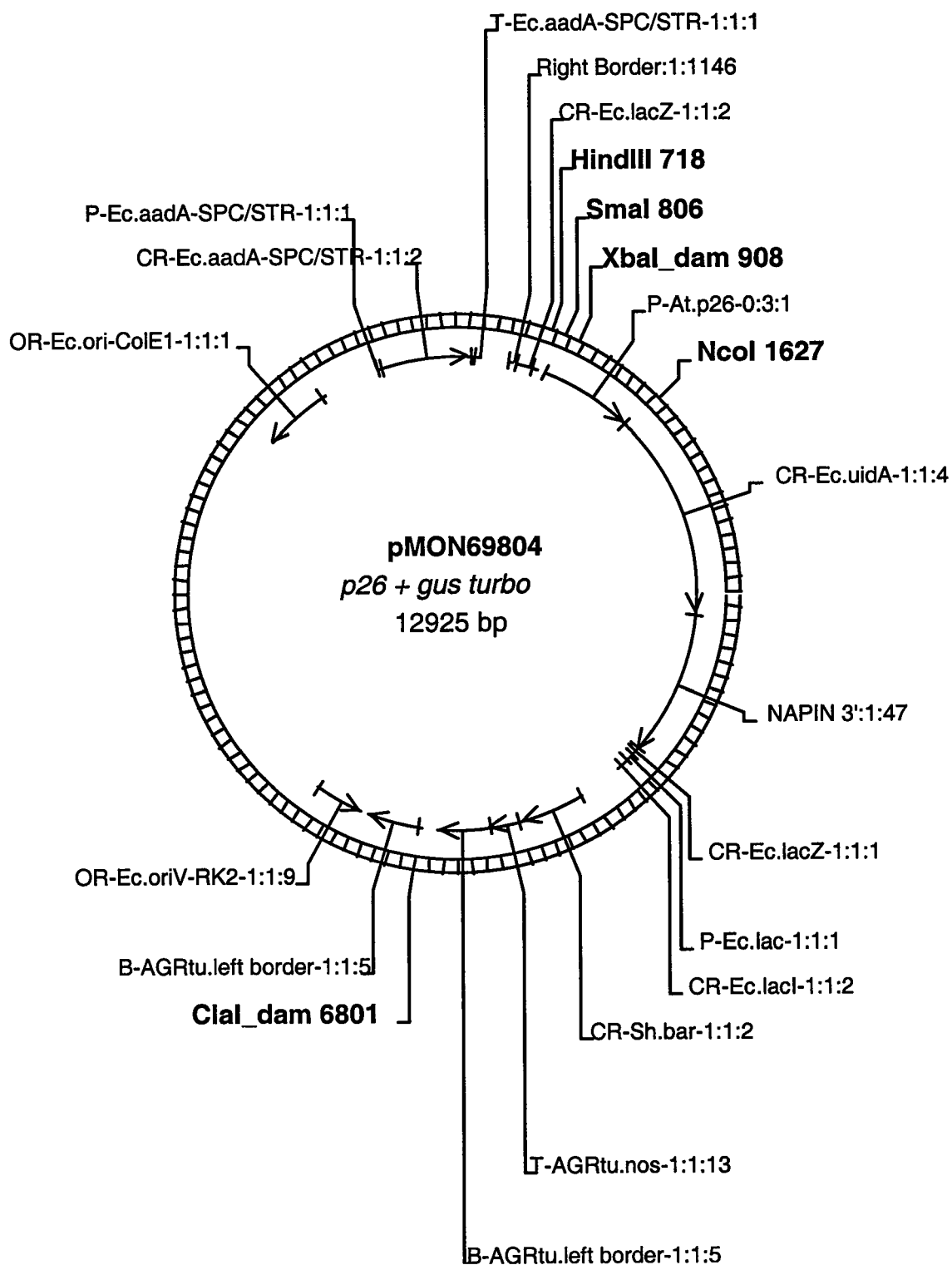
FIG. 2 is a schematic representation of pMON69804.

A 1007 bp fragment containing the p26 sequence was removed from pMON69803 by digestion with HindIII and NcoI. The fragment was ligated into pMON69802, which had also been digested with HindIII and NcoI. The resulting plasmid, containing the p26 promoter driving the *E. coli* uidA gene and with the napin 3' UTR was named pMON69804 (FIG. 2). The nucleic acid sequence was determined using known methodology and confirmed the integrity of the cloning junctions. This vector was used in the subsequent transformation of *Arabidopsis*.

pMON69815 (pBAN::GUS)

Figure 3:
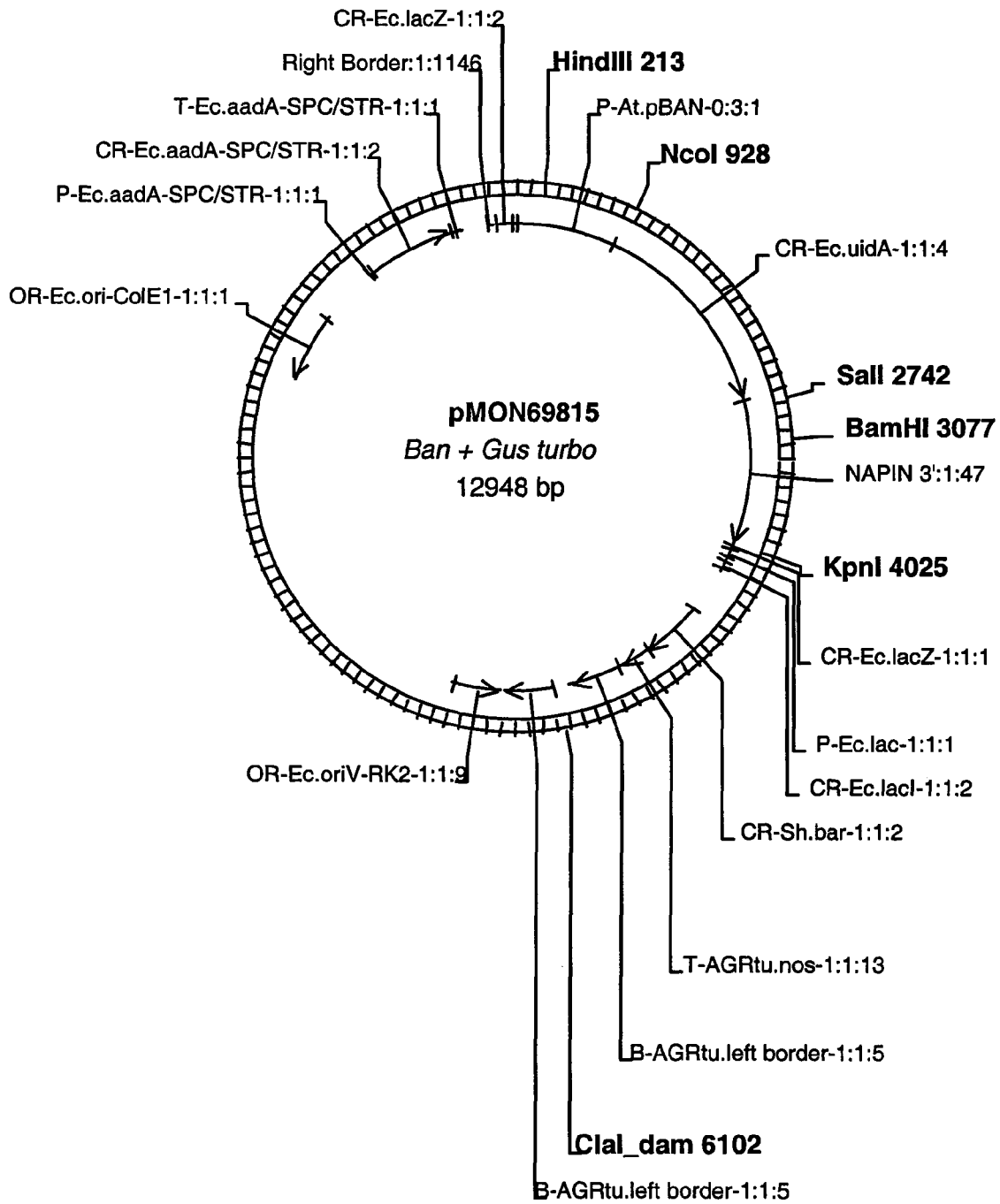
FIG. 3 is a schematic representation of pMON69815.

A 947 bp BstXI-NcoI fragment containing the pBAN promoter sequence was removed from pMON69809 by sequential digestion with BstXI followed by and NcoI. Prior to NcoI digestion and gel purification, the BstXI overhang was blunt ended using Pfu polymerase according to the manufacturer's instructions (Stratagene). The fragment was ligated into pMON69802, which had been sequentially digested with HindIII and NcoI. Prior to NcoI digestion and gel purification, the HindIII overhang from pMON69802 was blunt ended using Pfu polymerase according to the manufacturer's instructions (Stratagene). The resulting plasmid, containing the pBAN promoter driving the *E. coli* uidA gene and with the napin 3' UTR, was named pMON69815 (FIG. 3). The nucleic acid sequence was determined using known methodology and confirmed the integrity of the cloning junctions. This vector was used in the subsequent transformation of *Arabidopsis*.

pMON69812 (p63::GUS)

Figure 4:
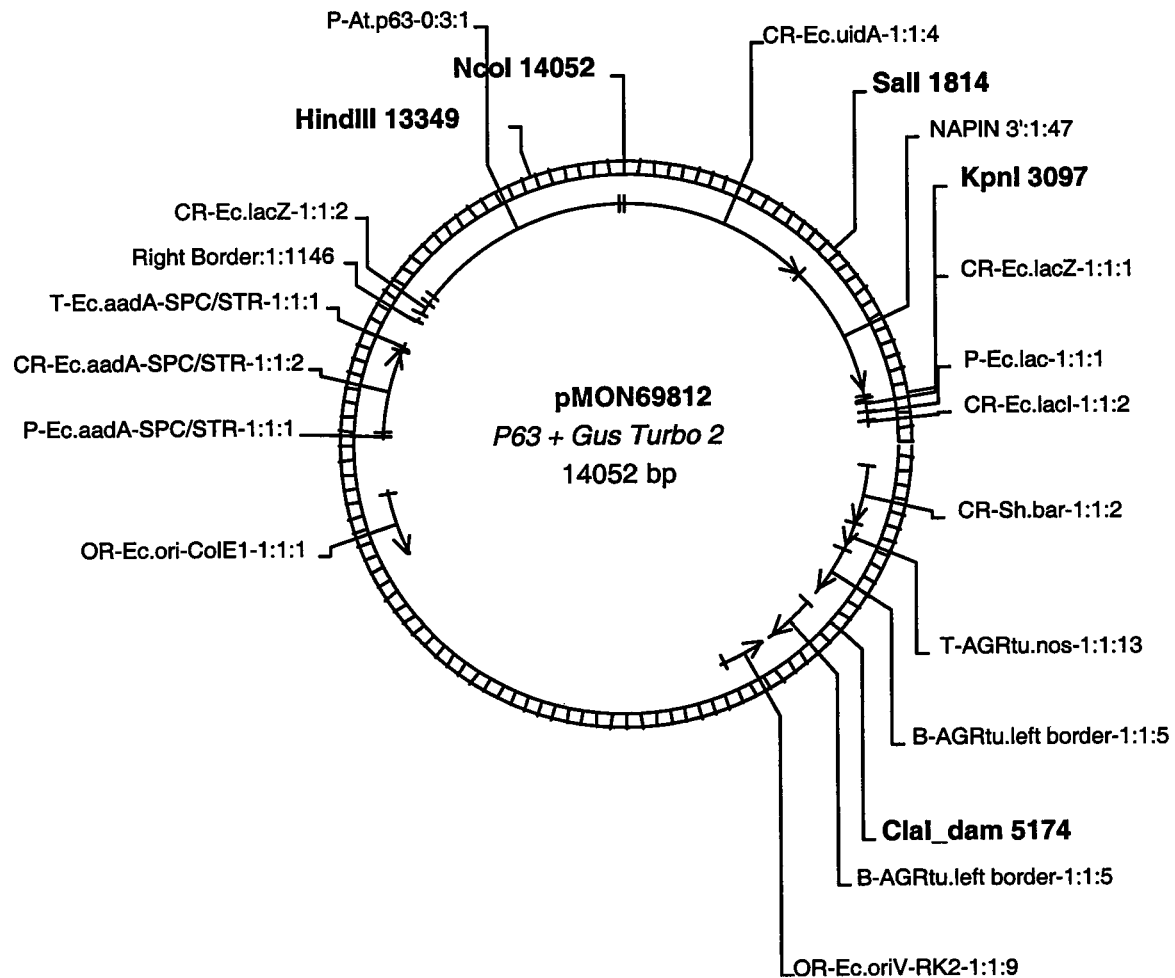
FIG. 4 is a schematic representation of pMON69812.

A 2031 base pair fragment containing the p63 sequence was cut out of pMON69811 by sequential digestion with BstXI and NcoI. Prior to NcoI digestion and gel purification, the BsatXI overhang was blunt ended using Pfu polymerase according to manufacturer's instructions (Stratagene). The fragment was ligated into pMON69802, which had been digested with HindIII, and also had the resulting overhang blunt ended with Pfu polymerase. The resulting plasmid, containing the p63 promoter driving the *E. coli* uidA gene and with the napin 3' UTR was named pMON69812 (FIG. 4). The nucleic acid sequence was determined using known methodology and confirmed the integrity of the cloning junctions. This vector was used in the subsequent transformation of *Arabidopsis*.

EXAMPLE 3

This example describes the transformation and subsequent regeneration of transgenic *Arabidopsis* plants expressing a heterologous gene of interest.

*Arabidopsis* plants were grown by sowing seeds onto 4 inch pots containing reverse osmosis water (ROW) saturated MetroMix 200 (The Scotts Company, Columbus, Ohio). The plants were vernalized by placing the pots in a covered flat, in a growth chamber at 4-7° C., 8 hours light/day for 4-7 days. The flats were transferred to a growth chamber at 22° C., 55% relative humidity, and 16 hours light/day at an average intensity of 160-200 µEinstein/s/m$^2$. The cover was lifted and slid back 1 inch after germination, and then was removed when the true leaves had formed. The plants were bottom watered, as needed, with ROW until 2-3 weeks after germination. Plants were then bottom watered, as needed, with Plantex 15-15-18 solution (Plantex Corporation Ottawa, Canada) at 50 ppm N$_2$. Pots were thinned so that 1 plant remained per pot at 2-3 weeks after germination. Once the plants began to bolt, the primary inflorescence was trimmed to encourage the growth of axillary bolts.

Transgenic *Arabidopsis thaliana* plants were obtained as described by Bent et al., *Science*, 265:1856-1860, 1994 or Bechtold et al., *C.R. Acad. Sci, Life Sciences*, 316:1194-1199, 1993. Cultures of *Agrobacterium tumefaciens* strain ABI containing one of the transformation vectors pMON69804, pMON69812, or pMON69815 were grown overnight in LB (10% bacto-tryptone, 5% yeast extract, and 10% NaCl with kanamycin (75 mg/L), chloramphenicol (25 mg/L), and spectinomycin (100 mg/L)). The bacterial culture was centrifuged and resuspended in 5% sucrose+0.05% Silwet-77 solution. The aerial portions of whole *Arabidopsis thaliana* plants (at about 5-7 weeks of age) were immersed in the resulting solution for 2-3 seconds. The excess solution was removed by blotting the plants on paper towels. The dipped plants were placed on their side in a covered flat and transferred to a growth chamber at 19° C. After 16 to 24 hours the dome was removed and the plants were set upright. When plants had reached maturity, water was withheld for 2-7 days prior to seed harvest. Harvested seed was passed through a stainless steel mesh screen (40 holes/inch) to remove debris. The harvested seed was stored in paper coin envelopes at room temperature until analysis.

The harvested seeds described above were sown onto flats containing ROW saturated MetroMix 200 (The Scotts Company). The plants were vernalized and germinated as described above. After true leaves had emerged, the aerial portion of the seedlings were sprayed with a solution containing a 1:200 dilution of Finale herbicide (The Scotts Company). Approximately 1 week after the first application, the plants were sprayed a second time. Up to 16 Finale resistant seedlings were transplanted to 2¼ inch pots, one seedling per pot, containing MetroMix 200 and were grown under the conditions described above until the initial siliques that had formed began to desiccate. Tissue (rosette leaf, cauline leaf, stem, flowers, floral buds, and developing siliques) was removed from each T1 plant for subsequent histochemical staining.

EXAMPLE 4

Expression of β-glucuronidase was analyzed in *Arabidopsis thaliana* plants transformed with pMON69815, pMON69812, or pMON69804 using histochemical staining. Tissues, prepared as described in Example 3, were incubated for approximately 24 hours at 37° C. in a solution containing 50 mM NaPO$_4$ (pH 7.2); 100 µM potassium ferricyanide; 100 µM potassium ferrocyanide, 0.03% Triton X-100; 20% methanol and 2.5 mg/ml 5-bromo-4-chloro-3-indoyl glucuronic acid (X-gluc). In some cases the potassium ferricyanide, potassium ferrocyanide, and methanol were omitted from the staining solution. The stained tissue was cleared of chlorophyll by an overnight incubation in 70% ethanol/30% H$_2$O at 37° C. Stained tissues were photographed immediately or transferred to a solution of 70% ethanol/30% glycerol (v/v) and stored at 4° C. until photographed. The results, summarized in Table 1 below, show that 4 out of the 11 individual T1 plants tested from pMON69804, (p26::GUS), showed GUS expression in the seed. For pMON69812, (p63::GUS), 13 of the 15 lines tested had expression in the seed. For pMON69815, (pBAN::GUS), 12 out of 12 lines tested had expression in the seed.

TABLE 1

| Construct | Promoter | # of Lines Tested | Lines with Seed Expression |
|---|---|---|---|
| pMON69804 | p26 | 11 | 4 |
| PMON69815 | pBan | 12 | 12 |
| pMON69812 | p63 | 15 | 13 |

To examine the developmental stage at which the promoters were active, seeds from the independent lines that were positive for GUS expression in the T1 generation (described above) were sown onto pots containing ROW saturated MetroMix 200. The plants were vernalized, in a growth chamber, at 4-7° C. and 8 hours of light/day for 4-7 days. The plants were transferred to a growth chamber at 22° C., 55% relative humidity, and 16 hours of light/day at an average intensity of 160-200 µEinstein/s/m$^2$. The plants were bottom watered, as needed, with ROW until well established, generally 2-3 weeks after germination. Plants were then bottom watered, as needed, with Plantex 15-15-18 at 50 ppm N$_2$. Pots were thinned so that 1 plant remained per 2¼ inch pot at 2-3 weeks after germination. At least 10 plants from each line were stained, as described above, at each time point. Visual observations of the GUS expression patterns were recorded. Qualitative expression was compared to the positive control plants containing a pNapin::GUS construct (labeled as 10908) and to the null segregants which served as the negative control plants. The results are shown in Table 2.

Expression driven by the napin promoter is detected from 7-18 days after flowering (daf). Expression driven by the p26 promoter, pBAN promoter, and the p63 promoter, was detected from 5-10, 1-14, and 4-14 daf, respectively. Hence, expression of all three promoters was detected earlier than that of the napin promoter.

TABLE 2

| | | Days after flowering | | | | | | | | | | | | |
|---|---|---|---|---|---|---|---|---|---|---|---|---|---|---|
| Line | promoter | 0 | 1 | 2 | 3 | 4 | 5 | 6 | 7 | 8 | 10 | 13 | 14 | 18 |
| 10908-7 | napin | − | − | ND | ND | ND | − | ND | + | ND | + | ND | + | + |
| 10908-10 | napin | − | − | − | ND | ND | − | ND | + | ND | + | ND | + | ND |
| 10908-16 | napin | − | − | − | − | ND | − | − | − | ND | + | ND | − | − |
| 69804-13 | p26 | − | − | − | − | − | ND | ND | + | ND | − | ND | − | − |
| 69804-14 | p26 | − | − | − | − | − | + | ND | + | + | + | ND | − | − |
| 69804-7 | p26 | − | − | − | ND | ND | + | ND | + | ND | − | ND | − | − |
| 69815-2 | pBan | − | + | + | + | ND | + | ND | + | ND | + | + | ND | − |
| 69815-9 | pBan | − | + | + | + | ND | + | ND | + | ND | + | ND | ND | − |
| 69815-14 | pBan | − | + | + | + | ND | + | ND | + | ND | + | ND | + | − |
| 69812-4 | p63 | − | − | − | − | − | + | ND | + | ND | + | ND | + | − |
| 69812-9 | p63 | − | − | − | − | ND | − | ND | − | ND | + | ND | + | − |
| 69812-16 | p63 | − | − | − | − | ND | − | ND | − | ND | + | ND | + | − |
| 69812-13 | p63 | ND | ND | ND | ND | + | + | ND | ND | ND | ND | ND | ND | ND |

ND: Not Determined

EXAMPLE 5

This example describes the vector construction and transformation of soy plants with reporter genes driven by promoters of the present invention.

Vector Construction pMON82350 (p63::GUS)

Figure 5:
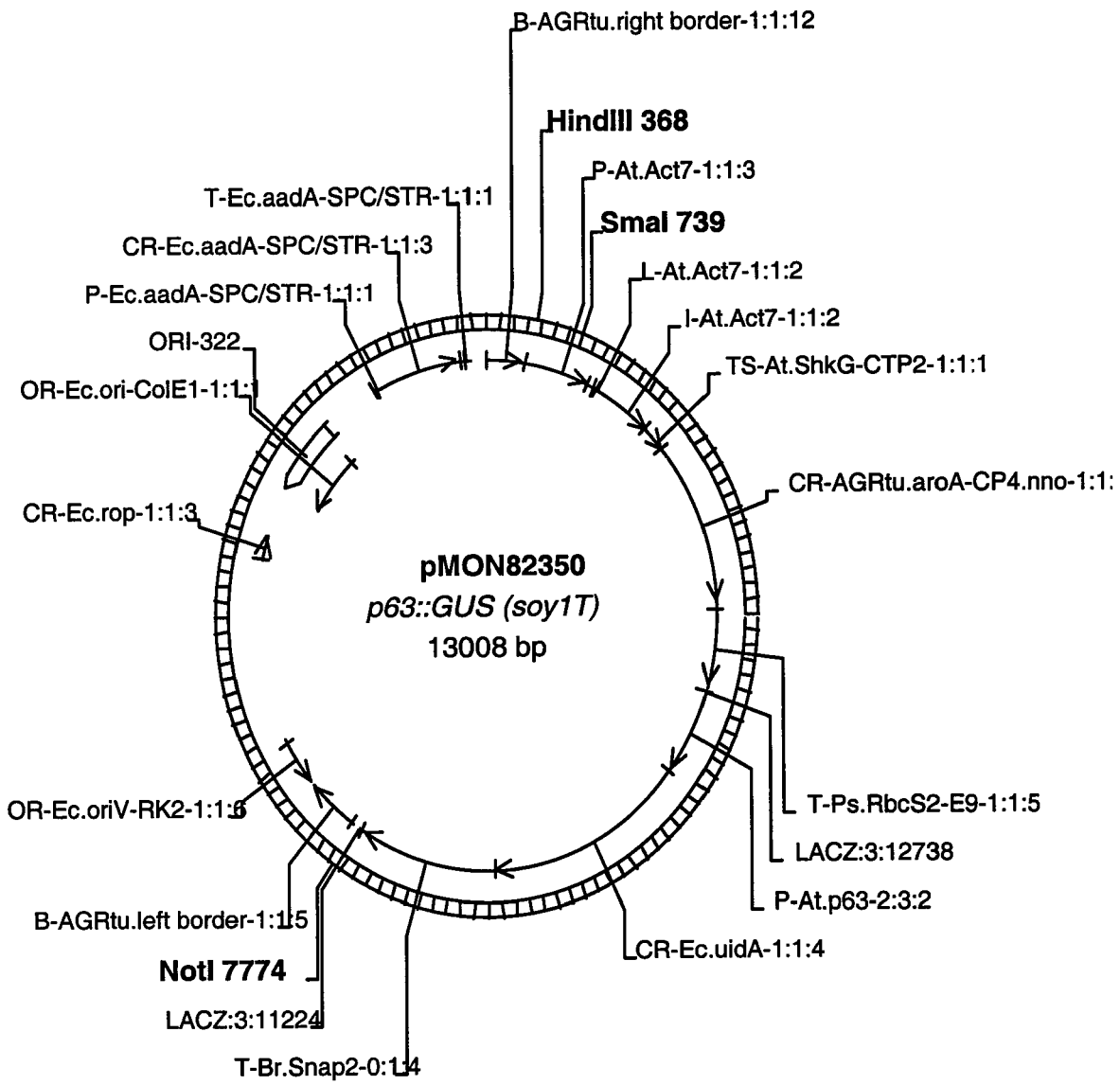
FIG. 5 is a schematic representation of pMON82350.
Figure 6:
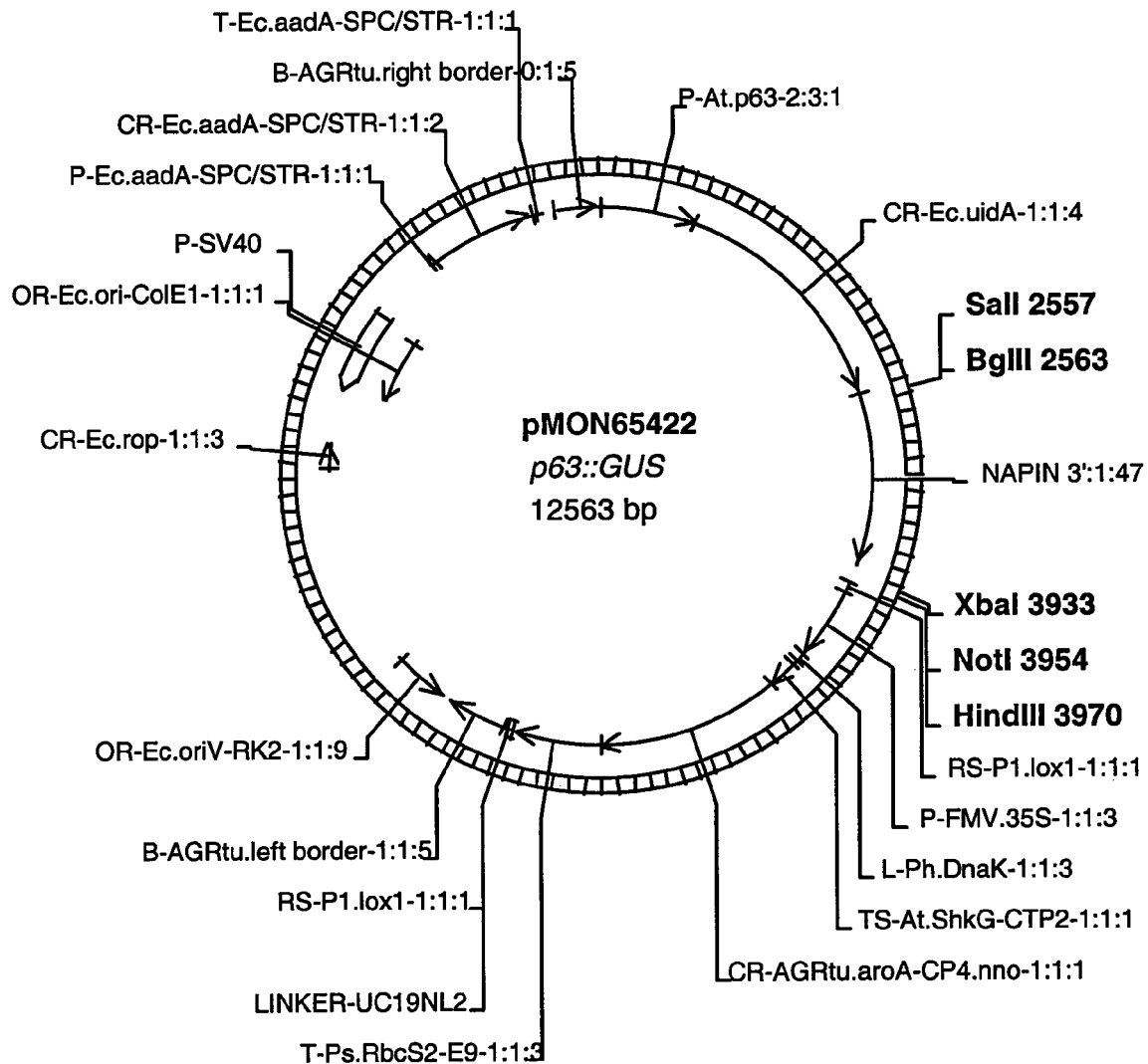
FIG. 6 is a schematic representation of pMON65422.

A 3859-base pair fragment containing p63 (SEQ ID NO: 3), the *Escherichia coli* uidA gene and the napin 3' UTR was removed from the vector pMON65415 by digestion with NotI and Sse8387I. The fragment was ligated in between the 3' UTR from the pea rbsc E9 gene and octopine T-DNA left border sequence in the vector pMON65448, which had been digested with NotI and Sse8387I. The vector pMON65448 contains a nopaline T-DNA right border sequence and octopine T-DNA left border sequence, in between which are the promoter, 5' UTR and first intron from the *Arabidopsis* act7 gene driving the expression of a CP4 EPSP synthase gene containing a CTP, linked to a synthetic EPSP synthase coding region and the 3' UTR from the pea rbsc E9 gene. The resulting plasmid was named pMON82350 (FIG. 5). The nucleic acid sequence was determined using standard sequencing methodology and confirmed the integrity of the cloning junctions.

pMON82350 was transformed into soy via *Agrobacterium*-mediated transformation as described by Martinell et al., U.S. Pat. No. 6,384,301. Transformed plant tissues are collected and stained as described in Example 4. Gus expression is detected in the seed.

EXAMPLE 6

This example describes the transformation and regeneration of canola plants with the heterologous gene of interest.

Vector Construction a. pMON65422

To analyze the expression of p63 in Canola, a binary vector was constructed. A 3796 base pair fragment containing 703 base pairs of the p63 promoter (p63tr) (SEQ ID NO: 4), the *E. coli* uidA gene and the napin 3' untranslated region (UTR) was removed from pMON69812 by digestion with HindIII and Asp718I. Prior to gel purification the HindIII and the Asp718I overhangs were blunt ended using Pfu polymerase (Stratagene). The fragment was ligated into a PmeI digested pMON70650 backbone. The vector pMON70650 contains a nopaline T-DNA right border sequence and octopine T-DNA left border sequence, with a 35S promoter from the Figwort Mosaic Virus (FMV) between the two T-DNA borders, driving the expression of a chimeric EPSP synthase gene containing a chloroplast targeting sequence from the *Arabidopsis* EPSP synthase gene (GenBank identifier number gi:16272) linked to a synthetic EPSP synthase coding region (U.S. Pat. No. 5,633,435) and the 3' untranslated region from the pea rbcS E9 gene. Additionally, pMON70650 contains recognition sites for cre recombinase. The recombinase sites are 5' of the FMV promoter and 3' of the E9 3'. The resulting plasmid was designated pMON65422. DNA sequence analysis confirmed the integrity of the cloning junctions.

b. pMON65428

To analyze expression of p26 in Canola, a binary vector was derived from the vector pCGN11123. The vector pCGN11123 contains a nopaline T-DNA right border sequence and an octopine T-DNA left border sequence, with an FMV-35S promoter, between the two T-DNA borders, driving the expression of a chimeric EPSP synthase gene containing a chloroplast targeting sequence from the *Arabidopsis* EPSP synthase gene (gi:16272) linked to a synthetic EPSP synthase coding region (U.S. Pat. No. 5,633,435), the 3' UTR from the pea rbcS E9 gene, and recognition sites for cre recombinase.

A 745 base pair fragment of DNA was amplified from pMON70650 using the following primers:

```
CP4-Dra
5'-ACTTCACTTGAGCGGAAGCCATAG-3'      (SEQ ID NO: 16)
``` and

```
CP4-Kpn
5'-TTTAAAACAATGGCGCAAGTTAGCAG-3'.   (SEQ ID NO: 17)
```

The CP4-Dra primer causes a single nucleotide substitution in the 5' UTR of EPSP synthase that eliminates an NcoI restriction site. The NcoI site was removed to facilitate later cloning. The product of the PCR reaction was purified according to standard methodology well known in the art and cloned into pCR2.1 Topo according to manufacturer's instructions (Invitrogen). The resulting plasmid was named pDMRUEZ033297. The sequence of this clone was determined using standard sequencing methodologies as set forth by PE Applied Biosystems.

A 737 base pair fragment containing the altered portion of the EPSP synthase gene was removed from pDMRUEZ033297 by digestion with KpnI and Dra I and ligated in place of the same size fragment of the vector pCGN11123. The resulting plasmid was named pDMRUEZ033298. A 3149 base pair fragment containing the *E. coli* uidA gene, and the napin 3' UTR was removed from pMON69802 by digestion with NotI and Asp718I. Prior to gel purification, the NotI and Asp718I overhangs were blunt ended using Pfu polymerase according to the manufacturer's instructions (Stratagene). The fragment was ligated into a NotI digested pDMRUEZ033298 vector backbone. Prior to ligation, the NotI overhangs were blunt ended using Pfu polymerase (Stratagene) according to the manufacturer's instructions. The resulting plasmid contains the nopaline T-DNA right border sequence, the *E. coli* uidA gene, and the napin 3' UTR followed by an expression cassette with an FMV-35S promoter, between the two T-DNA borders, driving the expression of a chimeric EPSP synthase gene containing a chloroplast targeting sequence from the *Arabidopsis* EPSP synthase gene (GenBank identifier number gi:16272) linked to a synthetic EPSP synthase coding region (U.S. Pat. No. 5,633,435), the 3' UTR from the pea rbcS E9 gene, and recognition sites for cre recombinase, followed by the octopine T-DNA left border sequence. This plasmid was named pMON65424. DNA sequence analysis confirmed the integrity of the cloning junctions.

Figure 7:
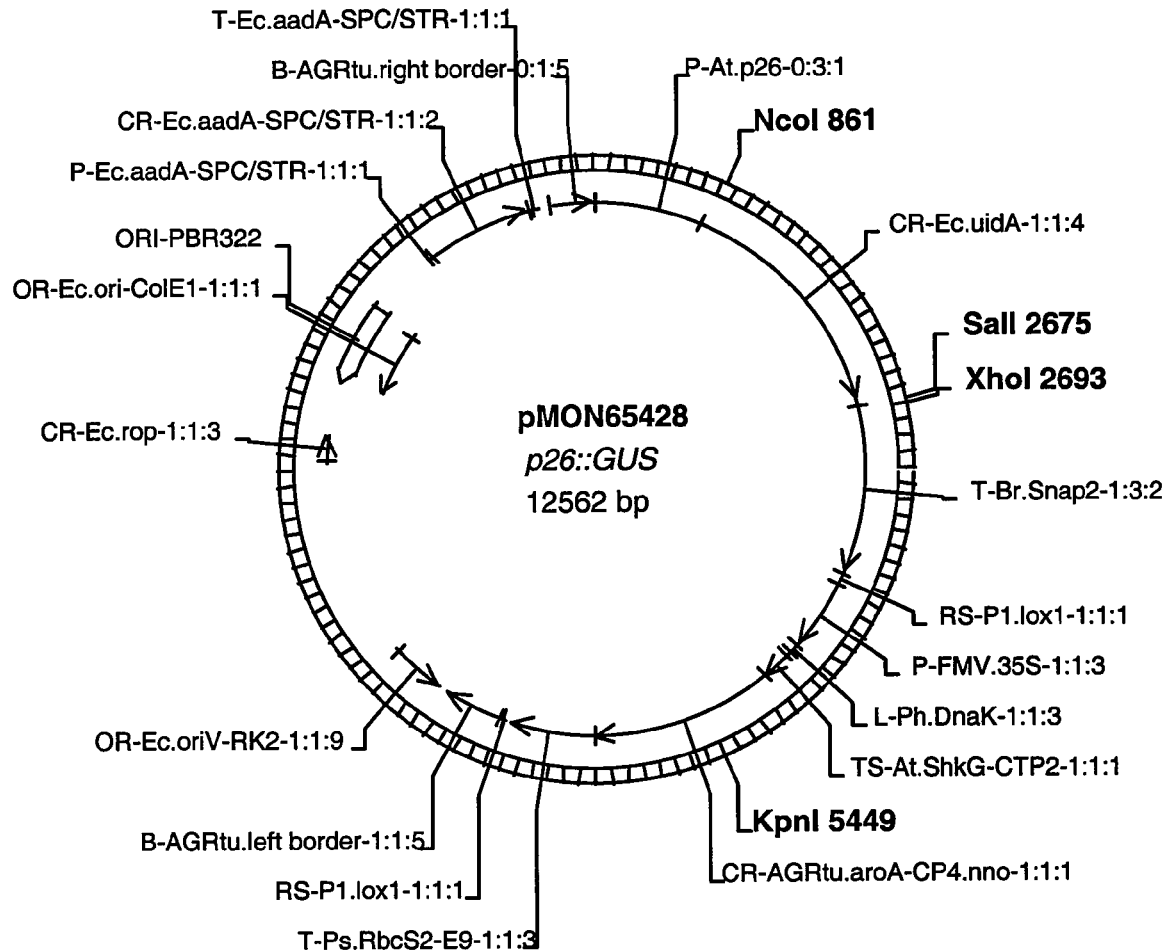
FIG. 7 is a schematic representation of pMON65428.

An 820 base pair fragment containing the p26 promoter sequence was removed from pMON69804 by digestion with SmaI and NcoI (FIG. 2, [SEQ ID NO: 2]). The fragment was ligated into a PmeI-NcoI digested pMON65424 vector backbone. The resulting plasmid was named pMON65428 (FIG. 7). The nucleic acid sequence was determined using known methodology and confirmed the integrity of the cloning junctions.

Canola Transformation

The vectors pMON65428 and pMON65422 are introduced into *Agrobacterium tumefaciens* strain ABI for transformation into *Brassica napus*. Canola plants are transformed using the protocol described by Moloney and Radke in U.S. Pat. No. 5,720,871. Briefly, seeds of *Brassica napus* cv Ebony are planted in 2 inch pots containing Metro Mix 350 (The Scotts Company, Columbus, Ohio). The plants are grown in a growth chamber at 24° C., and a 16/8 hour photoperiod, with light intensity of 400 $\mu Em^{-2}$ $sec^{-1}$ (HID lamps). After 2½ weeks, the plants are transplanted into 6 inch pots and grown in a growth chamber at 15/10° C. day/night temperature, 16/8 hour photoperiod, light intensity of 800 $\mu Em^{-2}$ $sect^{-1}$ (HID lamps).

Four terminal internodes from plants just prior to bolting or in the process of bolting but before flowering are removed and surface sterilized in 70% v/v ethanol for 1 minute, 2% w/v sodium hypochlorite for 20 minutes and rinsing 3 times with sterile deionized water. Six to seven stem segments are cut into 5 mm discs, maintaining orientation of basal end.

The *Agrobacterium* culture used to transform Canola is grown overnight on a rotator shaker at 24° C. in 2 mls of Luria Broth, LB, (10% bacto-tryptone, 5% yeast extract, and 10% NaCl) containing 50 mg/l kanamycin, 24 mg/l chloramphenicol, and 100 mg/l spectinomycin. A 1:10 dilution is made in MS media (Murashige and Skoog, *Physiol. Plant.*, 15:473-497, 1962) giving approximately $9 \times 10^8$ cells per ml. The stem discs (explants) are inoculated with 1.0 ml of *Agrobacterium* and the excess is aspirated from the explants.

The explants are placed basal side down in petri plates containing media comprising 1/10 MS salts, B5 vitamins (1% inositol; 0.1% thiamine HCl; 0.01% nicotinic acid; 0.01% pyridoxine-HCl), 3% sucrose, 0.8% agar, pH 5.7, 1.0 mg/l 6-benzyladenine (BA). The plates are layered with 1.5 ml of media containing MS salts, B5 vitamins, 3% sucrose, pH 5.7, 4.0 mg/l p-chlorophenoxyacetic acid, 0.005 mg/l kinetin and covered with sterile filter paper.

Following a 2 to 3 day co-culture, the explants are transferred to deep dish petri plates containing MS salts, B5 vitamins, 3% sucrose, 0.8% agar, pH 5.7, 1 mg/l BA, 500 mg/l carbenicillin, 50 mg/l cefotaxime, 200 mg/l kanamycin, or 175 mg/l gentamycin for selection. Seven explants are placed on each plate. After 3 weeks they are transferred to fresh media, 5 explants per plate. The explants are cultured in a growth room at 25° C., continuous light (Cool White).

The transformed plants are grown in a growth chamber at 22° C. in a 16-8 hours light-dark cycle with light intensity of 220 $\mu Em^{-2}s^{-1}$ for several weeks before transferring to the greenhouse. Plants are maintained in a greenhouse under standard conditions. Developing seed is harvested at various stages after pollination and stored at minus 70° C. Mature seed is collected and stored under controlled conditions consisting of about 17° C. and 30% humidity.

Up to 5 siliques are harvested from individual R0 plants at several time points after pollination. Siliques are scored with an 18 gauge needle to allow the staining solution to contact the developing seed. The siliques are incubated for approximately 24 hours at 37° C. in a solution containing 50 mM $NaPO_4$ (pH 7.2); 100 µM potassium ferricyanide; 100 µM potassium ferrocyanide, 0.03% Triton X-100; 20% methanol and 2.5 mg/ml 5-bromo-4-chloro-3-indoyl glucuronic acid (X-gluc). The stained tissue is cleared of chlorophyll by an overnight incubation in 70% ethanol/30% $H_2O$ at 37° C. Stained tissues are photographed immediately or transferred to a solution of 70% ethanol/30% glycerol (v/v) and stored at 4° C. until photographed. Samples were scored positive (+) or negative (−) for blue color.

Six out of 10 lines transformed with pMON65428 have detectable levels of activity in seeds from at least one time point. Ten out of 10 lines transformed with pMON65422 have detectable levels of activity in seeds from at least one time point. No staining is observed in seeds harvested from non-transgenic control plants. The data is illustrated in the tables below.

| p26 Expression in Developing Canola Seed | | | | | | | | | | |
|---|---|---|---|---|---|---|---|---|---|---|
| | Days After Pollination | | | | | | | | | |
| Construct | 3 | 6 | 9 | 12 | 15 | 20 | 25 | 30 | 35 | 40 |
| pMON65422 | + | + | + | + | + | + | + | + | + | + |
| pMON65422 | − | − | − | + | − | − | + | + | + | + |
| pMON65422 | + | + | + | + | + | + | + | + | − | − |
| pMON65422 | + | − | + | + | + | + | + | − | + | + |
| pMON65422 | − | − | − | − | − | + | + | + | + | + |
| pMON65422 | + | + | + | + | + | + | + | + | + | + |
| pMON65422 | + | + | + | + | + | + | + | + | + | + |
| pMON65422 | − | − | − | − | − | + | + | − | + | − |
| pMON65422 | − | + | + | + | + | + | + | + | + | + |
| pMON65422 | − | + | + | + | + | + | + | + | + | + |
| Control | − | − | − | − | − | − | − | − | − | − |

| p63 Expression in Developing Canola Seed | | | | | | | | | | |
|---|---|---|---|---|---|---|---|---|---|---|
| | Days After Pollination | | | | | | | | | |
| Construct | 3 | 6 | 9 | 12 | 15 | 20 | 25 | 30 | 35 | 40 |
| pMON65422 | + | + | + | + | + | + | + | + | + | + |
| pMON65422 | − | − | − | + | − | − | + | + | + | + |
| pMON65422 | + | + | + | + | + | + | + | + | − | − |
| pMON65422 | + | − | + | + | + | + | + | − | + | + |
| pMON65422 | − | − | − | − | − | + | + | + | + | + |
| pMON65422 | + | + | + | + | + | + | + | + | + | + |
| pMON65422 | + | + | + | + | + | + | + | + | + | + |
| pMON65422 | − | − | − | − | − | + | + | − | + | − |
| pMON65422 | − | + | + | + | + | + | + | + | + | + |
| pMON65422 | − | + | + | + | + | + | + | + | + | + |
| Control | − | − | − | − | − | − | − | − | − | − |

Having illustrated and described the principles of the present invention, it should be apparent to persons skilled in the art that the present invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

I claim:

1. A polynucleotide molecule comprising a sequence selected from the group consisting of:
   a) the sequence of SEQ ID NO: 3;
   b) a fragment of the sequence of SEQ ID NO: 3 with promoter function; and
   c) a polynucleotide sequence comprising at least about 95% identity to the sequence of SEQ ID NO:3, wherein the polynucleotide sequence has promoter function, wherein said polynucleotide molecule is operably linked to a heterologous transcribable polynucleotide molecule.

2. The polynucleotide molecule of claim 1, wherein said heterologous transcribable polynucleotide molecule is operably linked to a 3' transcription termination polynucleotide molecule.

3. The polynucleotide molecule of claim 1, wherein said heterologous transcribable polynucleotide molecule is a gene of agronomic interest.

4. The polynucleotide molecule of claim 1, wherein said heterologous transcribable polynucleotide molecule is a marker gene.

5. A transgenic plant stably transformed with the polynucleotide molecule of claim 1.

6. The transgenic plant of claim 5, wherein the plant is a transgenic dicotyledonous plant.

7. The transgenic plant of claim 5, wherein said heterologous transcribable polynucleotide molecule confers altered oil content in the seed to said transgenic plant.

8. The transgenic plant of claim 5, wherein said heterologous transcribable polynucleotide molecule confers altered protein quality in the seed to said transgenic plant.

9. The transgenic plant of claim 5, wherein said heterologous transcribable polynucleotide molecule confers altered micronutrient content in the seed to said transgenic plant.

10. A seed of said transgenic plant of claim 5, wherein the seed comprises said polynucleotide molecule.

11. Meal from said transgenic plant of claim 5, wherein the meal comprises said polynucleotide molecule.

12. A method of making a vegetable oil and meal, comprising the steps of:
   a) incorporating in the genome of a dicotyledonous seed producing, oil-containing plant a polynucleotide molecule according to claim 1, wherein the transcribable polynucleotide molecule confers altered oil content;
   b) growing the dicotyledonous plant to produce seeds; and
   c) extracting oil from the seed to produce extracted oil and meal.

13. The polynucleotide molecule of claim 1, wherein the polynucleotide sequence exhibits at least about 95% identity with the sequence of a).

14. The polynucleotide molecule of claim 1, wherein the polynucleotide sequence exhibits at least about 98% identity with the sequence of a).

15. The polynucleotide molecule of claim 1, wherein the polynucleotide sequence exhibits at least about 99% identity with the sequence of a).

16. The polynucleotide molecule of claim 1, wherein the polynucleotide sequence comprises a fragment of the sequence of SEQ ID NO: 3 with promoter function.

17. The transgenic dicotyledonous plant of claim 6, wherein said plant is a dicotyledonous plant selected from the group consisting of tobacco, tomato, potato, peanut, soybean, cotton, canola, rapeseed, safflower, flax, sugarbeet, *Arabidopsis, Brassica*, sunflower, and alfalfa.

* * * * *